US012454554B2

(12) United States Patent
Jongeneelen et al.

(10) Patent No.: US 12,454,554 B2
(45) Date of Patent: Oct. 28, 2025

(54) INFLUENZA VIRUS VACCINES AND USES THEREOF

(71) Applicant: JANSSEN VACCINES & PREVENTION B.V., Leiden (NL)

(72) Inventors: Mandy Antonia Catharina Jongeneelen, Leiden (NL); Tina Ritschel, Oegstgeest (NL); Ferdinand Jacobus Milder, Zwolle (NL); Indigo King, Seattle, WA (US); Yifan Song, Seattle, WA (US); Johannes Petrus Maria Langedijk, Amsterdam (NL); Boerries Brandenburg, Utrecht (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 909 days.

(21) Appl. No.: 17/753,506

(22) PCT Filed: Sep. 3, 2020

(86) PCT No.: PCT/EP2020/074539
§ 371 (c)(1),
(2) Date: Mar. 4, 2022

(87) PCT Pub. No.: WO2021/043869
PCT Pub. Date: Mar. 11, 2021

(65) Prior Publication Data

US 2023/0250135 A1 Aug. 10, 2023

Related U.S. Application Data

(60) Provisional application No. 62/896,244, filed on Sep. 5, 2019.

(51) Int. Cl.

| | |
|---|---|
| ***A61K 39/00*** | (2006.01) |
| ***A61K 39/145*** | (2006.01) |
| ***A61P 31/16*** | (2006.01) |
| ***C07K 14/005*** | (2006.01) |
| ***C07K 14/11*** | (2006.01) |

(52) U.S. Cl.
CPC ............ *C07K 14/005* (2013.01); *A61P 31/16* (2018.01); *A61K 39/00* (2013.01); *C07K 2319/42* (2013.01)

(58) Field of Classification Search
CPC ....... A61K 39/00; A61K 39/145; A61P 31/16; C07K 14/005; C07K 14/11; C07K 2319/42
See application file for complete search history.

(56) References Cited

FOREIGN PATENT DOCUMENTS

WO 2013079473 A1 6/2013

OTHER PUBLICATIONS

International Search Report issued Dec. 9, 2020 in corresponding PCT/EP2020/074539.
Written Opinion issued Dec. 9, 2020 in corresponding PCT/EP2020/074539.
Sutton, Troy C., et al., "Protective efficacy of influenza group 2 hemagglutinin stem-fragment immunogen vaccines," NPJ Vaccines, vol. 2, No. 1, Dec. 1, 2017.

*Primary Examiner* — Barry A Chestnut
(74) *Attorney, Agent, or Firm* — Ice Miller LLP

(57) ABSTRACT

Provided herein are group 2 influenza hemagglutinin stem polypeptides, nucleic acids encoding said polypeptides, vectors comprising said nucleic acid and pharmaceutical compositions comprising the same, as well as methods of their use, in particular in the prevention and/or treatment of influenza virus infections.

25 Claims, 26 Drawing Sheets

Specification includes a Sequence Listing.

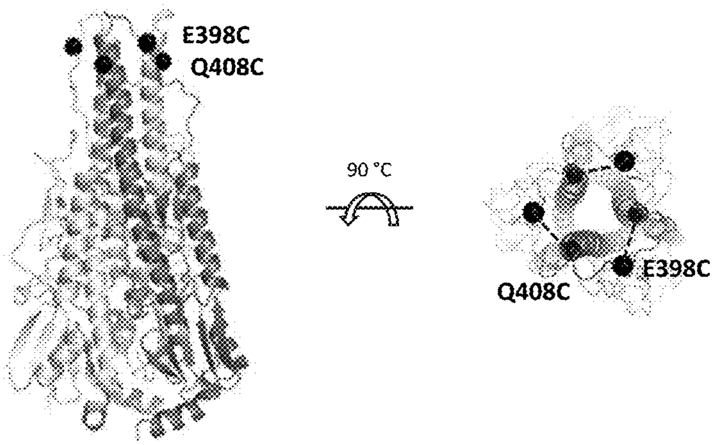
A
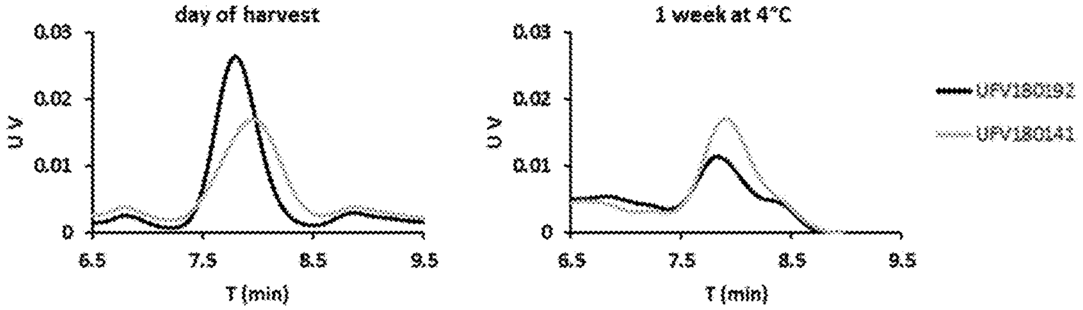
B
| 398 | 408 | ID. | Temperature stability ($Tm_{50}$) |
|---|---|---|---|
| - | - | UFV180192 | 50.8 °C |
| C | C | UFV180141 | 67.7 °C |
C
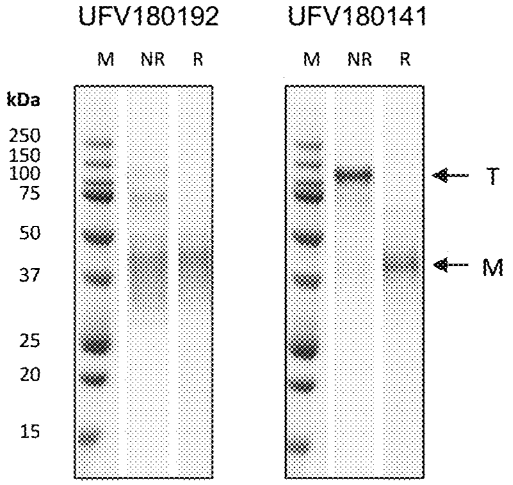
FIG. 4

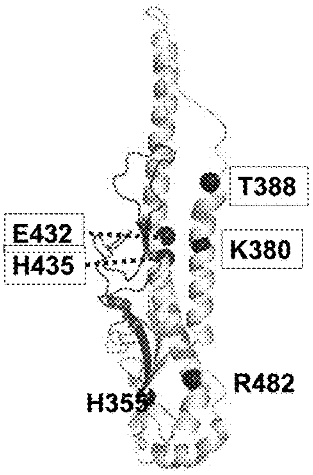
A
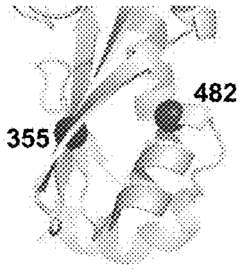
| | | | Normalized data (%) | | |
|---|---|---|---|---|---|
| 355 | 482 | ID. | Expression | CR9114 | CT149 |
| - | - | UFV161333 | 100 | 100 | 100 |
| W | - | UFV161739 | 196 | 1830 | 1579 |
| W | I | UFV161800 | 230 | 2063 | 1920 |
| F | I | UFV161804 | 153 | 707 | 903 |
B
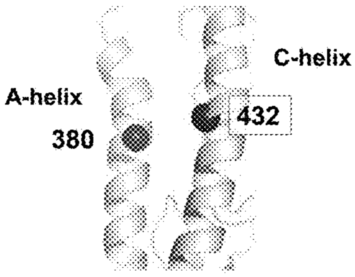
| 380 | 432 | ID. | Expression (%) | Trimer (%) | CR9114 (%) | CT149 (%) |
|---|---|---|---|---|---|---|
| - | - | UFV170991 | 100 | 100 | 100 | 100 |
| I | I | UFV171004 | 91 | 215 | 132 | 128 |
| F | F | UFV171190 | 92 | 110 | 108 | 84 |
| I | M | UFV171191 | 86 | 143 | 152 | 97 |
| F | I | UFV171192 | 112 | 138 | 104 | 79 |
| V | L | UFV171193 | 97 | 153 | 154 | 96 |
| M | - | UFV171194 | 99 | 77 | 64 | 58 |
| T | - | UFV171195 | 115 | 79 | 77 | 55 |
FIG. 5

C
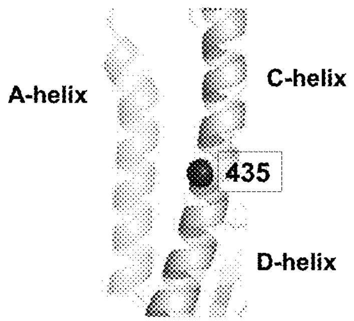
I.
| 435 | ID. | Expression (%) | Trimer (%) | CR9114 (%) | CT149 (%) |
|---|---|---|---|---|---|
| - | UFV170611 | 100 | 100 | 100 | 100 |
| K | UFV170612 | 123 | 71 | 99 | 96 |
| N | UFV170613 | 102 | 103 | 107 | 106 |
| Q | UFV170614 | 116 | 81 | 94 | 87 |
| R | UFV161908 | 87 | 78 | 113 | 108 |
II.
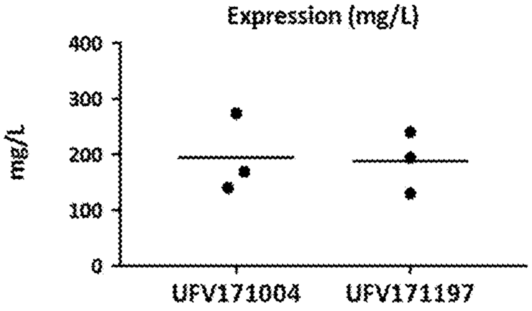
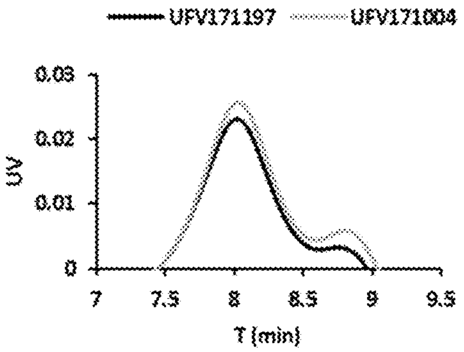
| Position 435 | ID. | CR9114 ($EC_{50}$) | CT149 ($EC_{50}$) | Temperature stability ($Tm_{50}$) |
|---|---|---|---|---|
| N | UFV171004 | 0.075 nM | 0.075 nM | 68.0 °C |
| R | UFV171197 | 0.084 nM | 0.075 nM | 64.1 °C |
FIG. 5 (Continued)

D
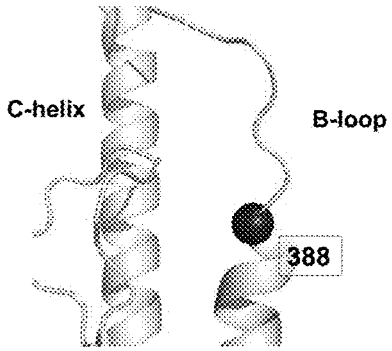
| ID.* | Position 388 | Expression (mg/L) |
|---|---|---|
| UFV180088 (R) | M | 475 |
| UFV180666 (WT) | T | 446 |
| UFV180667 | V | 332 |
| UFV180668 | I | 336 |
| UFV180669 | L | 427 |
| UFV180670 | F | 400 |
| UFV180671 | Y | 284 |
| UFV180672 | W | 287 |
| UFV180673 | H | 294 |
| UFV180674 | K | 245 |
| UFV180675 | R | 192 |
* Reference (R) containing a C-terminal C-tag. UFV180666 to UFV180675 contain a C-terminal Flag-Linker-His tag
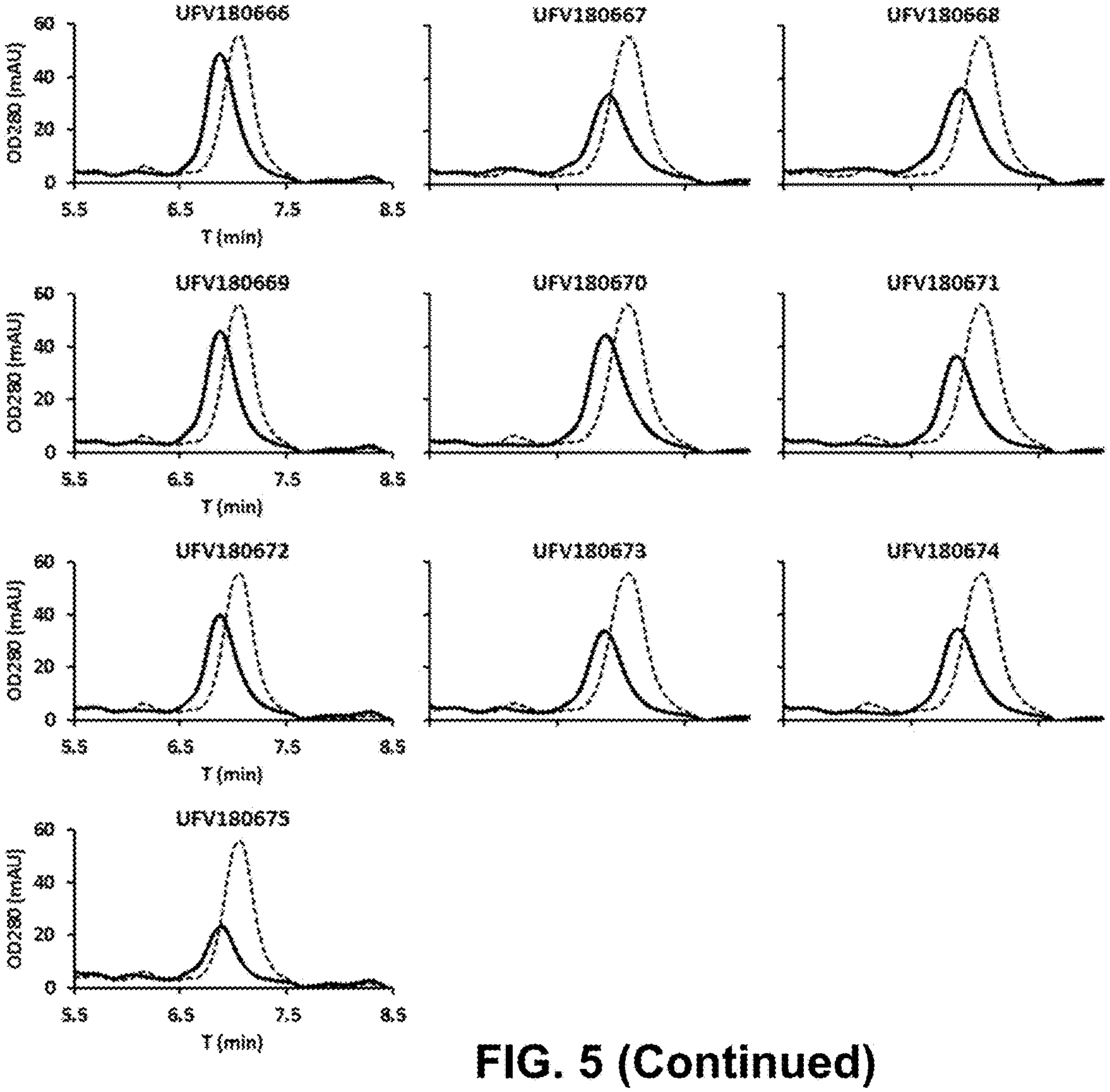
FIG. 5 (Continued)

B

| ID. | Connection | Expression (%) | CT149 binding (%) |
|---|---|---|---|
| UFV160653* | GPGS | 100 | 100 |
| UFV160764 | | 83 | 64 |
| UFV160765 | | 61 | 50 |
| UFV160766 | | 47 | 25 |
| UFV160674 | | 79 | 60 |
| UFV160675 | | 62 | 37 |
| UFV160767 | | 87 | 87 |
| UFV160768 | | 70 | 63 |
| UFV160769 | | 72 | 33 |
| UFV160770 | | 50 | 20 |
| UFV160771 | | 78 | 63 |
| UFV160772 | | 84 | 69 |

* Reference, ** Cysteine to glycine point mutation

C

| ID. | Connection | Expression (%) | CT149 binding (%) |
|---|---|---|---|
| UFV160321* | GGGG | 100 | 100 |
| UFV160403 | NPHR | 118 | 198 |
| UFV160404 | GDPH | 117 | 70 |
| UFV160405 | NGGS | 33 | 63 |
| UFV160406 | GGSN | 223 | 313 |
| UFV160407 | GSNA | 113 | 204 |
| UFV160408 | GPGS | 190 | 350 |
| UFV160409 | GSGF | 127 | 154 |
| UFV160410 | GSG | 100 | 165 |
| UFV160411 | GG | 118 | 248 |
| UFV160412 | GGS | 106 | 181 |
| UFV160413 | SGS | 110 | 161 |
| UFV160414 | HPST | 101 | 118 |
| UFV160415 | IPNI | 124 | 129 |
| UFV160416 | GLSS | 164 | 284 |
| UFV160417 | KPGD | 170 | 160 |
| UFV160418 | DAPI | 174 | 57 |
| UFV160419 | TPN | 86 | 124 |
| UFV160420 | TPNG | 125 | 258 |

* Reference

FIG. 6 (Continued)

| glycan introduction | | | ID. | Normalized data (%) | | | |
|---|---|---|---|---|---|---|---|
| 401 | 402 | 403 | | Expression | CR9114 | CT149 | SD15013 |
| E | V | E | UFV161686 | 100 | 100 | 100 | 100 |
| N | A | T | UFV161333 | 205 | 503 | 679 | 992 |
| Q | A | T | UFV161722 | 150 | 330 | 384 | 548 |
| N | A | Q | UFV161723 | 136 | 388 | 338 | 432 |

B

| ID. | Proline position | Expression (%) | CR9114 (%) | CT149 (%) | SD15013 (%) |
|---|---|---|---|---|---|
| UFV161333 | — | 100 | 100 | 100 | 100 |
| UFV161688 | **386** | 114 | 12 | 1 | 5 |
| UFV161689 | **387** | 111 | 4 | 2 | 3 |
| UFV161690 | **388** | 113 | 3 | 1 | 1 |
| UFV161691 | **389** | 106 | 28 | 16 | 3 |
| UFV161692 | **390** | 105 | 154 | 64 | 64 |
| UFV161693 | **391** | 106 | 129 | 74 | 58 |
| UFV161694 | **392** | 114 | 162 | 89 | 104 |
| UFV161695 | **393** | 128 | 150 | 84 | 82 |
| UFV161696 | **394** | 104 | 177 | 95 | 75 |
| UFV161697 | **395** | 100 | 156 | 99 | 113 |
| UFV161698 | **396** | 98 | 174 | 97 | 153 |
| UFV161699 | **397** | 101 | 119 | 92 | 58 |
| UFV161700 | **398** | 110 | 160 | 96 | 134 |
| UFV161701 | **399** | 104 | 158 | 110 | 158 |
| UFV161702 | **400** | 94 | 117 | 76 | 62 |
| UFV161703 | **401** | 99 | 103 | 61 | 58 |
| UFV161704 | **402** | 97 | 101 | 64 | 45 |
| UFV161705 | **403** | 98 | 109 | 68 | 50 |
| UFV161706 | **404** | 104 | 129 | 76 | 54 |
| UFV161707 | **405** | 113 | 147 | 90 | 55 |
| UFV161708 | **392+396** | 106 | 166 | 93 | 147 |
| UFV161709 | **392+398** | 107 | 140 | 86 | 115 |

C

| 2nd Glycan introduction | | | ID. | Normalized data (%) | | | |
|---|---|---|---|---|---|---|---|
| **393** | **394** | **395** | | **Expression** | **CR9114** | **CT149** | **SD15013** |
| H | Q | T | UFV161333 | 100 | 100 | 100 | 100 |
| N | Q | T | UFV161715 | 117 | 141 | 81 | 42 |
| **398** | **399** | **400** | | | | | |
| E | S | S | UFV161333 | 100 | 100 | 100 | 100 |
| N | S | S | UFV161721 | 109 | 147 | 97 | 83 |

D

| ID. | Glycan position(s) | Proline(s) | Expression (mg/L) | CR9114 (%) | CT149 (%) | SD15013 (%) |
|---|---|---|---|---|---|---|
| UFV171187 | 401 | — | 216 | 100 | 100 | 100 |
| UFV170991 | 401 | 405 | 81 | 71 | 72 | 63 |
| UFV171120 | 392+401 | 405 | 98 | 78 | 83 | 48 |
| UFV171121 | 392+401 | 399+405 | 109 | 101 | 91 | 85 |
| UFV170994 | 393+401 | 405 | 100 | 103 | 90 | 78 |
| UFV170995 | 393+401 | 399+405 | 130 | 107 | 97 | 88 |

E

```
AA         393          399  401        405
UFV180208  H Q T E K C F S N A T G R
UFV180217  N . . . . . P . . . . . P
```

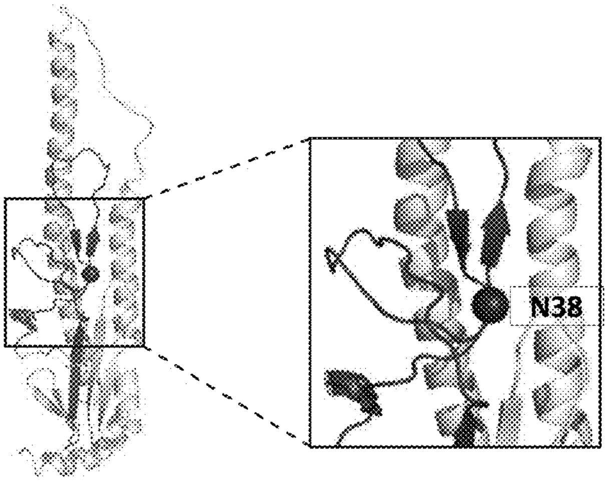
A
| 38 | 39 | 40 | ID. | Expression | CR9114 ($EC_{50}$) | CT149 ($EC_{50}$) |
|---|---|---|---|---|---|---|
| N | A | T | UFV170282 | 484 mg/L | 1.4 nM | 0.7 nM |
| N | A | I | UFV170278 | 255 mg/L | 0.7 nM | 0.7 nM |
B
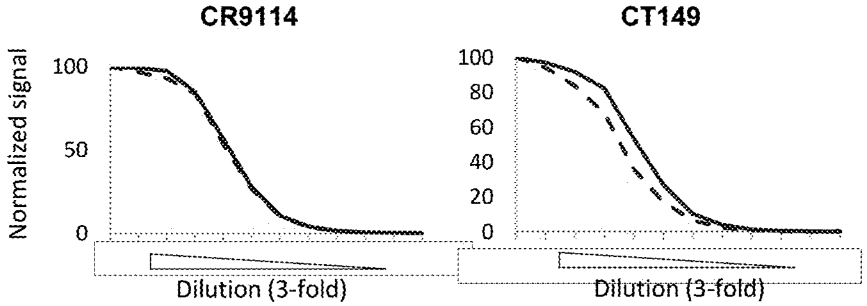
FIG. 8

A
UFV160595 UFV161196 UFV161198
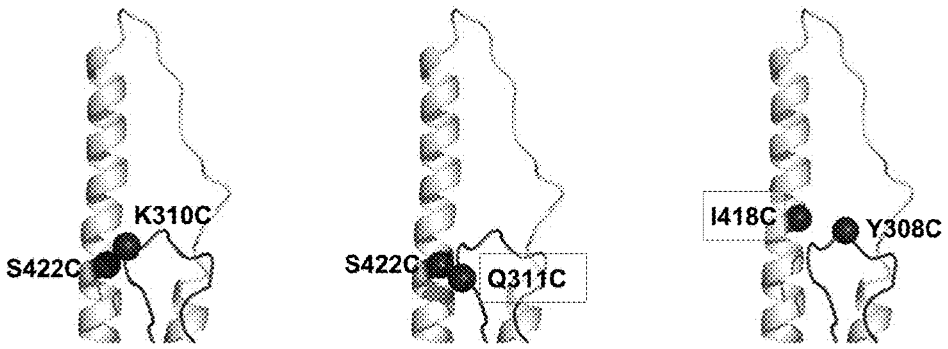
| 308 | 309 | 310 | 311 | 418 | 419 | 420 | 421 | 422 | ID. | Expression (%) | CR9114 (%) | CT149 (%) |
|---|---|---|---|---|---|---|---|---|---|---|---|---|
| - | - | C | - | - | - | - | - | C | UFV160595 | 100 | 100 | 100 |
| - | - | - | C | - | - | - | - | C | UFV161196 | 86 | 118 | 134 |
| C | - | - | - | C | - | - | - | - | UFV161198 | 80 | 69 | 110 |
B
UFV161169
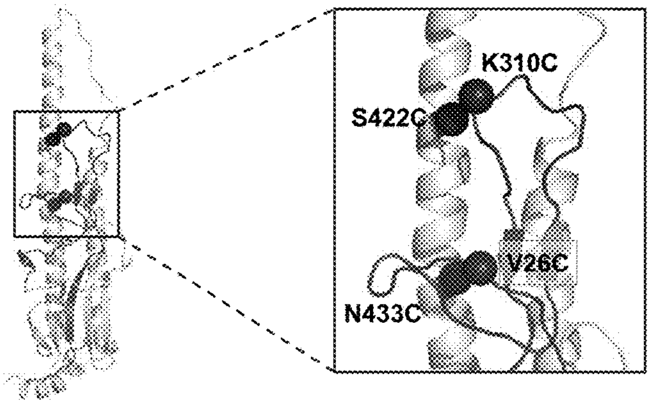
| 24 | 25 | 26 | 27 | 431 | 431 | 433 | 434 | ID. | Expression (%) | CR9114 (%) | CT149 (%) |
|---|---|---|---|---|---|---|---|---|---|---|---|
| - | - | - | - | - | - | - | - | UFV160595 | 100 | 100 | 100 |
| - | - | C | - | - | - | C | - | UFV161169 | 90 | 2 | 48 |
FIG. 9

| 396 | 397 | 398 | 405 | 406 | 407 | 408 | ID. | Expression (%) | Trimer (%) | CR9114 (%) | CT149 (%) |
|---|---|---|---|---|---|---|---|---|---|---|---|
| - | - | - | - | - | - | - | UFV170062 | 180 | 4 | 48 | 33 |
| - | - | C | - | - | - | C | UFV170051 | 100 | 100 | 100 | 100 |
| - | C | - | - | - | - | C | UFV161908 | 112 | 100 | 115 | 93 |
| C | - | - | - | - | - | C | UFV170428 | 108 | 78 | 94 | 95 |
| - | - | C | C | - | - | - | UFV170440 | 121 | 92 | 92 | 74 |

A
| 378 | 379 | 381 | ID. | Expression (%) | CR9114 (%) | CT149 (%) |
|---|---|---|---|---|---|---|
| **N** | **G** | **L** | WT H3 | | | |
| - | - | - | UFV161454 | 100 | 100 | 100 |
| - | **N** | - | UFV161453 | 130 | 61 | 24 |
| - | **A** | - | UFV161459 | 42 | 155 | 65 |
| - | **N** | **V** | UFV161451 | 163 | 947 | 561 |
| - | **A** | **V** | UFV161458 | 75 | 1072 | 589 |
| **T** | **N** | - | UFV161450 | 96 | 235 | 353 |
| **T** | **N** | **V** | UFV161448 | 84 | 1706 | 841 |
| **T** | **N** | **V** | WT H1 | | | |
B
| | | AA | | | | 378 | 379 | | 381 | | |
|---|---|---|---|---|---|---|---|---|---|---|---|
| **UFV171004** | **H1 A-helix** | | D | Q | I | T | N | I | V | N | R |
| **UFV171116** | **H3 A-helix** | | . | . | . | N | G | . | L | . | . |
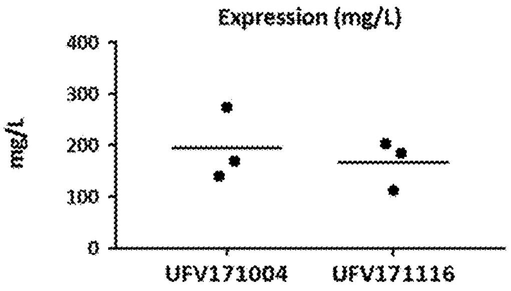
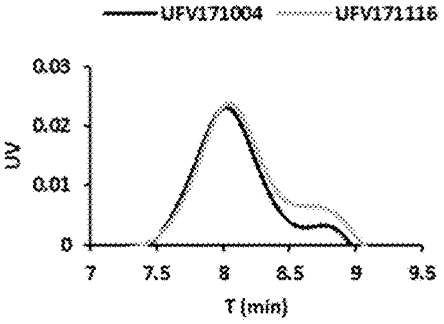
| ID. | Trimer % AUC | CR9114 ($EC_{50}$) | CT149 ($EC_{50}$) | Temperature stability ($Tm_{50}$) |
|---|---|---|---|---|
| UFV171004 | 87.3 | 0.075 nM | 0.075 nM | 68.0 °C |
| UFV171116 | 77.7 | 0.081 nM | 0.078 nM | 66.2 °C |
FIG. 12

A
| 25 | 27 | 367 | 379 | 381 | 475 | 476 | 479 | ID. | Trimer (%) | CR9114 (%) | CT149 (%) |
|---|---|---|---|---|---|---|---|---|---|---|---|
| L | K | L | **N** | **V** | N | A | E | UFV172561 | 100 | 100 | 100 |
| - | - | **Y** | - | - | **D** | **D** | **A** | UFV172563 | 78 | 118 | 118 |
| **K** | - | **Y** | - | - | **D** | **D** | **A** | UFV172564 | 63 | 115 | 105 |
| **K** | **N** | **Y** | - | - | - | **D** | **A** | UFV172571 | 62 | 77 | 81 |
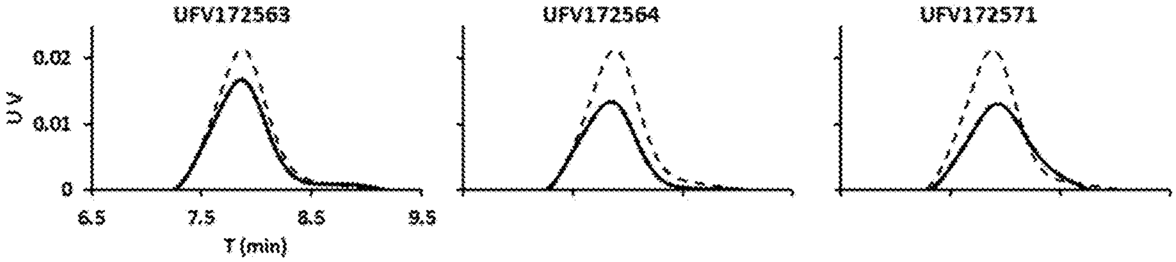
B
| 25 | 27 | 367 | 379 | 381 | 475 | 476 | 479 | ID. | Trimer (%) | CR9114 (%) | CT149 (%) |
|---|---|---|---|---|---|---|---|---|---|---|---|
| L | K | L | **G** | **L** | N | A | E | UFV172562 | 100 | 100 | 100 |
| **K** | - | **Y** | - | - | - | **D** | **A** | UFV172588 | 75 | 98 | 95 |
| **K** | - | **Y** | - | - | **D** | **D** | **A** | UFV172583 | 60 | 90 | 82 |
| **K** | **N** | **Y** | - | - | **D** | **D** | **A** | UFV172585 | 83* | 53 | 55 |
* Shifted trimer peak (see SEC pattern)
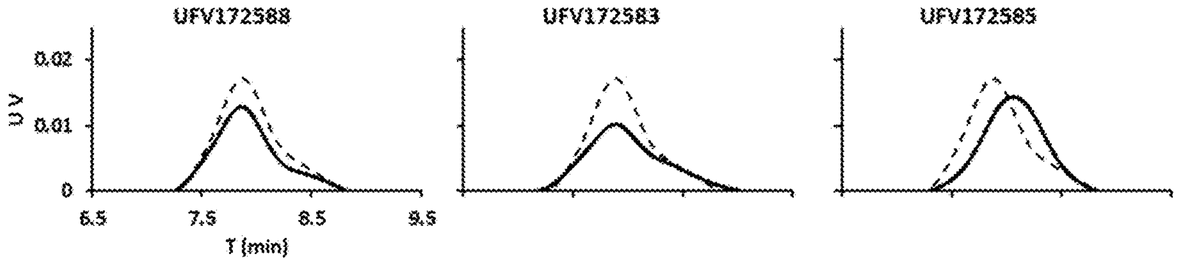
FIG. 13

| Design | Design elements | Mutations |
|---|---|---|
| I | GCN4 introduction | 405-RMKCIEDKIEEIESK-419 |
| | Intramolecular disulfide bridge | K310C + S422C |
| | interprotomeric disulfide bridge | E398C + D408C |
| | Beta-sheet optimization | H355W |
| | A-helix mutations | N378T, G379N, L381V |
| | Glycan introduction B-loop | EVE-401-403 to NAT |
| II | I + B-loop stabilizations | F392S, I395T, F399S |
| III | I + B-loop stabilizations | F392S, H393N, I395T, F399P, R405P |

| H3 strains | ID. | | |
|---|---|---|---|
| | I | II | III |
| A/Hong Kong/1/1968 | UFV180647 | UFV181117 | UFV181106 |
| A/Wisconsin/67/2005 | UFV180645 | UFV181118 | UFV181107 |
| A/Singapore/INFIMH/16/0019/2016 | UFV180642 | UFV181120 | UFV181109 |

A

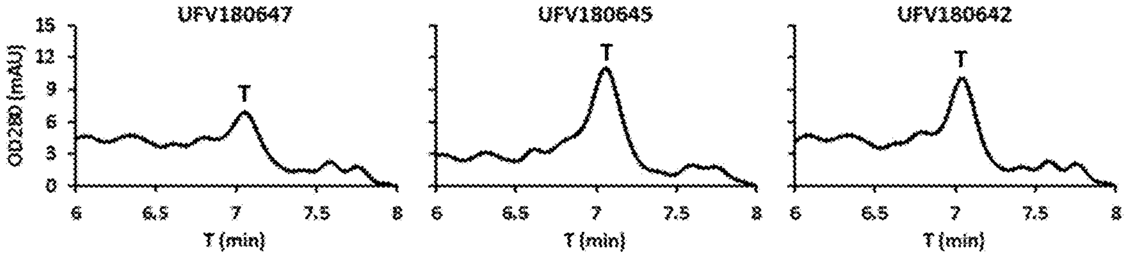

B

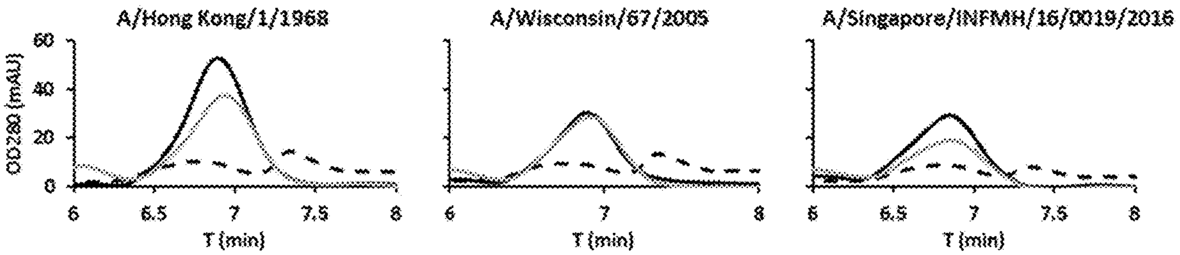

FIG. 14

SEQUENCE LISTING

<160> NUMBER OF SEQ ID NOS: 212

<210> SEQ ID NO 1
<211> LENGTH: 550
<212> TYPE: PRT
<213> ORGANISM: Influenza A virus

<400> SEQUENCE: 1

Gln Asp Leu Pro Gly Asn Asp Asn Ser Thr Ala Thr Leu Cys Leu Gly
1 5 10 15

His His Ala Val Pro Asn Gly Thr Leu Val Lys Thr Ile Thr Asp Asp
20 25 30

Gln Ile Glu Val Thr Asn Ala Thr Glu Leu Val Gln Ser Ser Ser Thr
35 40 45

Gly Lys Ile Cys Asn Asn Pro His Arg Ile Leu Asp Gly Ile Asp Cys
50 55 60

Thr Leu Ile Asp Ala Leu Leu Gly Asp Pro His Cys Asp Val Phe Gln
65 70 75 80

Asn Glu Thr Trp Asp Leu Phe Val Glu Arg Ser Lys Ala Phe Ser Asn
85 90 95

Cys Tyr Pro Tyr Asp Val Pro Asp Tyr Ala Ser Leu Arg Ser Leu Val
100 105 110

Ala Ser Ser Gly Thr Leu Glu Phe Ile Thr Glu Gly Phe Thr Trp Thr
115 120 125

Gly Val Thr Gln Asn Gly Gly Ser Asn Ala Cys Lys Arg Gly Pro Gly
130 135 140

Ser Gly Phe Phe Ser Arg Leu Asn Trp Leu Thr Lys Ser Gly Ser Thr
145 150 155 160

Tyr Pro Val Leu Asn Val Thr Met Pro Asn Asn Asp Asn Phe Asp Lys
165 170 175

Leu Tyr Ile Trp Gly Ile His His Pro Ser Thr Asn Gln Glu Gln Thr
180 185 190

Ser Leu Tyr Val Gln Ala Ser Gly Arg Val Thr Val Ser Thr Arg Arg
195 200 205

Ser Gln Gln Thr Ile Ile Pro Asn Ile Gly Ser Arg Pro Trp Val Arg
210 215 220

Gly Leu Ser Ser Arg Ile Ser Ile Tyr Trp Thr Ile Val Lys Pro Gly
225 230 235 240

Asp Val Leu Val Ile Asn Ser Asn Gly Asn Leu Ile Ala Pro Arg Gly
245 250 255

Tyr Phe Lys Met Arg Thr Gly Lys Ser Ser Ile Met Arg Ser Asp Ala
260 265 270

```
Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg Gly Leu Phe Gly Ala Ile Ala
                325                 330                 335

Gly Phe Ile Glu Asn Gly Trp Glu Gly Met Ile Asp Gly Trp Tyr Gly
            340                 345                 350

Phe Arg His Gln Asn Ser Glu Gly Thr Gly Gln Ala Ala Asp Leu Lys
        355                 360                 365

Ser Thr Gln Ala Ala Ile Asp Gln Ile Asn Gly Lys Leu Asn Arg Val
    370                 375                 380

Ile Glu Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Arg Arg Gln Leu Arg Glu Asn Ala Glu Glu Met Gly Asn
    450                 455                 460

Gly Cys Phe Lys Ile Tyr His Lys Cys Asp Asn Ala Cys Ile Glu Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Val Leu Leu Gly Phe Ile Met Trp Ala Cys Gln Arg Gly Asn Ile
    530                 535                 540

Arg Cys Asn Ile Cys Ile
545                 550


<210> SEQ ID NO 2
<211> LENGTH: 566
<212> TYPE: PRT
<213> ORGANISM: Influenza A virus

<400> SEQUENCE: 2

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95
```

```
Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Trp Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Asn Tyr Asp His Asp Val Tyr Arg Asp Glu Ala Leu
            500                 505                 510
```

Asn Asn Arg Phe Gln Ile Lys Gly Val Glu Leu Lys Ser Gly Tyr Lys
515 520 525

Asp Trp Ile Leu Trp Ile Ser Phe Ala Ile Ser Cys Phe Leu Leu Cys
530 535 540

Val Val Leu Leu Gly Phe Ile Met Trp Ala Cys Gln Arg Gly Asn Ile
545 550 555 560

Arg Cys Asn Ile Cys Ile
565

<210> SEQ ID NO 3
<211> LENGTH: 121
<212> TYPE: PRT
<213> ORGANISM: Artificial Sequence
<220> FEATURE:
<223> OTHER INFORMATION: CR6261 VH PROTEIN

<400> SEQUENCE: 3

Glu Val Gln Leu Val Glu Ser Gly Ala Glu Val Lys Lys Pro Gly Ser
1 5 10 15

Ser Val Lys Val Ser Cys Lys Ala Ser Gly Gly Pro Phe Arg Ser Tyr
20 25 30

Ala Ile Ser Trp Val Arg Gln Ala Pro Gly Gln Gly Pro Glu Trp Met
35 40 45

Gly Gly Ile Ile Pro Ile Phe Gly Thr Thr Lys Tyr Ala Pro Lys Phe
50 55 60

Gln Gly Arg Val Thr Ile Thr Ala Asp Asp Phe Ala Gly Thr Val Tyr
65 70 75 80

Met Glu Leu Ser Ser Leu Arg Ser Glu Asp Thr Ala Met Tyr Tyr Cys
85 90 95

Ala Lys His Met Gly Tyr Gln Val Arg Glu Thr Met Asp Val Trp Gly
100 105 110

Lys Gly Thr Thr Val Thr Val Ser Ser
115 120

<210> SEQ ID NO 4
<211> LENGTH: 111
<212> TYPE: PRT
<213> ORGANISM: Artificial Sequence
<220> FEATURE:
<223> OTHER INFORMATION: CR6261 VL PROTEIN

<400> SEQUENCE: 4

Gln Ser Val Leu Thr Gln Pro Pro Ser Val Ser Ala Ala Pro Gly Gln
1 5 10 15

Lys Val Thr Ile Ser Cys Ser Gly Ser Ser Ser Asn Ile Gly Asn Asp
20 25 30

Tyr Val Ser Trp Tyr Gln Gln Leu Pro Gly Thr Ala Pro Lys Leu Leu
35 40 45

Ile Tyr Asp Asn Asn Lys Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asn Tyr Tyr Cys Ala Thr Trp Asp Arg Arg Pro
85 90 95

Thr Ala Tyr Val Val Phe Gly Gly Gly Thr Lys Leu Thr Val Leu
100 105 110

<210> SEQ ID NO 5

<211> LENGTH: 122
<212> TYPE: PRT
<213> ORGANISM: Artificial Sequence
<220> FEATURE:
<223> OTHER INFORMATION: CR8020 VH PROTEIN

<400> SEQUENCE: 5

```
Gln Val Gln Leu Gln Gln Ser Gly Ala Glu Val Lys Thr Pro Gly Ala
1               5                   10                  15

Ser Val Lys Val Ser Cys Lys Ala Ser Gly Tyr Thr Phe Thr Ser Phe
            20                  25                  30

Gly Val Ser Trp Ile Arg Gln Ala Pro Gly Gln Gly Leu Glu Trp Ile
        35                  40                  45

Gly Trp Ile Ser Ala Tyr Asn Gly Asp Thr Tyr Tyr Ala Gln Lys Phe
    50                  55                  60

Gln Ala Arg Val Thr Met Thr Thr Asp Thr Ser Thr Thr Thr Ala Tyr
65                  70                  75                  80

Met Glu Met Arg Ser Leu Arg Ser Asp Asp Thr Ala Val Tyr Tyr Cys
                85                  90                  95

Ala Arg Glu Pro Pro Leu Phe Tyr Ser Ser Trp Ser Leu Asp Asn Trp
            100                 105                 110

Gly Gln Gly Thr Leu Val Thr Val Ser Ser
        115                 120
```

<210> SEQ ID NO 6
<211> LENGTH: 108
<212> TYPE: PRT
<213> ORGANISM: Artificial Sequence
<220> FEATURE:
<223> OTHER INFORMATION: CR8020 VL PROTEIN

<400> SEQUENCE: 6

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Asn
            20                  25                  30

Tyr Leu Ala Trp Phe Gln Gln Lys Pro Gly Gln Ala Pro Arg Leu Leu
        35                  40                  45

Ile Tyr Gly Ala Ser Arg Arg Ala Thr Gly Ile Pro Asp Arg Ile Ser
    50                  55                  60

Gly Ser Gly Ser Gly Thr Asp Phe Thr Leu Thr Ile Ser Arg Leu Glu
65                  70                  75                  80

Pro Ala Asp Phe Ala Val Tyr Tyr Cys Gln Gln Tyr Gly Thr Ser Pro
                85                  90                  95

Arg Thr Phe Gly Gln Gly Ala Lys Val Glu Ile Lys
            100                 105
```

<210> SEQ ID NO 7
<211> LENGTH: 121
<212> TYPE: PRT
<213> ORGANISM: Artificial Sequence
<220> FEATURE:
<223> OTHER INFORMATION: CR9114 VH PROTEIN

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30
```

```
Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

Ala Arg His Gly Asn Tyr Tyr Tyr Tyr Ser Gly Met Asp Val Trp Gly
            100                 105                 110

Gln Gly Thr Thr Val Thr Val Ser Ser
        115                 120


<210> SEQ ID NO 8
<211> LENGTH: 110
<212> TYPE: PRT
<213> ORGANISM: Artificial Sequence
<220> FEATURE:
<223> OTHER INFORMATION: CR9114 VL PROTEIN

<400> SEQUENCE: 8

Ser Tyr Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
            20                  25                  30

Ser Val Asn Trp Tyr Gln Gln Phe Pro Gly Thr Ala Pro Lys Leu Leu
        35                  40                  45

Ile Tyr Ser Asn Asp Gln Arg Pro Ser Val Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Ser Leu
                85                  90                  95

Lys Gly Ala Val Phe Gly Gly Gly Thr Gln Leu Thr Val Leu
            100                 105                 110


<210> SEQ ID NO 9
<211> LENGTH: 15
<212> TYPE: PRT
<213> ORGANISM: Artificial Sequence
<220> FEATURE:
<223> OTHER INFORMATION: heterologous trimerization domain

<400> SEQUENCE: 9

Arg Met Lys Gln Ile Glu Asp Lys Ile Glu Glu Ile Glu Ser Lys
1               5                   10                  15


<210> SEQ ID NO 10
<211> LENGTH: 15
<212> TYPE: PRT
<213> ORGANISM: Artificial Sequence
<220> FEATURE:
<223> OTHER INFORMATION: hetrologous trimerization domain

<400> SEQUENCE: 10

Pro Met Lys Gln Ile Glu Asp Lys Ile Glu Glu Ile Glu Ser Lys
1               5                   10                  15


<210> SEQ ID NO 11
<211> LENGTH: 15
<212> TYPE: PRT
```

<213> ORGANISM: Artificial Sequence
<220> FEATURE:
<223> OTHER INFORMATION: heterologous trimerization domain

<400> SEQUENCE: 11

Arg Met Lys Cys Ile Glu Asp Lys Ile Glu Glu Ile Glu Ser Lys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: heterologous trimerization domain

<400> SEQUENCE: 12

Pro Met Lys Cys Ile Glu Asp Lys Ile Glu Glu Ile Glu Ser Lys
1               5                   10                  15

<210> SEQ ID NO 13
<211> LENGTH: 566
<212> TYPE: PRT
<213> ORGANISM: Influenza A virus

<400> SEQUENCE: 13

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly

```
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 14
<211> LENGTH: 566
<212> TYPE: PRT
<213> ORGANISM: Influenza A virus

<400> SEQUENCE: 14

Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60
```

```
Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Lys Asn Glu Ser Phe Asn Trp Thr
    130                 135                 140

Gly Val Thr Gln Asn Gly Thr Ser Ser Ala Cys Ile Arg Gly Ser Ser
145                 150                 155                 160

Ser Ser Phe Phe Ser Arg Leu Asn Trp Leu Thr His Leu Asn Tyr Lys
                165                 170                 175

Tyr Pro Ala Leu Asn Val Thr Met Pro Asn Lys Glu Gln Phe Asp Lys
            180                 185                 190

Leu Tyr Ile Trp Gly Val His His Pro Gly Thr Asp Lys Asp Gln Ile
        195                 200                 205

Phe Pro Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Gly Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys His Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
```

```
                485                 490                 495

Ile Arg Asn Glu Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 15
<211> LENGTH: 566
<212> TYPE: PRT
<213> ORGANISM: Influenza A virus

<400> SEQUENCE: 15

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Lys Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Lys
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val Leu His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ser Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285
```

```
Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 16
<211> LENGTH: 566
<212> TYPE: PRT
<213> ORGANISM: Influenza A virus

<400> SEQUENCE: 16

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95
```

```
Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Pro Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510
```

Asn Asn Arg Phe Gln Ile Lys Gly Val Glu Leu Lys Ser Gly Tyr Lys
515 520 525

Asp Trp Ile Leu Trp Ile Ser Phe Ala Ile Ser Cys Phe Leu Leu Cys
530 535 540

Val Ala Leu Leu Gly Phe Ile Met Trp Ala Cys Gln Lys Gly Asn Ile
545 550 555 560

Arg Cys Asn Ile Cys Ile
565

<210> SEQ ID NO 17
<211> LENGTH: 566
<212> TYPE: PRT
<213> ORGANISM: Influenza A virus

<400> SEQUENCE: 17

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Ser Asn Gly Thr Leu Val Lys Thr Ile Thr Asn Asp
35 40 45

Gln Ile Glu Val Thr Asn Ala Thr Glu Leu Val Gln Ser Ser Ser Thr
50 55 60

Gly Arg Ile Cys Asp Ser Pro His Gln Ile Leu Asp Gly Glu Asn Cys
65 70 75 80

Thr Leu Ile Asp Ala Leu Leu Gly Asp Pro His Cys Asp Gly Phe Gln
85 90 95

Asn Lys Glu Trp Asp Leu Phe Val Glu Arg Ser Lys Ala Tyr Ser Asn
100 105 110

Cys Tyr Pro Tyr Asp Val Pro Asp Tyr Ala Ser Leu Arg Ser Leu Val
115 120 125

Ala Ser Ser Gly Thr Leu Glu Phe Asn Asn Glu Ser Phe Asn Trp Thr
130 135 140

Gly Val Ala Gln Asn Gly Thr Ser Ser Ala Cys Lys Arg Arg Ser Asn
145 150 155 160

Lys Ser Phe Phe Ser Arg Leu Asn Trp Leu His Gln Leu Lys Tyr Lys
165 170 175

Tyr Pro Ala Leu Asn Val Thr Met Pro Asn Asn Glu Lys Phe Asp Lys
180 185 190

Leu Tyr Ile Trp Gly Val His His Pro Ser Thr Asp Ser Asp Gln Ile
195 200 205

Ser Ile Tyr Ala Gln Ala Ser Gly Arg Val Thr Val Ser Thr Lys Arg
210 215 220

Ser Gln Gln Thr Val Ile Pro Asn Ile Gly Ser Ser Pro Trp Val Arg
225 230 235 240

Gly Val Ser Ser Arg Ile Ser Ile Tyr Trp Thr Ile Val Lys Pro Gly
245 250 255

Asp Ile Leu Leu Ile Asn Ser Thr Gly Asn Leu Ile Ala Pro Arg Gly
260 265 270

Tyr Phe Lys Ile Arg Ser Gly Lys Ser Ser Ile Met Arg Ser Asp Ala
275 280 285

Pro Ile Gly Lys Cys Asn Ser Glu Cys Ile Thr Pro Asn Gly Ser Ile
290 295 300

Pro Asn Asp Lys Pro Phe Gln Asn Val Asn Arg Ile Thr Tyr Gly Ala
305 310 315 320

```
Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565


<210> SEQ ID NO 18
<211> LENGTH: 16
<212> TYPE: PRT
<213> ORGANISM: Artificial Sequence
<220> FEATURE:
<223> OTHER INFORMATION: signal sequence

<400> SEQUENCE: 18

Met Lys Thr Ile Ile Ala Leu Ser Tyr Ile Phe Cys Leu Ala Leu Gly
1               5                   10                  15


<210> SEQ ID NO 19
<211> LENGTH: 16
<212> TYPE: PRT
<213> ORGANISM: Artificial Sequence
<220> FEATURE:
<223> OTHER INFORMATION: signal sequence

<400> SEQUENCE: 19

Met Lys Thr Ile Ile Ala Leu Ser Tyr Ile Leu Cys Leu Val Phe Ala
1               5                   10                  15


<210> SEQ ID NO 20
<211> LENGTH: 16
<212> TYPE: PRT
```

```
<213> ORGANISM: Artificial Sequence
<220> FEATURE:
<223> OTHER INFORMATION: signal sequence

<400> SEQUENCE: 20

Met Lys Thr Ile Ile Ala Leu Ser Tyr Ile Leu Cys Leu Val Phe Thr
1               5                   10                  15


<210> SEQ ID NO 21
<211> LENGTH: 16
<212> TYPE: PRT
<213> ORGANISM: Artificial Sequence
<220> FEATURE:
<223> OTHER INFORMATION: signal sequence

<400> SEQUENCE: 21

Met Lys Thr Ile Val Ala Leu Ser Tyr Ile Leu Cys Leu Val Phe Ala
1               5                   10                  15


<210> SEQ ID NO 22
<211> LENGTH: 6
<212> TYPE: PRT
<213> ORGANISM: Artificial Sequence
<220> FEATURE:
<223> OTHER INFORMATION: Histag

<400> SEQUENCE: 22

His His His His His His
1               5


<210> SEQ ID NO 23
<211> LENGTH: 7
<212> TYPE: PRT
<213> ORGANISM: Artificial Sequence
<220> FEATURE:
<223> OTHER INFORMATION: Histag

<400> SEQUENCE: 23

His His His His His His His
1               5


<210> SEQ ID NO 24
<211> LENGTH: 8
<212> TYPE: PRT
<213> ORGANISM: Artificial Sequence
<220> FEATURE:
<223> OTHER INFORMATION: FLAG tag

<400> SEQUENCE: 24

Asp Tyr Lys Asp Asp Asp Asp Lys
1               5


<210> SEQ ID NO 25
<211> LENGTH: 4
<212> TYPE: PRT
<213> ORGANISM: Artificial Sequence
<220> FEATURE:
<223> OTHER INFORMATION: C-Tag

<400> SEQUENCE: 25

Glu Pro Glu Ala
1


<210> SEQ ID NO 26
<211> LENGTH: 4
<212> TYPE: PRT
<213> ORGANISM: Artificial Sequence
```

<220> FEATURE:
<223> OTHER INFORMATION: linker

<400> SEQUENCE: 26

Ile Glu Gly Arg
1

<210> SEQ ID NO 27
<211> LENGTH: 6
<212> TYPE: PRT
<213> ORGANISM: Artificial Sequence
<220> FEATURE:
<223> OTHER INFORMATION: linker

<400> SEQUENCE: 27

Leu Val Pro Arg Gly Ser
1 5

<210> SEQ ID NO 28
<211> LENGTH: 27
<212> TYPE: PRT
<213> ORGANISM: Artificial Sequence
<220> FEATURE:
<223> OTHER INFORMATION: C-terminal domain

<400> SEQUENCE: 28

Gly Tyr Ile Pro Glu Ala Pro Arg Asp Gly Gln Ala Tyr Val Arg Lys
1 5 10 15

Asp Gly Glu Trp Val Leu Leu Ser Thr Phe Leu
20 25

<210> SEQ ID NO 29
<211> LENGTH: 54
<212> TYPE: PRT
<213> ORGANISM: Artificial Sequence
<220> FEATURE:
<223> OTHER INFORMATION: C-terminal domain

<400> SEQUENCE: 29

Ala Ala Ala Asp Tyr Lys Asp Asp Asp Asp Lys Leu Val Pro Arg Gly
1 5 10 15

Ser Pro Gly Ser Gly Tyr Ile Pro Glu Ala Pro Arg Asp Gly Gln Ala
20 25 30

Tyr Val Arg Lys Asp Gly Glu Trp Val Leu Leu Ser Thr Phe Leu Gly
35 40 45

His His His His His His
50

<210> SEQ ID NO 30
<211> LENGTH: 33
<212> TYPE: PRT
<213> ORGANISM: Artificial Sequence
<220> FEATURE:
<223> OTHER INFORMATION: FLAG- GS linker - His tag

<400> SEQUENCE: 30

Ala Ala Ala Asp Tyr Lys Asp Asp Asp Asp Lys Pro Gly Gly Gly Gly
1 5 10 15

Ser Gly Gly Gly Gly Ser Gly Gly Gly Gly Ser His His His His His
20 25 30

His

<210> SEQ ID NO 31

```
<211> LENGTH: 218
<212> TYPE: PRT
<213> ORGANISM: Artificial Sequence
<220> FEATURE:
<223> OTHER INFORMATION: Nanoluc - Strep tag

<400> SEQUENCE: 31

Glu Gly Arg Ala Ala Ala Gly Gly Ser Gly Gly Gly Gly Ser Met Val
1               5                   10                  15

Phe Thr Leu Glu Asp Phe Val Gly Asp Trp Arg Gln Thr Ala Gly Tyr
            20                  25                  30

Asn Leu Asp Gln Val Leu Glu Gln Gly Gly Val Ser Ser Leu Phe Gln
        35                  40                  45

Asn Leu Gly Val Ser Val Thr Pro Ile Gln Arg Ile Val Leu Ser Gly
    50                  55                  60

Glu Asn Gly Leu Lys Ile Asp Ile His Val Ile Ile Pro Tyr Glu Gly
65                  70                  75                  80

Leu Ser Gly Asp Gln Met Gly Gln Ile Glu Lys Ile Phe Lys Val Val
                85                  90                  95

Tyr Pro Val Asp Asp His His Phe Lys Val Ile Leu His Tyr Gly Thr
            100                 105                 110

Leu Val Ile Asp Gly Val Thr Pro Asn Met Ile Asp Tyr Phe Gly Arg
        115                 120                 125

Pro Tyr Glu Gly Ile Ala Val Phe Asp Gly Lys Lys Ile Thr Val Thr
    130                 135                 140

Gly Thr Leu Trp Asn Gly Asn Lys Ile Ile Asp Glu Arg Leu Ile Asn
145                 150                 155                 160

Pro Asp Gly Ser Leu Leu Phe Arg Val Thr Ile Asn Gly Val Thr Gly
                165                 170                 175

Trp Arg Leu Cys Glu Arg Ile Leu Ala Ala Ala Ala Trp Ser His Pro
            180                 185                 190

Gln Phe Glu Lys Gly Ala Ala Trp Ser His Pro Gln Phe Glu Lys Gly
        195                 200                 205

Ala Ala Trp Ser His Pro Gln Phe Glu Lys
    210                 215


<210> SEQ ID NO 32
<211> LENGTH: 192
<212> TYPE: PRT
<213> ORGANISM: Artificial Sequence
<220> FEATURE:
<223> OTHER INFORMATION: Nanoluc - C tag

<400> SEQUENCE: 32

Glu Gly Arg Ala Ala Ala Gly Gly Ser Gly Gly Gly Gly Ser Met Val
1               5                   10                  15

Phe Thr Leu Glu Asp Phe Val Gly Asp Trp Arg Gln Thr Ala Gly Tyr
            20                  25                  30

Asn Leu Asp Gln Val Leu Glu Gln Gly Gly Val Ser Ser Leu Phe Gln
        35                  40                  45

Asn Leu Gly Val Ser Val Thr Pro Ile Gln Arg Ile Val Leu Ser Gly
    50                  55                  60

Glu Asn Gly Leu Lys Ile Asp Ile His Val Ile Ile Pro Tyr Glu Gly
65                  70                  75                  80

Leu Ser Gly Asp Gln Met Gly Gln Ile Glu Lys Ile Phe Lys Val Val
                85                  90                  95

Tyr Pro Val Asp Asp His His Phe Lys Val Ile Leu His Tyr Gly Thr
```

-continued 100 105 110

Leu Val Ile Asp Gly Val Thr Pro Asn Met Ile Asp Tyr Phe Gly Arg
115 120 125

Pro Tyr Glu Gly Ile Ala Val Phe Asp Gly Lys Lys Ile Thr Val Thr
130 135 140

Gly Thr Leu Trp Asn Gly Asn Lys Ile Ile Asp Glu Arg Leu Ile Asn
145 150 155 160

Pro Asp Gly Ser Leu Leu Phe Arg Val Thr Ile Asn Gly Val Thr Gly
165 170 175

Trp Arg Leu Cys Glu Arg Ile Leu Ala Gly Ala Ala Glu Pro Glu Ala
180 185 190

<210> SEQ ID NO 33
<211> LENGTH: 36
<212> TYPE: PRT
<213> ORGANISM: Artificial Sequence
<220> FEATURE:
<223> OTHER INFORMATION: Strep tag

<400> SEQUENCE: 33

Glu Gly Arg Ala Ala Ala Trp Ser His Pro Gln Phe Glu Lys Gly Ala
1 5 10 15

Ala Trp Ser His Pro Gln Phe Glu Lys Gly Ala Ala Trp Ser His Pro
20 25 30

Gln Phe Glu Lys
35

<210> SEQ ID NO 34
<211> LENGTH: 19
<212> TYPE: PRT
<213> ORGANISM: Artificial Sequence
<220> FEATURE:
<223> OTHER INFORMATION: Sortase - C tag

<400> SEQUENCE: 34

Glu Gly Arg Ala Ala Ala Leu Pro Glu Thr Gly Gly Gly Ala Ala Glu
1 5 10 15

Pro Glu Ala

<210> SEQ ID NO 35
<211> LENGTH: 77
<212> TYPE: PRT
<213> ORGANISM: Artificial Sequence
<220> FEATURE:
<223> OTHER INFORMATION: FLAG - GS linker - Strep tag

<400> SEQUENCE: 35

Ser Gly Arg Asp Tyr Lys Asp Asp Asp Asp Lys Pro Gly Gly Gly Gly
1 5 10 15

Ser Gly Gly Gly Gly Ser Gly Gly Gly Gly Ser Gly Gly Gly Gly Ser
20 25 30

Gly Gly Gly Gly Ser Gly Gly Gly Gly Ser Gly Gly Gly Gly Ser Trp
35 40 45

Ser His Pro Gln Phe Glu Lys Gly Ala Ala Trp Ser His Pro Gln Phe
50 55 60

Glu Lys Gly Ala Ala Trp Ser His Pro Gln Phe Glu Lys
65 70 75

<210> SEQ ID NO 36
<211> LENGTH: 81

<212> TYPE: PRT
<213> ORGANISM: Artificial Sequence
<220> FEATURE:
<223> OTHER INFORMATION: Myc tag - GS linker - Strep tag

<400> SEQUENCE: 36

```
Glu Gly Arg Ala Ala Ala Glu Gln Lys Leu Ile Ser Glu Glu Asp Leu
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser Trp Ser His Pro Gln Phe Glu Lys Gly Ala Ala Trp Ser
    50                  55                  60

His Pro Gln Phe Glu Lys Gly Ala Ala Trp Ser His Pro Gln Phe Glu
65                  70                  75                  80

Lys
```

<210> SEQ ID NO 37
<211> LENGTH: 126
<212> TYPE: PRT
<213> ORGANISM: Artificial Sequence
<220> FEATURE:
<223> OTHER INFORMATION: CT149 VH PROTEIN

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Pro Glu Trp Val
        35                  40                  45

Gly Trp Ile Ser Ala Tyr Thr Gly Ile Thr Asp Tyr Ala Gln Lys Phe
    50                  55                  60

Gln Gly Arg Val Thr Leu Thr Thr Asp Ala Thr Thr Ala Thr Ala Phe
65                  70                  75                  80

Leu Asp Leu Arg Ser Leu Arg Pro Asp Asp Thr Ala Thr Tyr Phe Cys
                85                  90                  95

Ala Arg Asp Lys Val Gln Gly Arg Val Glu Val Gly Ser Gly Gly Arg
            100                 105                 110

His Asp Tyr Trp Gly Gln Gly Thr Leu Val Ile Val Ser Ser
        115                 120                 125
```

<210> SEQ ID NO 38
<211> LENGTH: 108
<212> TYPE: PRT
<213> ORGANISM: Artificial Sequence
<220> FEATURE:
<223> OTHER INFORMATION: CT149 VL PROTEIN

<400> SEQUENCE: 38

```
Glu Val Val Leu Thr Gln Ser Pro Gly Thr Leu Ala Leu Pro Pro Gly
1               5                   10                  15

Glu Arg Ala Thr Leu Ser Cys Arg Ala Ser His Arg Val Gly Ser Thr
            20                  25                  30

Tyr Ile Ala Trp Tyr Gln Gln Lys Ser Gly Gln Ala Pro Arg Arg Leu
        35                  40                  45

Ile Tyr Gly Ala Ser Asn Arg Ala Thr Asp Ile Pro Asp Arg Phe Ser
    50                  55                  60
```

Gly Ser Gly Ser Gly Thr Asp Phe Thr Leu Thr Ile Arg Arg Leu Glu
65 70 75 80

Pro Glu Asp Ser Ala Val Tyr Tyr Cys Gln Gln Phe Ser Val Ser Pro
85 90 95

Trp Thr Phe Gly Gln Gly Thr Arg Val Glu Ile Lys
100 105

<210> SEQ ID NO 39
<211> LENGTH: 155
<212> TYPE: PRT
<213> ORGANISM: Artificial Sequence
<220> FEATURE:
<223> OTHER INFORMATION: SD15013

<400> SEQUENCE: 39

Glu Val Gln Leu Val Glu Ser Gly Gly Gly Leu Val Gln Ala Gly Asp
1 5 10 15

Ser Leu Arg Ile Ser Cys Ala Ala Ser Gly Arg Thr Leu Ser Ile Tyr
20 25 30

Ser Met Gly Trp Phe Arg Gln Ala Pro Gly Lys Glu Arg Glu Phe Val
35 40 45

Ala Thr Ile Gly Trp Asn Ser Gly Arg Thr Phe Tyr Pro Asp Ser Leu
50 55 60

Lys Gly Arg Phe Thr Ile Ser Arg Asp Asn Ala Arg Asn Thr Leu Tyr
65 70 75 80

Leu Gln Met Asn Asn Leu Arg Pro Glu Asp Thr Ala Val Tyr Tyr Cys
85 90 95

Ala Ala Ala Lys Gly Pro Leu Arg Leu Ser Ser Gln Ala Asp Tyr Trp
100 105 110

Gly Gln Gly Thr Gln Val Thr Val Ser Ser Ala Ala Ala Trp Ser His
115 120 125

Pro Gln Phe Glu Lys Gly Ala Ala Trp Ser His Pro Gln Phe Glu Lys
130 135 140

Gly Ala Ala Trp Ser His Pro Gln Phe Glu Lys
145 150 155

<210> SEQ ID NO 40
<211> LENGTH: 265
<212> TYPE: PRT
<213> ORGANISM: Artificial Sequence
<220> FEATURE:
<223> OTHER INFORMATION: UFV180088

<400> SEQUENCE: 40

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln

```
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Pro Glu Ala
            260                 265


<210> SEQ ID NO 41
<211> LENGTH: 265
<212> TYPE: PRT
<213> ORGANISM: Artificial Sequence
<220> FEATURE:
<223> OTHER INFORMATION: UFV180089

<400> SEQUENCE: 41

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Tyr Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
```

```
        195                 200                 205

Arg Gln Leu Arg Glu Asn Ala Glu Asp Met Gly Asn Gly Cys Phe Lys
    210                 215                 220

Ile Tyr His Lys Cys Asp Asp Asp Cys Ile Ala Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Pro Glu Ala
            260                 265


<210> SEQ ID NO 42
<211> LENGTH: 265
<212> TYPE: PRT
<213> ORGANISM: Artificial Sequence
<220> FEATURE:
<223> OTHER INFORMATION: UFV180090

<400> SEQUENCE: 42

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Lys Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Tyr Lys Ser Thr Gln Ala
        115                 120                 125

Ala Ile Asp Gln Ile Thr Gly Ile Leu Asn Arg Val Ile Glu Lys Met
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Asp Cys Ile Ala Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Pro Glu Ala
            260                 265


<210> SEQ ID NO 43
<211> LENGTH: 294
<212> TYPE: PRT
```

```
<213> ORGANISM: Artificial Sequence
<220> FEATURE:
<223> OTHER INFORMATION: UFV180141

<400> SEQUENCE: 43

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 44
<211> LENGTH: 294
<212> TYPE: PRT
<213> ORGANISM: Artificial Sequence
<220> FEATURE:
<223> OTHER INFORMATION: UFV180192

<400> SEQUENCE: 44

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30
```

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Met
130 135 140

Asn Glu Lys Ser His Gln Thr Glu Lys Glu Ser Ser Asn Ala Thr Gly
145 150 155 160

Arg Met Lys Gln Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 45
<211> LENGTH: 294
<212> TYPE: PRT
<213> ORGANISM: Artificial Sequence
<220> FEATURE:
<223> OTHER INFORMATION: UFV180193

<400> SEQUENCE: 45

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

```
Asn Gly Trp Glu Gly Met Ile Asp Gly Trp Tyr Gly Phe Arg His Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 46
<211> LENGTH: 294
<212> TYPE: PRT
<213> ORGANISM: Artificial Sequence
<220> FEATURE:
<223> OTHER INFORMATION: UFV180194

<400> SEQUENCE: 46

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Lys Cys Ser Ser Asn Ala Thr Gly
145                 150                 155                 160
```

```
Arg Ile Gln Cys Leu Glu Lys Tyr Val Glu Asp Thr Lys Ile Asp Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

<210> SEQ ID NO 47
<211> LENGTH: 294
<212> TYPE: PRT
<213> ORGANISM: Artificial Sequence
<220> FEATURE:
<223> OTHER INFORMATION: UFV180195

<400> SEQUENCE: 47

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Lys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Ser Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220
```

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 48
<211> LENGTH: 294
<212> TYPE: PRT
<213> ORGANISM: Artificial Sequence
<220> FEATURE:
<223> OTHER INFORMATION: UFV180196

<400> SEQUENCE: 48

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Asn Gly Ile Leu Asn Arg Val Ile Glu Lys Met
130 135 140

Asn Glu Lys Ser His Gln Thr Glu Lys Cys Ser Ser Asn Ala Thr Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 49
<211> LENGTH: 294
<212> TYPE: PRT
<213> ORGANISM: Artificial Sequence
<220> FEATURE:
<223> OTHER INFORMATION: UFV180197

<400> SEQUENCE: 49

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Lys Val Asn Arg Val Ile Glu Lys Met
130 135 140

Asn Glu Lys Ser His Gln Thr Glu Lys Cys Ser Ser Asn Ala Thr Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Glu Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 50
<211> LENGTH: 294
<212> TYPE: PRT
<213> ORGANISM: Artificial Sequence
<220> FEATURE:
<223> OTHER INFORMATION: UFV180198

<400> SEQUENCE: 50

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

<210> SEQ ID NO 51
<211> LENGTH: 294
<212> TYPE: PRT
<213> ORGANISM: Artificial Sequence
<220> FEATURE:
<223> OTHER INFORMATION: UFV180199

<400> SEQUENCE: 51

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60
```

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Met
130 135 140

Asn Glu Lys Ser His Gln Thr Glu Lys Cys Ser Ser Asn Ala Thr Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Glu Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 52
<211> LENGTH: 294
<212> TYPE: PRT
<213> ORGANISM: Artificial Sequence
<220> FEATURE:
<223> OTHER INFORMATION: UFV180200

<400> SEQUENCE: 52

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Thr
130 135 140

Asn Glu Lys Ser His Gln Thr Glu Lys Cys Ser Ser Asn Ala Thr Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 53
<211> LENGTH: 294
<212> TYPE: PRT
<213> ORGANISM: Artificial Sequence
<220> FEATURE:
<223> OTHER INFORMATION: UFV180201

<400> SEQUENCE: 53

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Met
130 135 140

Asn Glu Lys Ser His Gln Thr Glu Lys Cys Ser Ser Glu Val Glu Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 54
<211> LENGTH: 294
<212> TYPE: PRT
<213> ORGANISM: Artificial Sequence
<220> FEATURE:
<223> OTHER INFORMATION: UFV180202

<400> SEQUENCE: 54

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Met
130 135 140

Asn Glu Lys Ser His Gln Ile Glu Lys Cys Ser Ser Asn Ala Thr Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

```
Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 55
<211> LENGTH: 294
<212> TYPE: PRT
<213> ORGANISM: Artificial Sequence
<220> FEATURE:
<223> OTHER INFORMATION: UFV180203

<400> SEQUENCE: 55

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln His Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 56
```

<211> LENGTH: 294
<212> TYPE: PRT
<213> ORGANISM: Artificial Sequence
<220> FEATURE:
<223> OTHER INFORMATION: UFV180204

<400> SEQUENCE: 56

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Leu Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

<210> SEQ ID NO 57
<211> LENGTH: 294
<212> TYPE: PRT
<213> ORGANISM: Artificial Sequence
<220> FEATURE:
<223> OTHER INFORMATION: UFV180205

<400> SEQUENCE: 57

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
```

```
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 58
<211> LENGTH: 294
<212> TYPE: PRT
<213> ORGANISM: Artificial Sequence
<220> FEATURE:
<223> OTHER INFORMATION: UFV180206

<400> SEQUENCE: 58

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
```

```
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Phe His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 59
<211> LENGTH: 294
<212> TYPE: PRT
<213> ORGANISM: Artificial Sequence
<220> FEATURE:
<223> OTHER INFORMATION: UFV180207

<400> SEQUENCE: 59

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Lys Cys Phe Ser Asn Ala Thr Gly
```

145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 60
<211> LENGTH: 267
<212> TYPE: PRT
<213> ORGANISM: Artificial Sequence
<220> FEATURE:
<223> OTHER INFORMATION: UFV181034

<400> SEQUENCE: 60

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Met
130 135 140

Asn Glu Lys Phe His Gln Ile Glu Lys Cys Phe Ser Asn Ala Thr Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln His Thr
180 185 190

Ile Asp Leu Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys

```
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val His His His His His His
            260                 265


<210> SEQ ID NO 61
<211> LENGTH: 267
<212> TYPE: PRT
<213> ORGANISM: Artificial Sequence
<220> FEATURE:
<223> OTHER INFORMATION: UFV181036

<400> SEQUENCE: 61

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Phe His Gln Ile Glu Lys Cys Phe Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Leu Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val His His His His His His
            260                 265


<210> SEQ ID NO 62
<211> LENGTH: 267
<212> TYPE: PRT
<213> ORGANISM: Artificial Sequence
<220> FEATURE:
<223> OTHER INFORMATION: UFV181038
```

<400> SEQUENCE: 62

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Met
130 135 140

Asn Glu Lys Phe His Gln Ile Glu Lys Cys Phe Ser Asn Ala Thr Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val His His His His His His
260 265

<210> SEQ ID NO 63
<211> LENGTH: 267
<212> TYPE: PRT
<213> ORGANISM: Artificial Sequence
<220> FEATURE:
<223> OTHER INFORMATION: UFV181040

<400> SEQUENCE: 63

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

```
Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln His Thr
            180                 185                 190

Ile Asp Leu Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val His His His His His His
            260                 265


<210> SEQ ID NO 64
<211> LENGTH: 267
<212> TYPE: PRT
<213> ORGANISM: Artificial Sequence
<220> FEATURE:
<223> OTHER INFORMATION: UFV181042

<400> SEQUENCE: 64

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175
```

```
Trp Cys Tyr Asn Ala Glu Leu Leu Val Ala Leu Ile Asn Gln His Thr
            180                 185                 190

Ile Asp Leu Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val His His His His His His
            260                 265


<210> SEQ ID NO 65
<211> LENGTH: 307
<212> TYPE: PRT
<213> ORGANISM: Artificial Sequence
<220> FEATURE:
<223> OTHER INFORMATION: UFV161333

<400> SEQUENCE: 65

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270
```

```
Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 66
<211> LENGTH: 307
<212> TYPE: PRT
<213> ORGANISM: Artificial Sequence
<220> FEATURE:
<223> OTHER INFORMATION: UFV161739

<400> SEQUENCE: 66

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 67
<211> LENGTH: 307
<212> TYPE: PRT
<213> ORGANISM: Artificial Sequence
<220> FEATURE:
<223> OTHER INFORMATION: UFV161800

<400> SEQUENCE: 67

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Ile Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 68
<211> LENGTH: 307
<212> TYPE: PRT
<213> ORGANISM: Artificial Sequence
<220> FEATURE:
<223> OTHER INFORMATION: UFV161804

<400> SEQUENCE: 68

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Phe Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Ile Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 69
<211> LENGTH: 304
<212> TYPE: PRT
<213> ORGANISM: Artificial Sequence
<220> FEATURE:
<223> OTHER INFORMATION: UFV170991

<400> SEQUENCE: 69

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45
```

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Lys Val Asn Arg Val Ile Glu Lys Met
130 135 140

Asn Glu Lys Ser His Gln Thr Glu Cys Glu Ser Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Glu Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Glu Leu Lys Ser Gly Tyr Lys Asp Trp Ile Ala
260 265 270

Ala Ala Asp Tyr Lys Asp Asp Asp Asp Lys Pro Gly Gly Gly Gly Ser
275 280 285

Gly Gly Gly Gly Ser Gly Gly Gly Gly Ser His His His His His His
290 295 300

<210> SEQ ID NO 70
<211> LENGTH: 304
<212> TYPE: PRT
<213> ORGANISM: Artificial Sequence
<220> FEATURE:
<223> OTHER INFORMATION: UFV171004

<400> SEQUENCE: 70

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

```
Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300
```

<210> SEQ ID NO 71
<211> LENGTH: 304
<212> TYPE: PRT
<213> ORGANISM: Artificial Sequence
<220> FEATURE:
<223> OTHER INFORMATION: UFV171190

<400> SEQUENCE: 71

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Phe Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175
```

Trp Cys Tyr Asn Ala Glu Leu Leu Val Ala Leu Phe Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Glu Leu Lys Ser Gly Tyr Lys Asp Trp Ile Ala
260 265 270

Ala Ala Asp Tyr Lys Asp Asp Asp Asp Lys Pro Gly Gly Gly Gly Ser
275 280 285

Gly Gly Gly Gly Ser Gly Gly Gly Gly Ser His His His His His His
290 295 300

<210> SEQ ID NO 72
<211> LENGTH: 304
<212> TYPE: PRT
<213> ORGANISM: Artificial Sequence
<220> FEATURE:
<223> OTHER INFORMATION: UFV171191

<400> SEQUENCE: 72

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Met
130 135 140

Asn Glu Lys Ser His Gln Thr Glu Cys Glu Ser Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Met Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

```
Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300


<210> SEQ ID NO 73
<211> LENGTH: 304
<212> TYPE: PRT
<213> ORGANISM: Artificial Sequence
<220> FEATURE:
<223> OTHER INFORMATION: UFV171192

<400> SEQUENCE: 73

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Phe Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300
```

<210> SEQ ID NO 74
<211> LENGTH: 304
<212> TYPE: PRT
<213> ORGANISM: Artificial Sequence
<220> FEATURE:
<223> OTHER INFORMATION: UFV171193

<400> SEQUENCE: 74

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Val Val Asn Arg Val Ile Glu Lys Met
130 135 140

Asn Glu Lys Ser His Gln Thr Glu Cys Glu Ser Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Leu Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Glu Leu Lys Ser Gly Tyr Lys Asp Trp Ile Ala
260 265 270

Ala Ala Asp Tyr Lys Asp Asp Asp Asp Lys Pro Gly Gly Gly Gly Ser
275 280 285

Gly Gly Gly Gly Ser Gly Gly Gly Gly Ser His His His His His His
290 295 300

<210> SEQ ID NO 75
<211> LENGTH: 304
<212> TYPE: PRT
<213> ORGANISM: Artificial Sequence
<220> FEATURE:
<223> OTHER INFORMATION: UFV171194

<400> SEQUENCE: 75

Met Lys Thr Ile Ile Ala Leu Ser Tyr Ile Phe Cys Leu Ala Leu Gly

```
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Met Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300


<210> SEQ ID NO 76
<211> LENGTH: 304
<212> TYPE: PRT
<213> ORGANISM: Artificial Sequence
<220> FEATURE:
<223> OTHER INFORMATION: UFV171195

<400> SEQUENCE: 76

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
```

```
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Thr Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300
```

<210> SEQ ID NO 77
<211> LENGTH: 307
<212> TYPE: PRT
<213> ORGANISM: Artificial Sequence
<220> FEATURE:
<223> OTHER INFORMATION: UFV170611

<400> SEQUENCE: 77

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Arg Val Ile
```

```
    130                 135                 140

Glu Lys Met Asn Glu Lys Ser His Gln Thr Glu Cys Glu Ser Ser Asn
145                 150                 155                 160

Ala Thr Gly Arg Met Lys Cys Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln His Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 78
<211> LENGTH: 307
<212> TYPE: PRT
<213> ORGANISM: Artificial Sequence
<220> FEATURE:
<223> OTHER INFORMATION: UFV170612

<400> SEQUENCE: 78

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Arg Val Ile
    130                 135                 140

Glu Lys Met Asn Glu Lys Ser His Gln Thr Glu Cys Glu Ser Ser Asn
145                 150                 155                 160

Ala Thr Gly Arg Met Lys Cys Ile Glu Asp Lys Ile Glu Glu Ile Glu
                165                 170                 175

Ser Lys Leu Trp Cys Tyr Asn Ala Glu Leu Leu Val Ala Leu Glu Asn
```

```
            180                 185                 190

Gln Lys Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 79
<211> LENGTH: 307
<212> TYPE: PRT
<213> ORGANISM: Artificial Sequence
<220> FEATURE:
<223> OTHER INFORMATION: UFV170613

<400> SEQUENCE: 79

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Arg Val Ile
    130                 135                 140

Glu Lys Met Asn Glu Lys Ser His Gln Thr Glu Cys Glu Ser Ser Asn
145                 150                 155                 160

Ala Thr Gly Arg Met Lys Cys Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Asn Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
```

```
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 80
<211> LENGTH: 307
<212> TYPE: PRT
<213> ORGANISM: Artificial Sequence
<220> FEATURE:
<223> OTHER INFORMATION: UFV170614

<400> SEQUENCE: 80

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Arg Val Ile
    130                 135                 140

Glu Lys Met Asn Glu Lys Ser His Gln Thr Glu Cys Glu Ser Ser Asn
145                 150                 155                 160

Ala Thr Gly Arg Met Lys Cys Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Gln Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
```

```
        275                 280                 285

Gly Gly Ser Gly Gly Gly Gly Ser Gly Gly Gly Gly Ser His His His
    290                 295                 300

His His His
305


<210> SEQ ID NO 81
<211> LENGTH: 307
<212> TYPE: PRT
<213> ORGANISM: Artificial Sequence
<220> FEATURE:
<223> OTHER INFORMATION: UFV161908

<400> SEQUENCE: 81

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Arg Val Ile
    130                 135                 140

Glu Lys Met Asn Glu Lys Ser His Gln Thr Glu Cys Glu Ser Ser Asn
145                 150                 155                 160

Ala Thr Gly Arg Met Lys Cys Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

```
<210> SEQ ID NO 82
<211> LENGTH: 304
<212> TYPE: PRT
<213> ORGANISM: Artificial Sequence
<220> FEATURE:
<223> OTHER INFORMATION: UFV171197

<400> SEQUENCE: 82

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Arg Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300


<210> SEQ ID NO 83
<211> LENGTH: 294
<212> TYPE: PRT
<213> ORGANISM: Artificial Sequence
<220> FEATURE:
<223> OTHER INFORMATION: UFV180666

<400> SEQUENCE: 83

Met Lys Thr Ile Ile Ala Leu Ser Tyr Ile Phe Cys Leu Ala Leu Gly
1               5                   10                  15
```

```
Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Thr
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

<210> SEQ ID NO 84
<211> LENGTH: 294
<212> TYPE: PRT
<213> ORGANISM: Artificial Sequence
<220> FEATURE:
<223> OTHER INFORMATION: UFV180667

<400> SEQUENCE: 84

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80
```

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Val
130 135 140

Asn Glu Lys Ser Asn Gln Thr Glu Lys Cys Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 85
<211> LENGTH: 294
<212> TYPE: PRT
<213> ORGANISM: Artificial Sequence
<220> FEATURE:
<223> OTHER INFORMATION: UFV180668

<400> SEQUENCE: 85

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Ile
130 135 140

Asn Glu Lys Ser Asn Gln Thr Glu Lys Cys Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 86
<211> LENGTH: 294
<212> TYPE: PRT
<213> ORGANISM: Artificial Sequence
<220> FEATURE:
<223> OTHER INFORMATION: UFV180669

<400> SEQUENCE: 86

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Leu
130 135 140

Asn Glu Lys Ser Asn Gln Thr Glu Lys Cys Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

```
Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 87
<211> LENGTH: 294
<212> TYPE: PRT
<213> ORGANISM: Artificial Sequence
<220> FEATURE:
<223> OTHER INFORMATION: UFV180670

<400> SEQUENCE: 87

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Phe
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270
```

```
Pro Gly Gly Gly Gly Ser Gly Gly Gly Gly Ser Gly Gly Gly Gly Ser
        275                 280                 285

His His His His His His
    290


<210> SEQ ID NO 88
<211> LENGTH: 294
<212> TYPE: PRT
<213> ORGANISM: Artificial Sequence
<220> FEATURE:
<223> OTHER INFORMATION: UFV180671

<400> SEQUENCE: 88

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Tyr
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 89
<211> LENGTH: 294
<212> TYPE: PRT
<213> ORGANISM: Artificial Sequence
<220> FEATURE:
```

<223> OTHER INFORMATION: UFV180672

<400> SEQUENCE: 89

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Trp
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

<210> SEQ ID NO 90
<211> LENGTH: 294
<212> TYPE: PRT
<213> ORGANISM: Artificial Sequence
<220> FEATURE:
<223> OTHER INFORMATION: UFV180673

<400> SEQUENCE: 90

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45
```

```
Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys His
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

<210> SEQ ID NO 91
<211> LENGTH: 294
<212> TYPE: PRT
<213> ORGANISM: Artificial Sequence
<220> FEATURE:
<223> OTHER INFORMATION: UFV180674

<400> SEQUENCE: 91

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110
```

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Lys
130 135 140

Asn Glu Lys Ser Asn Gln Thr Glu Lys Cys Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 92
<211> LENGTH: 294
<212> TYPE: PRT
<213> ORGANISM: Artificial Sequence
<220> FEATURE:
<223> OTHER INFORMATION: UFV180675

<400> SEQUENCE: 92

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Arg
130 135 140

Asn Glu Lys Ser Asn Gln Thr Glu Lys Cys Pro Ser Asn Ala Thr Gly
145 150 155 160

Pro Met Lys Cys Ile Glu Asp Lys Ile Glu Glu Ile Glu Ser Lys Leu
165 170 175

```
Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 93
<211> LENGTH: 303
<212> TYPE: PRT
<213> ORGANISM: Artificial Sequence
<220> FEATURE:
<223> OTHER INFORMATION: UFV170636

<400> SEQUENCE: 93

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Lys Tyr Val
    50                  55                  60

Cys Gln Asn Thr Leu Lys Leu Ala Thr Gly Met Arg Asn Val Pro Glu
65                  70                  75                  80

Lys Gln Thr Arg Gly Leu Phe Gly Ala Ile Ala Gly Phe Ile Glu Asn
                85                  90                  95

Gly Trp Glu Gly Met Ile Asp Gly Trp Tyr Gly Phe Arg Trp Gln Asn
            100                 105                 110

Ser Glu Gly Thr Gly Gln Ala Ala Asp Leu Lys Ser Thr Gln Ala Ala
        115                 120                 125

Ile Asp Gln Ile Thr Asn Lys Val Asn Arg Val Ile Glu Lys Met Asn
    130                 135                 140

Glu Lys Ser His Gln Thr Glu Cys Glu Ser Ser Asn Ala Thr Gly Arg
145                 150                 155                 160

Met Lys Cys Ile Glu Asp Lys Ile Glu Glu Ile Glu Ser Lys Leu Trp
                165                 170                 175

Cys Tyr Asn Ala Glu Leu Leu Val Ala Leu Glu Asn Gln Arg Thr Ile
            180                 185                 190

Asp Tyr Thr Asp Ser Glu Met Asn Lys Leu Phe Glu Lys Thr Arg Arg
        195                 200                 205

Gln Leu Arg Glu Asn Ala Glu Asp Met Gly Asn Gly Cys Phe Lys Ile
    210                 215                 220

Tyr His Lys Cys Asp Asn Ala Cys Ile Glu Ser Ile Arg Asn Gly Thr
225                 230                 235                 240
```

```
Tyr Asp His Asp Val Tyr Arg Asp Glu Ala Leu Asn Asn Arg Phe Gln
                245                 250                 255

Ile Lys Gly Val Glu Leu Lys Ser Gly Tyr Lys Asp Trp Ile Ala Ala
            260                 265                 270

Ala Asp Tyr Lys Asp Asp Asp Asp Lys Pro Gly Gly Gly Gly Ser Gly
        275                 280                 285

Gly Gly Gly Ser Gly Gly Gly Gly Ser His His His His His His
    290                 295                 300


<210> SEQ ID NO 94
<211> LENGTH: 304
<212> TYPE: PRT
<213> ORGANISM: Artificial Sequence
<220> FEATURE:
<223> OTHER INFORMATION: UFV170637

<400> SEQUENCE: 94

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Arg Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Arg Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300
```

<210> SEQ ID NO 95
<211> LENGTH: 305
<212> TYPE: PRT
<213> ORGANISM: Artificial Sequence
<220> FEATURE:
<223> OTHER INFORMATION: UFV170638

<400> SEQUENCE: 95

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Ser Ser Lys
50 55 60

Tyr Val Cys Gln Asn Thr Leu Lys Leu Ala Thr Gly Met Arg Asn Val
65 70 75 80

Pro Glu Lys Gln Thr Arg Gly Leu Phe Gly Ala Ile Ala Gly Phe Ile
85 90 95

Glu Asn Gly Trp Glu Gly Met Ile Asp Gly Trp Tyr Gly Phe Arg Trp
100 105 110

Gln Asn Ser Glu Gly Thr Gly Gln Ala Ala Asp Leu Lys Ser Thr Gln
115 120 125

Ala Ala Ile Asp Gln Ile Thr Asn Lys Val Asn Arg Val Ile Glu Lys
130 135 140

Met Asn Glu Lys Ser His Gln Thr Glu Cys Glu Ser Ser Asn Ala Thr
145 150 155 160

Gly Arg Met Lys Cys Ile Glu Asp Lys Ile Glu Glu Ile Glu Ser Lys
165 170 175

Leu Trp Cys Tyr Asn Ala Glu Leu Leu Val Ala Leu Glu Asn Gln Arg
180 185 190

Thr Ile Asp Tyr Thr Asp Ser Glu Met Asn Lys Leu Phe Glu Lys Thr
195 200 205

Arg Arg Gln Leu Arg Glu Asn Ala Glu Asp Met Gly Asn Gly Cys Phe
210 215 220

Lys Ile Tyr His Lys Cys Asp Asn Ala Cys Ile Glu Ser Ile Arg Asn
225 230 235 240

Gly Thr Tyr Asp His Asp Val Tyr Arg Asp Glu Ala Leu Asn Asn Arg
245 250 255

Phe Gln Ile Lys Gly Val Glu Leu Lys Ser Gly Tyr Lys Asp Trp Ile
260 265 270

Ala Ala Ala Asp Tyr Lys Asp Asp Asp Asp Lys Pro Gly Gly Gly Gly
275 280 285

Ser Gly Gly Gly Gly Ser Gly Gly Gly Gly Ser His His His His His
290 295 300

His
305

<210> SEQ ID NO 96
<211> LENGTH: 306
<212> TYPE: PRT
<213> ORGANISM: Artificial Sequence
<220> FEATURE:
<223> OTHER INFORMATION: UFV170639

<400> SEQUENCE: 96

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Ser Ser Thr
50 55 60

Lys Tyr Val Cys Gln Asn Thr Leu Lys Leu Ala Thr Gly Met Arg Asn
65 70 75 80

Val Pro Glu Lys Gln Thr Arg Gly Leu Phe Gly Ala Ile Ala Gly Phe
85 90 95

Ile Glu Asn Gly Trp Glu Gly Met Ile Asp Gly Trp Tyr Gly Phe Arg
100 105 110

Trp Gln Asn Ser Glu Gly Thr Gly Gln Ala Ala Asp Leu Lys Ser Thr
115 120 125

Gln Ala Ala Ile Asp Gln Ile Thr Asn Lys Val Asn Arg Val Ile Glu
130 135 140

Lys Met Asn Glu Lys Ser His Gln Thr Glu Cys Glu Ser Ser Asn Ala
145 150 155 160

Thr Gly Arg Met Lys Cys Ile Glu Asp Lys Ile Glu Glu Ile Glu Ser
165 170 175

Lys Leu Trp Cys Tyr Asn Ala Glu Leu Leu Val Ala Leu Glu Asn Gln
180 185 190

Arg Thr Ile Asp Tyr Thr Asp Ser Glu Met Asn Lys Leu Phe Glu Lys
195 200 205

Thr Arg Arg Gln Leu Arg Glu Asn Ala Glu Asp Met Gly Asn Gly Cys
210 215 220

Phe Lys Ile Tyr His Lys Cys Asp Asn Ala Cys Ile Glu Ser Ile Arg
225 230 235 240

Asn Gly Thr Tyr Asp His Asp Val Tyr Arg Asp Glu Ala Leu Asn Asn
245 250 255

Arg Phe Gln Ile Lys Gly Val Glu Leu Lys Ser Gly Tyr Lys Asp Trp
260 265 270

Ile Ala Ala Ala Asp Tyr Lys Asp Asp Asp Asp Lys Pro Gly Gly Gly
275 280 285

Gly Ser Gly Gly Gly Gly Ser Gly Gly Gly Gly Ser His His His His
290 295 300

His His
305

<210> SEQ ID NO 97
<211> LENGTH: 307
<212> TYPE: PRT
<213> ORGANISM: Artificial Sequence
<220> FEATURE:
<223> OTHER INFORMATION: UFV170640

<400> SEQUENCE: 97

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp

```
        35                  40                  45

Gln Val Glu Val Thr Asn Ala Ile Glu Leu Val Gln Ser Ser Ser Thr
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Arg Val Ile
    130                 135                 140

Glu Lys Met Asn Glu Lys Ser His Gln Thr Glu Cys Glu Ser Ser Asn
145                 150                 155                 160

Ala Thr Gly Arg Met Lys Cys Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 98
<211> LENGTH: 307
<212> TYPE: PRT
<213> ORGANISM: Artificial Sequence
<220> FEATURE:
<223> OTHER INFORMATION: UFV160653

<400> SEQUENCE: 98

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
```

```
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 99
<211> LENGTH: 304
<212> TYPE: PRT
<213> ORGANISM: Artificial Sequence
<220> FEATURE:
<223> OTHER INFORMATION: UFV160764

<400> SEQUENCE: 99

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Pro Lys Tyr
    50                  55                  60

Val Cys Gln Asn Thr Leu Lys Leu Ala Thr Gly Met Arg Asn Val Pro
65                  70                  75                  80

Glu Lys Gln Thr Arg Gly Leu Phe Gly Ala Ile Ala Gly Phe Ile Glu
                85                  90                  95

Asn Gly Trp Glu Gly Met Ile Asp Gly Trp Tyr Gly Phe Arg His Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Ser Val Ile Glu Lys Met
```

```
    130                 135                 140

Asn Glu Lys Ser His Gln Thr Glu Lys Glu Ser Ser Asn Ala Thr Gly
145                 150                 155                 160

Arg Met Lys Gln Ile Glu Asp Lys Ile Glu Glu Ile Glu Ser Lys Leu
                165                 170                 175

Trp Cys Tyr Asn Ala Glu Leu Leu Val Ala Leu Glu Asn Gln Arg Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300


<210> SEQ ID NO 100
<211> LENGTH: 305
<212> TYPE: PRT
<213> ORGANISM: Artificial Sequence
<220> FEATURE:
<223> OTHER INFORMATION: UFV160765

<400> SEQUENCE: 100

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Cys Pro Lys
    50                  55                  60

Tyr Val Cys Gln Asn Thr Leu Lys Leu Ala Thr Gly Met Arg Asn Val
65                  70                  75                  80

Pro Glu Lys Gln Thr Arg Gly Leu Phe Gly Ala Ile Ala Gly Phe Ile
                85                  90                  95

Glu Asn Gly Trp Glu Gly Met Ile Asp Gly Trp Tyr Gly Phe Arg His
            100                 105                 110

Gln Asn Ser Glu Gly Thr Gly Gln Ala Ala Asp Leu Lys Ser Thr Gln
        115                 120                 125

Ala Ala Ile Asp Gln Ile Thr Asn Lys Val Asn Ser Val Ile Glu Lys
    130                 135                 140

Met Asn Glu Lys Ser His Gln Thr Glu Lys Glu Ser Ser Asn Ala Thr
145                 150                 155                 160

Gly Arg Met Lys Gln Ile Glu Asp Lys Ile Glu Glu Ile Glu Ser Lys
                165                 170                 175

Leu Trp Cys Tyr Asn Ala Glu Leu Leu Val Ala Leu Glu Asn Gln Arg
            180                 185                 190

Thr Ile Asp Tyr Thr Asp Ser Glu Met Asn Lys Leu Phe Glu Lys Thr
```

```
        195                 200                 205

Arg Arg Gln Leu Arg Glu Asn Ala Glu Asp Met Gly Asn Gly Cys Phe
    210                 215                 220

Lys Ile Tyr His Lys Cys Asp Asn Ala Cys Ile Glu Ser Ile Arg Asn
225                 230                 235                 240

Gly Thr Tyr Asp His Asp Val Tyr Arg Asp Glu Ala Leu Asn Asn Arg
                245                 250                 255

Phe Gln Ile Lys Gly Val Glu Leu Lys Ser Gly Tyr Lys Asp Trp Ile
            260                 265                 270

Ala Ala Ala Asp Tyr Lys Asp Asp Asp Asp Lys Pro Gly Gly Gly Gly
        275                 280                 285

Ser Gly Gly Gly Gly Ser Gly Gly Gly Gly Ser His His His His His
    290                 295                 300

His
305


<210> SEQ ID NO 101
<211> LENGTH: 306
<212> TYPE: PRT
<213> ORGANISM: Artificial Sequence
<220> FEATURE:
<223> OTHER INFORMATION: UFV160766

<400> SEQUENCE: 101

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ala Cys Pro
    50                  55                  60

Lys Tyr Val Cys Gln Asn Thr Leu Lys Leu Ala Thr Gly Met Arg Asn
65                  70                  75                  80

Val Pro Glu Lys Gln Thr Arg Gly Leu Phe Gly Ala Ile Ala Gly Phe
                85                  90                  95

Ile Glu Asn Gly Trp Glu Gly Met Ile Asp Gly Trp Tyr Gly Phe Arg
            100                 105                 110

His Gln Asn Ser Glu Gly Thr Gly Gln Ala Ala Asp Leu Lys Ser Thr
        115                 120                 125

Gln Ala Ala Ile Asp Gln Ile Thr Asn Lys Val Asn Ser Val Ile Glu
    130                 135                 140

Lys Met Asn Glu Lys Ser His Gln Thr Glu Lys Glu Ser Ser Asn Ala
145                 150                 155                 160

Thr Gly Arg Met Lys Gln Ile Glu Asp Lys Ile Glu Glu Ile Glu Ser
                165                 170                 175

Lys Leu Trp Cys Tyr Asn Ala Glu Leu Leu Val Ala Leu Glu Asn Gln
            180                 185                 190

Arg Thr Ile Asp Tyr Thr Asp Ser Glu Met Asn Lys Leu Phe Glu Lys
        195                 200                 205

Thr Arg Arg Gln Leu Arg Glu Asn Ala Glu Asp Met Gly Asn Gly Cys
    210                 215                 220

Phe Lys Ile Tyr His Lys Cys Asp Asn Ala Cys Ile Glu Ser Ile Arg
225                 230                 235                 240

Asn Gly Thr Tyr Asp His Asp Val Tyr Arg Asp Glu Ala Leu Asn Asn
```

```
            245                 250                 255

Arg Phe Gln Ile Lys Gly Val Glu Leu Lys Ser Gly Tyr Lys Asp Trp
            260                 265                 270

Ile Ala Ala Ala Asp Tyr Lys Asp Asp Asp Asp Lys Pro Gly Gly Gly
        275                 280                 285

Gly Ser Gly Gly Gly Gly Ser Gly Gly Gly Gly Ser His His His His
    290                 295                 300

His His
305


<210> SEQ ID NO 102
<211> LENGTH: 307
<212> TYPE: PRT
<213> ORGANISM: Artificial Sequence
<220> FEATURE:
<223> OTHER INFORMATION: UFV160674

<400> SEQUENCE: 102

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Ala Gly
    50                  55                  60

Pro Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
```

290 295 300

His His His
305

<210> SEQ ID NO 103
<211> LENGTH: 307
<212> TYPE: PRT
<213> ORGANISM: Artificial Sequence
<220> FEATURE:
<223> OTHER INFORMATION: UFV160675

<400> SEQUENCE: 103

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Gly Ala Cys
50 55 60

Pro Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 104
<211> LENGTH: 307
<212> TYPE: PRT

<213> ORGANISM: Artificial Sequence
<220> FEATURE:
<223> OTHER INFORMATION: UFV160767

<400> SEQUENCE: 104

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Ala Cys
50 55 60

Pro Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 105
<211> LENGTH: 306
<212> TYPE: PRT
<213> ORGANISM: Artificial Sequence
<220> FEATURE:
<223> OTHER INFORMATION: UFV160768

<400> SEQUENCE: 105

Met Lys Thr Ile Ile Ala Leu Ser Tyr Ile Phe Cys Leu Ala Leu Gly
1 5 10 15

```
Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Cys Pro
    50                  55                  60

Lys Tyr Val Cys Gln Asn Thr Leu Lys Leu Ala Thr Gly Met Arg Asn
65                  70                  75                  80

Val Pro Glu Lys Gln Thr Arg Gly Leu Phe Gly Ala Ile Ala Gly Phe
                85                  90                  95

Ile Glu Asn Gly Trp Glu Gly Met Ile Asp Gly Trp Tyr Gly Phe Arg
            100                 105                 110

His Gln Asn Ser Glu Gly Thr Gly Gln Ala Ala Asp Leu Lys Ser Thr
        115                 120                 125

Gln Ala Ala Ile Asp Gln Ile Thr Asn Lys Val Asn Ser Val Ile Glu
    130                 135                 140

Lys Met Asn Glu Lys Ser His Gln Thr Glu Lys Glu Ser Ser Asn Ala
145                 150                 155                 160

Thr Gly Arg Met Lys Gln Ile Glu Asp Lys Ile Glu Glu Ile Glu Ser
                165                 170                 175

Lys Leu Trp Cys Tyr Asn Ala Glu Leu Leu Val Ala Leu Glu Asn Gln
            180                 185                 190

Arg Thr Ile Asp Tyr Thr Asp Ser Glu Met Asn Lys Leu Phe Glu Lys
        195                 200                 205

Thr Arg Arg Gln Leu Arg Glu Asn Ala Glu Asp Met Gly Asn Gly Cys
    210                 215                 220

Phe Lys Ile Tyr His Lys Cys Asp Asn Ala Cys Ile Glu Ser Ile Arg
225                 230                 235                 240

Asn Gly Thr Tyr Asp His Asp Val Tyr Arg Asp Glu Ala Leu Asn Asn
                245                 250                 255

Arg Phe Gln Ile Lys Gly Val Glu Leu Lys Ser Gly Tyr Lys Asp Trp
            260                 265                 270

Ile Ala Ala Ala Asp Tyr Lys Asp Asp Asp Asp Lys Pro Gly Gly Gly
        275                 280                 285

Gly Ser Gly Gly Gly Gly Ser Gly Gly Gly Gly Ser His His His His
    290                 295                 300

His His
305
```

<210> SEQ ID NO 106
<211> LENGTH: 308
<212> TYPE: PRT
<213> ORGANISM: Artificial Sequence
<220> FEATURE:
<223> OTHER INFORMATION: UFV160769

<400> SEQUENCE: 106

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Ala
    50                  55                  60
```

Cys Pro Lys Tyr Val Cys Gln Asn Thr Leu Lys Leu Ala Thr Gly Met
65 70 75 80

Arg Asn Val Pro Glu Lys Gln Thr Arg Gly Leu Phe Gly Ala Ile Ala
85 90 95

Gly Phe Ile Glu Asn Gly Trp Glu Gly Met Ile Asp Gly Trp Tyr Gly
100 105 110

Phe Arg His Gln Asn Ser Glu Gly Thr Gly Gln Ala Ala Asp Leu Lys
115 120 125

Ser Thr Gln Ala Ala Ile Asp Gln Ile Thr Asn Lys Val Asn Ser Val
130 135 140

Ile Glu Lys Met Asn Glu Lys Ser His Gln Thr Glu Lys Glu Ser Ser
145 150 155 160

Asn Ala Thr Gly Arg Met Lys Gln Ile Glu Asp Lys Ile Glu Glu Ile
165 170 175

Glu Ser Lys Leu Trp Cys Tyr Asn Ala Glu Leu Leu Val Ala Leu Glu
180 185 190

Asn Gln Arg Thr Ile Asp Tyr Thr Asp Ser Glu Met Asn Lys Leu Phe
195 200 205

Glu Lys Thr Arg Arg Gln Leu Arg Glu Asn Ala Glu Asp Met Gly Asn
210 215 220

Gly Cys Phe Lys Ile Tyr His Lys Cys Asp Asn Ala Cys Ile Glu Ser
225 230 235 240

Ile Arg Asn Gly Thr Tyr Asp His Asp Val Tyr Arg Asp Glu Ala Leu
245 250 255

Asn Asn Arg Phe Gln Ile Lys Gly Val Glu Leu Lys Ser Gly Tyr Lys
260 265 270

Asp Trp Ile Ala Ala Ala Asp Tyr Lys Asp Asp Asp Asp Lys Pro Gly
275 280 285

Gly Gly Gly Ser Gly Gly Gly Gly Ser Gly Gly Gly Gly Ser His His
290 295 300

His His His His
305

<210> SEQ ID NO 107
<211> LENGTH: 307
<212> TYPE: PRT
<213> ORGANISM: Artificial Sequence
<220> FEATURE:
<223> OTHER INFORMATION: UFV160770

<400> SEQUENCE: 107

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Ser Cys
50 55 60

Pro Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

```
Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 108
<211> LENGTH: 305
<212> TYPE: PRT
<213> ORGANISM: Artificial Sequence
<220> FEATURE:
<223> OTHER INFORMATION: UFV160771

<400> SEQUENCE: 108

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Pro Lys
    50                  55                  60

Tyr Val Cys Gln Asn Thr Leu Lys Leu Ala Thr Gly Met Arg Asn Val
65                  70                  75                  80

Pro Glu Lys Gln Thr Arg Gly Leu Phe Gly Ala Ile Ala Gly Phe Ile
                85                  90                  95

Glu Asn Gly Trp Glu Gly Met Ile Asp Gly Trp Tyr Gly Phe Arg His
            100                 105                 110

Gln Asn Ser Glu Gly Thr Gly Gln Ala Ala Asp Leu Lys Ser Thr Gln
        115                 120                 125

Ala Ala Ile Asp Gln Ile Thr Asn Lys Val Asn Ser Val Ile Glu Lys
    130                 135                 140

Met Asn Glu Lys Ser His Gln Thr Glu Lys Glu Ser Ser Asn Ala Thr
145                 150                 155                 160
```

```
Gly Arg Met Lys Gln Ile Glu Asp Lys Ile Glu Glu Ile Glu Ser Lys
                165                 170                 175

Leu Trp Cys Tyr Asn Ala Glu Leu Leu Val Ala Leu Glu Asn Gln Arg
            180                 185                 190

Thr Ile Asp Tyr Thr Asp Ser Glu Met Asn Lys Leu Phe Glu Lys Thr
        195                 200                 205

Arg Arg Gln Leu Arg Glu Asn Ala Glu Asp Met Gly Asn Gly Cys Phe
    210                 215                 220

Lys Ile Tyr His Lys Cys Asp Asn Ala Cys Ile Glu Ser Ile Arg Asn
225                 230                 235                 240

Gly Thr Tyr Asp His Asp Val Tyr Arg Asp Glu Ala Leu Asn Asn Arg
                245                 250                 255

Phe Gln Ile Lys Gly Val Glu Leu Lys Ser Gly Tyr Lys Asp Trp Ile
            260                 265                 270

Ala Ala Ala Asp Tyr Lys Asp Asp Asp Asp Lys Pro Gly Gly Gly Gly
        275                 280                 285

Ser Gly Gly Gly Gly Ser Gly Gly Gly Gly Ser His His His His His
    290                 295                 300

His
305


<210> SEQ ID NO 109
<211> LENGTH: 306
<212> TYPE: PRT
<213> ORGANISM: Artificial Sequence
<220> FEATURE:
<223> OTHER INFORMATION: UFV160772

<400> SEQUENCE: 109

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Pro
    50                  55                  60

Lys Tyr Val Cys Gln Asn Thr Leu Lys Leu Ala Thr Gly Met Arg Asn
65                  70                  75                  80

Val Pro Glu Lys Gln Thr Arg Gly Leu Phe Gly Ala Ile Ala Gly Phe
                85                  90                  95

Ile Glu Asn Gly Trp Glu Gly Met Ile Asp Gly Trp Tyr Gly Phe Arg
            100                 105                 110

His Gln Asn Ser Glu Gly Thr Gly Gln Ala Ala Asp Leu Lys Ser Thr
        115                 120                 125

Gln Ala Ala Ile Asp Gln Ile Thr Asn Lys Val Asn Ser Val Ile Glu
    130                 135                 140

Lys Met Asn Glu Lys Ser His Gln Thr Glu Lys Glu Ser Ser Asn Ala
145                 150                 155                 160

Thr Gly Arg Met Lys Gln Ile Glu Asp Lys Ile Glu Glu Ile Glu Ser
                165                 170                 175

Lys Leu Trp Cys Tyr Asn Ala Glu Leu Leu Val Ala Leu Glu Asn Gln
            180                 185                 190

Arg Thr Ile Asp Tyr Thr Asp Ser Glu Met Asn Lys Leu Phe Glu Lys
        195                 200                 205
```

```
Thr Arg Arg Gln Leu Arg Glu Asn Ala Glu Asp Met Gly Asn Gly Cys
    210                 215                 220

Phe Lys Ile Tyr His Lys Cys Asp Asn Ala Cys Ile Glu Ser Ile Arg
225                 230                 235                 240

Asn Gly Thr Tyr Asp His Asp Val Tyr Arg Asp Glu Ala Leu Asn Asn
                245                 250                 255

Arg Phe Gln Ile Lys Gly Val Glu Leu Lys Ser Gly Tyr Lys Asp Trp
            260                 265                 270

Ile Ala Ala Ala Asp Tyr Lys Asp Asp Asp Asp Lys Pro Gly Gly Gly
        275                 280                 285

Gly Ser Gly Gly Gly Gly Ser Gly Gly Gly Gly Ser His His His His
    290                 295                 300

His His
305


<210> SEQ ID NO 110
<211> LENGTH: 307
<212> TYPE: PRT
<213> ORGANISM: Artificial Sequence
<220> FEATURE:
<223> OTHER INFORMATION: UFV160321

<400> SEQUENCE: 110

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255
```

```
Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 111
<211> LENGTH: 307
<212> TYPE: PRT
<213> ORGANISM: Artificial Sequence
<220> FEATURE:
<223> OTHER INFORMATION: UFV160403

<400> SEQUENCE: 111

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Asn Pro His
    50                  55                  60

Arg Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300
```

His His His
305

<210> SEQ ID NO 112
<211> LENGTH: 307
<212> TYPE: PRT
<213> ORGANISM: Artificial Sequence
<220> FEATURE:
<223> OTHER INFORMATION: UFV160404

<400> SEQUENCE: 112

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Gly Asp Pro
50 55 60

His Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Leu Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 113
<211> LENGTH: 307
<212> TYPE: PRT
<213> ORGANISM: Artificial Sequence
<220> FEATURE:

<223> OTHER INFORMATION: UFV160405

<400> SEQUENCE: 113

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Asn Gly Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Leu Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 114
<211> LENGTH: 307
<212> TYPE: PRT
<213> ORGANISM: Artificial Sequence
<220> FEATURE:
<223> OTHER INFORMATION: UFV160406

<400> SEQUENCE: 114

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Gly Gly Ser
50 55 60

Asn Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Leu Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 115
<211> LENGTH: 307
<212> TYPE: PRT
<213> ORGANISM: Artificial Sequence
<220> FEATURE:
<223> OTHER INFORMATION: UFV160407

<400> SEQUENCE: 115

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Gly Ser Asn
50 55 60

Ala Lys Tyr Val Cys Gln Asn Thr Leu Lys Leu Ala Thr Gly Met Arg
65 70 75 80

```
Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 116
<211> LENGTH: 307
<212> TYPE: PRT
<213> ORGANISM: Artificial Sequence
<220> FEATURE:
<223> OTHER INFORMATION: UFV160408

<400> SEQUENCE: 116

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125
```

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Leu Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 117
<211> LENGTH: 307
<212> TYPE: PRT
<213> ORGANISM: Artificial Sequence
<220> FEATURE:
<223> OTHER INFORMATION: UFV160409

<400> SEQUENCE: 117

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Gly Ser Gly
50 55 60

Phe Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

```
Ser Lys Leu Trp Cys Tyr Asn Ala Glu Leu Leu Val Ala Leu Glu Asn
            180                 185                 190

Gln Arg Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 118
<211> LENGTH: 306
<212> TYPE: PRT
<213> ORGANISM: Artificial Sequence
<220> FEATURE:
<223> OTHER INFORMATION: UFV160410

<400> SEQUENCE: 118

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Ser Gly
    50                  55                  60

Lys Tyr Val Cys Gln Asn Thr Leu Lys Leu Ala Thr Gly Met Arg Asn
65                  70                  75                  80

Val Pro Glu Lys Gln Thr Arg Gly Leu Phe Gly Ala Ile Ala Gly Phe
                85                  90                  95

Ile Glu Asn Gly Trp Glu Gly Met Ile Asp Gly Trp Tyr Gly Phe Arg
            100                 105                 110

His Gln Asn Ser Glu Gly Thr Gly Gln Ala Ala Asp Leu Lys Ser Thr
        115                 120                 125

Gln Ala Ala Ile Asp Gln Ile Thr Asn Lys Val Asn Ser Val Ile Glu
    130                 135                 140

Lys Met Asn Glu Lys Ser His Gln Thr Glu Lys Glu Ser Ser Asn Ala
145                 150                 155                 160

Thr Gly Arg Met Lys Gln Ile Glu Asp Lys Ile Glu Glu Ile Glu Ser
                165                 170                 175

Lys Leu Trp Cys Tyr Asn Ala Glu Leu Leu Val Ala Leu Glu Asn Gln
            180                 185                 190

Arg Thr Ile Asp Leu Thr Asp Ser Glu Met Asn Lys Leu Phe Glu Lys
        195                 200                 205

Thr Arg Arg Gln Leu Arg Glu Asn Ala Glu Asp Met Gly Asn Gly Cys
    210                 215                 220
```

```
Phe Lys Ile Tyr His Lys Cys Asp Asn Ala Cys Ile Glu Ser Ile Arg
225                 230                 235                 240

Asn Gly Thr Tyr Asp His Asp Val Tyr Arg Asp Glu Ala Leu Asn Asn
                245                 250                 255

Arg Phe Gln Ile Lys Gly Val Glu Leu Lys Ser Gly Tyr Lys Asp Trp
            260                 265                 270

Ile Ala Ala Ala Asp Tyr Lys Asp Asp Asp Asp Lys Pro Gly Gly Gly
        275                 280                 285

Gly Ser Gly Gly Gly Gly Ser Gly Gly Gly Gly Ser His His His His
    290                 295                 300

His His
305


<210> SEQ ID NO 119
<211> LENGTH: 305
<212> TYPE: PRT
<213> ORGANISM: Artificial Sequence
<220> FEATURE:
<223> OTHER INFORMATION: UFV160411

<400> SEQUENCE: 119

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Lys
    50                  55                  60

Tyr Val Cys Gln Asn Thr Leu Lys Leu Ala Thr Gly Met Arg Asn Val
65                  70                  75                  80

Pro Glu Lys Gln Thr Arg Gly Leu Phe Gly Ala Ile Ala Gly Phe Ile
                85                  90                  95

Glu Asn Gly Trp Glu Gly Met Ile Asp Gly Trp Tyr Gly Phe Arg His
            100                 105                 110

Gln Asn Ser Glu Gly Thr Gly Gln Ala Ala Asp Leu Lys Ser Thr Gln
        115                 120                 125

Ala Ala Ile Asp Gln Ile Thr Asn Lys Val Asn Ser Val Ile Glu Lys
    130                 135                 140

Met Asn Glu Lys Ser His Gln Thr Glu Lys Glu Ser Ser Asn Ala Thr
145                 150                 155                 160

Gly Arg Met Lys Gln Ile Glu Asp Lys Ile Glu Glu Ile Glu Ser Lys
                165                 170                 175

Leu Trp Cys Tyr Asn Ala Glu Leu Leu Val Ala Leu Glu Asn Gln Arg
            180                 185                 190

Thr Ile Asp Leu Thr Asp Ser Glu Met Asn Lys Leu Phe Glu Lys Thr
        195                 200                 205

Arg Arg Gln Leu Arg Glu Asn Ala Glu Asp Met Gly Asn Gly Cys Phe
    210                 215                 220

Lys Ile Tyr His Lys Cys Asp Asn Ala Cys Ile Glu Ser Ile Arg Asn
225                 230                 235                 240

Gly Thr Tyr Asp His Asp Val Tyr Arg Asp Glu Ala Leu Asn Asn Arg
                245                 250                 255

Phe Gln Ile Lys Gly Val Glu Leu Lys Ser Gly Tyr Lys Asp Trp Ile
            260                 265                 270
```

```
Ala Ala Ala Asp Tyr Lys Asp Asp Asp Asp Lys Pro Gly Gly Gly Gly
        275                 280                 285

Ser Gly Gly Gly Gly Ser Gly Gly Gly Gly Ser His His His His His
    290                 295                 300

His
305


<210> SEQ ID NO 120
<211> LENGTH: 306
<212> TYPE: PRT
<213> ORGANISM: Artificial Sequence
<220> FEATURE:
<223> OTHER INFORMATION: UFV160412

<400> SEQUENCE: 120

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Ser
    50                  55                  60

Lys Tyr Val Cys Gln Asn Thr Leu Lys Leu Ala Thr Gly Met Arg Asn
65                  70                  75                  80

Val Pro Glu Lys Gln Thr Arg Gly Leu Phe Gly Ala Ile Ala Gly Phe
                85                  90                  95

Ile Glu Asn Gly Trp Glu Gly Met Ile Asp Gly Trp Tyr Gly Phe Arg
            100                 105                 110

His Gln Asn Ser Glu Gly Thr Gly Gln Ala Ala Asp Leu Lys Ser Thr
        115                 120                 125

Gln Ala Ala Ile Asp Gln Ile Thr Asn Lys Val Asn Ser Val Ile Glu
    130                 135                 140

Lys Met Asn Glu Lys Ser His Gln Thr Glu Lys Glu Ser Ser Asn Ala
145                 150                 155                 160

Thr Gly Arg Met Lys Gln Ile Glu Asp Lys Ile Glu Glu Ile Glu Ser
                165                 170                 175

Lys Leu Trp Cys Tyr Asn Ala Glu Leu Leu Val Ala Leu Glu Asn Gln
            180                 185                 190

Arg Thr Ile Asp Leu Thr Asp Ser Glu Met Asn Lys Leu Phe Glu Lys
        195                 200                 205

Thr Arg Arg Gln Leu Arg Glu Asn Ala Glu Asp Met Gly Asn Gly Cys
    210                 215                 220

Phe Lys Ile Tyr His Lys Cys Asp Asn Ala Cys Ile Glu Ser Ile Arg
225                 230                 235                 240

Asn Gly Thr Tyr Asp His Asp Val Tyr Arg Asp Glu Ala Leu Asn Asn
                245                 250                 255

Arg Phe Gln Ile Lys Gly Val Glu Leu Lys Ser Gly Tyr Lys Asp Trp
            260                 265                 270

Ile Ala Ala Ala Asp Tyr Lys Asp Asp Asp Asp Lys Pro Gly Gly Gly
        275                 280                 285

Gly Ser Gly Gly Gly Gly Ser Gly Gly Gly Gly Ser His His His His
    290                 295                 300

His His
305
```

<210> SEQ ID NO 121
<211> LENGTH: 306
<212> TYPE: PRT
<213> ORGANISM: Artificial Sequence
<220> FEATURE:
<223> OTHER INFORMATION: UFV160413

<400> SEQUENCE: 121

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Gly Ser
    50                  55                  60

Lys Tyr Val Cys Gln Asn Thr Leu Lys Leu Ala Thr Gly Met Arg Asn
65                  70                  75                  80

Val Pro Glu Lys Gln Thr Arg Gly Leu Phe Gly Ala Ile Ala Gly Phe
                85                  90                  95

Ile Glu Asn Gly Trp Glu Gly Met Ile Asp Gly Trp Tyr Gly Phe Arg
            100                 105                 110

His Gln Asn Ser Glu Gly Thr Gly Gln Ala Ala Asp Leu Lys Ser Thr
        115                 120                 125

Gln Ala Ala Ile Asp Gln Ile Thr Asn Lys Val Asn Ser Val Ile Glu
    130                 135                 140

Lys Met Asn Glu Lys Ser His Gln Thr Glu Lys Glu Ser Ser Asn Ala
145                 150                 155                 160

Thr Gly Arg Met Lys Gln Ile Glu Asp Lys Ile Glu Glu Ile Glu Ser
                165                 170                 175

Lys Leu Trp Cys Tyr Asn Ala Glu Leu Leu Val Ala Leu Glu Asn Gln
            180                 185                 190

Arg Thr Ile Asp Leu Thr Asp Ser Glu Met Asn Lys Leu Phe Glu Lys
        195                 200                 205

Thr Arg Arg Gln Leu Arg Glu Asn Ala Glu Asp Met Gly Asn Gly Cys
    210                 215                 220

Phe Lys Ile Tyr His Lys Cys Asp Asn Ala Cys Ile Glu Ser Ile Arg
225                 230                 235                 240

Asn Gly Thr Tyr Asp His Asp Val Tyr Arg Asp Glu Ala Leu Asn Asn
                245                 250                 255

Arg Phe Gln Ile Lys Gly Val Glu Leu Lys Ser Gly Tyr Lys Asp Trp
            260                 265                 270

Ile Ala Ala Ala Asp Tyr Lys Asp Asp Asp Asp Lys Pro Gly Gly Gly
        275                 280                 285

Gly Ser Gly Gly Gly Gly Ser Gly Gly Gly Gly Ser His His His His
    290                 295                 300

His His
305
```

<210> SEQ ID NO 122
<211> LENGTH: 307
<212> TYPE: PRT
<213> ORGANISM: Artificial Sequence
<220> FEATURE:
<223> OTHER INFORMATION: UFV160414

<400> SEQUENCE: 122

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser His Pro Ser
    50                  55                  60

Thr Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305

<210> SEQ ID NO 123
<211> LENGTH: 307
<212> TYPE: PRT
<213> ORGANISM: Artificial Sequence
<220> FEATURE:
<223> OTHER INFORMATION: UFV160415

<400> SEQUENCE: 123

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp 35 40 45

Gln Ile Glu Val Thr Asn Ala Thr Glu Leu Val Gln Ser Ile Pro Asn
50 55 60

Ile Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Leu Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 124
<211> LENGTH: 307
<212> TYPE: PRT
<213> ORGANISM: Artificial Sequence
<220> FEATURE:
<223> OTHER INFORMATION: UFV160416

<400> SEQUENCE: 124

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Gly Leu Ser
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly

```
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

```
<210> SEQ ID NO 125
<211> LENGTH: 307
<212> TYPE: PRT
<213> ORGANISM: Artificial Sequence
<220> FEATURE:
<223> OTHER INFORMATION: UFV160417

<400> SEQUENCE: 125

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Lys Pro Gly
    50                  55                  60

Asp Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
```

```
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 126
<211> LENGTH: 307
<212> TYPE: PRT
<213> ORGANISM: Artificial Sequence
<220> FEATURE:
<223> OTHER INFORMATION: UFV160418

<400> SEQUENCE: 126

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Asp Ala Pro
    50                  55                  60

Ile Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
```

```
            180                 185                 190

Gln Arg Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 127
<211> LENGTH: 306
<212> TYPE: PRT
<213> ORGANISM: Artificial Sequence
<220> FEATURE:
<223> OTHER INFORMATION: UFV160419

<400> SEQUENCE: 127

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Thr Pro Asn
    50                  55                  60

Lys Tyr Val Cys Gln Asn Thr Leu Lys Leu Ala Thr Gly Met Arg Asn
65                  70                  75                  80

Val Pro Glu Lys Gln Thr Arg Gly Leu Phe Gly Ala Ile Ala Gly Phe
                85                  90                  95

Ile Glu Asn Gly Trp Glu Gly Met Ile Asp Gly Trp Tyr Gly Phe Arg
            100                 105                 110

His Gln Asn Ser Glu Gly Thr Gly Gln Ala Ala Asp Leu Lys Ser Thr
        115                 120                 125

Gln Ala Ala Ile Asp Gln Ile Thr Asn Lys Val Asn Ser Val Ile Glu
    130                 135                 140

Lys Met Asn Glu Lys Ser His Gln Thr Glu Lys Glu Ser Ser Asn Ala
145                 150                 155                 160

Thr Gly Arg Met Lys Gln Ile Glu Asp Lys Ile Glu Glu Ile Glu Ser
                165                 170                 175

Lys Leu Trp Cys Tyr Asn Ala Glu Leu Leu Val Ala Leu Glu Asn Gln
            180                 185                 190

Arg Thr Ile Asp Leu Thr Asp Ser Glu Met Asn Lys Leu Phe Glu Lys
        195                 200                 205

Thr Arg Arg Gln Leu Arg Glu Asn Ala Glu Asp Met Gly Asn Gly Cys
    210                 215                 220

Phe Lys Ile Tyr His Lys Cys Asp Asn Ala Cys Ile Glu Ser Ile Arg
```

```
225                 230                 235                 240

Asn Gly Thr Tyr Asp His Asp Val Tyr Arg Asp Glu Ala Leu Asn Asn
                245                 250                 255

Arg Phe Gln Ile Lys Gly Val Glu Leu Lys Ser Gly Tyr Lys Asp Trp
            260                 265                 270

Ile Ala Ala Ala Asp Tyr Lys Asp Asp Asp Asp Lys Pro Gly Gly Gly
        275                 280                 285

Gly Ser Gly Gly Gly Gly Ser Gly Gly Gly Gly Ser His His His His
    290                 295                 300

His His
305


<210> SEQ ID NO 128
<211> LENGTH: 307
<212> TYPE: PRT
<213> ORGANISM: Artificial Sequence
<220> FEATURE:
<223> OTHER INFORMATION: UFV160420

<400> SEQUENCE: 128

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Thr Pro Asn
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
```

```
        275                 280                 285

Gly Gly Ser Gly Gly Gly Gly Ser Gly Gly Gly Gly Ser His His His
    290                 295                 300

His His His
305


<210> SEQ ID NO 129
<211> LENGTH: 307
<212> TYPE: PRT
<213> ORGANISM: Artificial Sequence
<220> FEATURE:
<223> OTHER INFORMATION: UFV161686

<400> SEQUENCE: 129

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Glu
145                 150                 155                 160

Val Glu Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 130
<211> LENGTH: 307
<212> TYPE: PRT
<213> ORGANISM: Artificial Sequence
<220> FEATURE:
<223> OTHER INFORMATION: UFV161722

<400> SEQUENCE: 130

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Gln
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305

<210> SEQ ID NO 131
<211> LENGTH: 307
<212> TYPE: PRT
<213> ORGANISM: Artificial Sequence
<220> FEATURE:
<223> OTHER INFORMATION: UFV161723

<400> SEQUENCE: 131

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Gln Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 132
<211> LENGTH: 307
<212> TYPE: PRT
<213> ORGANISM: Artificial Sequence
<220> FEATURE:
<223> OTHER INFORMATION: UFV161688

<400> SEQUENCE: 132

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45
```

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Pro Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305

<210> SEQ ID NO 133
<211> LENGTH: 307
<212> TYPE: PRT
<213> ORGANISM: Artificial Sequence
<220> FEATURE:
<223> OTHER INFORMATION: UFV161689

<400> SEQUENCE: 133

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Pro Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 134
<211> LENGTH: 307
<212> TYPE: PRT
<213> ORGANISM: Artificial Sequence
<220> FEATURE:
<223> OTHER INFORMATION: UFV161690

<400> SEQUENCE: 134

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Pro Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 135
<211> LENGTH: 307
<212> TYPE: PRT
<213> ORGANISM: Artificial Sequence
<220> FEATURE:
<223> OTHER INFORMATION: UFV161691

<400> SEQUENCE: 135

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Pro Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

```
Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 136
<211> LENGTH: 307
<212> TYPE: PRT
<213> ORGANISM: Artificial Sequence
<220> FEATURE:
<223> OTHER INFORMATION: UFV161692

<400> SEQUENCE: 136

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Pro Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240
```

```
Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 137
<211> LENGTH: 307
<212> TYPE: PRT
<213> ORGANISM: Artificial Sequence
<220> FEATURE:
<223> OTHER INFORMATION: UFV161693

<400> SEQUENCE: 137

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Pro Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285
```

Gly Gly Ser Gly Gly Gly Gly Ser Gly Gly Gly Gly Ser His His His
    290                 295                 300

His His His
305

<210> SEQ ID NO 138
<211> LENGTH: 307
<212> TYPE: PRT
<213> ORGANISM: Artificial Sequence
<220> FEATURE:
<223> OTHER INFORMATION: UFV161694

<400> SEQUENCE: 138

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Pro His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305

<210> SEQ ID NO 139
<211> LENGTH: 307

<212> TYPE: PRT
<213> ORGANISM: Artificial Sequence
<220> FEATURE:
<223> OTHER INFORMATION: UFV161695

<400> SEQUENCE: 139

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser Pro Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 140
<211> LENGTH: 307
<212> TYPE: PRT
<213> ORGANISM: Artificial Sequence
<220> FEATURE:
<223> OTHER INFORMATION: UFV161696

<400> SEQUENCE: 140

```
Met Lys Thr Ile Ile Ala Leu Ser Tyr Ile Phe Cys Leu Ala Leu Gly
1               5                   10                  15
```

```
Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Pro Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 141
<211> LENGTH: 307
<212> TYPE: PRT
<213> ORGANISM: Artificial Sequence
<220> FEATURE:
<223> OTHER INFORMATION: UFV161697

<400> SEQUENCE: 141

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60
```

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Pro Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 142
<211> LENGTH: 307
<212> TYPE: PRT
<213> ORGANISM: Artificial Sequence
<220> FEATURE:
<223> OTHER INFORMATION: UFV161698

<400> SEQUENCE: 142

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Pro Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 143
<211> LENGTH: 307
<212> TYPE: PRT
<213> ORGANISM: Artificial Sequence
<220> FEATURE:
<223> OTHER INFORMATION: UFV161699

<400> SEQUENCE: 143

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Pro Glu Ser Ser Asn
145 150 155 160

```
Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 144
<211> LENGTH: 307
<212> TYPE: PRT
<213> ORGANISM: Artificial Sequence
<220> FEATURE:
<223> OTHER INFORMATION: UFV161700

<400> SEQUENCE: 144

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Pro Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205
```

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305

<210> SEQ ID NO 145
<211> LENGTH: 307
<212> TYPE: PRT
<213> ORGANISM: Artificial Sequence
<220> FEATURE:
<223> OTHER INFORMATION: UFV161701

<400> SEQUENCE: 145

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Pro Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 146
<211> LENGTH: 307
<212> TYPE: PRT
<213> ORGANISM: Artificial Sequence
<220> FEATURE:
<223> OTHER INFORMATION: UFV161702

<400> SEQUENCE: 146

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Pro Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 147
<211> LENGTH: 307
<212> TYPE: PRT
<213> ORGANISM: Artificial Sequence
<220> FEATURE:
<223> OTHER INFORMATION: UFV161703

<400> SEQUENCE: 147

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Pro
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 148
<211> LENGTH: 307
<212> TYPE: PRT
<213> ORGANISM: Artificial Sequence

<220> FEATURE:
<223> OTHER INFORMATION: UFV161704

<400> SEQUENCE: 148

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Pro Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 149
<211> LENGTH: 307
<212> TYPE: PRT
<213> ORGANISM: Artificial Sequence
<220> FEATURE:
<223> OTHER INFORMATION: UFV161705

<400> SEQUENCE: 149

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly

```
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Pro Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 150
<211> LENGTH: 307
<212> TYPE: PRT
<213> ORGANISM: Artificial Sequence
<220> FEATURE:
<223> OTHER INFORMATION: UFV161706

<400> SEQUENCE: 150

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
```

```
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Pro Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 151
<211> LENGTH: 307
<212> TYPE: PRT
<213> ORGANISM: Artificial Sequence
<220> FEATURE:
<223> OTHER INFORMATION: UFV161707

<400> SEQUENCE: 151

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
```

```
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Glu Ser Ser Asn
145                 150                 155                 160

Ala Thr Gly Pro Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 152
<211> LENGTH: 307
<212> TYPE: PRT
<213> ORGANISM: Artificial Sequence
<220> FEATURE:
<223> OTHER INFORMATION: UFV161708

<400> SEQUENCE: 152

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Pro His Gln Thr Pro Lys Glu Ser Ser Asn
145                 150                 155                 160

Ala Thr Gly Arg Met Lys Gln Ile Glu Asp Lys Ile Glu Glu Ile Glu
```

165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 153
<211> LENGTH: 307
<212> TYPE: PRT
<213> ORGANISM: Artificial Sequence
<220> FEATURE:
<223> OTHER INFORMATION: UFV161709

<400> SEQUENCE: 153

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Pro His Gln Thr Glu Lys Pro Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly

```
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 154
<211> LENGTH: 307
<212> TYPE: PRT
<213> ORGANISM: Artificial Sequence
<220> FEATURE:
<223> OTHER INFORMATION: UFV161715

<400> SEQUENCE: 154

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser Asn Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
```

```
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 155
<211> LENGTH: 306
<212> TYPE: PRT
<213> ORGANISM: Artificial Sequence
<220> FEATURE:
<223> OTHER INFORMATION: UFV161721

<400> SEQUENCE: 155

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Ser Val Ile
    130                 135                 140

Glu Lys Met Asn Glu Lys Ser His Gln Thr Glu Lys Asn Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr His Asp Val Tyr Arg Asp Glu Ala Leu Asn Asn
                245                 250                 255

Arg Phe Gln Ile Lys Gly Val Glu Leu Lys Ser Gly Tyr Lys Asp Trp
            260                 265                 270

Ile Ala Ala Ala Asp Tyr Lys Asp Asp Asp Asp Lys Pro Gly Gly Gly
        275                 280                 285

Gly Ser Gly Gly Gly Gly Ser Gly Gly Gly Gly Ser His His His His
    290                 295                 300

His His
```

305

<210> SEQ ID NO 156
<211> LENGTH: 304
<212> TYPE: PRT
<213> ORGANISM: Artificial Sequence
<220> FEATURE:
<223> OTHER INFORMATION: UFV171187

<400> SEQUENCE: 156

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Lys Val Asn Arg Val Ile Glu Lys Met
130 135 140

Asn Glu Lys Ser His Gln Thr Glu Cys Glu Ser Ser Asn Ala Thr Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Glu Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Glu Leu Lys Ser Gly Tyr Lys Asp Trp Ile Ala
260 265 270

Ala Ala Asp Tyr Lys Asp Asp Asp Asp Lys Pro Gly Gly Gly Gly Ser
275 280 285

Gly Gly Gly Gly Ser Gly Gly Gly Gly Ser His His His His His His
290 295 300

<210> SEQ ID NO 157
<211> LENGTH: 304
<212> TYPE: PRT
<213> ORGANISM: Artificial Sequence
<220> FEATURE:
<223> OTHER INFORMATION: UFV171120

<400> SEQUENCE: 157

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Asn His Thr Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300
```

<210> SEQ ID NO 158
<211> LENGTH: 304
<212> TYPE: PRT
<213> ORGANISM: Artificial Sequence
<220> FEATURE:
<223> OTHER INFORMATION: UFV171121

<400> SEQUENCE: 158

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60
```

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Lys Val Asn Arg Val Ile Glu Lys Met
130 135 140

Asn Glu Lys Asn His Thr Thr Glu Cys Glu Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Glu Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Glu Leu Lys Ser Gly Tyr Lys Asp Trp Ile Ala
260 265 270

Ala Ala Asp Tyr Lys Asp Asp Asp Asp Lys Pro Gly Gly Gly Gly Ser
275 280 285

Gly Gly Gly Gly Ser Gly Gly Gly Gly Ser His His His His His His
290 295 300

<210> SEQ ID NO 159
<211> LENGTH: 304
<212> TYPE: PRT
<213> ORGANISM: Artificial Sequence
<220> FEATURE:
<223> OTHER INFORMATION: UFV170994

<400> SEQUENCE: 159

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

```
Ala Ile Asp Gln Ile Thr Asn Lys Val Asn Arg Val Ile Glu Lys Met
    130                 135                 140

Asn Glu Lys Ser Asn Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300


<210> SEQ ID NO 160
<211> LENGTH: 304
<212> TYPE: PRT
<213> ORGANISM: Artificial Sequence
<220> FEATURE:
<223> OTHER INFORMATION: UFV170995

<400> SEQUENCE: 160

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser Asn Gln Thr Glu Cys Glu Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190
```

```
Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300


<210> SEQ ID NO 161
<211> LENGTH: 294
<212> TYPE: PRT
<213> ORGANISM: Artificial Sequence
<220> FEATURE:
<223> OTHER INFORMATION: UFV180208

<400> SEQUENCE: 161

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Phe His Gln Thr Glu Lys Cys Phe Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln His Thr
            180                 185                 190

Ile Asp Leu Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255
```

```
Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 162
<211> LENGTH: 294
<212> TYPE: PRT
<213> ORGANISM: Artificial Sequence
<220> FEATURE:
<223> OTHER INFORMATION: UFV180217

<400> SEQUENCE: 162

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Phe Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln His Thr
            180                 185                 190

Ile Asp Leu Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290


<210> SEQ ID NO 163
<211> LENGTH: 281
```

<212> TYPE: PRT
<213> ORGANISM: Artificial Sequence
<220> FEATURE:
<223> OTHER INFORMATION: UFV170278

<400> SEQUENCE: 163

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg Trp Gln Asn Ser Glu Gly Thr Gly Gln Ala Ala Asp Leu Lys Ser
115 120 125

Thr Gln Ala Ala Ile Asp Gln Ile Thr Asn Lys Val Asn Arg Val Ile
130 135 140

Glu Lys Met Asn Glu Lys Ser His Gln Thr Glu Lys Cys Ser Ser Asn
145 150 155 160

Ala Thr Gly Arg Met Lys Cys Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Gly Ala Ala Glu Pro Glu Ala
275 280

<210> SEQ ID NO 164
<211> LENGTH: 281
<212> TYPE: PRT
<213> ORGANISM: Artificial Sequence
<220> FEATURE:
<223> OTHER INFORMATION: UFV170282

<400> SEQUENCE: 164

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

```
Gln Val Glu Val Thr Asn Ala Thr Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Arg Val Ile
    130                 135                 140

Glu Lys Met Asn Glu Lys Ser His Gln Thr Glu Lys Cys Ser Ser Asn
145                 150                 155                 160

Ala Thr Gly Arg Met Lys Cys Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Gly Ala Ala Glu Pro Glu Ala
        275                 280


<210> SEQ ID NO 165
<211> LENGTH: 307
<212> TYPE: PRT
<213> ORGANISM: Artificial Sequence
<220> FEATURE:
<223> OTHER INFORMATION: UFV160595

<400> SEQUENCE: 165

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125
```

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 166
<211> LENGTH: 307
<212> TYPE: PRT
<213> ORGANISM: Artificial Sequence
<220> FEATURE:
<223> OTHER INFORMATION: UFV161196

<400> SEQUENCE: 166

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Ile Glu Leu Val Gln Ser Gly Pro Gly
50 55 60

Ser Lys Gly Pro Lys Cys Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 167
<211> LENGTH: 307
<212> TYPE: PRT
<213> ORGANISM: Artificial Sequence
<220> FEATURE:
<223> OTHER INFORMATION: UFV161198

<400> SEQUENCE: 167

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Ile Glu Leu Val Gln Ser Gly Pro Gly
50 55 60

Ser Lys Cys Val Pro Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Cys Lys Leu Trp Ala Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 168
<211> LENGTH: 307
<212> TYPE: PRT
<213> ORGANISM: Artificial Sequence
<220> FEATURE:
<223> OTHER INFORMATION: UFV161169

<400> SEQUENCE: 168

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Cys Lys Thr Ile Thr Asp Asp
35 40 45

Gln Ile Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Val Asn Ser Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Cys
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 169
<211> LENGTH: 307
<212> TYPE: PRT
<213> ORGANISM: Artificial Sequence
<220> FEATURE:
<223> OTHER INFORMATION: UFV170062

<400> SEQUENCE: 169

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg Trp Gln Asn Ser Glu Gly Thr Gly Gln Ala Ala Asp Leu Lys Ser
115 120 125

Thr Gln Ala Ala Ile Asp Gln Ile Thr Asn Lys Val Asn Arg Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 170
<211> LENGTH: 307
<212> TYPE: PRT
<213> ORGANISM: Artificial Sequence
<220> FEATURE:
<223> OTHER INFORMATION: UFV170051

<400> SEQUENCE: 170

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg Trp Gln Asn Ser Glu Gly Thr Gly Gln Ala Ala Asp Leu Lys Ser
115 120 125

Thr Gln Ala Ala Ile Asp Gln Ile Thr Asn Lys Val Asn Arg Val Ile
130 135 140

Glu Lys Met Asn Glu Lys Ser His Gln Thr Glu Lys Cys Ser Ser Asn
145 150 155 160

Ala Thr Gly Arg Met Lys Cys Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 171
<211> LENGTH: 307
<212> TYPE: PRT
<213> ORGANISM: Artificial Sequence
<220> FEATURE:
<223> OTHER INFORMATION: UFV170428

<400> SEQUENCE: 171

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg Trp Gln Asn Ser Glu Gly Thr Gly Gln Ala Ala Asp Leu Lys Ser
115 120 125

Thr Gln Ala Ala Ile Asp Gln Ile Thr Asn Lys Val Asn Arg Val Ile
130 135 140

Glu Lys Met Asn Glu Lys Ser His Gln Thr Cys Lys Glu Ser Ser Asn
145 150 155 160

Ala Thr Gly Arg Met Lys Cys Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 172
<211> LENGTH: 307
<212> TYPE: PRT
<213> ORGANISM: Artificial Sequence
<220> FEATURE:
<223> OTHER INFORMATION: UFV170440

<400> SEQUENCE: 172

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp

```
        35                  40                  45

Gln Val Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg Trp Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Arg Val Ile
    130                 135                 140

Glu Lys Met Asn Glu Lys Ser His Gln Thr Glu Lys Cys Ser Ser Asn
145                 150                 155                 160

Ala Thr Gly Cys Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 173
<211> LENGTH: 271
<212> TYPE: PRT
<213> ORGANISM: Artificial Sequence
<220> FEATURE:
<223> OTHER INFORMATION: UFV171272

<400> SEQUENCE: 173

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
```

```
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile
            260                 265                 270


<210> SEQ ID NO 174
<211> LENGTH: 269
<212> TYPE: PRT
<213> ORGANISM: Artificial Sequence
<220> FEATURE:
<223> OTHER INFORMATION: UFV171273

<400> SEQUENCE: 174

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
```

```
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp
            260                 265
```

<210> SEQ ID NO 175
<211> LENGTH: 267
<212> TYPE: PRT
<213> ORGANISM: Artificial Sequence
<220> FEATURE:
<223> OTHER INFORMATION: UFV171274

<400> SEQUENCE: 175

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr
            260                 265
```

<210> SEQ ID NO 176
<211> LENGTH: 265
<212> TYPE: PRT
<213> ORGANISM: Artificial Sequence
<220> FEATURE:
<223> OTHER INFORMATION: UFV171275

<400> SEQUENCE: 176

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser
            260                 265
```

<210> SEQ ID NO 177
<211> LENGTH: 263
<212> TYPE: PRT
<213> ORGANISM: Artificial Sequence
<220> FEATURE:
<223> OTHER INFORMATION: UFV171276

<400> SEQUENCE: 177

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45
```

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Lys Val Asn Arg Val Ile Glu Lys Met
130 135 140

Asn Glu Lys Ser His Gln Thr Glu Cys Glu Ser Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Glu Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Glu Leu
260

<210> SEQ ID NO 178
<211> LENGTH: 261
<212> TYPE: PRT
<213> ORGANISM: Artificial Sequence
<220> FEATURE:
<223> OTHER INFORMATION: UFV171277

<400> SEQUENCE: 178

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Lys Val Asn Arg Val Ile Glu Lys Met
130 135 140

Asn Glu Lys Ser His Gln Thr Glu Cys Glu Ser Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Glu Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val
260

<210> SEQ ID NO 179
<211> LENGTH: 259
<212> TYPE: PRT
<213> ORGANISM: Artificial Sequence
<220> FEATURE:
<223> OTHER INFORMATION: UFV171278

<400> SEQUENCE: 179

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Lys Val Asn Arg Val Ile Glu Lys Met
130 135 140

Asn Glu Lys Ser His Gln Thr Glu Cys Glu Ser Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Glu Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

```
Thr Tyr Asp His Asp Val Tyr Arg Asp Glu Ala Leu Asn Asn Arg Phe
                245                 250                 255

Gln Ile Lys


<210> SEQ ID NO 180
<211> LENGTH: 257
<212> TYPE: PRT
<213> ORGANISM: Artificial Sequence
<220> FEATURE:
<223> OTHER INFORMATION: UFV171279

<400> SEQUENCE: 180

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln


<210> SEQ ID NO 181
<211> LENGTH: 255
<212> TYPE: PRT
<213> ORGANISM: Artificial Sequence
<220> FEATURE:
<223> OTHER INFORMATION: UFV171280

<400> SEQUENCE: 181

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
```

```
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Lys Val Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg
                245                 250                 255
```

<210> SEQ ID NO 182
<211> LENGTH: 307
<212> TYPE: PRT
<213> ORGANISM: Artificial Sequence
<220> FEATURE:
<223> OTHER INFORMATION: UFV161454

<400> SEQUENCE: 182

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Ile
```

```
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 183
<211> LENGTH: 307
<212> TYPE: PRT
<213> ORGANISM: Artificial Sequence
<220> FEATURE:
<223> OTHER INFORMATION: UFV161453

<400> SEQUENCE: 183

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Asn Lys Leu Asn Arg Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
```

180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305

<210> SEQ ID NO 184
<211> LENGTH: 307
<212> TYPE: PRT
<213> ORGANISM: Artificial Sequence
<220> FEATURE:
<223> OTHER INFORMATION: UFV161459

<400> SEQUENCE: 184

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Ala Lys Leu Asn Arg Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile

```
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305


<210> SEQ ID NO 185
<211> LENGTH: 307
<212> TYPE: PRT
<213> ORGANISM: Artificial Sequence
<220> FEATURE:
<223> OTHER INFORMATION: UFV161451

<400> SEQUENCE: 185

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Asn Lys Val Asn Arg Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
```

```
        275                 280                 285

Gly Gly Ser Gly Gly Gly Gly Ser Gly Gly Gly Gly Ser His His His
    290                 295                 300

His His His
305


<210> SEQ ID NO 186
<211> LENGTH: 307
<212> TYPE: PRT
<213> ORGANISM: Artificial Sequence
<220> FEATURE:
<223> OTHER INFORMATION: UFV161458

<400> SEQUENCE: 186

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Ala Lys Val Asn Arg Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 187
<211> LENGTH: 307
<212> TYPE: PRT
<213> ORGANISM: Artificial Sequence
<220> FEATURE:
<223> OTHER INFORMATION: UFV161450

<400> SEQUENCE: 187

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Ile Glu Leu Val Gln Ser Gly Pro Gly
50 55 60

Ser Lys Tyr Val Cys Gln Asn Thr Leu Lys Leu Ala Thr Gly Met Arg
65 70 75 80

Asn Val Pro Glu Lys Gln Thr Arg Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Thr Asn Lys Leu Asn Arg Val Ile
130 135 140

Glu Lys Met Asn Glu Lys Ser His Gln Thr Glu Lys Glu Ser Ser Asn
145 150 155 160

Ala Thr Gly Arg Met Lys Gln Ile Glu Asp Lys Ile Glu Glu Ile Glu
165 170 175

Ser Lys Leu Trp Cys Tyr Asn Ala Glu Leu Leu Val Ala Leu Glu Asn
180 185 190

Gln Arg Thr Ile Asp Tyr Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Ala Ala Ala Asp Tyr Lys Asp Asp Asp Asp Lys Pro Gly Gly
275 280 285

Gly Gly Ser Gly Gly Gly Gly Ser Gly Gly Gly Gly Ser His His His
290 295 300

His His His
305

<210> SEQ ID NO 188
<211> LENGTH: 307
<212> TYPE: PRT
<213> ORGANISM: Artificial Sequence
<220> FEATURE:
<223> OTHER INFORMATION: UFV161448

<400> SEQUENCE: 188

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Ile Glu Leu Val Gln Ser Gly Pro Gly
    50                  55                  60

Ser Lys Tyr Val Cys Gln Asn Thr Leu Lys Leu Ala Thr Gly Met Arg
65                  70                  75                  80

Asn Val Pro Glu Lys Gln Thr Arg Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Thr Asn Lys Val Asn Arg Val Ile
    130                 135                 140

Glu Lys Met Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln Arg Thr Ile Asp Tyr Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Ala Ala Ala Asp Tyr Lys Asp Asp Asp Asp Lys Pro Gly Gly
        275                 280                 285

Gly Gly Ser Gly Gly Gly Gly Ser Gly Gly Gly Gly Ser His His His
    290                 295                 300

His His His
305
```

<210> SEQ ID NO 189
<211> LENGTH: 304
<212> TYPE: PRT
<213> ORGANISM: Artificial Sequence
<220> FEATURE:
<223> OTHER INFORMATION: UFV171116

<400> SEQUENCE: 189

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45
```

```
Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Asn Gly Ile Leu Asn Arg Val Ile Glu Lys Met
    130                 135                 140

Asn Glu Lys Ser His Gln Thr Glu Cys Glu Ser Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Ala
            260                 265                 270

Ala Ala Asp Tyr Lys Asp Asp Asp Asp Lys Pro Gly Gly Gly Gly Ser
        275                 280                 285

Gly Gly Gly Gly Ser Gly Gly Gly Gly Ser His His His His His His
    290                 295                 300
```

<210> SEQ ID NO 190
<211> LENGTH: 294
<212> TYPE: PRT
<213> ORGANISM: Artificial Sequence
<220> FEATURE:
<223> OTHER INFORMATION: UFV172561

<400> SEQUENCE: 190

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110
```

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Met
130 135 140

Asn Glu Lys Ser Asn Gln Thr Glu Cys Glu Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Arg Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 191
<211> LENGTH: 294
<212> TYPE: PRT
<213> ORGANISM: Artificial Sequence
<220> FEATURE:
<223> OTHER INFORMATION: UFV172563

<400> SEQUENCE: 191

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Tyr Lys Ser Thr Gln Ala
115 120 125

Ala Ile Asp Gln Ile Thr Asn Ile Val Asn Arg Val Ile Glu Lys Met
130 135 140

Asn Glu Lys Ser Asn Gln Thr Glu Cys Glu Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Arg Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asp Asp Cys Ile Ala Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 192
<211> LENGTH: 294
<212> TYPE: PRT
<213> ORGANISM: Artificial Sequence
<220> FEATURE:
<223> OTHER INFORMATION: UFV172564

<400> SEQUENCE: 192

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Lys Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Tyr Lys Ser Thr Gln Ala
115 120 125

Ala Ile Asp Gln Ile Thr Asn Ile Val Asn Arg Val Ile Glu Lys Met
130 135 140

Asn Glu Lys Ser Asn Gln Thr Glu Cys Glu Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Arg Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asp Asp Cys Ile Ala Ser Ile Arg Asn Gly
225 230 235 240

```
Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

<210> SEQ ID NO 193
<211> LENGTH: 294
<212> TYPE: PRT
<213> ORGANISM: Artificial Sequence
<220> FEATURE:
<223> OTHER INFORMATION: UFV172571

<400> SEQUENCE: 193

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Lys Val Asn Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Tyr Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser Asn Gln Thr Glu Cys Glu Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Arg Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Asp Cys Ile Ala Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

<210> SEQ ID NO 194
<211> LENGTH: 294
<212> TYPE: PRT
<213> ORGANISM: Artificial Sequence
<220> FEATURE:
<223> OTHER INFORMATION: UFV172562

<400> SEQUENCE: 194

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Gly Ile Leu Asn Arg Val Ile Glu Lys Met
130 135 140

Asn Glu Lys Ser Asn Gln Thr Glu Cys Glu Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Arg Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 195
<211> LENGTH: 294
<212> TYPE: PRT
<213> ORGANISM: Artificial Sequence
<220> FEATURE:
<223> OTHER INFORMATION: UFV172588

<400> SEQUENCE: 195

Met Lys Thr Ile Ile Ala Leu Ser Tyr Ile Phe Cys Leu Ala Leu Gly
1 5 10 15

```
Gln Asp Leu Pro Gly Asn Asp Asn Ser Thr Ala Thr Leu Cys Leu Gly
            20                  25                  30

His His Ala Val Pro Asn Gly Thr Lys Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Tyr Lys Ser Thr Gln Ala
        115                 120                 125

Ala Ile Asp Gln Ile Thr Gly Ile Leu Asn Arg Val Ile Glu Lys Met
    130                 135                 140

Asn Glu Lys Ser Asn Gln Thr Glu Cys Glu Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Arg Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Asp Cys Ile Ala Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

```
<210> SEQ ID NO 196
<211> LENGTH: 294
<212> TYPE: PRT
<213> ORGANISM: Artificial Sequence
<220> FEATURE:
<223> OTHER INFORMATION: UFV172583

<400> SEQUENCE: 196

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Lys Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80
```

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Tyr Lys Ser Thr Gln Ala
115 120 125

Ala Ile Asp Gln Ile Thr Gly Ile Leu Asn Arg Val Ile Glu Lys Met
130 135 140

Asn Glu Lys Ser Asn Gln Thr Glu Cys Glu Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Arg Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asp Asp Cys Ile Ala Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val Ala Ala Ala Asp Tyr Lys Asp Asp Asp Asp Lys
260 265 270

Pro Gly Gly Gly Gly Ser Gly Gly Gly Gly Ser Gly Gly Gly Gly Ser
275 280 285

His His His His His His
290

<210> SEQ ID NO 197
<211> LENGTH: 294
<212> TYPE: PRT
<213> ORGANISM: Artificial Sequence
<220> FEATURE:
<223> OTHER INFORMATION: UFV172585

<400> SEQUENCE: 197

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Lys Val Asn Thr Ile Thr Glu Asp
35 40 45

Gln Val Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Tyr Lys Ser Thr Gln Ala
115 120 125

Ala Ile Asp Gln Ile Thr Gly Ile Leu Asn Arg Val Ile Glu Lys Met
130 135 140

```
Asn Glu Lys Ser Asn Gln Thr Glu Cys Glu Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Arg Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asp Asp Cys Ile Ala Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Ala Ala Ala Asp Tyr Lys Asp Asp Asp Asp Lys
            260                 265                 270

Pro Gly Gly Gly Gly Ser Gly Gly Gly Gly Ser Gly Gly Gly Gly Ser
        275                 280                 285

His His His His His His
    290
```

<210> SEQ ID NO 198
<211> LENGTH: 267
<212> TYPE: PRT
<213> ORGANISM: Artificial Sequence
<220> FEATURE:
<223> OTHER INFORMATION: UFV180642

<400> SEQUENCE: 198

```
Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Arg Tyr
    50                  55                  60

Val Cys His Ser Thr Leu Lys Leu Ala Thr Gly Met Arg Asn Val Pro
65                  70                  75                  80

Glu Lys Gln Thr Gln Gly Ile Phe Gly Ala Ile Ala Gly Phe Ile Glu
                85                  90                  95

Asn Gly Trp Glu Gly Met Val Asp Gly Trp Tyr Gly Phe Arg Trp Gln
            100                 105                 110

Asn Ser Glu Gly Arg Gly Gln Ala Ala Asp Leu Lys Ser Thr Gln Ala
        115                 120                 125

Ala Ile Asp Gln Ile Thr Asn Lys Val Asn Arg Leu Ile Gly Lys Met
    130                 135                 140

Asn Glu Lys Phe His Gln Ile Glu Lys Cys Phe Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln His Thr
            180                 185                 190

Ile Asp Leu Thr Asp Ser Glu Met Asn Lys Leu Phe Glu Lys Thr Lys
        195                 200                 205
```

```
Lys Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Glu
225                 230                 235                 240

Thr Tyr Asp His Asn Val Tyr Arg Asp Glu Ala Leu Asn Asn Arg Phe
                245                 250                 255

Gln Ile Lys Gly Val His His His His His His
            260                 265


<210> SEQ ID NO 199
<211> LENGTH: 267
<212> TYPE: PRT
<213> ORGANISM: Artificial Sequence
<220> FEATURE:
<223> OTHER INFORMATION: UFV180645

<400> SEQUENCE: 199

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Arg Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Ile Phe Gly Ala Ile Ala Gly Phe Ile Glu
                85                  90                  95

Asn Gly Trp Glu Gly Met Val Asp Gly Trp Tyr Gly Phe Arg Trp Gln
            100                 105                 110

Asn Ser Glu Gly Ile Gly Gln Ala Ala Asp Leu Lys Ser Thr Gln Ala
        115                 120                 125

Ala Ile Asn Gln Ile Thr Asn Lys Val Asn Arg Leu Ile Gly Lys Met
    130                 135                 140

Asn Glu Lys Phe His Gln Ile Glu Lys Cys Phe Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Glu Asn Gln His Thr
            180                 185                 190

Ile Asp Leu Thr Asp Ser Glu Met Asn Lys Leu Phe Glu Arg Thr Lys
        195                 200                 205

Lys Gln Leu Arg Glu Asn Ala Glu Asp Met Gly Asn Gly Cys Phe Lys
    210                 215                 220

Ile Tyr His Lys Cys Asp Asn Ala Cys Ile Gly Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val His His His His His His
            260                 265


<210> SEQ ID NO 200
<211> LENGTH: 267
<212> TYPE: PRT
<213> ORGANISM: Artificial Sequence
```

<220> FEATURE:
<223> OTHER INFORMATION: UFV180647

<400> SEQUENCE: 200

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro
65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Lys Val Asn Arg Val Ile Glu Lys Met
130 135 140

Asn Glu Lys Phe His Gln Ile Glu Lys Cys Phe Ser Asn Ala Thr Gly
145 150 155 160

Arg Met Lys Cys Ile Glu Asp Lys Ile Glu Glu Ile Glu Ser Lys Leu
165 170 175

Trp Cys Tyr Asn Ala Glu Leu Leu Val Ala Leu Glu Asn Gln His Thr
180 185 190

Ile Asp Leu Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val His His His His His His
260 265

<210> SEQ ID NO 201
<211> LENGTH: 267
<212> TYPE: PRT
<213> ORGANISM: Artificial Sequence
<220> FEATURE:
<223> OTHER INFORMATION: UFV181106

<400> SEQUENCE: 201

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Lys Tyr
50 55 60

Val Cys Gln Asn Thr Leu Lys Leu Ala Thr Gly Met Arg Asn Val Pro 65 70 75 80

Glu Lys Gln Thr Gln Gly Leu Phe Gly Ala Ile Ala Gly Phe Ile Glu
85 90 95

Asn Gly Trp Glu Gly Met Ile Asp Gly Trp Tyr Gly Phe Arg Trp Gln
100 105 110

Asn Ser Glu Gly Thr Gly Gln Ala Ala Asp Leu Lys Ser Thr Gln Ala
115 120 125

Ala Ile Asp Gln Ile Thr Asn Ile Val Asn Arg Val Ile Glu Lys Met
130 135 140

Asn Glu Lys Ser Asn Gln Thr Glu Lys Cys Pro Ser Asn Ala Thr Gly
145 150 155 160

Pro Met Lys Cys Ile Glu Asp Lys Ile Glu Glu Ile Glu Ser Lys Leu
165 170 175

Trp Cys Tyr Asn Ala Glu Leu Leu Val Ala Leu Ile Asn Gln Asn Thr
180 185 190

Ile Asp Tyr Thr Asp Ser Glu Met Asn Lys Leu Phe Glu Lys Thr Arg
195 200 205

Arg Gln Leu Arg Glu Asn Ala Glu Asp Met Gly Asn Gly Cys Phe Lys
210 215 220

Ile Tyr His Lys Cys Asp Asn Ala Cys Ile Glu Ser Ile Arg Asn Gly
225 230 235 240

Thr Tyr Asp His Asp Val Tyr Arg Asp Glu Ala Leu Asn Asn Arg Phe
245 250 255

Gln Ile Lys Gly Val His His His His His His
260 265

<210> SEQ ID NO 202
<211> LENGTH: 267
<212> TYPE: PRT
<213> ORGANISM: Artificial Sequence
<220> FEATURE:
<223> OTHER INFORMATION: UFV181107

<400> SEQUENCE: 202

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Gln Ile Glu Val Thr Asn Ala Thr Glu Leu Val Gln Ser Ser Arg Tyr
50 55 60

Val Cys Gln Asn Thr Leu Lys Leu Ala Thr Gly Met Arg Asn Val Pro
65 70 75 80

Glu Lys Gln Thr Gln Gly Ile Phe Gly Ala Ile Ala Gly Phe Ile Glu
85 90 95

Asn Gly Trp Glu Gly Met Val Asp Gly Trp Tyr Gly Phe Arg Trp Gln
100 105 110

Asn Ser Glu Gly Ile Gly Gln Ala Ala Asp Leu Lys Ser Thr Gln Ala
115 120 125

Ala Ile Asn Gln Ile Thr Asn Ile Val Asn Arg Leu Ile Gly Lys Met
130 135 140

Asn Glu Lys Ser Asn Gln Thr Glu Lys Cys Pro Ser Asn Ala Thr Gly
145 150 155 160

Pro Met Lys Cys Ile Glu Asp Lys Ile Glu Glu Ile Glu Ser Lys Leu

```
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Arg Thr Lys
        195                 200                 205

Lys Gln Leu Arg Glu Asn Ala Glu Asp Met Gly Asn Gly Cys Phe Lys
    210                 215                 220

Ile Tyr His Lys Cys Asp Asn Ala Cys Ile Gly Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val His His His His His His
            260                 265


<210> SEQ ID NO 203
<211> LENGTH: 267
<212> TYPE: PRT
<213> ORGANISM: Artificial Sequence
<220> FEATURE:
<223> OTHER INFORMATION: UFV181109

<400> SEQUENCE: 203

Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Arg Tyr
    50                  55                  60

Val Cys His Ser Thr Leu Lys Leu Ala Thr Gly Met Arg Asn Val Pro
65                  70                  75                  80

Glu Lys Gln Thr Gln Gly Ile Phe Gly Ala Ile Ala Gly Phe Ile Glu
                85                  90                  95

Asn Gly Trp Glu Gly Met Val Asp Gly Trp Tyr Gly Phe Arg Trp Gln
            100                 105                 110

Asn Ser Glu Gly Arg Gly Gln Ala Ala Asp Leu Lys Ser Thr Gln Ala
        115                 120                 125

Ala Ile Asp Gln Ile Thr Asn Ile Val Asn Arg Leu Ile Gly Lys Met
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Lys
        195                 200                 205

Lys Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Glu
225                 230                 235                 240

Thr Tyr Asp His Asn Val Tyr Arg Asp Glu Ala Leu Asn Asn Arg Phe
                245                 250                 255

Gln Ile Lys Gly Val His His His His His His
```

```
            260                 265


<210> SEQ ID NO 204
<211> LENGTH: 267
<212> TYPE: PRT
<213> ORGANISM: Artificial Sequence
<220> FEATURE:
<223> OTHER INFORMATION: UFV181117

<400> SEQUENCE: 204

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val His His His His His His
            260                 265


<210> SEQ ID NO 205
<211> LENGTH: 267
<212> TYPE: PRT
<213> ORGANISM: Artificial Sequence
<220> FEATURE:
<223> OTHER INFORMATION: UFV181118

<400> SEQUENCE: 205

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30
```

```
His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Arg Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Ile Phe Gly Ala Ile Ala Gly Phe Ile Glu
                85                  90                  95

Asn Gly Trp Glu Gly Met Val Asp Gly Trp Tyr Gly Phe Arg Trp Gln
            100                 105                 110

Asn Ser Glu Gly Ile Gly Gln Ala Ala Asp Leu Lys Ser Thr Gln Ala
        115                 120                 125

Ala Ile Asn Gln Ile Thr Asn Ile Val Asn Arg Leu Ile Gly Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Arg Thr Lys
        195                 200                 205

Lys Gln Leu Arg Glu Asn Ala Glu Asp Met Gly Asn Gly Cys Phe Lys
    210                 215                 220

Ile Tyr His Lys Cys Asp Asn Ala Cys Ile Gly Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val His His His His His His
            260                 265
```

<210> SEQ ID NO 206
<211> LENGTH: 267
<212> TYPE: PRT
<213> ORGANISM: Artificial Sequence
<220> FEATURE:
<223> OTHER INFORMATION: UFV181120

<400> SEQUENCE: 206

```
Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Arg Tyr
    50                  55                  60

Val Cys His Ser Thr Leu Lys Leu Ala Thr Gly Met Arg Asn Val Pro
65                  70                  75                  80

Glu Lys Gln Thr Gln Gly Ile Phe Gly Ala Ile Ala Gly Phe Ile Glu
                85                  90                  95

Asn Gly Trp Glu Gly Met Val Asp Gly Trp Tyr Gly Phe Arg Trp Gln
            100                 105                 110

Asn Ser Glu Gly Arg Gly Gln Ala Ala Asp Leu Lys Ser Thr Gln Ala
        115                 120                 125
```

```
Ala Ile Asp Gln Ile Thr Asn Ile Val Asn Arg Leu Ile Gly Lys Met
    130                 135                 140

Asn Glu Lys Ser His Gln Thr Glu Lys Cys Ser Ser Asn Ala Thr Gly
145                 150                 155                 160

Arg Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Lys
        195                 200                 205

Lys Gln Leu Arg Glu Asn Ala Glu Asp Met Gly Asn Gly Cys Phe Lys
    210                 215                 220

Ile Tyr His Lys Cys Asp Asn Ala Cys Ile Glu Ser Ile Arg Asn Glu
225                 230                 235                 240

Thr Tyr Asp His Asn Val Tyr Arg Asp Glu Ala Leu Asn Asn Arg Phe
                245                 250                 255

Gln Ile Lys Gly Val His His His His His His
            260                 265


<210> SEQ ID NO 207
<211> LENGTH: 306
<212> TYPE: PRT
<213> ORGANISM: Artificial Sequence
<220> FEATURE:
<223> OTHER INFORMATION: UFV180480 (UFV180088 + native trans-membrane
      (TM) domain)

<400> SEQUENCE: 207

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Glu Asp
        35                  40                  45

Gln Val Glu Val Thr Asn Ala Thr Glu Leu Val Gln Ser Ser Lys Tyr
    50                  55                  60

Val Cys Gln Asn Thr Leu Lys Leu Ala Thr Gly Met Arg Asn Val Pro
65                  70                  75                  80

Glu Lys Gln Thr Gln Gly Leu Phe Gly Ala Ile Ala Gly Phe Ile Glu
                85                  90                  95

Asn Gly Trp Glu Gly Met Ile Asp Gly Trp Tyr Gly Phe Arg Trp Gln
            100                 105                 110

Asn Ser Glu Gly Thr Gly Gln Ala Ala Asp Leu Lys Ser Thr Gln Ala
        115                 120                 125

Ala Ile Asp Gln Ile Thr Asn Ile Val Asn Arg Val Ile Glu Lys Met
    130                 135                 140

Asn Glu Lys Ser Asn Gln Thr Glu Lys Cys Pro Ser Asn Ala Thr Gly
145                 150                 155                 160

Pro Met Lys Cys Ile Glu Asp Lys Ile Glu Glu Ile Glu Ser Lys Leu
                165                 170                 175

Trp Cys Tyr Asn Ala Glu Leu Leu Val Ala Leu Ile Asn Gln Asn Thr
            180                 185                 190

Ile Asp Tyr Thr Asp Ser Glu Met Asn Lys Leu Phe Glu Lys Thr Arg
        195                 200                 205

Arg Gln Leu Arg Glu Asn Ala Glu Asp Met Gly Asn Gly Cys Phe Lys
    210                 215                 220
```

```
Ile Tyr His Lys Cys Asp Asn Ala Cys Ile Glu Ser Ile Arg Asn Gly
225                 230                 235                 240

Thr Tyr Asp His Asp Val Tyr Arg Asp Glu Ala Leu Asn Asn Arg Phe
                245                 250                 255

Gln Ile Lys Gly Val Glu Leu Lys Ser Gly Tyr Lys Asp Trp Ile Leu
            260                 265                 270

Trp Ile Ser Phe Ala Ile Ser Cys Phe Leu Leu Cys Val Val Leu Leu
        275                 280                 285

Gly Phe Ile Met Trp Ala Cys Gln Arg Gly Asn Ile Arg Cys Asn Ile
    290                 295                 300

Cys Ile
305
```

<210> SEQ ID NO 208
<211> LENGTH: 801
<212> TYPE: DNA
<213> ORGANISM: Artificial Sequence
<220> FEATURE:
<223> OTHER INFORMATION: nucleotide sequence encoding UFV180088

<400> SEQUENCE: 208

```
atgaaaacca ttatcgcact gagttacatc ttctgcctgg ctctgggaca ggatctgcct     60

gggaacgaca acagcacagc aacactgtgc ctgggacacc atgctgtgcc caacgggacc    120

ctggtcaaga ccatcacaga ggatcaggtg gaagtgacta atgcaaccga actggtccag    180

agctccaagt acgtgtgcca gaacaccctg aaactggcca caggcatgag aaatgtccct    240

gagaagcaga cccaggggct gttcggcgct atcgcaggct tcatcgagaa cggatgggaa    300

gggatgatcg acggctggta tggattccgg tggcagaatt ccgagggaac agggcaggcc    360

gctgacctga agtctactca ggcagccatc gatcagatta ccaacatcgt gaatcgcgtc    420

atcgagaaga tgaacgaaaa aagcaatcag acagagaagt gcccctccaa tgccactggc    480

cccatgaagt gtattgagga taagatcgag gaaatcgaaa gtaaactgtg gtgctacaac    540

gccgagctgc tggtggctct gatcaatcag aatacaatcg actatactga ttcagagatg    600

aacaagctgt tcgaaaaaac taggagacag ctgcgagaga acgcagaaga catgggcaat    660

ggatgtttta agatctacca caaatgcgat aacgcctgta tcgagtctat taggaatggc    720

acatacgacc atgacgtgta ccgggacgaa gcactgaaca atcgctttca gatcaagggg    780

gtggaaccag aggcataata a                                              801
```

<210> SEQ ID NO 209
<211> LENGTH: 924
<212> TYPE: DNA
<213> ORGANISM: Artificial Sequence
<220> FEATURE:
<223> OTHER INFORMATION: nucleotide sequence encoding UFV180480
(UFV180088 + TM domain)

<400> SEQUENCE: 209

```
atgaagacca tcatcgccct gtcttacatc ttctgcctgg ccctgggaca ggacctgcca     60

ggcaacgata atagcaccgc caccctgtgc ctgggacacc acgcagtgcc caacggcacc    120

ctggtgaaga ccatcacaga ggaccaggtg gaggtgacca atgccacaga gctggtgcag    180

agctccaagt acgtgtgcca gaacaccctg aagctggcca caggcatgag aaatgtgccc    240

gagaagcaga cccagggcct gttcggagcc atcgccggct ttatcgagaa cggctgggag    300

ggcatgatcg atggctggta tggctttcgg tggcagaata gcgagggaac aggacaggca    360
```

```
gcagacctga agtccaccca ggcagccatc gatcagatca caaacatcgt gaatagagtg    420

atcgagaaga tgaacgagaa gtccaatcag accgagaagt gcccctctaa cgccacaggc    480

cctatgaagt gtatcgagga caagatcgag gagatcgagt ccaagctgtg gtgctacaac    540

gccgagctgc tggtggccct gatcaaccag aataccatcg actatacaga ttctgagatg    600

aataagctgt tcgagaagac ccggagacag ctgagggaga acgccgagga catgggcaat    660

ggctgtttta agatctacca caagtgcgat aacgcctgta tcgagagcat ccgcaatggc    720

acatacgacc acgacgtgta ccgggacgag gccctgaaca atagattcca gatcaagggc    780

gtggagctga agtccggcta taaggattgg atcctgtgga tctctttcgc catcagctgc    840

tttctgctgt gcgtggtgct gctgggcttt atcatgtggg cctgtcagag gggcaacatc    900

cgctgcaata tctgtatctg ataa                                           924
```

```
<210> SEQ ID NO 210
<211> LENGTH: 245
<212> TYPE: PRT
<213> ORGANISM: Artificial Sequence
<220> FEATURE:
<223> OTHER INFORMATION: minimal sequence of UFV180088

<400> SEQUENCE: 210

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Glu Asp
            20                  25                  30

Gln Val Glu Val Thr Asn Ala Thr Glu Leu Val Gln Ser Ser Lys Tyr
        35                  40                  45

Val Cys Gln Asn Thr Leu Lys Leu Ala Thr Gly Met Arg Asn Val Pro
    50                  55                  60

Glu Lys Gln Thr Gln Gly Leu Phe Gly Ala Ile Ala Gly Phe Ile Glu
65                  70                  75                  80

Asn Gly Trp Glu Gly Met Ile Asp Gly Trp Tyr Gly Phe Arg Trp Gln
                85                  90                  95

Asn Ser Glu Gly Thr Gly Gln Ala Ala Asp Tyr Lys Ser Thr Gln Ala
            100                 105                 110

Ala Ile Asp Gln Ile Thr Asn Ile Val Asn Arg Val Ile Glu Lys Met
        115                 120                 125

Asn Glu Lys Ser Asn Gln Thr Glu Lys Cys Pro Ser Asn Ala Thr Gly
    130                 135                 140

Pro Met Lys Cys Ile Glu Asp Lys Ile Glu Glu Ile Glu Ser Lys Leu
145                 150                 155                 160

Trp Cys Tyr Asn Ala Glu Leu Leu Val Ala Leu Ile Asn Gln Asn Thr
                165                 170                 175

Ile Asp Tyr Thr Asp Ser Glu Met Asn Lys Leu Phe Glu Lys Thr Arg
            180                 185                 190

Arg Gln Leu Arg Glu Asn Ala Glu Asp Met Gly Asn Gly Cys Phe Lys
        195                 200                 205

Ile Tyr His Lys Cys Asp Asp Asp Cys Ile Ala Ser Ile Arg Asn Gly
    210                 215                 220

Thr Tyr Asp His Asp Val Tyr Arg Asp Glu Ala Leu Asn Asn Arg Phe
225                 230                 235                 240

Gln Ile Lys Gly Val
                245
```

<210> SEQ ID NO 211
<211> LENGTH: 245
<212> TYPE: PRT
<213> ORGANISM: Artificial Sequence
<220> FEATURE:
<223> OTHER INFORMATION: minimal sequence of UFV180089

<400> SEQUENCE: 211

```
Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Glu Asp
            20                  25                  30

Gln Val Glu Val Thr Asn Ala Thr Glu Leu Val Gln Ser Ser Lys Tyr
        35                  40                  45

Val Cys Gln Asn Thr Leu Lys Leu Ala Thr Gly Met Arg Asn Val Pro
    50                  55                  60

Glu Lys Gln Thr Gln Gly Leu Phe Gly Ala Ile Ala Gly Phe Ile Glu
65                  70                  75                  80

Asn Gly Trp Glu Gly Met Ile Asp Gly Trp Tyr Gly Phe Arg Trp Gln
                85                  90                  95

Asn Ser Glu Gly Thr Gly Gln Ala Ala Asp Tyr Lys Ser Thr Gln Ala
            100                 105                 110

Ala Ile Asp Gln Ile Thr Asn Ile Val Asn Arg Val Ile Glu Lys Met
        115                 120                 125

Asn Glu Lys Ser Asn Gln Thr Glu Lys Cys Pro Ser Asn Ala Thr Gly
    130                 135                 140

Pro Met Lys Cys Ile Glu Asp Lys Ile Glu Glu Ile Glu Ser Lys Leu
145                 150                 155                 160

Trp Cys Tyr Asn Ala Glu Leu Leu Val Ala Leu Ile Asn Gln Asn Thr
                165                 170                 175

Ile Asp Tyr Thr Asp Ser Glu Met Asn Lys Leu Phe Glu Lys Thr Arg
            180                 185                 190

Arg Gln Leu Arg Glu Asn Ala Glu Asp Met Gly Asn Gly Cys Phe Lys
        195                 200                 205

Ile Tyr His Lys Cys Asp Asp Asp Cys Ile Ala Ser Ile Arg Asn Gly
    210                 215                 220

Thr Tyr Asp His Asp Val Tyr Arg Asp Glu Ala Leu Asn Asn Arg Phe
225                 230                 235                 240

Gln Ile Lys Gly Val
                245
```

<210> SEQ ID NO 212
<211> LENGTH: 245
<212> TYPE: PRT
<213> ORGANISM: Artificial Sequence
<220> FEATURE:
<223> OTHER INFORMATION: minimal sequence of UFV180090

<400> SEQUENCE: 212

```
Gln Asp Leu Pro Gly Asn Asp Asn Ser Thr Ala Thr Leu Cys Leu Gly
1               5                   10                  15

His His Ala Val Pro Asn Gly Thr Lys Val Lys Thr Ile Thr Glu Asp
            20                  25                  30

Gln Val Glu Val Thr Asn Ala Thr Glu Leu Val Gln Ser Ser Lys Tyr
        35                  40                  45

Val Cys Gln Asn Thr Leu Lys Leu Ala Thr Gly Met Arg Asn Val Pro
    50                  55                  60
```

-continued

```
Glu Lys Gln Thr Gln Gly Leu Phe Gly Ala Ile Ala Gly Phe Ile Glu
65                  70                  75                  80

Asn Gly Trp Glu Gly Met Ile Asp Gly Trp Tyr Gly Phe Arg Trp Gln
                85                  90                  95

Asn Ser Glu Gly Thr Gly Gln Ala Ala Asp Tyr Lys Ser Thr Gln Ala
            100                 105                 110

Ala Ile Asp Gln Ile Thr Gly Ile Leu Asn Arg Val Ile Glu Lys Met
        115                 120                 125

Asn Glu Lys Ser Asn Gln Thr Glu Lys Cys Pro Ser Asn Ala Thr Gly
    130                 135                 140

Pro Met Lys Cys Ile Glu Asp Lys Ile Glu Glu Ile Glu Ser Lys Leu
145                 150                 155                 160

Trp Cys Tyr Asn Ala Glu Leu Leu Val Ala Leu Ile Asn Gln Asn Thr
                165                 170                 175

Ile Asp Tyr Thr Asp Ser Glu Met Asn Lys Leu Phe Glu Lys Thr Arg
            180                 185                 190

Arg Gln Leu Arg Glu Asn Ala Glu Asp Met Gly Asn Gly Cys Phe Lys
        195                 200                 205

Ile Tyr His Lys Cys Asp Asn Asp Cys Ile Ala Ser Ile Arg Asn Gly
    210                 215                 220

Thr Tyr Asp His Asp Val Tyr Arg Asp Glu Ala Leu Asn Asn Arg Phe
225                 230                 235                 240

Gln Ile Lys Gly Val
                245
```

INFLUENZA VIRUS VACCINES AND USES THEREOF

CROSS-REFERENCE TO RELATED APPLICATIONS

This application is a Section 371 of International Application No. PCT/EP2020/074539 filed Sep. 3, 2020, which was published in the English language Mar. 11, 2021, under International Publication No. WO 2021/043869 A1, which claims priority under 35 U.S.C. § 119(b) to U.S. Patent Application No. 62/896,244 filed Sep. 5, 2019, the disclosures of which are incorporated herein by reference in their entireties.

This invention was made, at least in part, with Government support under Agreement HHSO100201700018C, awarded by HHS. The Government has certain rights in the invention.

REFERENCE TO SEQUENCE LISTING SUBMITTED ELECTRONICALLY

This application contains a sequence listing, which is submitted electronically via EFS-Web as an ASCII formatted sequence listing with a file name of "CRU6017WOPCT1_ST25" creation date of Sep. 3, 2020 and having a size of 496 KB. The sequence listing submitted via EFS-Web is part of the specification and is herein incorporated by reference in its entirety.

INTRODUCTION

The invention relates to the field of medicine. Provided herein are influenza A hemagglutinin (HA) stem domain polypeptides, nucleic acids encoding said polypeptides, pharmaceutical compositions comprising the same, and methods of their use.

BACKGROUND

Influenza viruses are major human pathogens, causing a respiratory disease (commonly referred to as "influenza" or "the flu") that ranges in severity from sub-clinical infection to primary viral pneumonia which can result in death. The clinical effects of infection vary with the virulence of the influenza strain and the exposure, history, age, and immune status of the host. Every year it is estimated that approximately 1 billion people worldwide undergo infection with influenza virus, leading to severe illness in 3-5 million cases and an estimated 300,000 to 500,000 of influenza related deaths. The bulk of these infections can be attributed to influenza A viruses carrying H1 or H3 hemagglutinin subtypes, with a smaller contribution from Influenza B viruses, and therefore representatives of these are typically included in the seasonal vaccine. The current immunization practice relies on early identification of circulating influenza viruses to allow for timely production of an effective seasonal influenza vaccine. Apart from the inherent difficulties in predicting the strains that will be dominant during the next season, antiviral resistance and immune escape also play a role in failure of current vaccines to prevent morbidity and mortality. In addition, the possibility of a pandemic caused by a highly virulent viral strain originating from animal reservoirs and reassorted to increase human to human spread, still poses a significant and realistic threat to global health.

Influenza viruses are enveloped RNA viruses that belong to the family of Orthomyxoviridae. Their genomes consist of eight single-stranded RNA segments that code for 11 different proteins, one nucleoprotein (NP), three polymerase proteins (PA, PB1, and PB2), two matrix proteins (M1 and M2), three non-structural proteins (NS1, NS2, and PB1-F2), and two external glycoproteins: hemagglutinin (HA) and neuraminidase (NA).

Influenza A viruses are widely distributed in nature and can infect a variety of birds and mammals. The viruses are classified based on differences in antigenic structure of the HA and NA proteins, with their different combinations representing unique virus subtypes that are further classified into specific influenza virus strains. Although all known subtypes can be found in birds, currently circulating human influenza A subtypes are H1N1 and H3N2. Phylogenetic analysis of influenza A viruses has demonstrated a subdivision of hemagglutinins into two main, so-called phylogenetic groups: inter alia the H1, H2, H5 and H9 subtypes in phylogenetic group 1 (the group 1 viruses) and inter alia the H3, H4 and H7 subtypes in phylogenetic group 2 (group 2 viruses).

The influenza type B virus strains are strictly human. The antigenic variation in HA within the influenza type B virus strains is smaller than those observed within the type A strains. Two genetically and antigenically distinct lineages of influenza B virus are circulating in humans, as represented by the B/Yamagata/16/88 (also referred to as B/Yamagata) and B/Victoria/2/87 (B/Victoria) lineages. Although the spectrum of disease caused by influenza B viruses is generally milder than that caused by influenza A viruses, severe illness requiring hospitalization is still frequently observed with influenza B infection.

It is known that antibodies that neutralize the influenza virus are primarily directed against hemagglutinin (HA). Hemagglutinin or HA is a trimeric glycoprotein that is anchored in the viral membrane and has a dual function: it is responsible for binding to the cell surface receptor sialic acid and, after uptake, it mediates the fusion of viral and endosomal membrane leading to the release of viral RNA into the cytosol of the target cell. HA comprises a large head domain and a smaller stem domain. The stem domain is anchored in the viral membrane via a C-terminal transmembrane domain sequence. The protein is post-translationally cleaved to yield two HA polypeptides, HA1 and HA2 (the full sequence is referred to as HA0) (FIG. 1A, 1B). The membrane distal head domain is mainly derived from HA1 and the membrane proximal stem domain primarily from HA2. Cleavage of the HA precursor molecule HA0 is required to activate virus infectivity, and the distribution of activating proteases in the host is one of the determinants of pathogenicity of the influenza virus. The HAs of mammalian and nonpathogenic avian viruses are cleaved extracellularly, which limits their spread in hosts to tissues where the appropriate proteases are encountered. On the other hand, the HAs of pathogenic viruses are cleaved intracellularly by ubiquitously occurring proteases and therefore have the capacity to infect various cell types and cause systemic infections.

The reason that the seasonal influenza vaccine must be updated every year is the large variability of the virus. In the HA protein this variation is particularly manifested in the head domain where antigenic drift and shift have resulted in large numbers of different variants. Since this is also the area that is immunodominant, most neutralizing antibodies are directed against this domain and those antibodies act by interfering with receptor binding. The combination of immunodominance and large variation of the head domain explains why infection with one particular strain does not lead to immunity to other strains: the antibodies elicited by the first infection only recognize a limited number of strains closely related to the virus of the primary infection.

Recently, influenza hemagglutinin stem polypeptides, lacking the complete influenza hemagglutinin globular head domain or a substantial part of it, have been described and have been used to generate an immune response to one or more conserved epitopes of the stem domain polypeptide. It is believed that epitopes of the stem polypeptide are less immunogenic than the highly immunogenic regions of a globular head domain, and that the absence of a globular head domain in the stem polypeptide might allow an immune response against one or more epitopes of the stem polypeptide to develop (Steel et al., 2010). Steel et al. thus created an influenza HA stem polypeptide by deleting amino acid residue 53 to 276 from the HA1 domain of the A/Puerto Rico/8/1934 (H1N1) and A/Hong Kong/1/1968 (H3N2) strains and by replacing the deleted sequence with a short flexible linking sequence: GGGG. Vaccination of mice with the H3 HK68 construct did not elicit antisera that were cross-reactive with group 1 HAs. In addition, as explained in WO2013/079473, the stem polypeptides were unstable and did not adopt the correct conformation as proven by the lack of binding of antibodies that were previously shown to bind to conserved epitopes in the full-length wild type HA stem region.

Bommakanti et al. (2010) described an HA2 based polypeptide comprising amino acid residues 330-501 (HA2), a 7-amino acid linker (GSAGSAG), amino acid residues 16-55 of HA1, a 6-amino acid linker GSAGSA, followed by residues 290-321 of HA1, with the mutations V297T, 1300E, Y302T and C305T in HA1. The design was based on the sequence of H3 HA (A/Hong Kong/1/1968). The polypeptide did only provide cross-protection against another influenza virus strain within the H3 subtype (A/Phil/2/82 but not against an H1 subtype (A/PR/8/34). In a more recent paper by Bommakanti et al. (2012), a stem polypeptide based on HA from H1N1 A/Puerto Rico/8/1934 (H1HA0HA6) was described. In this polypeptide, the equivalent of amino acid residues 48 to 288 have been deleted and mutations I297T, V300T, I302N, C305S, F392D, F395T, and L402D have been made. Both the H3 and H1 based polypeptides were expressed in *E. coli* and therefore lack the glycans that are part of the naturally occurring HA proteins.

Corbett et al. (2019) has described influenza A virus H3 and H7 HA stem trimers displayed on self-assembling ferritin nanoparticles which elicited protective, homosubtypic antibodies in mice. Although immunogenic, the HA antigens fused to ferritin also may induce unwanted responses against the carrier nanoparticle which could lead to reduced HA directed immune response and longevity thereof after repeated immunization. Furthermore, expression levels and purification challenges of HA-ferritin fusion proteins may hamper the production of large amount of vaccine dosages. Also, the accessibility of HA epitopes (such as the binding site of CR8020) close to the surface of such nanoparticles may reduce the immune response to these favorable conserved HA surfaces.

Until now, influenza continues to be a significant global health burden, even though the technology for conventional egg-grown, whole inactivated influenza virus vaccines was developed more than 70 years ago. Constant antigenic drift of the influenza virus hemagglutinin (HA) coupled with immunodominant strain-specific antibody responses directed to the variable HA head domain results in conventional vaccine effectiveness ranging from 10 to 60% and the need for seasonal updates of virus strains included in licensed vaccines. Furthermore, current vaccine approaches provide minimal protection against pandemic influenza virus strains.

The need for a better group 2 vaccine is particularly acute, as vaccine effectiveness against H3N2 over the past decade has averaged only 33% (Belongia et al. (2016)), recent H3N2 strains have exhibited increased virulence (Garten et al. (2017)), and H7 viruses represent one of the greatest pandemic threats from nonseasonal strains.

There thus exists a need for a safe and effective "universal" vaccine that stimulates the production of a robust, broadly neutralizing antibody response and that offers protection against a broad set of current and future influenza virus strains (both seasonal and pandemic), in particular a vaccine that provides protection against one or more influenza A virus subtypes within phylogenetic group 2, for the effective prevention of influenza.

SUMMARY

The present invention provides novel monomeric and multimeric, in particular trimeric, polypeptides derived from group 2 influenza hemagglutinin (HA), which polypeptides comprise the influenza HA stem domain and lack the globular head region, herein referred to as influenza hemagglutinin (HA) stem polypeptides or mini-HAs. The polypeptides induce a cellular and/or humoral immune response against at least group 2 influenza viruses when administered to a subject, in particular a human subject. The polypeptides of the invention are thermostable and present conserved epitopes of the membrane proximal stem of the group 2 HA molecule to the immune system in the absence of dominant epitopes that are present in the membrane distal head domain.

Thus, in the HA stem polypeptides of the invention part of the primary sequence of the HA0 protein, i.e. the part making up the head domain has been deleted, and the remaining amino acid sequence has been reconnected, either directly or, in some embodiments, by introducing a short flexible linking sequence ('linker') to restore the continuity of the polypeptide chain. The resulting amino acid sequence is further modified by introducing specific modifications that stabilize the native 3-dimensional structure of the remaining part of the HA molecule.

In a first aspect, the present invention relates to monomeric influenza A hemagglutinin (HA) stem polypeptides, comprising an HA1 and a HA2 domain of an HA of a group 2 influenza A virus, said HA stem polypeptides comprising an amino acid sequence which comprises:

(i) a deletion of the head region from the HA1 domain;

(ii) a modification of the trimerization region in the HA2 domain;

(iii) at least two cysteine residues capable of forming at least one intramonomeric cysteine bridge;

and wherein in the amino acid sequence the amino acid at position 355 is W;

wherein the numbering of the amino acid positions in the HA stem polypeptide amino acid sequence is H3 numbering according to the HA nomenclature of Winter et al. (1981), which corresponds to the full-length HA numbering of the reference strain H3N2 A/Aichi/2/68 (SEQ ID NO: 1).

In certain embodiments, the present invention relates to group 2 influenza A hemagglutinin (HA) stem polypeptides comprising an HA1 and an HA2 domain, wherein said HA stem polypeptides comprise an amino acid sequence which comprises, (i) a deletion of the head region in the HA1 domain, said deletion comprising at least the amino acid sequence from the amino acid corresponding to the amino acid at position 50 up to and including the amino acid corresponding to the amino acid at position 302;

(ii) a modification of the trimerization region in the HA2 domain, preferably a modification of the trimerization region in the C-helix, said trimerization region comprising the amino acid sequence from the amino acid corresponding to the amino acid at position 405 up to and including the amino acid corresponding to the amino acid at position 419;

(iii) a cysteine at the amino acid position corresponding to position 310 in combination with a cysteine at the position corresponding to position 422; or a cysteine at the amino acid corresponding to position 311 in combination with a cysteine at the position corresponding to position 422; or a cysteine at the amino acid position corresponding to position 308 in combination with a cysteine at the position corresponding to position 418 (capable of) forming an intramonomeric disulphide bridge;

and wherein in the amino acid sequence the amino acid at position 355 is W;

wherein the numbering of the amino acid positions in the HA stem polypeptide amino acid sequence is H3 numbering according to the HA nomenclature of Winter et al., supra, corresponding to the full-length HA numbering of the reference strain H3N2 A/Aichi/2/68 (SEQ ID NO: 1).

According to the present invention it has surprisingly been shown that the novel group 2 influenza HA stem polypeptides of the invention can be recombinantly expressed in high levels, are trimeric in cell culture supernatant in the absence of additional artificial C-terminal trimerization domains, and/or have an increased melting temperature which indicates a greater thermostability. In addition, the group 2 HA stem polypeptides of the invention mimic the stem of the full-length group 2 HA by stably presenting the epitope of HA stem binding antibodies binding to group 2 HA, such as CR9114 (as described in WO2013/007770) and/or CR8020 (as described in WO2010/130636).

In a second aspect, the invention relates to multimeric influenza A hemagglutinin (HA) stem polypeptide, comprising at least two HA stem polypeptide monomers as described herein.

In a further aspect, the present invention provides nucleic acid molecules encoding the group 2 influenza HA stem polypeptides.

In yet another aspect, the invention provides vectors, in particular recombinant adenoviral vectors, comprising nucleic acids encoding the influenza HA stem polypeptides.

In a further aspect, the invention provides methods for inducing an immune response against a group 2 influenza HA in a subject in need thereof, the method comprising administering to the subject an influenza HA stem polypeptide, a nucleic acid molecule, and/or a vector according to the invention.

In another aspect, the invention provides pharmaceutical compositions comprising an influenza HA stem polypeptide, a nucleic acid molecule and/or a vector according to the invention, and a pharmaceutically acceptable carrier.

In a further aspect, the invention provides group 2 influenza HA stem polypeptides, nucleic acid molecules encoding said influenza HA stem polypeptides, and/or vectors comprising said nucleic acid molecules for use in inducing an immune response against an influenza virus, in particular for use as a vaccine for the prevention of a disease or condition caused by an influenza virus A strain from phylogenetic group 2.

BRIEF DESCRIPTION OF THE FIGURES

FIG. 4. Stability of trimeric stem polypeptide with and without inter-protomeric disulfide bridge. A. SEC analysis of culture supernatants of Expi293F cells (left panel) at time of harvest and of culture supernatant of EXPI-CHO cells expressing purified polypeptides after one-week incubation at 4° C. without (UFV180192) and with (UFV180141) introduced cysteine residues at position 398 and 408 (as indicated in structural mini-HA model at the top of this figure); B. Temperature stability of purified polypeptides as determined by Differential Scanning Fluorimetry; C. SDS-PAGE analysis of protein purity under non-reduced and reduced conditions. As shown, the introduced cysteines form inter-protomeric disulfide bridges and increase the temperature stability.

FIG. 5. A. Protein expression levels and antibody binding as determined by AlphaLISA of culture supernatants of EXPI-293 expressed polypeptides that differ at positions 355 and 482. Values are determined by AlphaLISA and are normalized to reference (UFV161333); B. Protein expression, trimer content and antibody binding as determined by AlphaLISA of culture supernatants of EXPI-293 expressed polypeptides mutated at position 380 and 432. Values are normalized to reference (UFV170991); C. I. Protein expression, trimer content and antibody binding as determined by AlphaLISA of culture supernatants of EXPI-293 expressed polypeptides mutated at position 435. Values are normalized to reference (UFV170611), C. II. Protein expression levels of constructs UFV171004 (435N) and UFV171197 (435R)

expressed in EXPI-CHO culture supernatants as determined by OCTET (left panel) and SEC analysis (right panel). In vitro characterization of purified polypeptides (bottom panel): binding of mAbs CR9114 and mAb CT149 (ELISA, $EC_{50}$ values) and temperature stability (Differential Scanning Fluorimetry, $Tm_{50}$ values in ° C.); D. Protein expression levels of polypeptides mutated at position 388 as determined by OCTET and SEC analysis of EXPI-CHO culture supernatants.

Figure 6:
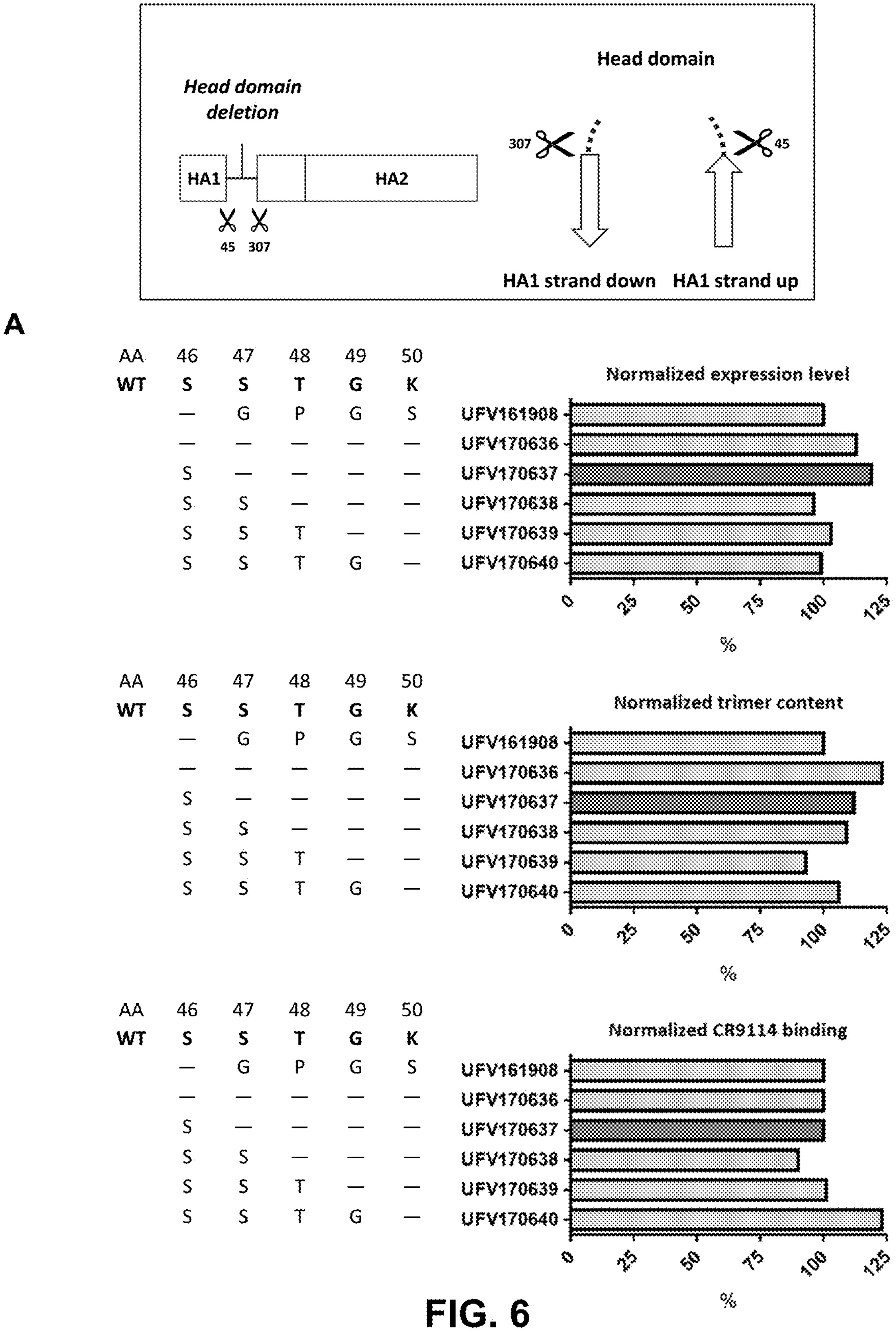

FIG. 6. Schematic representation of the HA head domain (HA1) removal. Expression levels, trimer content and mAb binding as determined by AlphaLISA of culture supernatants of EXPI-293 cells expressed polypeptides. All data is normalized to reference designs UFV161908 (A), UFV160653 (B), and UFV160321 (C). A. In reference design (UFV161908) part of the head domain starting with the amino acid on position 46 up till and including the amino acid at position 306 was removed and the two HA1 ends were connected by an artificial "GPGS-linker". Various alternative cutting positions for HA head domain removal (HA1 strain up) and direct connections of the HA1 ends (i.e. the connection of the N-terminal HA1 segment to the C-terminal HA1 segment after deletion of the head) are shown. In construct UFV170637 (dark grey) the head domain starting with the amino acid at position 47 up till and including the amino acid at position 306 was deleted similar to the preferred constructs UFV180088, UFV180089, and UFV180090); B. Direct connection of HA1 up and/or down strain after HA head domain removal; C. Connection of the HA1 N-terminal and C-terminal ends by means of a homologous linker sequence originating from the head domain. All constructs have a deletion of the amino acid sequence from the amino acid at position 46 up to and including the amino acid at position 306.

Figure 7:
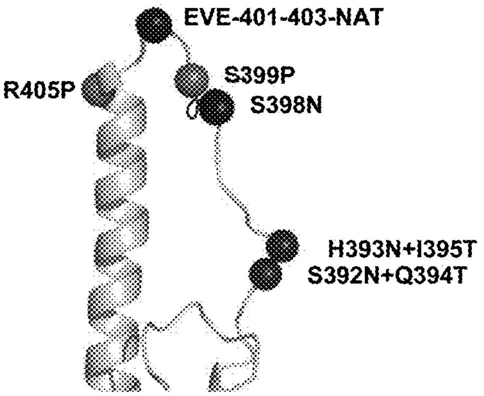
Figure 7:
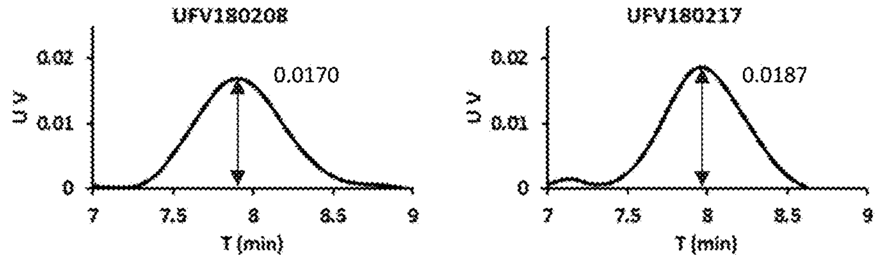

FIG. 7. Expression level and mAb binding as determined by AlphaLISA of culture supernatants of EXPI-293 expressed trimeric stem polypeptides with mutations to stabilize the B-loop. All data is normalized to reference designs UFV161686 (A), UFV161333 (B, C), and UFV171187 (D); A. Optimizing and shielding the B-loop by introducing a glycosylation motif at position 401-403 for N-linked glycosylation at position 401; B. Introducing proline residues by point mutations to stabilize the B-loop; C. Introduction of a second glycosylation motif (for N-linked glycosylation at position 393) to further shield the B-loop; D. Combining added N-linked glycosylation motifs (at position 401 and 392 or 393) with proline substitutions. Protein expression levels as determined by OCTET (anti-His2); E. SEC profiles of culture supernatants of EXPI-293 cells expressing polypeptides show that the introduction of one glycan (UFV180208) or two glycans and two prolines (UFV180217) are well accepted. The retention time and height of the peak corresponding to the trimeric polypeptide is indicated in grey.

FIG. 8. Expression level and mAb binding of EXPI-CHO expressed trimeric stem polypeptides with and without the motif for an N-linked glycan at position 38. A. Expression level as determined by OCTET (anti C-tag) and antibody binding as determined by ELISA ($EC_{50}$ values); B. ELISA dilution curves of UFV170282 (solid line) and UFV170278 (dashed line).

FIG. 9. Analysis of EXPI-293 culture supernatants expressing polypeptides with variations in the position of the introduced intra-protomeric disulfide bridge. Protein expression and antibody binding as determined by AlphaLISA normalized to reference UFV160595. A. Alternative cysteines introduced near the position as present in reference construct UFV160595; B. Alternative second disulfide bridge introduced in the region below the first disulfide bridge.

Figure 10:
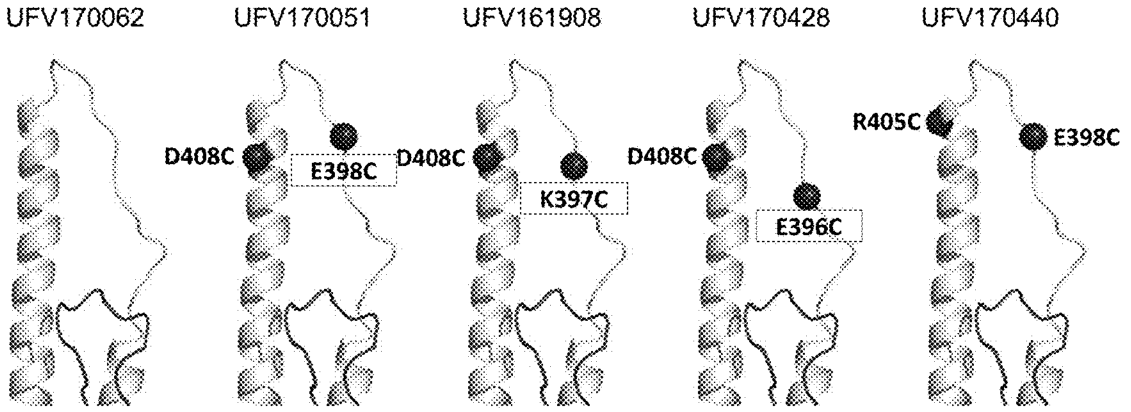

FIG. 10. Analysis of EXPI-293 culture supernatants expressing polypeptides with variations in the position of the introduced inter-protomeric disulfide bridge. Protein expression and antibody binding as determined by AlphaLISA normalized to reference design UFV170051.

Figure 11:
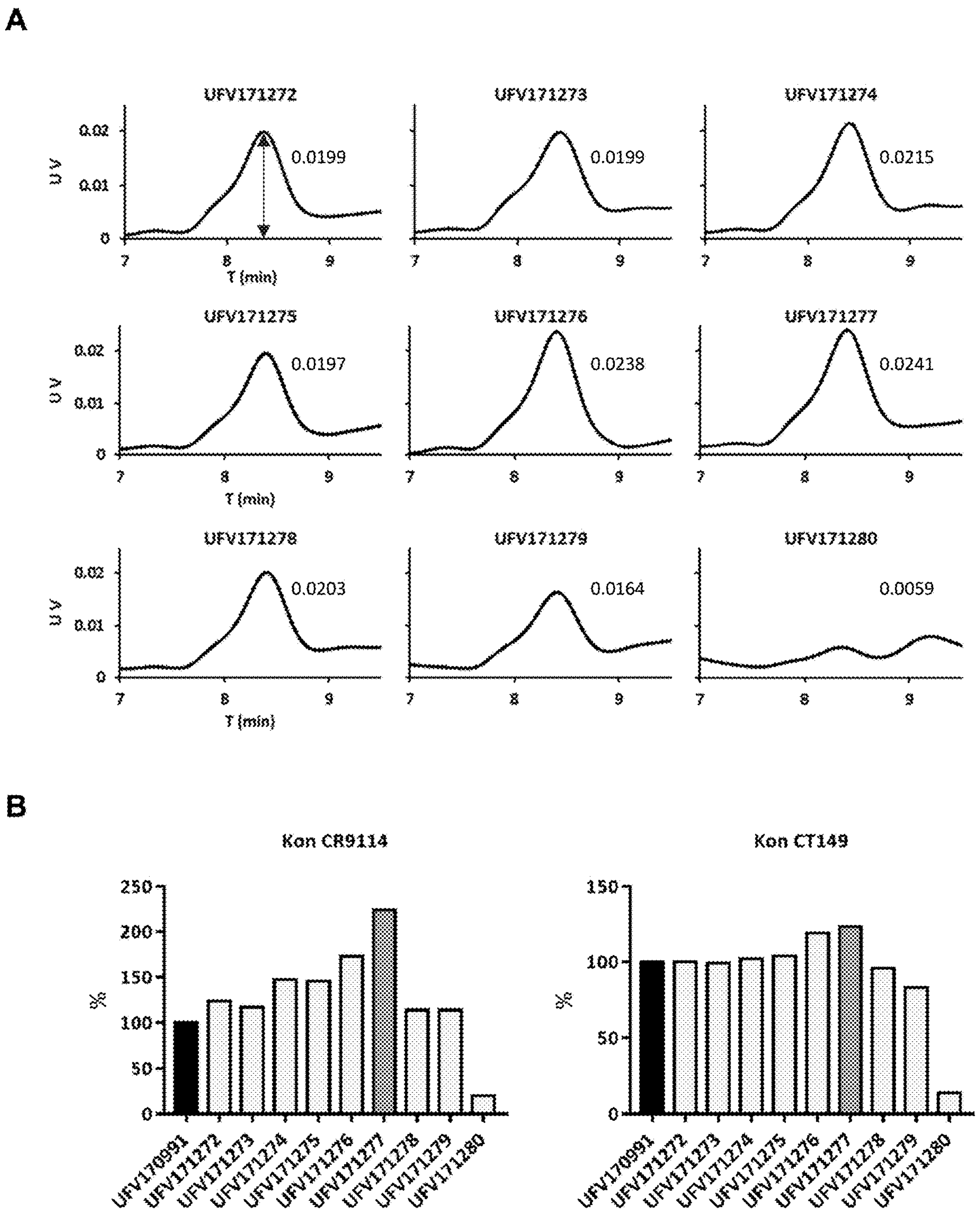

FIG. 11. Analysis of EXPI-293 culture supernatants expressing soluble trimeric polypeptide variants with alternative C-terminal truncations (at position 515 in UFV171272, and stepwise up to position 499 in UFV171280). A. SEC profiles with the trimeric peak retention time and height indicated in grey; B. Binding of polypeptides to broadly neutralizing antibody CR9114 and CT149 as determined by OCTET; shown are relative $K_{ON}$ values of the polypeptides compared to reference UFV170991 (black).

FIG. 12. In vitro characterization of polypeptides of the invention with residue substitutions in the A-helix from H3 wild type (WT) towards H1. A. Protein expression levels and antibody binding as determined by AlphaLISA of EXPI-293 cell culture supernatants containing expressed polypeptides. Values are normalized to reference (UFV161454); B. Protein expression levels of three independent EXPI-CHO culture supernatants as determined by OCTET (anti-His2, left panel) and SEC-MALS analysis (right panel). In vitro characterization of purified polypeptides (bottom panel): binding of mAbs CR9114 and CT149 (ELISA, $EC_{50}$ values) and temperature stability (Differential Scanning Fluorimetry, $Tm_{50}$ values).

FIG. 13. Culture supernatant analysis of EXPI-293 cells expressing trimeric stem polypeptides with stem surface mutations towards H7 HA. Trimer content and antibody binding determined by AlphaLISA. All data is normalized to reference design UFV172561 containing A-helix mutations 379 and 381 towards H1 (A) or reference design UFV172562 containing wild type H3 A-helix residues at position 379 and 381 (B). The references are indicated as a dotted line in the SEC profiles.

FIG. 14. SEC analysis of culture supernatants of EXPI-293 cells expressing polypeptides derived from different Group 2 H3 strains containing relevant design elements for the generation of soluble trimeric stem polypeptides. A. SEC profiles of mini-HA polypeptides containing set I design elements and based on A/Hong Kong/1/1968, A/Wisconsin/67/05, or A/Singapore/INFIMH/16/0019/2016 (Trimer peak indicated with 'T'); B. SEC profiles of polypeptides containing additional stabilizing mutations in the B-loop: design I (dotted line), design II (grey) and design III (black) elements.

Figure 15:
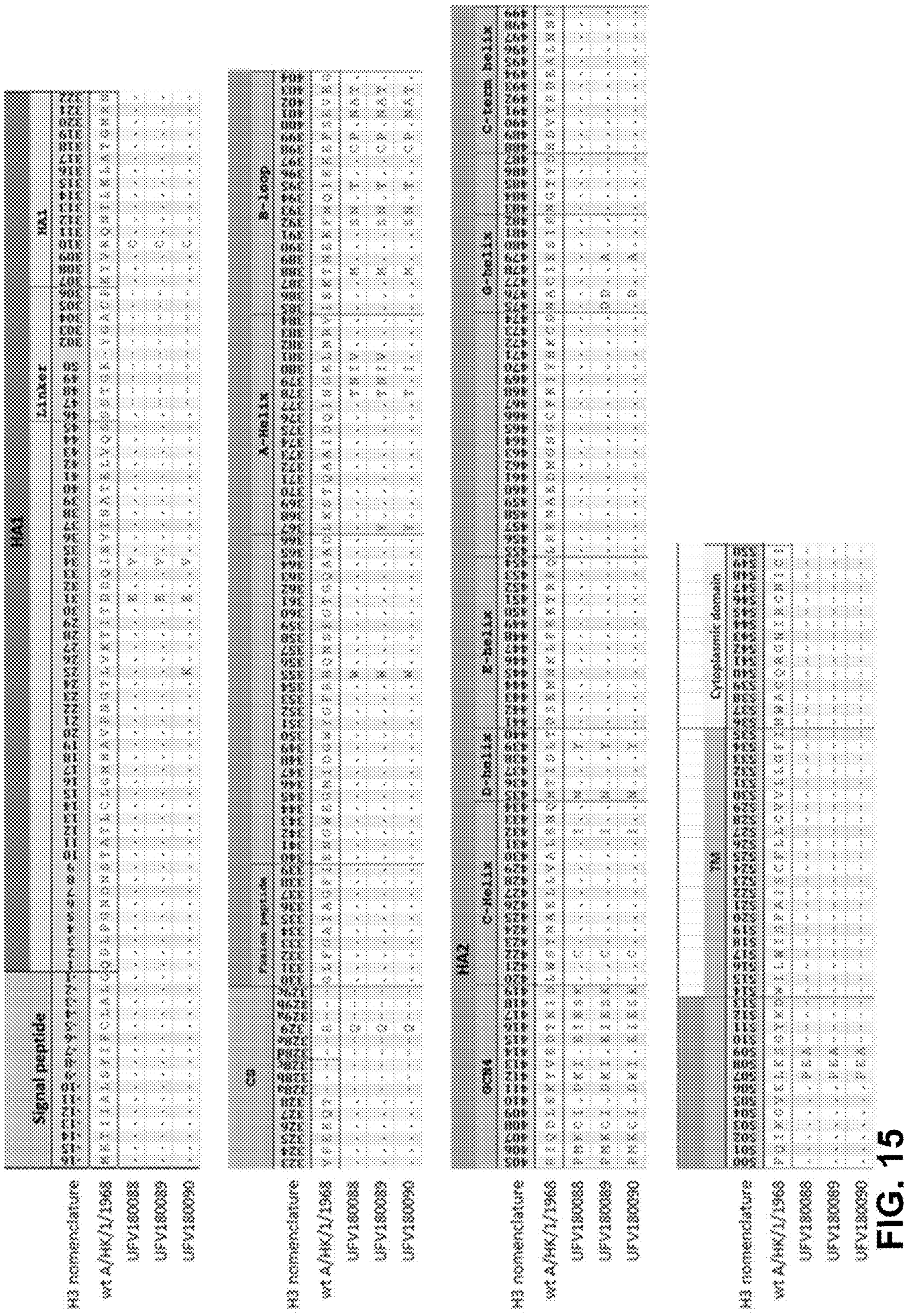

FIG. 15. Numbering of amino acid positions in wild type H3 A/Hong Kong/1/1968 (wt A/HK/1/1968) and in H3 derived mini-HA designs UFV180088, UFV180089, and UFV180090 according to H3 numbering of Winter et al. (1981).

Figure 16:
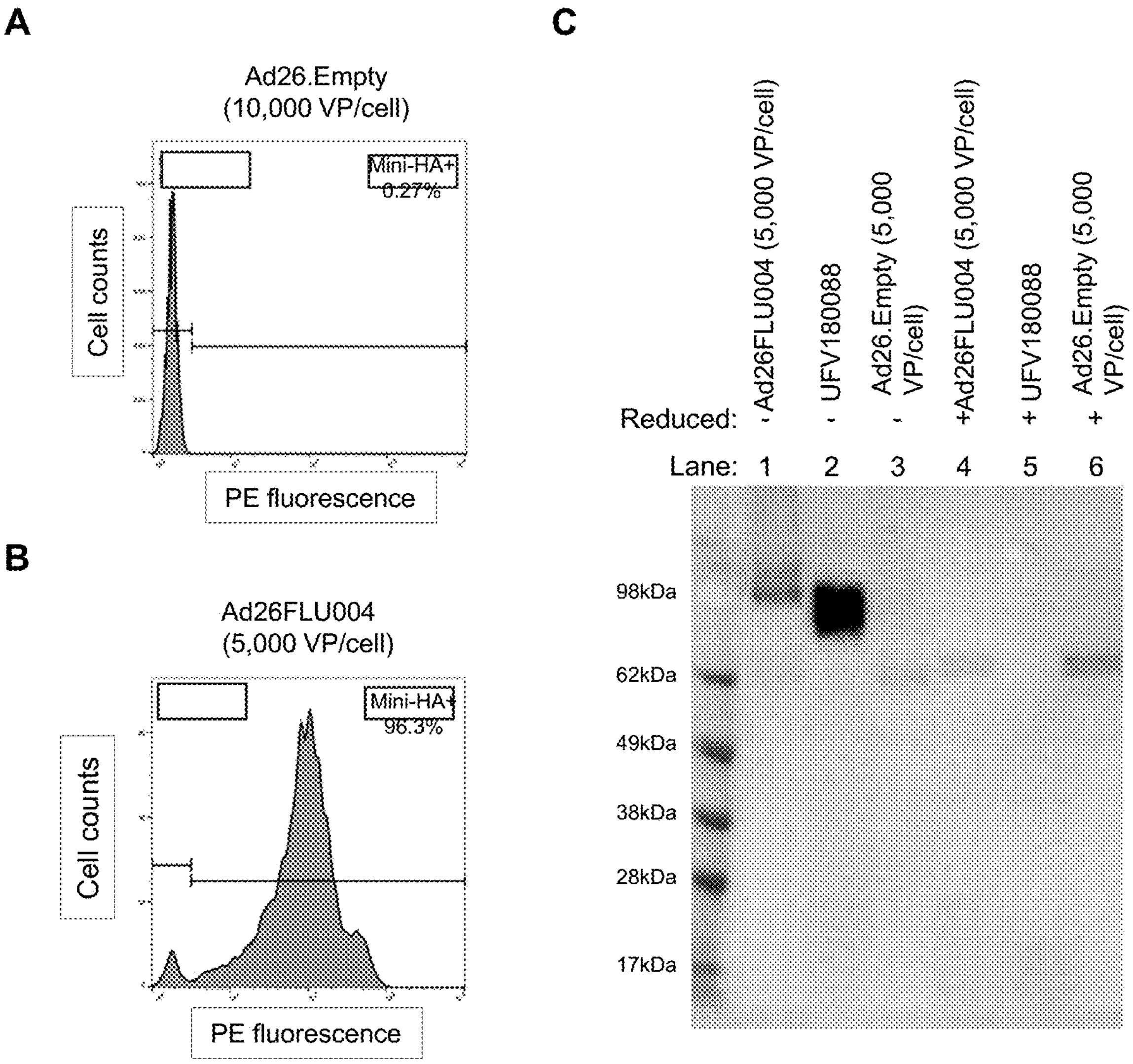

FIG. 16. Adenovirus (Ad26.FLU.004) driven expression and folding of UFV180480 (UFV18088 with native transmembrane domain). FACS analysis of transduced MRC-5 cells with A) Ad26.Empty (10,000 VP/cell, negative control) and B) Ad26.FLU.004 (5,000 VP/cell). The transduced MRC-5 cells were stained with CR9114 antibody; C. Western blot analysis of MRC-5 cell lysates transduced with either Ad26.FLU.004 (5,000 VP/cell) or Ad26.Empty (5,000 VP/cell). As a positive control, UFV180088 (200 ng/lane) was loaded. All samples were run under non-reduced (lane 1-3) or reduced (lane 4-6) conditions. Antibody CR9114 was used to detect the expressed mini-HA.

Figure 17:
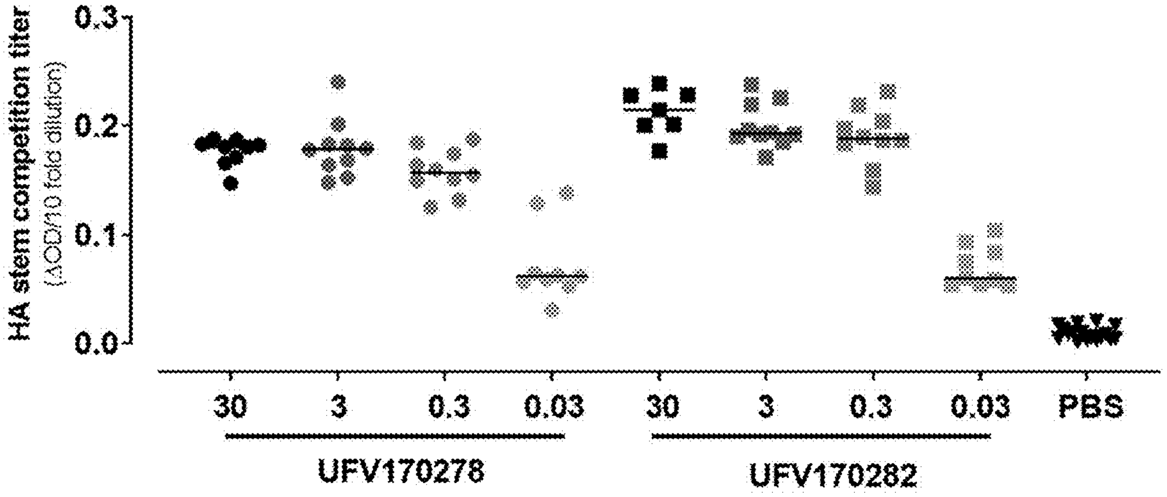
Figure 17:
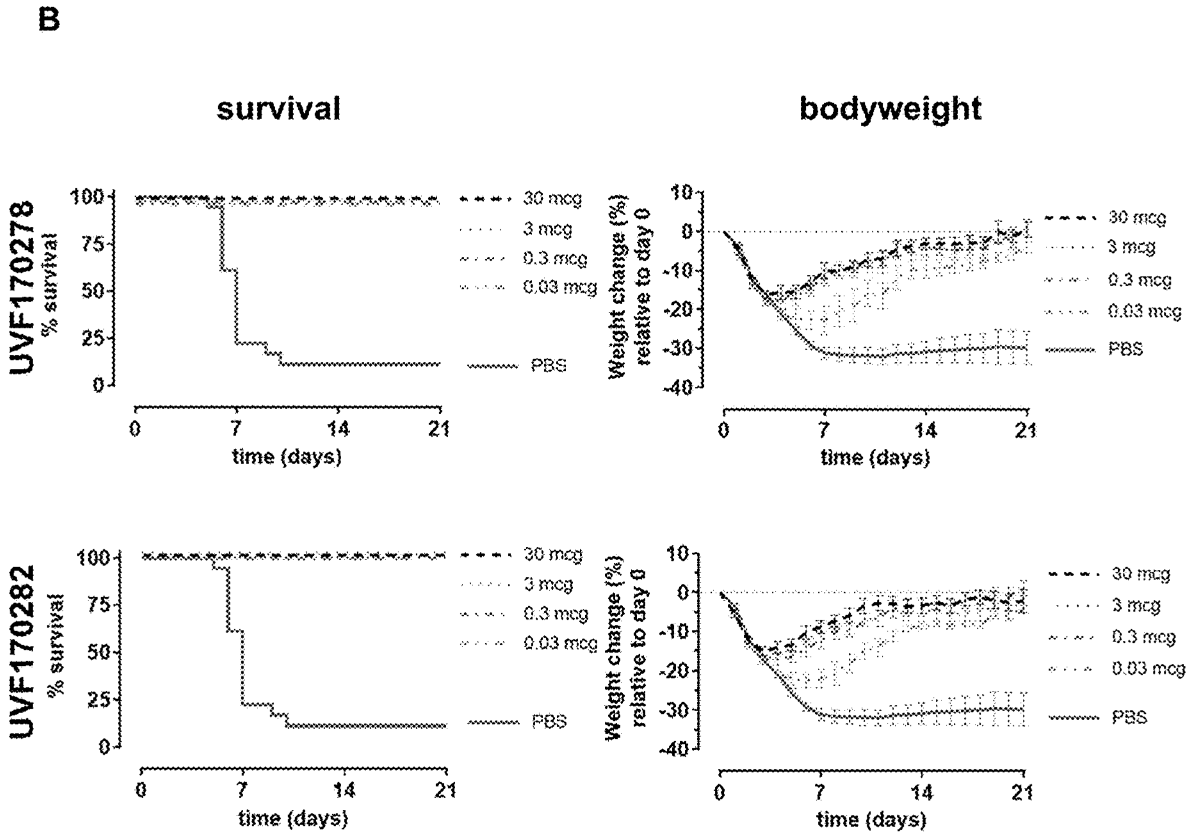

FIG. 17. In vivo characterization of the polypeptides UFV170278, a polypeptide that contains the wild type motif 38-NAT-40 for N-linked glycosylation and UFV170282, a polypeptide in which this glycan motif was knocked-out by point mutation T40I. A. H3 A/Hong Kong/1/1968 FL HA stem-specific antibody titers 4 weeks after the third immunization of mice with polypeptides of the invention or PBS. Horizontal line per group denotes group median. B. Left panels: Survival proportion during the follow-up period after H3N2 A/Hong Kong/1/1968 challenge of mice immunized with indicated polypeptides of the invention or PBS; UFV170278 top panel, UFV170282 bottom panel. Right panels: Relative bodyweight during the follow-up period after H3N2 A/Hong Kong/1/1968 challenge of mice immunized with indicated polypeptides of the invention or PBS; UFV170278 top panel, UFV170282 bottom panel. Relative bodyweight change was expressed relative to Day 0. Cumulative bodyweight loss during the follow-up period was determined by calculating the Area Under the Curve (AUC). Error bars denote 95% confidence interval.

Figure 18:
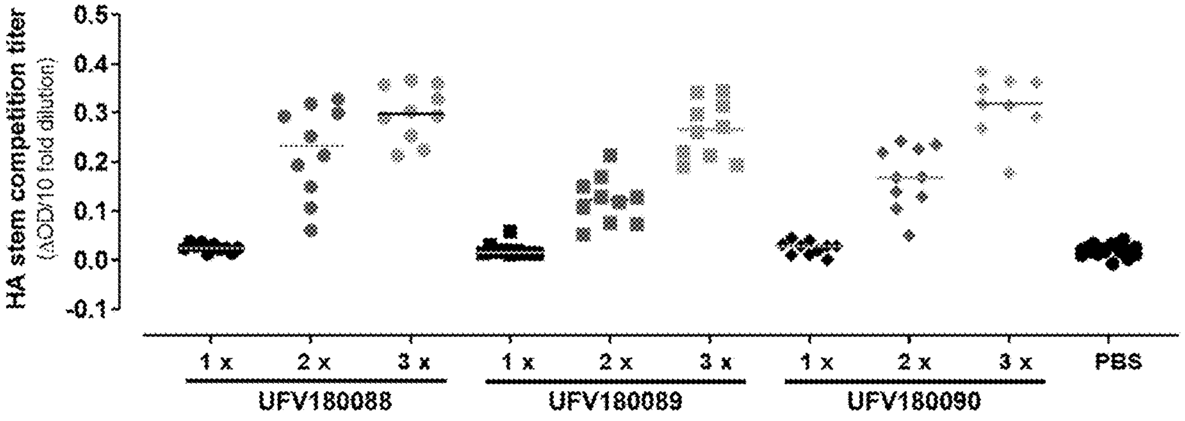
Figure 18:
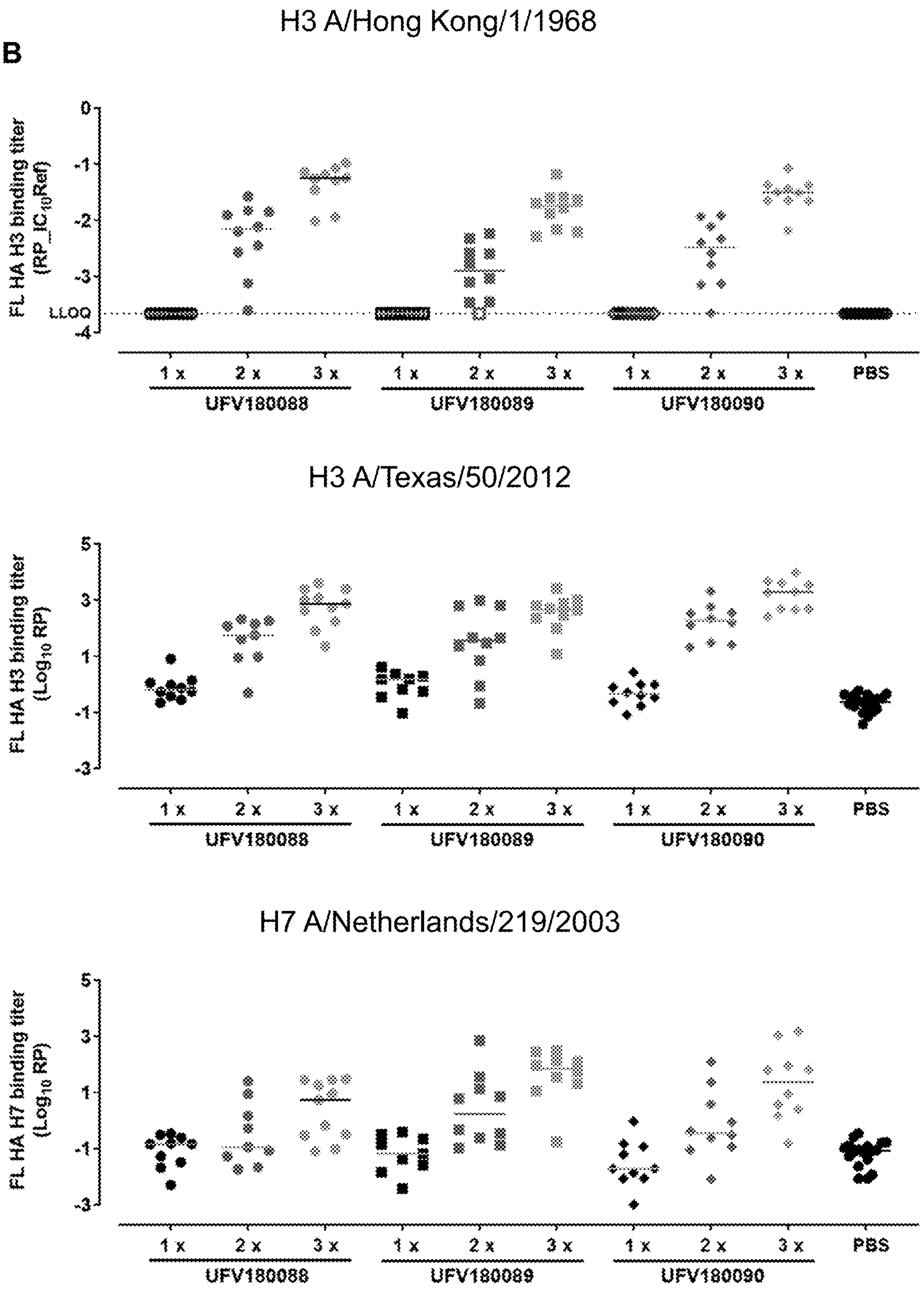

FIG. 18. In vivo characterization of the immunogenicity of polypeptides UFV180088, UFV180089 and UFV180090 of the invention in a naïve mouse model. A. H3 A/Hong Kong/1/1968 FL HA stem-specific antibody titers after one (1×), two (2×), or three (3×) immunizations of mice with polypeptides of the invention or PBS. Horizontal line per group denotes group median. B FL HA H3 A/Hong Kong/1/1968, H3 A/Texas/50/2012 and H7 A/Netherlands/219/2003 antibody titers after one (1×), two (2×), or three (3×) immunizations of mice with polypeptides of the invention or PBS. Horizontal line per group denotes group median. Dashed line denotes LLOQ with open symbols indicating values at LLOQ.

Figure 19:
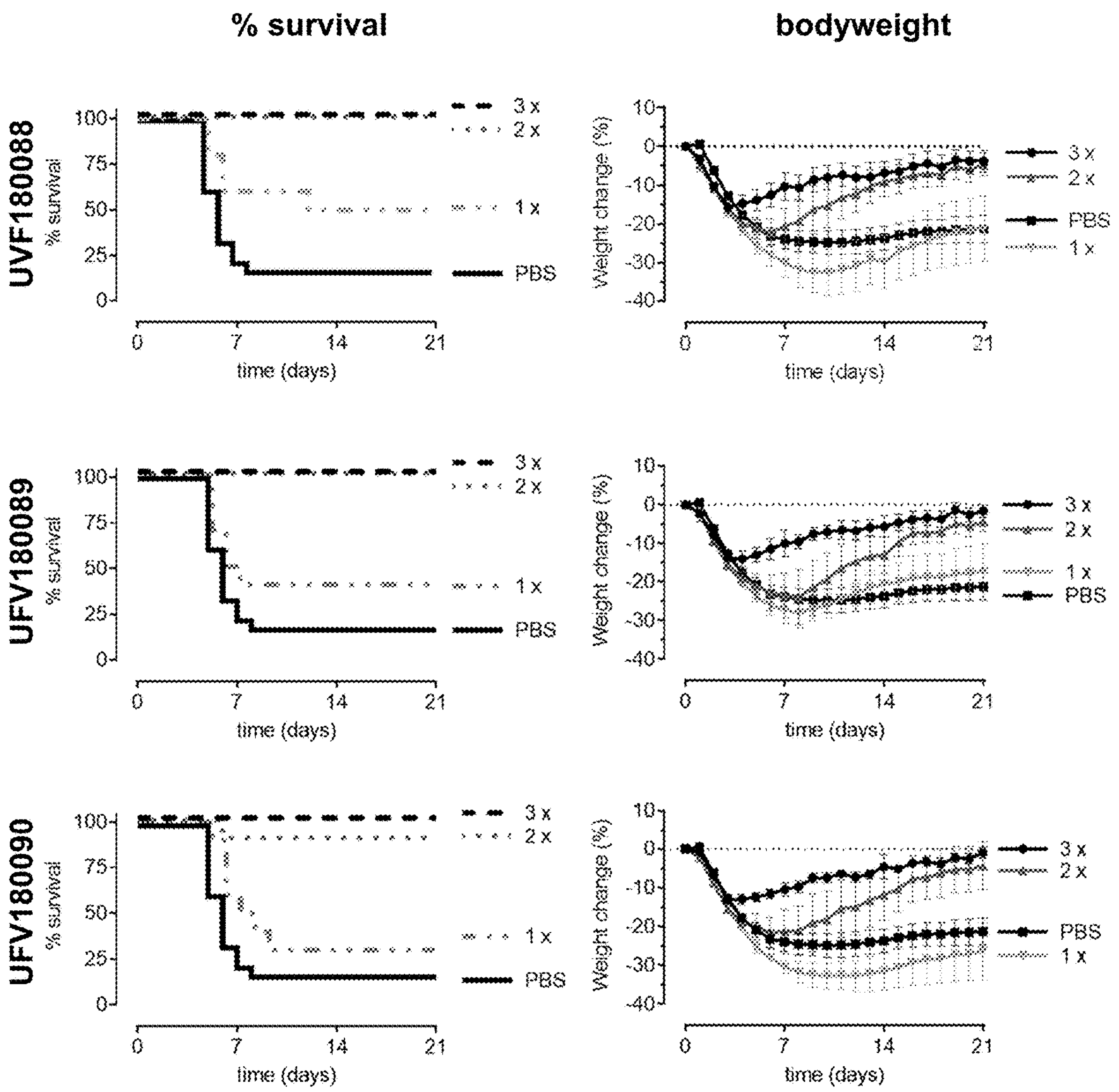

FIG. 19. In vivo characterization of the polypeptides UFV180088, UFV180089 and UFV180090 of the invention in a. H3N2 lethal naïve mouse model. Left panels: Survival proportion during the follow-up period after H3N2 A/Hong Kong/1/1968 challenge of mice immunized with indicated polypeptides of the invention or PBS; UFV180088 top panel, UFV180089 middle panel and UFV180090 bottom panel. Right panels: Relative bodyweight during the follow-up period after H3N2 A/Hong Kong/1/1968 challenge of mice immunized with indicated polypeptides of the invention or PBS. Relative bodyweight change was expressed relative to Day 0. Cumulative bodyweight loss during the follow-up period was determined by calculating the Area Under the Curve (AUC). Error bars denote 95% confidence interval. H7N9 lethal naïve mouse model.

DEFINITIONS

Definitions of terms as used in the present invention are given below.

An amino acid according to the invention can be any of the twenty naturally occurring (or 'standard' amino acids) or variants thereof, such as e.g. D-proline (the D-enantiomer of proline), or any variants that are not naturally found in proteins, such as e.g. norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that forms a cycle to the polypeptide backbone, and glycine that is more flexible than other amino acids. Table 7 shows the abbreviations and properties of the standard amino acids.

The term "included" or "including" as used herein is deemed to be followed by the words "without limitation".

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

Influenza viruses are typically classified into influenza virus types: genus A, B and C. The term "influenza virus subtype" as used herein refers to influenza A virus variants that are characterized by combinations of the hemagglutinin (H) and neuraminidase (N) viral surface proteins. According to the present invention influenza virus subtypes may be referred to by their H number, such as for example "influenza virus comprising HA of the H3 subtype", "influenza virus of the H3 subtype" or "H3 influenza", or by a combination of a H number and an N number, such as for example "influenza virus subtype H3N2" or "H3N2". The term "subtype" specifically includes all individual "strains", within each subtype, which usually result from mutations and show different pathogenic profiles, including natural isolates as well as man-made mutants or reassortants and the like. Such strains may also be referred to as various "isolates" of a viral subtype. Accordingly, as used herein, the terms "strains" and "isolates" may be used interchangeably. The current nomenclature for human influenza virus strains or isolates includes the type (genus) of virus, i.e. A, B or C, the geographical location of the first isolation, strain number and year of isolation, usually with the antigenic description of HA and NA given in brackets, e.g. A/Moscow/10/00 (H3N2). Non-human strains also include the host of origin in the nomenclature.

The influenza A virus subtypes can further be classified by reference to their phylogenetic group. Phylogenetic analysis has demonstrated a subdivision of hemagglutinins into two main groups: inter alia the H1, H2, H5 and H9 subtypes in phylogenetic group 1 ("group 1" influenza viruses) and inter alia the H3, H4, H7 and H10 subtypes in phylogenetic group 2 ("group 2" influenza viruses).

As used herein, the term "influenza virus disease" or "influenza" refers to the pathological condition resulting from the presence of an influenza virus, e.g. an influenza A or B virus, in a subject. As used herein, the terms "disease" and "disorder" are used interchangeably. In specific embodiments, the term refers to a respiratory illness caused by the infection of the subject by the influenza virus.

As used herein, the term "nucleic acid" or "nucleic acid molecule" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded. The nucleic acid molecules may be modified chemically or biochemically or may contain non-natural or derivatized nucleotide bases, as will be readily appreciated by those skilled in the art. Such modifications include, for example, labels, methylation, substitution of one or more of the naturally occurring nucleotides with an analog, inter-nucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

Figure 2:
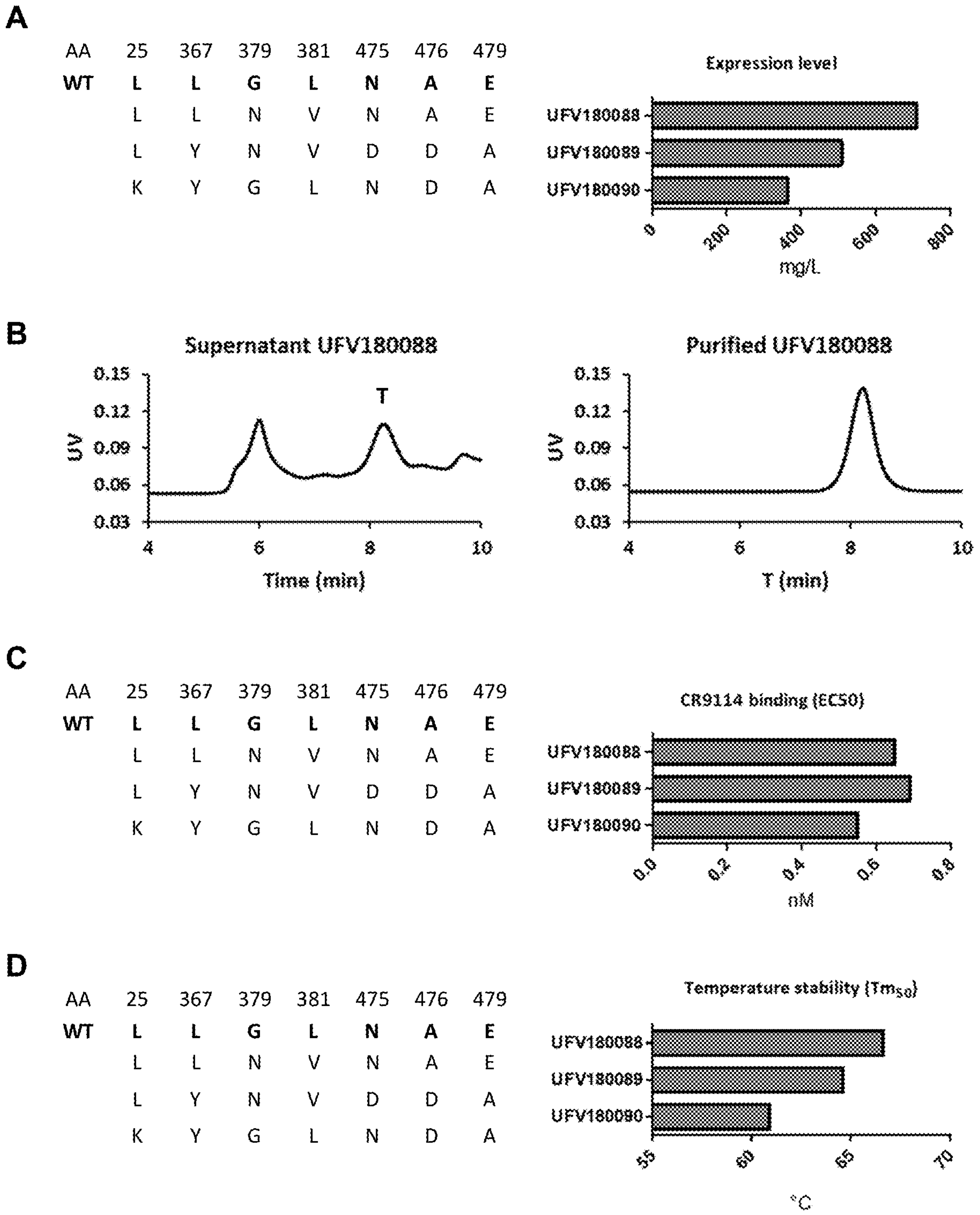
FIG. 2. A. Protein expression levels of EXPI-CHO culture supernatants as determined by OCTET (anti C-tag); B. SEC analysis of culture supernatants of EXPI-CHO cells expressing construct 180088 (left panel) and SEC-MALS analysis of purified 180088; C. Binding of mAb CR9114 to purified polypeptides by ELISA ($EC_{50}$ values); D. Temperature stability analysis of purified polypeptides by Differential Scanning Fluorimetry.

As used herein, the numbering of the amino acids in HA is based on H3 numbering, as described by Winter et al. (1981). The numbering of the amino acid residues or amino acid positions thus refers to the numbering in the full length H3 HA (in particular, the numbering of amino acid positions in A/Aichi/2/68), as described by and shown in FIG. 2 in Winter et al. (1981). The numbering thus is based on the full-length HA numbering of the reference strain H3N2 A/Aichi/2/68 (SEQ ID NO: 1). The numbering in particular refers to the numbering of the amino acid positions in SEQ ID NO: 1. For example, the wording 'the amino acid at position 392" or "the amino acid corresponding to the amino acid at position 392" (which are used interchangeably throughout this application) refers to the amino acid residue that is at position 392 according to the H3 numbering of Winter et al. (1981). It is noted that, because in the polypeptides of the invention part of the HA1 domain (the head domain) has been deleted, the numbering, as used herein, does not necessarily refer to the actual positions of the amino acids in the HA stem polypeptides of the invention but instead refers to the position of said amino acid in the full-length HA molecule (i.e. without the head deletion). It will furthermore be understood by the skilled person that equivalent amino acids (i.e. amino acids corresponding to the amino acid at a particular position in SEQ ID NO: 1) in other influenza virus strains and/or subtypes, and in the stem polypeptides of the invention, can be determined by sequence alignment.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked and O-linked glycosylation), protease cleavage and lipid modification (e.g. S-palmitoylation).

"HA stem polypeptide" refers to a HA derived polypeptide which does not comprise the head domain of a naturally-occurring (or wild-type) hemagglutinin (HA).

As used herein, the term "wild-type" refers to HA from influenza viruses that are circulating naturally.

DETAILED DESCRIPTION

Influenza viruses have a significant impact on global public health, causing millions of cases of severe illness each year, thousands of deaths, and considerable economic losses. Current trivalent or quadrivalent influenza vaccines elicit a potent neutralizing antibody response to the vaccine strains and closely related isolates, but rarely extend to more diverged strains within a subtype or to other subtypes. In addition, selection of the appropriate vaccine strains presents many challenges and frequently results in sub-optimal protection. Furthermore, predicting the subtype of the next pandemic virus, including when and where it will arise, is currently still impossible.

Hemagglutinin (HA) is the major envelope glycoprotein from influenza viruses which is the major target of neutralizing antibodies. Hemagglutinin has two main functions during the entry process. First, hemagglutinin mediates attachment of the virus to the surface of target cells through interactions with sialic acid receptors. Second, after endocytosis of the virus, hemagglutinin subsequently triggers the fusion of the viral and endosomal membranes to release its genome into the cytoplasm of the target cell. HA comprises a large ectodomain of ~500 amino acids that is cleaved by host-derived enzymes to generate 2 polypeptides (HA1 and HA2) that remain linked by a disulfide bond. The majority of the N-terminal fragment (the HA1 domain, ~320-330 amino acids) forms a membrane-distal globular "head domain" that contains the receptor-binding site and most determinants recognized by virus neutralizing antibodies. The smaller C-terminal portion (HA2 domain, ~180 amino acids) forms a stem-like structure (the stem domain) that anchors the globular domain to the cellular or viral membrane. The degree of sequence identity between subtypes is smaller in the HA1 polypeptides (34%-59% identity between subtypes) than in the HA2 polypeptide (51% 80% identity). The most conserved region is the sequence around the protease cleavage site, particularly the HA2 N-terminal 23 amino acids, which sequence is conserved among all influenza A virus subtypes (Lorieau et al., 2010). Part of this region is exposed as a surface loop in the HA precursor molecule (HA0) but becomes inaccessible when HA0 is cleaved into HA1 and HA2.

Most neutralizing antibodies bind to the loops that surround the receptor binding site and thereby interfere with receptor binding and attachment. Since these loops are highly variable, most antibodies targeting these regions are strain-specific, explaining why current vaccines elicit such limited, strain-specific immunity. Fully human monoclonal antibodies against influenza virus hemagglutinin with broad cross-neutralizing potency were generated, such as e.g. CR6261 (WO2008/028946). Functional and structural analysis have revealed that these antibodies interfere with the membrane fusion process and are directed against highly conserved epitopes in the stem domain of group 1 influenza HA protein (Throsby et al., 2008; Ekiert et al. 2009, WO 2008/028946). With the identification of CR9114 (as described in WO2013/007770) which cross-reacts with many group 1 and 2 HA molecules, it has become clear that it is possible for the human immune system to elicit very broad neutralizing antibodies against influenza viruses. However, given the need for a yearly vaccination scheme these antibodies are apparently not always elicited to a protective level, following infection by or vaccination with (seasonal) influenza viruses of subtypes H1 and/or H3.

According to the present invention novel HA stem polypeptides are provided that mimic the specific epitopes of e.g. the antibody CR9114 (comprising a heavy chain variable region of SEQ ID NO: 7 and a light chain variable region of SEQ ID NO: 8) and/or CR8020 (comprising a heavy chain variable region of SEQ ID NO: 5 and a light chain variable region of SEQ ID NO: 6). The polypeptides of the invention can be used to elicit influenza virus binding and/or neutralizing antibodies, preferably cross-binding and/or cross-neutralizing antibodies when administered in vivo, either alone, or in combination with other prophylactic and/or therapeutic treatments. With "cross-binding and/or cross-neutralizing antibodies", antibodies are meant that are capable of binding to and/or neutralizing at least two, preferably at least three, four, or five different subtypes of influenza A viruses from phylogenetic group 2, or antibodies that are capable of binding to and/or neutralizing at least one group 1 influenza virus, and at least one group 2 influenza virus.

Influenza HA stem polypeptides, stably presenting the epitopes of the antibodies CR6261 and/or CR9114, have previously been described in WO2013/079473. At least some of these HA stem polypeptides were capable of stably presenting the epitope of CR6261 and/or CR9114 and were shown to be immunogenic in mice. Additional HA stem domain polypeptides, capable of stably presenting the epitope of CR6261 and/or CR9114 were described in WO2014/191435, WO2016/005480 and WO2016/005482. These stem polypeptides are based on HA of group 1 influenza A viruses and induce an immune response against group 1 influenza A viruses only.

In the research that led to the present invention it has been shown that the modifications that were introduced in the group 1 HA stem polypeptides did not lead to stable and trimeric stem polypeptides when HA of group 2 influenza viruses was used.

The present invention now provides group 2 influenza HA stem polypeptides comprising novel modifications which polypeptides can be well expressed in mammalian cells, are trimeric (e.g. as measured by AlphaLISA and SEC) and thermostable (e.g. as measured by, e.g. Dynamic Scanning Fluorimetry/Differential Scanning Calorimetry (DSF/DSC)). In addition, the group 2 stem polypeptides of the invention have been shown to induce neutralizing antibodies in vivo. In addition, the affinity of all tested broadly neutralizing antibodies (bnAb) to the polypeptides of the invention is less than 1 nM (as measured by Octet and ELISA), which is similar to the affinity of the antibodies to full-length HA, which clearly shows that the polypeptides mimic the stem of native, full length HA. The novel HA stem polypeptides furthermore can comprise but do not require any artificial linkers, tags, nor N- or C-terminal trimerization domains.

In a first aspect, the present invention thus provides monomeric influenza A hemagglutinin (HA) stem polypeptides, comprising an HA1 and a HA2 domain of an HA of a group 2 influenza A virus, said HA stem polypeptides comprising an amino acid sequence which comprises:

(i) a deletion of the head region from the HA1 domain;
(ii) a modification of the trimerization region in the HA2 domain;
(iii) at least two cysteine residues capable of forming at least one intramonomeric cysteine bridge;

and wherein in the amino acid sequence the amino acid at position 355 is W;

wherein the numbering of the amino acid positions in the HA stem polypeptides amino acid sequence is H3 numbering according to the HA nomenclature of Winter et al., corresponding to the full-length HA numbering of the reference strain H3N2 A/Aichi/2/68 (SEQ ID NO: 1).

The present invention thus provides HA stem polypeptides (i.e. headless HA polypeptides), comprising a modification of the trimerization region in the HA2 domain, preferably a modification in the C-helix, and at least 2 cysteine residues forming an intramonomeric disulphide bridge; wherein in the amino acid sequence the amino acid at position 355 is W; and wherein the numbering of the amino acid positions in the HA stem polypeptides amino acid sequence is H3 numbering according to the HA nomenclature of Winter et al. based on the full-length HA numbering of the reference strain H3N2 A/Aichi/2/68 (SEQ ID NO: 1).

In certain embodiments, the invention provides monomeric influenza A hemagglutinin (HA) stem polypeptides, comprising an HA1 and a HA2 domain of an HA of a group 2 influenza A virus, said HA stem polypeptides comprising an amino acid sequence which comprises:

(i) a deletion of the head region from the HA1 domain;
(ii) a modification of the trimerization region in the HA2 domain;
(iii) at least two cysteine residues capable of forming at least one intramonomeric cysteine bridge;

and wherein the polypeptides comprise a mutation of the amino acid at position 355 into W;

wherein the numbering of the amino acid positions in the HA stem polypeptides amino acid sequence is H3 numbering according to the HA nomenclature of Winter et al., corresponding to the full-length HA numbering of the reference strain H3N2 A/Aichi/2/68 (SEQ ID NO: 1).

In certain embodiments, the amino acid at position 355 is W and the amino acid at position 432 is I, or the amino acid at position 355 is W and the amino acid at position 432 is I and the amino acid at position 380 is I. In certain embodiments, the polypeptides comprise a mutation of the amino acid at position 355 into W and a mutation of the amino acid at position 432 into I, or a mutation of the amino acid at position 355 into W and a mutation of the amino acid at position 432 into I and a mutation of the amino acid at position 380 into I. According to the invention it has been shown that the presence of these amino acids increases trimer levels of the polypeptides of the invention.

In certain other embodiments, the amino acid at position 355 is (a mutation into) W and the amino acid at position 378 is (a mutation into) T, the amino acid at position 379 is (a mutation into) N and/or the amino acid at position 381 is (a mutation into) V. The presence of these amino acids has been shown to increase expression and binding of the broadly neutralizing antibodies.

In certain embodiments, the polypeptides further comprise an introduced glycosylation motif (NxT) for N-linked glycosylation at position 401 to shield potential neoepitopes within the B-loop. Thus, according to the invention, the polypeptides comprise a glycosylation motif (NxT) at positions 401-403 for N-linked glycosylation at position 401.

In particular embodiments, the present invention provides group 2 influenza A hemagglutinin (HA) stem polypeptides comprising an HA1 and an HA2 domain, wherein said HA stem polypeptides comprise an amino acid sequence which comprises, (i) a deletion of the head region in the HA1 domain, said deletion comprising at least the amino acid sequence from the amino acid corresponding to the amino acid at position 50 up to and including the amino acid corresponding to the amino acid at position 302;
(ii) a modification of the trimerization region in the HA2 domain, preferably a modification of the trimerization region in the C-helix, said trimerization region comprising the amino acid sequence from the amino acid corresponding to the amino acid at position 405 up to and including the amino acid corresponding to the amino acid at position 419;

(iii) a cysteine at the amino acid position corresponding to position 310 in combination with a cysteine at the position corresponding to position 422; or a cysteine at the amino acid corresponding to position 311 in combination with a cysteine at the position corresponding to position 422; or a cysteine at the amino acid position corresponding to position 308 in combination with a cysteine at the position corresponding to position 418, said cysteine residues (being capable of) forming an intramonomeric disulphide bridge; wherein in the amino acid sequence the amino acid at position 355 is W; and wherein the numbering of the amino acid positions in the HA stem polypeptide amino acid sequence is H3 numbering according to the HA nomenclature of Winter et al. (supra) based on the full-length HA numbering of the reference strain H3N2 A/Aichi/2/68 (SEQ ID NO: 1).

According to the present invention, it has surprisingly been found that group 2 influenza HA stem polypeptides having an amino acid sequence wherein the amino acid at position 355 is W, showed high expression levels in mammalian cells, had an increased propensity to trimerize and/or an increased thermostability, compared to previously generated group 2 HA stem polypeptides. In addition, the HA stem polypeptides of the invention induce a humoral and/or cellular immune response against group 2 influenza virus in vivo.

As is known to those skilled in the art, a full-length influenza hemagglutinin (HA0) typically comprises an HA1 domain and an HA2 domain. In addition, a full-length influenza hemagglutinin (HA0) typically comprises a stem domain and a head domain. The stem domain is formed by two segments of the HA1 domain and most or all of the HA2 domain. The two segments of the HA1 domain are separated, in the primary sequence, by the globular head domain. As described herein, the HA stem polypeptides of the invention comprise an amino acid sequence which comprises several modifications in the HA1 and/or HA2 domain, as compared to the amino acid sequence of the wild-type, full-length HA polypeptide (HA0), in particular the amino acid sequence of a group 2 HA. As used throughout this application the numbering of the amino acid positions in the HA stem polypeptide amino acid sequence is H3 numbering according to the HA nomenclature of Winter et al., supra (i.e. corresponding to the full-length HA numbering of the reference strain H3N2 A/Aichi/2/68 (SEQ ID NO: 1)).

According to the invention, at least part of the highly variable and immunodominant head in the HA1 domain of the influenza HA polypeptide, said part comprising at least the amino acid sequence starting with the amino acid at position 50 up to and including the amino acid at position 302, has been deleted from the HA1 domain of the full-length HA (HA0) protein to create a stem polypeptide, also called “mini-HA”. The remaining parts of the HA1 domain (i.e. the N-terminal segment of the HA1 domain and the C-terminal segment of the HA1 domain) are linked, either directly (i.e. without a linker) or through a linker of 1 to 10 amino acids. Thus, for example, when the amino acid sequence from the amino acid at position 50 up to and including the amino acid at position 302 is deleted, the amino acid at position 49 (the last amino acid of the N-terminal HA1 segment) is linked to the amino acid at position 303 (the first amino acid of the C-terminal HA1 segment), either directly, or through replacement of the deleted head region with a linker of 1 to 10 amino acids. The deletion of the amino acid sequence from the amino acid at position 50 up to and including the amino acid at position 302 is the minimal deletion in the HA1 domain. According to the invention, also a larger part of the HA1 domain may be deleted, e.g. the amino acid sequence starting with the amino acid at position 47 up to and including the amino acid at position 306, as shown in FIG. 1A, lower construct.

In a preferred embodiment, the deletion in the HA1 domain comprises at least the amino acid sequence from the amino acid at position 47 up to and including the amino acid at position 306. In this embodiment, the stem polypeptide thus comprises a N-terminal HA1 segment up till and including the amino acid at position 46, and a C-terminal HA1 segment starting from the amino acid at position 307 (dark grey parts in FIG. 1A).

In a preferred embodiment, the deletion in the HA1 domain consists of the amino acid sequence from the amino acid at position 47 up to and including the amino acid at position 306.

In some embodiments, the deletion in the HA1 domain has been replaced by a linking sequence of 1 to 10 amino acids.

In addition, as described herein, the HA stem polypeptides of the invention comprise a modification of the trimerization region in the HA2 domain, preferably a modification in the C-helix, to improve trimerization of the HA stem polypeptides after deletion of the head region. In certain preferred embodiments, said modification in the HA2 domain is a modification that enhances trimerization of the HA stem polypeptide.

In certain embodiments, said modification comprises the introduction of a heterologous trimerization domain in the C-helix. It is generally understood that the C-helix comprises the amino acid sequence from the amino acid at position 405 up to and including the amino acid at position 434 (H3 numbering). In a preferred embodiment, said heterologous trimerization domain has been introduced at a position corresponding to the amino acid sequence from the amino acid at position 405 up to and including the amino acid at position 419 (FIG. 1A). Thus, in certain embodiments, the original (wt) amino acid sequence in the HA2 domain from position 405 up to position 419 has been replaced by a heterologous trimerization sequence of the same length, i.e. with an identical number of amino acids.

In certain embodiments, the heterologous trimerization domain is a GCN4 sequence.

In certain preferred embodiments, the modified trimerization region (i.e. comprising the heterologous trimerization domain) comprises an amino acid sequence selected from the group consisting of:

(SEQ ID NO: 9)

$_{405}$RMKQIEDKIEEIESK$_{419}$ and (SEQ ID NO: 10)

$_{405}$PMKQIEDKIEEIESK$_{419}$

In some embodiments, at least one of the amino acids of the heterologous trimerization sequence has been mutated into C, enabling the formation of an intermonomeric cysteine bridge (as described below). Thus, in certain preferred embodiments, the trimerization region thus comprises an amino acid sequence selected from the group consisting of: $_{405}$RMKCIEDKIEEIESK$_{419}$ (SEQ ID NO: 11) and $_{405}$PMKCIEDKIEEIESK$_{419}$ (SEQ ID NO: 12). In a preferred embodiment, the trimerization region consists of the amino acid sequence $_{405}$PMKCIEDKIEEIESK$_{419}$ (SEQ ID NO: 12).

In certain embodiments, the modification comprises an alteration, preferably an optimization, of the heptad repeat sequence in the C-helix, preferably in the trimerization region comprising the amino acid sequence from the amino acid at position 405 up to and including the amino acid at position 419. A heptad repeat, denoted $[abcdefg]_n$, typically has hydrophobic residues at a and d, and polar/charged residues at e and g. These motifs are the basis for most coiled coil structures, which are a structural motif in proteins in which alpha-helices are coiled together like the strands of a rope (dimers and trimers are the most common types) (Ciani et al., 2010).

As a further modification, the HA stem polypeptides according to the invention comprise at least two cysteine residues (capable of) forming an intramonomeric (or intraprotomeric) cysteine (or disulphide) bridge. An engineered cysteine bridge can be introduced by mutating at least one (if the other is already a cysteine), but usually by mutating two residues that are spatially close into cysteine, which will spontaneously or by active oxidation form a covalent bond between the sulfur atoms of these residues. In a preferred embodiment, the polypeptides comprise a cysteine at position 310 and a cysteine at position 422, or a cysteine at the amino acid corresponding to position 311 in combination with a cysteine at the position corresponding to position 422; or a cysteine at the amino acid position corresponding to position 308 in combination with a cysteine at the position corresponding to position 418, enabling the formation of an intramonomeric cysteine bridge. In certain embodiments, the polypeptides comprise a mutation of the amino acid at the positions corresponding to the positions 310 and/or 422 into C, or a mutation of the amino acid at the positions 311 and/or 422 into C, or a mutation of the amino acid at the amino acid position corresponding to position 308 and/or 418 into C, said cysteine residues creating said intramonomeric cysteine bridge. These cysteine residues thus form an intramonomeric (or intraprotomeric) cysteine (or disulphide) bridge which stabilizes the protein. In a preferred embodiment, the polypeptides comprise a (mutation into) cysteine at position 310 and a (mutation into) cysteine at position 422 forming the at least one intramonomeric cysteine bridge.

The polypeptides according to the invention, typically comprise at least 4 native (i.e. naturally occurring) glycosylation (or glycan) motifs (NxT) for N-linked glycosylation, e.g. a glycan motif at positions: 8-10 ($_{8}NST_{10}$), positions 22-24 ($_{22}NGT_{24}$), positions 38-40 ($_{38}NAT_{40}$), and 483-485 ($_{483}NGT_{485}$) In certain embodiments, the polypeptides comprise at least one introduced glycan motif at position 401-403 for N-linked glycosylation at position 401, as described above. In certain embodiments, the polypeptides comprise at least one additional introduced glycosylation motif. Thus, in certain embodiments, the at least one additional N-linked glycosylation motif is present and/or introduced at positions 392-394 for N-linked glycosylation at position 392 and/or at positions 393-395 for N-linked glycosylation at position 393. In a preferred embodiment, the polypeptides comprise a glycosylation motif at position 401-403 for N-linked glycosylation at position 401 and a glycosylation motif at positions 393-395 for N-linked glycosylation at position 393.

In further embodiments, the amino acid at the position corresponding to the position 388 is M. In certain embodiments, the amino acid at the position corresponding to the position 388 is mutated into M. However, other amino acids at this position are also possible, including, but not limited to T, V, I, L, F, Y, W, H, K and R.

Furthermore, in certain embodiments, the polypeptides comprise an amino acid sequence, wherein:

the amino acid at position 31 is E and the amino acid at position 34 is V;

the amino acid at position 392 is S or P;

the amino acid at position 395 is T or P;

the amino acid at position 399 is S or P;

the amino acid at position 435 is N or R; and/or the amino acid at position 439 is Y.

Thus, in certain embodiments, the amino acid at position 31 is E and the amino acid at position 34 is V. In certain embodiments, the polypeptides comprise an amino acid sequence comprising a mutation of the amino acid at position 31 into E and a mutation of the amino acid at position 34 into V. According to the invention, it has been found that the presence of these amino acid residues (i.e. 31E and 34V) optimizes the hydrogen bonding network which is an important contributor to the stability of the polypeptides of the invention. The polypeptides may further comprise an amino acid sequence wherein the amino acid at position 392 is (a mutation into) S or P; the amino acid at position 395 is (a mutation ino) T or P; and/or the amino acid at position 399 is (a mutation into) S or P. The polypeptides of the invention thus may comprise one or more mutations in the so-called B-loop, which B-loop comprises the amino acid sequence starting from the amino acid at position 385 up to and including the amino acid at position 404 (see FIG. 1C). The B-loop mutations increase the solubility of the polypeptides by reducing the hydrophobicity. In certain preferred embodiments, the polypeptides, as compared to a wild-type HA polypeptide, thus comprise at least one additional mutation in the B-loop selected from the group consisting of:

a mutation of the amino acid corresponding to the amino acid at position 392 into S or P, preferably into S;

a mutation of the amino acid corresponding to the amino acid at position 395 into T or P; preferably into T; and a mutation of the amino acid corresponding to the amino acid at position 399 into S or P, preferably into P.

The polypeptides may further comprise a mutation of the amino acid corresponding to the amino acid at position 435 into N or R, preferably into N; and/or a mutation of the amino acid corresponding to the amino acid at position 439 into Y. These mutations are believed to optimize the trimer interface contributing to the trimer stability in solution.

It is again noted that as used herein the numbering of the amino acid positions is based on H3 numbering according to Winter et al. (1981). It is also again noted that the numbering of the amino acid positions as used herein is based on the numbering of the positions in a full length H3 HA polypeptide (HA0). Thus, as used herein, "an amino acid at position 434" refers to the amino acid at position 434 in H3 HA0. The numbering thus does not refer to the actual positions of the amino acids in the HA stem polypeptides of the invention, due to deletion of the head domain (see FIG. 15).

According to the invention, the HA stem polypeptide is a group 2 HA polypeptide. Thus, according to the invention, the modifications described herein have been introduced in HA of an influenza virus from phylogenetic group 2, such as an influenza virus comprising HA of the H3, H7 or H10 subtype, resulting in the HA stem polypeptides of the invention. In certain embodiments, the HA stem polypeptide is an H3 HA polypeptide. Thus, in certain embodiments, the HA stem polypeptide is derived from HA of an influenza A virus comprising HA of a H3 subtype, such as from the influenza virus the influenza virus A/Hong Kong/1/68 with the amino acid sequence SEQ ID NO:2, or A/Wisconsin/

67/2005 with the amino acid sequence of SEQ ID NO: 13, or A/Singapore/INFMH/16/0019/2016 with the amino acid sequence of SEQ ID NO: 14. It will be understood by the skilled person that the polypeptides of the invention may also be derived from HA of other H3 influenza A virus strains, including but not limited to A/Perth/16/2009 (SEQ ID NO: 15), A/Brisbane/10/2007 (SEQ ID NO: 16), or A/Panama/2007/1999 (SEQ ID NO: 17).

As described above, the stem polypeptides may or may not comprise a linking sequence of 1-10 amino acid residues replacing the deleted HA1 head sequence and thereby linking the two remaining HA1 parts. In certain embodiments, the linking sequence comprises from 1 to 5 amino acids. In certain embodiments, the linking sequence comprises 2, 3 or 4 amino acids. The linking sequence may be a heterologous linking sequence, i.e. an amino acid sequence that does not occur in naturally occurring, or wild-type, HA, such as, but not limited to GGGG and GPSG.

In certain embodiments, the linking sequence is a homologous linking sequence, i.e. an amino acid sequence derived from the deleted corresponding head region such as, but not limited to NPHR, GDPH, NGGS, GGSN, GSNA, GPGS, GSGF, GSG, GG, GGS, SGS, HPST, IPNI, GLSS, KPGD, DAPI, TPN, and TPNG.

In preferred embodiments, the polypeptides do not comprise a linking sequence.

As described above, cleavage of the influenza HA0 protein (in HA1 and HA2) is required for its activity, facilitating the entry of the viral genome into the target cells by causing the fusion of the host endosomal membrane with the viral membrane.

In certain embodiments, the polypeptides of the invention comprise the natural protease cleavage site. Thus, it is known that the Arg (R)-Gly (G) sequence spanning HA1 and HA2 (i.e. amino acid positions 329 and 330) is a recognition site for trypsin and trypsin-like proteases and is typically cleaved for hemagglutinin activation (FIG. 1A).

In certain embodiments, the polypeptides do not comprise a protease cleavage site. Thus, in certain preferred embodiments, the protease cleavage site has been removed by mutation of the amino acid residue at position 329 into any amino acid other than arginine (R) or lysine (K). In certain embodiments, the amino acid residue at position 329 is not arginine (R). In a preferred embodiment, the polypeptides comprise a mutation of the amino acid at position 329 into glutamine (Q). Thus, in certain preferred embodiments, the polypeptides of the invention comprise the cleavage site knock-out mutation R329Q to prevent putative cleavage of the molecule during production in vitro or in vivo after administration.

In other embodiments, the polypeptides comprise a polybasic cleavage site, e.g. a Furin cleavage site. Thus, the polypeptides can be cleaved by furin-like proteases within the cell to produce a cleaved mini-HA, similar to a natively folded and processed HA.

In certain embodiments, the polypeptides do not comprise a signal sequence. The signal sequence (sometimes referred to as signal peptide, targeting signal, localization signal, localization sequence, transit peptide, leader sequence or leader peptide) is a short peptide (usually 16-30 amino acids long) that is present at the N-terminus of most newly synthesized proteins that are destined towards the secretory pathway. Signal sequences function to prompt a cell to translocate the protein, usually to the cellular membrane. In many instances the amino acids comprising the signal peptide are cleaved off the protein once its final destination has been reached. In influenza HA, the signal sequences typically comprise the first 16 amino acids of the amino acid sequence of the full-length HA0 (corresponding to the amino acids from position −6 to position 10 according to H3 numbering, see FIG. 15).

In certain embodiments, the polypeptides comprise (part of) a signal sequence.

The polypeptides may comprise (part of) the wild-type signal sequence or may comprise (part of) alternative signal sequences, such as, but not limited to a signal sequence selected from the group of:

```
                                        (SEQ ID NO: 18)
MKTIIALSYIFCLALG;

                                        (SEQ ID NO: 19)
MKTIIALSYILCLVFA;

                                        (SEQ ID NO: 20)
MKTIIALSYILCLVFT;
and

                                        (SEQ ID NO: 21)
MKTIVALSYILCLVFA
```

In preferred embodiments, the (soluble) polypeptides do not comprise the signal sequence.

In a preferred embodiment, the polypeptides of the invention comprise (i) a deletion of the head region from the HA1 domain, said deletion consisting of the amino acid sequence from the amino acid at position 47 up to and including the amino acid at position 306, wherein the amino acid at position 46 is directly linked to the amino acid at position 307;

(ii) an introduction of a heterologous trimerization domain comprising the amino acid sequence $_{405}$PMKCIEDKIEEIESK$_{419}$ (SEQ ID NO:12) replacing the original amino acid sequence from the amino acid at position 405 up to and including the amino acid at position 419;

(iii) a (mutation into) cysteine at the amino acid position corresponding to position 310 in combination with a (mutation into) cysteine at the position corresponding to position 422;

(iv) introduced glycosylation motifs at positions: 393-395 (i.e. $_{393}$NQT$_{395}$) and 401-403 (i.e. $_{401}$NAT$_{403}$);

and wherein furthermore in the amino acid sequence:

(a) the amino acid at position 355 is (a mutation into) W;

(b) the amino acid at position 432 is (a mutation into) I and the amino acid at position 380 is (a mutation into) I;

(c) the amino acid at position 378 is (a mutation into) T and the amino acid at position 379 is (a mutation into) N and/or the amino acid at position 381 is (a mutation into) V;

(d) the amino acid at position 388 is (a mutation into) M;

(e) the amino acid at position 31 is (a mutation into) E and the amino acid at position 34 is (a mutation into) V;

(f) the amino acid at position 392 is (a mutation into) S;

(g) the amino acid at position 395 is (a mutation into) T;

(h) the amino acid at position 398 is (a mutation into) C;

(i) the amino acid at position 399 is (a mutation into) P;

(j) the amino acid at position 408 is (a mutation into) C;

(k) the amino acid at position 435 is (a mutation into) N;

(l) the amino acid at position 439 is (a mutation into) Y; and (m) the amino acid at position 329 is (a mutation into) Q;

wherein the numbering of the amino acid positions in the HA stem polypeptide amino acid sequence is H3 numbering corresponding to the full-length HA numbering of the reference strain H3N2 A/Aichi/2/68 (SEQ ID NO: 1).

In a particular embodiment, the HA1 and HA2 domains are from an influenza virus comprising HA of the H3 subtype, preferably from the influenza virus A/Hong Kong/1/68.

In certain preferred embodiments, the HA1 and HA2 domains are from an influenza virus comprising HA of the H3 subtype, preferably from the influenza virus A/Hong Kong/1/68, wherein one or more of the amino acids in said H3 HA1 and HA2 domains have been mutated into the corresponding amino acids of an H7 HA.

Thus, in certain embodiments, the HA1 and HA2 domains are from an influenza virus comprising HA of the H3 subtype, preferably from the influenza virus A/Hong Kong/1/68 to claim 19, wherein:

(a) the amino acid at position 25 is (a mutation into) K;
(b) the amino acid at position 367 is (a mutation into) Y;
(c) the amino acid at position 378 is (a mutation into) T;
(d) the amino acid at position 475 is (a mutation into) D;
(e) the amino acid at position 476 is (a mutation into) D; and/or
(f) the amino acid at position 479 is (a mutation into) A.

Although not wishing to be bound to theory, it is believed that by resurfacing a stabilized H3 derived stem polypeptide with desirable characteristics such as expression, folding, and thermostability towards H7 HA, an antibody response could be induced that could be more protective against the more distant H7 viruses, without having to switch completely to a less favorably behaving H7 derived stem polypeptide, i.e. which is more difficult to manufacture, has lower expression levels and lower stability.

In certain embodiments, the polypeptides comprise an HA2 domain including the transmembrane (TM) and cytoplasmic (CD) domain (said TM and CD domain comprising the amino acid sequence corresponding to the amino acid sequence starting with the amino acid corresponding to the amino acid at position 514 up to and including the amino acid corresponding to the amino acid at position 550 (H3 numbering)). Thus membrane-bound mini-HA polypeptides are provided.

To produce secreted soluble stem polypeptides, in certain embodiments the polypeptides do not comprise the transmembrane and cytoplasmic domain. Thus, in certain embodiments, the polypeptides comprise a truncated HA2 domain, in particular an HA2 domain that is truncated at the C-terminal end. A truncated HA2 domain according to the invention thus is shorter than the full length HA2 sequence, by deletion of one or more amino acid residues at the C-terminal end of the HA2 domain.

In certain embodiments, the C-terminal part of the HA2 domain starting with the amino acid corresponding to the amino acid at position 514 has been deleted, thus removing substantially the full transmembrane and cytoplasmic domain.

In certain embodiments, also a part of the C-terminal helix has been deleted. According to the present invention it has been found that even when a larger part of the HA2 domain is deleted, stable soluble HA stem polypeptides can be provided. Thus, in certain embodiments, the C-terminal part of the HA2 domain starting at amino acid position 500, 501, 502, 503, 504, 505, 506, 507, 508, 509, 510, 511, 512, 513, or 514 has been deleted (again numbering according to H3 numbering as described by Winter et al., supra) to produce a soluble polypeptide following expression in cells.

In a preferred embodiment, the C-terminal part of the HA2 domain starting from the position corresponding to 506 has been deleted.

Optionally, a heterologous amino acid sequence (i.e. an amino acid sequence that does not naturally occur in influenza HA) can be linked to the (truncated) HA2 domain.

Thus, in certain embodiments, His-tag sequences, e.g. HHHHHH (SEQ ID NO: 22) or HHHHHHH (SEQ ID NO: 23), or a FLAG tag DYKDDDDK (SEQ ID NO: 24), or C-tag EPEA (SEQ ID NO: 25), or a combination of these, have been linked to the C-terminal amino acid of the (optionally truncated) HA2 domain for detection and/or purification purposes. In certain embodiments, the heterologous amino acid sequence, such as the His-tag sequence, may be connected to the (truncated) HA2 domain through a linker. In certain embodiments, the linker may contain (part of) a proteolytic cleavage site, e.g. the amino acid sequence IEGR (SEQ ID NO: 26) or LVPRGS (SEQ ID NO: 27) to enzymatically remove the His-tag sequence after purification.

In certain embodiments, the heterologous amino acid sequence that is linked to the C-terminal amino acid of the (truncated) HA2 domain comprises an amino acid sequence selected from the group consisting of:

```
                                        (SEQ ID NO: 28)
GYIPEAPRDGQAYVRKDGEWVLLSTFL,

                                        (SEQ ID NO: 29.)
AAADYKDDDDKLVPRGSPGSGYIPEAPRDGQAYVRKDGEWVLLSTFLGH
HHHHH,

                                        (SEQ ID NO: 30)
AAADYKDDDDKPGGGGSGGGGSGGGGSHHHHHH (FLAG-GS
linker-His tag),,

                                        (SEQ ID NO: 31)
EGRAAAGGSGGGGSMVFTLEDFVGDWRQTAGYNLDQVLEQGGVSSLFQN
LGVSVTPIQRIVLSGENGLKIDIHVIIPYEGLSGDQMGQIEKIFKVVYP
VDDHHFKVILHYGTLVIDGVTPNMIDYFGRPYEGIAVFDGKKITVTGTL
WNGNKIIDERLINPDGSLLFRVTINGVTGWRLCERILAAAAWSHPQFEK
GAAWSHPQFEKGAAWSHPQFEK (Nanoluc-Strep tag),,

                                        (SEQ ID NO: 32)
EGRAAAGGSGGGGSMVFTLEDFVGDWRQTAGYNLDQVLEQGGVSSLFQN
LGVSVTPIQRIVLSGENGLKIDIHVIIPYEGLSGDQMGQIEKIFKVVYP
VDDHHFKVILHYGTLVIDGVTPNMIDYFGRPYEGIAVFDGKKITVTGTL
WNGNKIIDERLINPDGSLLFRVTINGVTGWRLCERILAGAAEPEA
(Nanoluc-C tag),,

                                         SEQ ID NO: 33)
EGRAAAWSHPQFEKGAAWSHPQFEKGAAWSHPQFEK (Strep tag),,

                                        (SEQ ID NO: 34)
EGRAAALPETGGGAAEPEA (Sortase-C tag),,

                                        (SEQ ID NO: 35)
SGRDYKDDDDKPGGGGSGGGGSGGGGSGGGGSGGGGSGGGGSGGGGSWS
HPQFEKGAAWSHPQFEKGAAWSHPQFEK (FLAG-GS linker-
Strep tag),,
```

-continued and

```
                                        (SEQ ID NO: 36)
EGRAAAEQKLISEEDLGGGGSGGGGSGGGGSGGGGSGGGGSGGGGSGGG

GSWSHPQFEKGAAWSHPQFEKGAAWSHPQFEK (Myc tag-GS

linker-Strep tag),.
```

In certain embodiments, a heterologous trimerization domain has been linked to the C-terminal amino acid of the (optionally truncated) HA2 domain, such as, but not limited to a "Foldon" trimerization domain (as described by Letarov et al. (1993); S-Guthe et al. (2004)).

In certain embodiments, the HA stem polypeptides of the invention comprise an amino acid sequence selected from SEQ ID NO: 40-44, 46-64, 66, 67, 69-97, 156-164, 169-181 and 189-212.

In a preferred embodiment, the polypeptide comprises an amino acid sequence selected from SEQ ID NO: 40-42, 207 and 210-212, preferably an amino acid sequence selected from 210-212, more preferably SEQ ID NO: 210.

In certain embodiments, the polypeptides are glycosylated when expressed in suitable cells (e.g. mammalian cells). The polypeptides of the invention typically contain 4 native glycosylation motifs (NxT), as described above. As also described above, according to the invention, in certain embodiments the polypeptides comprise at least one introduced glycosylation motif at position 401-403 for N-linked glycosylation at position 401. The polypeptides preferably comprise an additional introduced glycosylation motif at position 393-395 for N-linked glycosylaton at position 393.

In a further aspect, the invention provides multimeric, preferably trimeric, HA stem polypeptides. In order to obtain stable trimeric HA stem polypeptides, the polypeptides of the invention preferably comprise at least two cysteine residues (capable of) forming an intermonomeric (also referred to as interprotomeric) cysteine bridge. Thus, in certain embodiments, the polypeptides comprise a cysteine at the position corresponding to position 396 in combination with a cysteine at the position corresponding to position 408, or a cysteine at the position corresponding to position 397 in combination with a cysteine at the position corresponding to position 408, or a cysteine at the position corresponding to position 398 in combination with a cysteine at the position corresponding to position 408, or a cysteine at the position corresponding to position 398 in combination with a cysteine at the position corresponding to position 405.

In certain embodiments, the polypeptides comprise a mutation of the amino acid at position 396 into C and a mutation of the amino acid at position 408 into C; or a mutation of the amino acid at position 397 into C and a mutation of the amino acid at position 408 into C; or a mutation of the amino acid at position 398 into C and a mutation of the amino acid at position 408 into C; or a mutation of the amino acid at position 398 into C and a mutation of the amino acid at position 405 into C; creating an intermonomeric cysteine bridge between the cysteine at position 396 of a first monomer and the cysteine at position 408 of a second monomer; or between the cysteine at position 397 of a first monomer and the cysteine at position 408 of a second monomer; or between the cysteine at position 398 of a first monomer and the cysteine at position 408 of a second monomer; or between the cysteine at position 398 of a first monomer and the cysteine at position 405 of a second monomer. It is noted that, in some embodiments, the amino acid at position 405 or 408 are within the heterologous trimerization sequence.

In a preferred embodiment, the polypeptides comprise a cysteine at position 398 and a cysteine at position 408, creating an intermonomeric cysteine bridge between the cysteine at position 398 of a first monomer and the amino acid at position 408 of a second monomer.

The invention further provides nucleic acid molecules encoding the influenza HA stem polypeptides of the invention. It is understood by a skilled person that numerous different nucleic acid molecules can encode the same polypeptide as a result of the degeneracy of the genetic code. It is also understood that skilled persons may, using routine techniques, make nucleotide substitutions that do not affect the polypeptide sequence encoded by the polynucleotides described to reflect the codon usage of any particular host organism in which the polypeptides are to be expressed. Therefore, unless otherwise specified, a "nucleic acid molecule encoding an amino acid sequence" includes all nucleotide sequences that are degenerate versions of each other and that encode the same amino acid sequence.

In certain embodiments, the nucleic acid molecules encoding the influenza HA stem polypetides are codon optimized for expression in mammalian cells, such as human cells. Methods of codon-optimization are known and have been described previously (e.g. WO 96/09378).

In certain embodiments, the nucleic acid molecules encoding the influenza HA stem polypeptide comprise a nucleic acid sequence selected from SEQ ID NO: 208 and SEQ ID NO: 209.

The influenza hemagglutinin stem domain polypeptides can be prepared according to any technique deemed suitable to one of skill, including techniques described below. Thus, the polypeptides of the invention may be synthesized as DNA sequences by standard methods known in the art and cloned and subsequently expressed, in vitro or in vivo, using suitable restriction enzymes and methods known in the art.

The invention further relates to vectors comprising a nucleic acid molecule encoding a polypeptide of the invention. In certain embodiments, a nucleic acid molecule according to the invention thus is part of a vector, e.g. a plasmid. Such vectors can easily be manipulated by methods well known to the person skilled in the art and are for instance designed to be capable of replication in prokaryotic and/or eukaryotic cells. The vector used can be any vector that is suitable for cloning DNA and can be used for transcription of the nucleic acid of interest. When host cells are used, it is preferred that the vector is an integrating vector. Alternatively, the vector may be an episomally replicating vector. The person skilled in the art is capable of choosing suitable expression vectors and inserting the nucleic acid sequences of the invention in a functional manner. To obtain expression of nucleic acid sequences encoding polypeptides, it is well known to those skilled in the art that sequences capable of driving expression can be functionally linked to the nucleic acid sequences encoding the polypeptide, resulting in recombinant nucleic acid molecules encoding a protein or polypeptide in expressible format. Sequences driving expression may include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al, 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001), actin promoter, an immunoglobulin promoter, heat shock promoters, and the like. Testing for promoter function and strength of a promoter is a matter of routine for a person skilled in the art, and in general may for instance encompass cloning a test gene such as lacZ, luciferase, GFP, etc. behind the promoter sequence, and test for expression of the test gene. Of course, promoters may be altered by deletion, addition, mutation of sequences therein, and tested for functionality, to find new, attenuated, or improved promoter sequences. According to the present invention, strong promoters that give high transcription levels in the eukaryotic cells of choice are preferred.

The constructs may be transfected into eukaryotic cells (e.g. plant, fungal, yeast or animal cells) or suitable prokaryotic expression systems like *E. coli* using methods that are well known to persons skilled in the art. In some cases, a suitable 'tag' sequence (such as for example, but not limited to, a his-, myc-, strep-, sortase, c-, or flag-tag) or complete protein (such as for example, but not limited to, maltose binding protein or glutathione S transferase) may be added to the sequences of the invention, as described above, to allow for purification and/or identification of the polypeptides from the cells or supernatant. Optionally a sequence containing a specific proteolytic site can be included to afterwards remove the tag by proteolytic digestion.

In preferred embodiments, the polypeptides are produced in mammalian cells.

Purified polypeptides can be analyzed by spectroscopic methods known in the art (e.g. circular dichroism spectroscopy, Fourier Transform Infrared spectroscopy and NMR spectroscopy or X-ray crystallography) to investigate the presence of desired structures like helices and beta sheets. ELISA, AlphaLISA, label free biolayer interferometry (Octet) and FACS and the like can be used to investigate binding of the polypeptides of the invention to the broadly neutralizing antibodies, such as CR8020 and/or CR9114. Thus, polypeptides according to the invention having the correct conformation can be selected. Trimeric content can be analyzed for example by using SDS gel electrophoresis under non-reducing conditions, size exclusion chromatography in the presence of antibody Fab fragments of broadly neutralizing antibodies, such as CR8020 and/or CR9114, as well as AlphaLISA using differently labled antibodies. Stability of the polypeptides can be assessed as decribed above after temperature stress, freeze-thaw cycles, increased protein concentration, or agitation. The melting temperature of the polypeptide can further be assed by Differential Scanning Fluorimetry (DSF) and/or Differential Scanning Calorimetry (DSC).

In certain embodiments, the nucleic acid is inserted in a recombinant vector which can be used as a vaccine component. Preferably, the recombinant vector is a human adenovirus, e.g. a human adenovirus of serotype 26 (Ad26). The present invention thus also provides recombinant adenoviral vectors comprising a nucleic acid molecule encoding a HA stem polypeptide according to the invention. In a preferred embodiment, the nucleic acid molecule encoding the stem polypeptide comprises a nucleic acid sequence selected from the group consisting of SEQ ID NO: 208 and SEQ ID NO: 209.

The preparation of recombinant adenoviral vectors is well known in the art. The term 'recombinant' for an adenovirus, as used herein implicates that it has been modified by the hand of man, e.g. it has altered terminal ends actively cloned therein and/or it comprises a heterologous gene, i.e. it is not a naturally occurring wild type adenovirus. In certain embodiments, an adenoviral vector according to the invention is deficient in at least one essential gene function of the E1 region, e.g. the Ela region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913.

In certain embodiments, the adenovirus is a human adenovirus of the serotype 26 or 35.

The invention further provides pharmaceutical composition comprising a polypeptide, a nucleic acid, and/or a vector according to the invention, and pharmaceutically acceptable carrier. In particular, the invention relates to pharmaceutical compositions comprising a therapeutically effective amount of the polypeptides, nucleic acids, and/or vectors of the invention. The pharmaceutical compositions further comprise a pharmaceutically acceptable carrier. In the present context, the term "pharmaceutically acceptable" means that the carrier, at the dosages and concentrations employed, will not cause unwanted or harmful effects in the subjects to which they are administered. Such pharmaceutically acceptable carriers and excipients are well known in the art (see for example Remington: The Science and Practice of Pharmacy—22nd edition, Loyd V. Ed. Allen, Pharmaceutical Press [2013]; Pharmaceutical Formulation Development of Peptides and Proteins, S. Frokjaer and L. Hovgaard, Eds, Taylor & Francis [2000]; Remington: Essentials of Pharmaceutics, Linda Felton, Pharmaceutical Press [2013], and Handbook of Pharmaceutical Excipients, 3rd edition, A. Kibbe, Ed., Pharmaceutical Press [2000]). The term "carrier" refers to a diluent, excipient, or vehicle with which the polypeptides, nucleic acids, and/or vectors are administered. Saline solutions and aqueous dextrose and glycerol solutions can e.g. be employed as liquid carriers, particularly for injectable solutions.

The polypeptides or nucleic acid molecules of the invention may also be administered in combination with or conjugated to nanoparticles, such as e.g. polymers, liposomes, virosomes, virus-like particles. The polypeptides, or nucleci acid molecules, may be combined with, encapsidated in or conjugated (e.g. covalently linked or adsorbed) to the nanoparticles.

The invention further relates to polypeptides, nucleic acids, and/or vectors as described herein for use as a medicament.

The invention in particular relates to polypeptides, nucleic acids, and/or vectors as described herein for use in inducing an immune response against an influenza virus, preferably a group 2 influenza virus.

The invention also relates to methods for inducing an immune response against an influenza A virus in a subject in need thereof, the method comprising administering to said subject, a therapeutically effective amount of a polypeptide, nucleic acid molecule and/or vector as described herein. A subject according to the invention preferably is a mammal that is capable of being infected with an influenza virus, or otherwise can benefit from the induction of an immune response, such subject for instance being a rodent, e.g. a mouse, a ferret, or a domestic or farm animal, or a non-human-primate, or a human. Preferably, the subject is a human subject.

In certain embodiments, the invention provides methods for inducing an immune response against a group 2 influenza A virus. The immune response may comprise a humoral (i.e. the induction of influenza virus neutralizing antibodies) and/or a cellular immune response. In certain embodiments, the invention provides methods for inducing an immune response against at least one, two, three, four, five or six subtypes of a group 2 influenza virus. In certain embodiments, the invention provides methods for inducing an immune response against an influenza virus comprising HA of the H3 subtype.

In certain embodiments, the immune response induced is effective to prevent an influenza virus infection caused by a group 2 influenza A virus, such as an influenza A virus comprising HA of the H3 subtype, and/or an influenza A virus comprising HA of the H7 subtype. In certain embodiments, the immune response induced is effective to prevent an influenza virus infection caused by an influenza A virus comprising HA of the H3 subtype. In certain embodiments, the immune response induced is effective to prevent an influenza virus infection caused by an influenza A virus comprising HA of the H3 and H7 subtype.

The invention further relates to polypeptides, nucleic acids, and/or vectors as described herein for use as an influenza vaccine, in particular for use as a vaccine against influenza caused by a group 2 influenza virus strain.

In certain embodiments, the polypeptides, nucleic acid molecules and/or vectors of the invention are administered in combination with an adjuvant. The adjuvant for may be administered before, concomitantly with, or after administration of the polypeptides, nucleic acid molecules and/or vectors of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), optionally formulated in a liposome, CpG-motif containing oligonucleotides, ADP-ribosylating bacterial toxins or mutants thereof, such as *E. coli* heat labile enterotoxin LT, cholera toxin CT, pertussis toxin PT, or tetanus toxoid TT, Matrix M, or combinations thereof. In addition, known immunopotentiating technologies may be used, such as fusing the polypeptides of the invention to proteins known in the art to enhance immune response (e.g. tetanus toxoid, CRM197, rCTB, bacterial flagellins or others) or including the polypeptides in virosomes, or combinations thereof.

Administration of the polypeptides, nucleic acid molecules, and/or vectors according to the invention can be performed using standard routes of administration. Non-limiting examples include parenteral administration, such as intravenous, intradermal, transdermal, intramuscular, subcutaneous, etc, or mucosal administration, e.g. intranasal, oral, and the like. The skilled person will be capable to determine the various possibilities to administer the polypeptides, nucleic acid molecules, and/or vectors according to the invention, in order to induce an immune response.

In certain embodiments, the polypeptide, nucleic acid molecule, and/or vector is administered more than one time, i.e. in a so-called homologous prime-boost regimen. The administration of the second dose can be performed, for example, one week after the administration of the first dose, two weeks after the administration of the first dose, three weeks after the administration of the first dose, one month after the administration of the first dose, six weeks after the administration of the first dose, two months after the administration of the first dose, 3 months after the administration of the first dose, or 4 months or more after the administration of the first dose, etc, up to several years after the administration of the first dose of the polypeptide, nucleic acid molecule, and/or vector of the invention. It is also possible to administer the polypeptides, nucleic acid molecules and/or vectors more than twice, e.g. three times, four times, etc, so that the first priming administration is followed by more than one boosting administration.

The polypeptides, nucleic acid molecules, and/or vectors may also be administered, either as prime, or as boost, in a heterologous prime-boost regimen.

The invention further provides methods for preventing an influenza virus disease in a subject in need thereof, comprising administering to said subject a therapeutically effective amount of a polypeptide, a nucleic acid molecule and/or a vector as described herein. A therapeutically effective amount refers to an amount of the polypeptide, nucleic acid, and/or vector that is effective for preventing, ameliorating and/or treating a disease or condition resulting from infection by an influenza virus. Prevention encompasses inhibiting or reducing the spread of influenza virus or inhibiting or reducing the onset, development or progression of one or more of the symptoms associated with infection by an influenza virus. Ameliorion as used in herein may refer to the reduction of visible or perceptible disease symptoms, viremia, or any other measurable manifestation of influenza infection.

A subject in need of treatment includes subjects that are already inflicted with a condition resulting from infection with an influenza virus, as well as those in which infection with influenza virus is to be prevented. The polypeptides, nucleic acids and/or vectors of the invention thus may be administered to a naive subject, i.e., a subject that does not have a disease caused by an influenza virus infection or has not been and has not been currently infected with an influenza virus infection, or to subjects that already have been infected with an influenza virus.

In an embodiment, prevention may be targeted at patient groups that are susceptible to influenza virus infection. Such patient groups include, but are not limited to e.g., the elderly (e.g. ≥50 years old, ≥60 years old, and preferably ≥65 years old), the young (e.g. ≤5 years old, ≤1 year old), hospitalized patients, immunocompromised subjects, and patients who have been treated with an antiviral compound but have shown an inadequate antiviral response.

The polypeptides, nucleic acid molecules and/or vectors of the invention may be administered to a subject in combination with one or more other active agents, such as alternative influenza vaccines, monoclonal antibodies, antiviral agents, antibacterial agents, and/or immunomodulatory agents. The one or more other active agents may be beneficial in the treatment and/or prevention of an influenza virus disease or may ameliorate a symptom or condition associated with an influenza virus disease. In some embodiments, the one or more other active agents are pain relievers, anti-fever medications, or therapies that alleviate or assist with breathing.

The invention is further illustrated in the following examples and figures. The examples are not intended to limit the scope of the invention in any way.

EXAMPLES

Example 1: HA Stem-Based Polypeptides—Structure and Design Elements of Preferred Polypeptides of the Invention, UFV180088, UFV 180089 and UFV180090

The polypeptide UFV180088, representing the stem (or stalk) of the uncleaved influenza virus haemagglutinin ($HA_0$) from the H3 influenza virus A/Hong Kong/1/68, was created by deleting (at least part of) the head domain from HA1, in particular the region comprising the amino acids starting from position 47 up to and including the amino acid at position 306 (FIGS. 1A and 1B). It is noted that for the numbering of the amino acid positions in the current invention the H3 numbering by Winter el al. supra is used. The main structural elements of the polypeptide of the invention (mini-HA) including the A-helix, the B-loop, and the C-, D-, and E-helix are indicated in FIG. 1C.

When expressed as soluble ectodomain the polypeptides of the invention are C-terminally truncated after the last helix (which ends at position 499). UFV180088 was truncated at position 506, i.e. the C-terminal part of the HA sequence starting with the amino acid at position 506 was deleted.

The polypeptide of the invention, UFV 180088, as described in this example was made resistant to protease cleavage by a mutation of the natural monobasic cleavage site amino acid arginine (R) at position 329 (i.e. the C-terminal amino acid of the HA1 domain, see FIG. 1) into, e.g. glutamine (Q). In contrast to the native full-length HA, polypeptides of the invention containing mutation R329Q cannot be cleaved anymore and cannot undergo the associated conformational change that buries the hydrophobic fusion peptide in the interior of the protein.

The removal of the head domain leaves a part of the HA molecule that was previously shielded from the aqueous solvent exposed. For this reason, several amino acid residues in the B-loop, i.e. the region comprising the amino acids 385-404 (FIG. 1C) were mutated as compared to the parental wild-type full-length HA from A/Hong Kong/1/1968 to stabilize the stem polypeptide. In particular, the amino acid at position 388 was mutated into M, and the amino acid at position 392 was mutated into S.

Further, to reduce the helix propensity of the B-loop, a proline was introduced, in particular a proline at position 399. Lastly, to shield potential neoepitopes within the B-loop one or two N-linked glycosylation motives (i.e. NxT) were introduced in the B-loop, in particular a glycosylation motif at positions 393-395 for N-linked glycosylation at position 393 and a glycosylation motif at positions 401-403 for N-linked glycosylation at position 401.

Furthermore, to facilitate stable trimerization of the soluble HA stem derived polypeptide, the GCN4 derived trimerization domain sequence 405PMKCIEDKIEE-$IESK_{419}$ (SEQ ID NO: 12) was introduced in the $HA_2$ domain, in particular in the C-helix, replacing the original (i.e. wild type) amino acid sequence from the amino acid at position 405 up to and including the amino acid at position 419.

In addition, cysteines (if not yet present) were introduced at position 398 and 408 (it is noted that position 408 is located in the introduced GCN4 sequence) to form interprotomeric disulfide bridges between the cysteine at position 398 of a first monomer and the cysteine at position 408 of an adjacent monomer to covalently link the monomers into a trimeric stem polypeptide.

To further stabilize and increase the expression of the polypeptide UFV180088, as well as to ensure correct folding similar to the stem of the wild type full-length HA, additional mutations were introduced in the polypeptide, in particular at positions 31 (D31E), 34 (134V), 310 (K310C), 355 (H355W), 378 (N378T), 379 (379N), 380 (K3801), 381 (L381V), 422 (S422C), 432 (E4321), 435 (H435R), and 439 (L439Y) (FIG. 1D).

Variants of the polypeptide UFV180088 were prepared, i.e. UFV 180089 and UFV180090. These polypeptides comprised additional mutations compared to UFV180088. Thus, UFV180089 comprised the additional mutations (as compared to UFV180088) L367Y, N475D, A476D and E479A. UFV180090 comprised the additional (as compared to UFV 180088) mutations L25K, L367Y, A476D and E479A, and did not comprise the mutations G379N and L381V.

Example 2: Expression, Purification and In Vitro Characterization of the Trimeric Polypeptides of the Invention Protein Expression in Mammalian Cells DNA fragments encoding the polypeptides of the invention UFV180088, UFV180089 and UFV180090 (as described in Example 1) were synthesized (Genscript) and cloned in the pcDNA2004 expression vector (in-house modified pcDNA3 plasmid with an enhanced CMV promotor). The polypeptides were produced in ExpiCHO suspension cells cultured in ExpiCHO™ expression medium by transient transfection of respective industrial grade DNA using ExpiFectamine™ transfection reagent (Gibco, ThermoFisher Scientific) according to the manufacturer's protocol. ExpiFectamine CHO Enhancer and ExpiCHO Feed (Gibco, ThermoFisher Scientific) were added to the cell cultures 1 day post transfection according to the manufacturer's protocol. Culture supernatants containing the secreted polypeptides were harvested between day 7-11 and clarified by centrifugation, followed by filtration over a 0.2 m bottle top filter (Corning).

Protein Purification

The polypeptides were purified by means of a two-step protocol. First, the harvested and clarified culture supernatant was loaded on a HiScale 16/20 column (GE Healthcare) packed with an affinity resin (Capture Select) that consists of a C-tag specific single domain antibody, immobilized on Agarose based bead (ThermoFisher Scientific). This resin is highly specific for the C-tag, a four-residue acid peptide (E-P-E-A (SEQ ID NO: 25) that was fused to the C-terminus of the polypeptides. The amount of applied polypeptide in the harvested culture supernatant was determined by OCTET prior to purification (see paragraph; Culture supernatant and, purified protein analysis). Elution of the C-tagged proteins was performed using a TRIS buffer containing 2M $MgCl_2$. Based on the UV signal (A280) the elution fractions were pooled and filtered through a Millex-GV 0.22 μm filter membrane (Merck Millipore). Subsequently, the collected elution peak was applied to a Superdex 200 pg 26/60 column (GE Healthcare) equilibrated in running buffer (20 mM Tris, 150 mM NaCl, pH7.8) to remove potential multimeric and/or monomeric protein impurities. The trimer fractions were pooled, and purity was assessed by analytical SEC-MALS.

Culture Supernatant and Purified Protein Analysis

As described above, the level of expressed stem polypeptide in the harvested culture supernatant was assessed prior to purification through Bio-Layer Interferometry using the OCTET platform (ForteBio). In short, CaptureSelect™ Biotin Anti-C-tag conjugate (ThermoFisher Scientific) was immobilized on Streptavidin (SA) biosensors (ForteBio) after which a standard curve was established by assessing the binding shift of a dilution series of a well-defined reference batch of purified homologous polypeptide. Subsequently, the binding shift of pre-diluted harvested culture supernatants (10 and 30-fold diluted in kinetics buffer (ForteBio)) containing the polypeptides of the invention was measured and the concentration of the polypeptides was calculated using the established standard curve.

The trimer content of the polypeptides in the culture supernatant and of purified polypeptides was assessed by Size Exclusion Chromatography Multi Angle Light Scattering (SEC-MALS) analysis using a High Performance Liquid Chromatography (HPLC) Infinity 1260 series setup (Agilent). Of each purified polypeptide 40 μg was run (1 mL/min.) over a TSK gel G3000SWx1 column (Sigma-Aldrich) and the molar mass of the eluted material was measured by a miniDAWN Treos Multi Angle Light Scattering detector and Optilab T-rEx differential refractometer (Wyatt Technology). The data were analyzed by the Astra 6 software package (Wyatt Technology) and molecular weight calculations were derived from the refractive index signal.

The correct folding of the purified polypeptides of the invention was assessed by ELISA ($EC_{50}$ values of antibody binding). To this end, the stem polypeptides were coated at a concentration of 10 nM and incubated with a dilution series of monoclonal antibody (mAb) CR9114 (as described in WO2013/007770) using 70 nM as starting concentration. Antibody binding was determined by incubation with a secondary anti-human Fc HRP antibody (Mouse anti Human IgG, Jackson ImmunoResearch) and was visualized by addition of POD substrate. Read out was performed using the EnSight™ multimode plate reader (PerkinElner). The $EC_{50}$ values were calculated using the Spotfire suite (Tibco Software Inc.).

Thermostability of the purified polypeptides was determined by Differential Scanning Fluorimetry (DSF) by monitoring the fluorescent emission of Sypro Orange Dye (ThermoFisher Scientific) added to a 6 μg polypeptide solution. Upon gradual increase of the temperature, from 25° C. to 95° C. (60° C. per hour), the polypeptides unfold and the fluorescent dye binds to the exposed hydrophobic residues leading to a characteristic change in the emission. The melting curves were measured using a ViiA7 real time PCR machine (Applied BioSystems) and the $Tm_{50}$ values were calculated by the Spotfire suite (Tibco Software Inc.). The $Tm_{50}$ values represent the temperature at which 50% of the protein has been unfolded and thus are a measure for the temperature stability of the polypeptides.

Results and Conclusion

The expression level and trimer content of the polypeptides were determined in two independent 70 mL ExpiCHO transfections at day 9 post transfection (FIG. 2A). All polypeptides expressed well. The H3N2 A/Hong Kong/1/68 derived polypeptide UFV180088 expressed at a level of ~700 mg/L culture supernatant. Polypeptide UFV180089 and UFV180090, similar in design to polypeptide UFV180088, and comprising further alterations in surface amino acids (i.e. changing the surface to more closely resemble an H7 HA): L367Y, N475D, A476D and E479A and alterations L25K, L367Y, N379G, V381L, A476D, and E479A, expressed at a level of ~500 mg/L and ~350 mg/L respectively.

The analysis of crude cell culture supernatant by analytical SEC (FIG. 2B, left panel) indicated the presence of a well-defined soluble trimeric polypeptide population (~8.3 minutes retention time). Similar analysis also indicated that the two-step purification protocol yields very pure trimeric polypeptide (FIG. 2B, right panel). Furthermore, the trimeric polypeptides were correctly folded and displayed the epitope of broadly neutralizing monoclonal antibody CR9114. This is evident by ELISA analysis showing strong CR9114 binding with $EC_{50}$ values below 1 nM (FIG. 2C). Additionally, the temperature at which 50% of the polypeptide unfolds was determined by DSF. All polypeptides were temperature stable and displayed $Tm_{50}$ values of 66.6° C., 64.6° C. and 60.9° C. for UFV180088, UFV180089 and UFV180090, respectively (FIG. 2D).

In conclusion, the polypeptides of the invention described in this example expressed well and were purified from the cell culture supernatant as properly folded trimeric polypeptides.

Example 3: Characterization of Single Point Mutations in Polypeptides of the Invention (SEC Profiles)

Designs

To assess the contribution of mutations introduced in the trimeric polypeptides of the invention (schematically shown in FIG. 1), amino acids were mutated back to the original amino acids in the backbone strain A/Hong Kong/1/1968 (Table 1, FIG. 3A), starting from polypeptide UFV 180141 (comprising all features of UFV180088, i.e.: a deletion of the head region starting from the amino acid at position 47 up to an including the amino acid at position 306 (i.e. deletion 47-306), an introduced trimerization region in the HA2 domain at positions 405-419 (it is noted that the introduced GCN4 sequence is slightly different as compared to UFV180088: i.e. $405RMKCIEDKIEEIESK_{419}$ (SEQ ID NO: 11), comprising a cysteine at the amino acid position corresponding to position 310 in combination with a cysteine at the position corresponding to position 422 (forming an intra-protomeric disulphide bridge), comprising a Q at position 329 (protease cleavage resistant), and wherein the amino acid at position 355 is W; and the amino acid at position 378 is T and the amino acid at position 379 is N and the amino acid at position 381 is V; and comprising a glycan motif at positions 401-403), and comprising a cysteine at the position corresponding to position 398 in combination with a cysteine at the position corresponding to position 408 (in the GCN4 sequence), forming an inter-protomeric disulphide bridge, and comprising an M at position 388, an E at position 31 and a V at position 34, an I at positions 380 and 432, an S at position 392, a T at position 395, an S at position 399, and N at position 435 and a Y at position 439). Like UFV180088, the polypeptide UFV180141 was truncated after the amino acid at position 506. However, UFV180141 does not comprise the additional glycosylation motif at position 393-395, the B-loop stabilizing prolines at position 405 and carries 399S instead of 399P. In addition, UFV180088 comprised the C-terminal tag EPEA (SEQ ID NO: 25), whereas UFV180141 comprised a different C-terminal tag.

An exception is the C408Q mutation, which is not a mutation back to wild type H3, but which was mutated back to the introduced GCN4 trimerization domain sequence (introduced at position 405-419). The impact of the absence of specific mutations was assessed by analytical SEC.

An alternative approach to assess the beneficial effect of selected mutations is their stepwise introduction into a minimal design polypeptide, i.e. UFV180647, comprising the following features: a deletion of the head region starting from the amino acid at position 47 up to an including the amino acid at position 306 (i.e. deletion 47-306), an introduced trimerization region in the HA2 domain, i.e. $_{405}$RMKCIEDKIEEIESK$_{419}$ (SEQ ID NO:11) introduced at positions 405-419; a cysteine at the amino acid position corresponding to position 310 in combination with a cysteine at the position corresponding to position 422 (forming an intra-protomeric disulphide bridge), comprising a Q at position 329 (protease cleavage resistant), and wherein the amino acid at position 355 is W; the amino acid at position 378 is T, the amino acid at position 379 is N and the amino acid at position 381 is V; and comprising a glycan motif at positions 401-403, and comprising a cysteine at the position corresponding to position 398 in combination with a cysteine at the position corresponding to position 408 (forming an inter-protomeric disulphide bridge), and comprising an M at position 388. Constructs with added mutations were analyzed by analytical SEC and compared to the minimal design polypeptide (Table 2, FIG. 3C).

TABLE 1

Reversion of selected mutations back to wild type A/Hong Kong/1968 residues in stabilized trimeric polypeptide UFV180141

| UFV# | Mutation(s) |
|---|---|
| UFV180141 | As described above |
| UFV180192 | C398E, C408Q (interprotomeric disulfide bridge) |
| UFV180193 | W355H |
| UFV180194 | GCN4 deletion |
| UFV180195 | C310K, C422S (intramolecular disulfide bridge) |
| UFV180196 | T378N, N379G, V381L (A-helix mutations) |
| UFV180197 | I380K, 1432E |
| UFV180198 | I380K |
| UFV180199 | I432E |
| UFV180200 | M388T |
| UFV180201 | N401E, A402V, T403E (B-loop glycan) |
| UFV180202 | T395I |
| UFV180203 | N435H |
| UFV180204 | Y439L |
| UFV180205 | E31D, V34I |
| UFV180206 | S392F |
| UFV180207 | S399F |

TABLE 2

Stepwise introduction of selected mutations to the minimal design polypeptide UFV180647

| UFV# | Mutations |
|---|---|
| UFV180647 | As described above |
| UFV181034 | K380I, E432I |
| UFV181036 | K380I, E432I, H435N |
| UFV181038 | K380I, E432I, H435N, L439Y |
| UFV181040 | Stabilized B-Loop (F392S, H393N, I395T, F399P, R405P) |
| UFV181042 | K380I, E432I, stabilized B-Loop (F392S, H393N, I395T, F399P, R405P) |

Protein Expression in Mammalian Expi293F Cells

DNA fragments encoding the polypeptides listed in Table 1 and 2 were synthesized as described in Example 2. The polypeptides, including a C-terminal FLAG-Linker-His tag for screening purposes and purification, were produced in the eukaryotic suspension cell line Expi293F at micro scale (200 μL). In short, cells were transiently transfected with industrial grade DNA in 96-halfdeepwell plates (System Duetz) at a cell density of 2.5E+06 vc/mL using the Expi-Fectamine 293 transfection kit (Gibco, ThermoFisher Scientific) and incubated in shaker flasks containing Expi293 Expression Medium (Gibco, ThermoFisher Scientific) at 37° C., 250 rpm, 8% $CO_2$ and 75% humidity. Cell culture supernatants containing secreted polypeptides were harvested at day 3 and clarified by centrifugation (10 min. at 400 xg) followed by filtration (96-well Filter plates, 0.22 μm PVDF membrane, Corning).

Culture Supernatant Analysis

Figure 3:
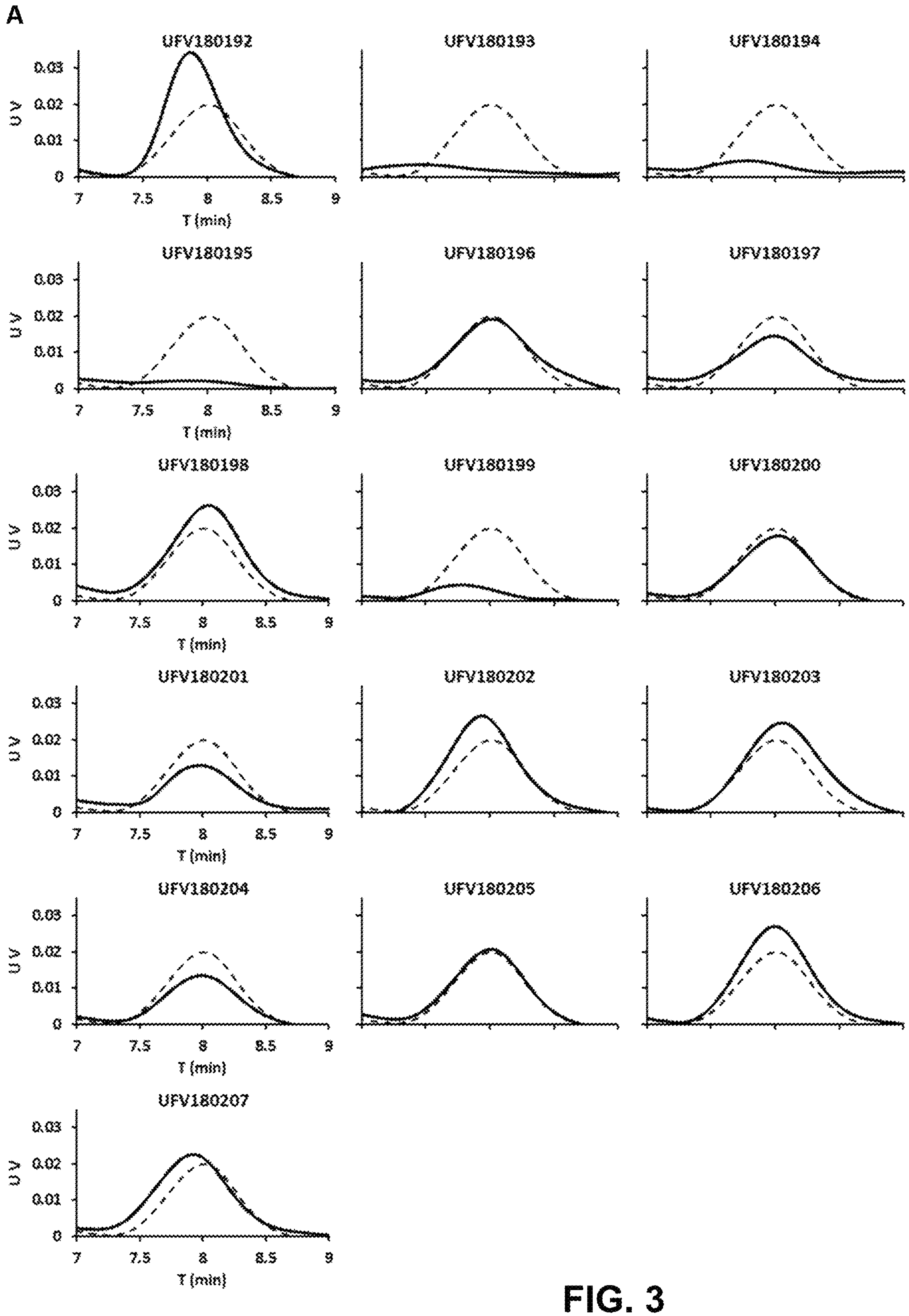
FIG. 3. SEC profiles and elution analysis of culture supernatants of EXPI-293 cells expressing several stem polypeptides of the invention. A. SEC profiles of polypeptides with backmutations to wild type (WT) residues; dotted line is stabilized head-less mini-HA reference (UFV180141), black line is mutated mini-HA to WT sequence; B. Elution time (left) and trimer peak height (right) of SEC profiles in panel A; C. SEC profiles of minimal design polypeptides and stepwise introduction of selected mutations from UFV180088; dotted line is minimal design mini-HA reference (UFV180647), black line is mutated mini-HA; D. Elution time and peak height of SEC profiles in panel C.
Figure 3:
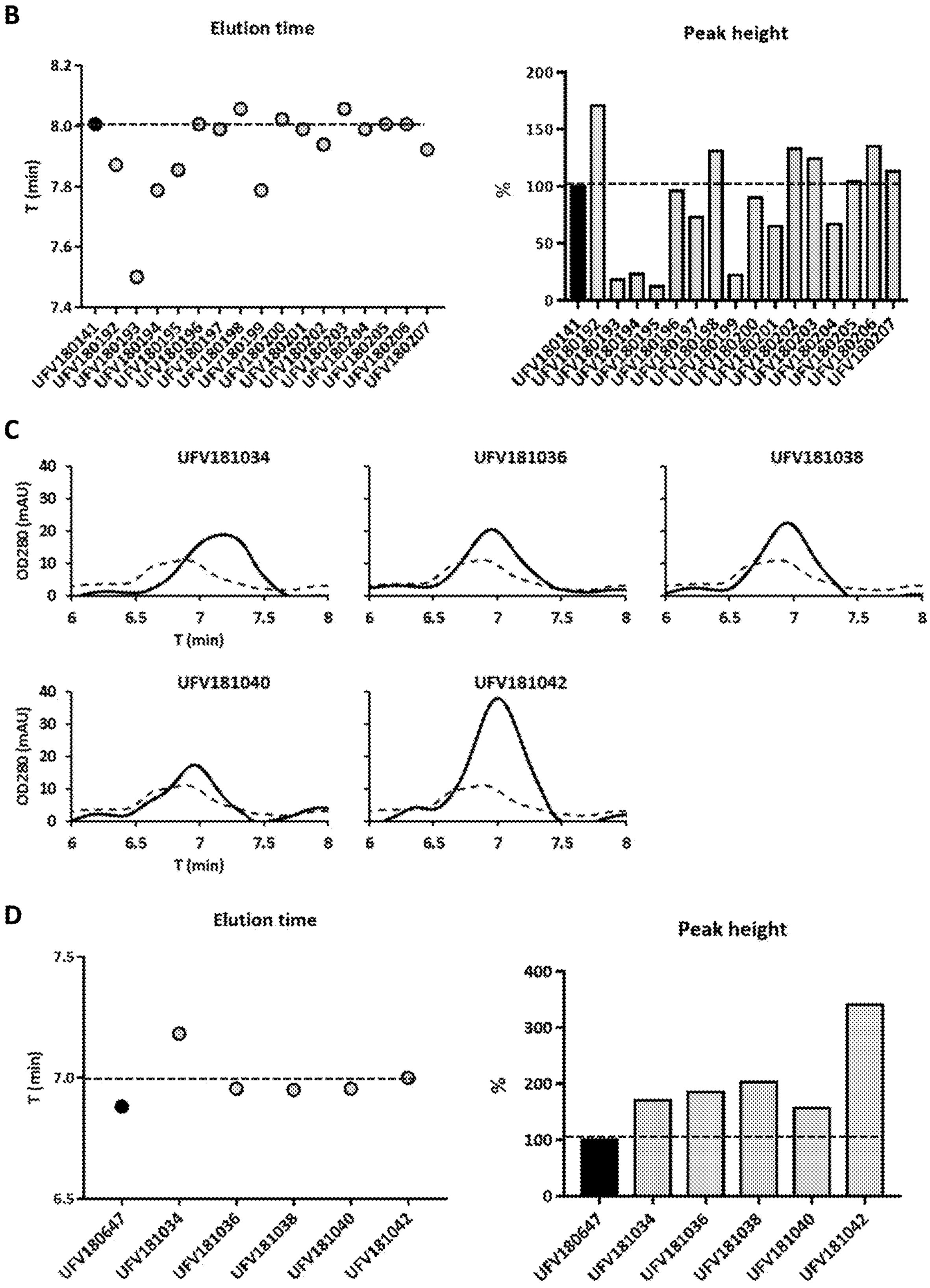

The content of the polypeptides of the invention in the Expi-293 cell culture harvests was assessed by analytical SEC in a High-Performance Liquid Chromatography (HPLC) Infinity 1260 series setup (Agilent). An injection volume of 100 μL culture supernatant was run (1 mL/min.) over a TSK gel G3000SWx1 column (Sigma-Aldrich) and the elution was monitored by UV detection (FIG. 3A). Alternatively, samples were analyzed by Ultra High Performance Liquid Chromatography (UHPLC) using a Vanquish system (ThermoFisher Scientific) with a BEH 200A column (Waters, injection volume 40 μL, flow 0.35 mL/min.) and elution fractions were monitored by a Helios light scattering detector (Wyatt Technologies, FIG. 3C). The SEC profiles were analyzed by the Astra 6 software package (Wyatt Technology). The elution time and the trimeric peak (height and shape) of the SEC profiles are visualized in FIG. 3B and FIG. 3D.

Results and Conclusion

A subset of the back mutations appeared to be detrimental for expression of the stem polypeptides, e.g. shown by UFV180193 (W355H back mutation), UFV180194 (GCN4 deletion), UFV180195 (deletion of intramolecular disulfide bridge) and UFV180199 (I432E back mutation) whereas other backmutations were tolerated (FIGS. 3A and 3B).

Polypeptides lacking the stabilizing mutations introduced in UFV180088 (Table 2) showed significant improvements in the expression level of a minimal trimeric stem polypeptide upon incremental addition of mutations of the invention (towards UFV180088 design). For example, as shown in FIG. 3C, the trimeric peak of polypeptide UFV1801034 shifted in elution time and increased in height upon introduction of mutations K380I, E4321 (FIG. 3D). Incremental addition of the stabilizing mutation in the B-Loop (UFV181042: F392S, H393N, I395T, F399P, R405P) further increased the expression of trimeric polypeptide.

This Example shows that at least the following amino acid positions (e.g. mutations): i.e. a (mutation into) W at position 355 and/or a (mutation into) T at position 378, a (mutation into) N at position 379, and a (mutation into) V at position 381 and/or a (mutation into) I at position 432, or a (mutation into) I at position 432 and 380, and a glycosylation motif at positions 401-403 for N-linked glycosylation at position 401, are beneficial for obtaining high levels of desired soluble trimeric polypeptides. Adding stabilizing mutation in the B-Loop (e.g. F392S, H393N, I395T, and F399P) further increases the expression of the trimeric polypeptide.

Example 4: Interprotomeric Disulfide Bridge; Stability of the Polypeptide of the Invention Designs To assess the contribution of introduced cysteines in the B-loop and C-helix which form interprotomeric disulfide bridges in the polypeptides of the invention (schematically shown in FIG. 4), the cysteines were mutated back to their respective wild type residue (Glutamic acid) as present in backbone strain A/Hong Kong/1/1968 (position 398) and to Glutamine (residue 408) as present in the introduced GCN4 trimerization domain sequence (405-419). The impact of the omission of the cysteines and subsequent disulfide bridge was assessed by analytical SEC, DSF and SDS-PAGE.

Protein Expression, Purification and Characterization

DNA fragments encoding the polypeptides UFV180192 and UFV180141 were produced at micro scale in Expi293F cells as described in Example 3 and at medium scale in ExpiCHO cells as described in Example 2 (~60 mL, harvest at day 8). Culture supernatant was analyzed by analytical SEC, as in Example 2, at the day of harvest (micro scale) or after a 1-week incubation period of the harvested culture supernatant at 4° C. (medium scale). From the harvested culture supernatants (medium scale) the his-tagged polypeptides were purified in a two-step protocol using an ÅKTA Avant 25 system (GE Healthcare Life Sciences). First, immobilized metal affinity chromatography was performed using a pre-packed cOmplete His-tag Purification Column (Roche), washed with 1 mM Imidazole and eluted with 300 mM Imidazole. Second, Size Exclusion Chromatography using an SRT-10C SEC-300 Column (Sepax Technologies) was performed and trimer peak fractions collected. The thermo-stability of the purified proteins was determined by DSF (as in Example 2) and purity of the proteins was assessed by Sodium Dodecyl Sulfate Polyacrylamide Gel Electrophoresis (SDS-PAGE) under non-reducing and reducing conditions by running a 10% Bis-Tris Gel using the Bolt system and following the manufacturer's instructions (Invitrogen).

Results and Conclusion

Assessment of the cell culture supernatant by analytical SEC indicated that both the polypeptides with (UFV180141) and without (UFV180192) introduced cysteines in the B-loop (at position 398) and C-helix (position 408) expressed trimeric polypeptide in solution (FIG. 4A; left panel). Polypeptide UFV180192 was more abundant compared to peptide UFV180141 at the day of harvest 3 days after transfection at small scale. Nevertheless, at higher scale, harvest at day 8 and after storing UFV180192 containing supernatant for one week at 4° C., a second, non-trimer peak appeared (~8.5 min retention time) indicating structural instability of the construct lacking the interprotomeric disulfide bridge (FIG. 4A; right panel). The differences in stability were confirmed by DSF assessment of the purified polypeptides. The polypeptide lacking the interprotomeric disulfide bridge (UFV180192) unfolded at 50.8° C. while the polypeptide with the introduced cysteines at position 398 and 408 unfolded at 67.7° C. (FIG. 4B). SDS-PAGE analysis of the purified polypeptides showed that the polypeptide without the cysteines at position 398 and 408 runs, as expected, at monomer height of ~40 kDa under both non-reduced and reduced conditions. In contrast, the main band for the polypeptide with the two introduced cysteines is observed under non-reducing conditions at ~120 kDa, as expected for a covalently bound trimer, and under reducing conditions at the expected monomer height of ~40 kDa (FIG. 4C).

Data shown in this example demonstrate that covalently linking monomers by introducing two cysteines at position 398 and position 408 to form inter-protomeric disulfide bonds results in a significantly more stable soluble trimeric polypeptide.

Example 5: Alternative Substitutions for Positions 355, 380 and 342, 435 and 388

Designs

Alternative substitutions for optimization of the polypeptides of the invention were tested at position 355 (FIG. 5A), at position 380 and 432 (FIG. 5B), at position 435 (FIG. 5C), and at position 388 (FIG. 5D). Expression and folding of the polypeptides were assessed in Expi293F cell culture supernatant.

Protein Expression in Mammalian Cells

DNA fragments encoding the polypeptides were synthesized as described in Example 2. The polypeptides, including a C-terminal FLAG-Linker-His tag for screening purposes, were produced in eukaryotic Expi293F cells at micro scale (200p L) as described in Example 3 with an exception of polypeptides described in FIG. 5C II and FIG. 5D which were produced in the eukaryotic ExpiCHO cell line as described in Example 2 (at medium scale, respectively 50 mL and 30 mL).

Culture Supernatant Analysis

Expression, folding and trimer content of the polypeptides of the invention were assessed by amplified luminescent proximity homogeneous assay (AlphaLISA, FIGS. 5A, 5B, 5C I) according to the manufacturer's instructions (PerkinElmer). This in-solution and in-binding-equilibrium assay is based on successful binding of both a donor and acceptor bead to the polypeptide. When in close proximity, laser irradiation of the donor bead at 680 nm generates a flow of singlet oxygen, triggering chemical events in nearby acceptor bead, resulting in a chemiluminescent emission at 615 nm. Expression levels were measured via the Expression-AlphaLISA setup by simultaneous addition of Nickel donor beads (anti-His tag) and anti-FLAG tag acceptor beads to the cell culture supernatant. This Expression-AlphaLISA setup recognizes the C-terminal Flag-Linker-His tag irrespective of the folding of the polypeptides. The correct folding of the polypeptides was assessed in a Binding-AlphaLISA by simultaneous addition of Nickel donor beads, human IgG CR9114 (2 nM) or CT149 (1 nM), and anti-human IgG acceptor beads to the cell culture supernatant. A signal can only be obtained if the polypeptide correctly folds and permits the binding of the influenza virus HA specific IgGs.

The trimer-AlphaLISA setup was used to determine the content of trimeric polypeptides present in the culture supernatant. It relies on human IgGs such as CT149 or CR9114 which specifically bind to monomeric HA. If a 1:1 mix of differently labeled IgG CT149 or CR9114 is added to HA an AlphaLISA signal can only be detected if a multimer, permitting binding of at least two antibodies, but not a monomer, permitting binding of only a single antibody, is present. Trimer-AlphaLISA was performed by simultaneous addition of Streptavidin donor beads and anti-DIG IgG acceptor beads to culture supernatant in the presence of biotinylated- and DIG-labelled CT149 or CR9114 IgGs (each 0.5 nM, 1:1 ratio).

For all AlphaLISA setups the detector beads were added at a concentration of 10 µg/mL. The culture supernatants were tested at different dilutions to avoid the hook-effect according to the manufacturer's instructions. Readout was performed 2 hours after incubation at room temperature in the dark using the EnSight™ multimode plate reader (PerkinElmer). All data was normalized to their respective reference constructs that was set to 100%.

The level of expressed polypeptide in the cell culture supernatant was also assessed by Bio-Layer Interferometry using the OCTET platform according to the manufacturer's instructions (FortéBio). In short, a standard curve was established using anti-HIS (HIS2) biosensors (FortéBio) by assessing the binding shift of a dilution series of a well-defined reference batch of purified homologous polypeptide. Subsequently, the binding shift of pre-diluted (in kinetics buffer, FortéBio) cell culture supernatants containing the polypeptides of the invention was measured and the concentration of the polypeptides was calculated using the established standard curve (FIGS. 5C II, 5D). The content of the polypeptides of the invention in the culture harvests was further characterized by analytical SEC in HPLC (FIG. 5C II) and UHPLC (FIG. 5D, 10 µL injection volume) as described in Example 4. After purification of the selected polypeptides UFV171004 and UFV171197 the binding of monoclonal antibodies CR9114 and CT149 was assessed by ELISA. Lastly, the thermostability of these purified polypeptides was determined by DSF (both methods as described in Example 2, FIG. 5C II).

Results and Conclusion

Introducing a tryptophan (W) at position 355 in polypeptide UFV161739 resulted in a strong increase in expression and binding of antibody CR9114 and CT149 compared to the construct with the wild type histidine at position 355 (UFV161333). Simultaneous introduction of 355W and isoleucine (I) at position 482 (UFV161800) further increased expression and antibody binding compared to a construct with only the single mutation 355W. Simultaneous introduction of phenylalanine (F) at position 355 and 4821 was well tolerated but resulted in a smaller increase in expression and antibody binding compared to the control construct with the respective wild type residues at position 355 and 482 (FIG. 5A).

Multiple amino acid residues and combinations thereof were assessed for positions 380 and 432. Overall, the tested amino acid substitutions were well tolerated; with minimal effects on expression level, trimer content, and antibody binding (FIG. 5B). Simultaneous introduction of isoleucine at positions 380 and 432 in a polypeptide (UFV171004) resulted in the highest trimer yield (215%) compared to the reference.

At position 435, four different amino acid substitutions (K, N, Q, R) showed to be well tolerated. The respective polypeptides and the reference polypeptide UFV170611 containing the wild type histidine at position 435 showed comparable AlphaLISA levels for expression, trimer content and binding of monoclonal antibodies CR9114 and CT149 (FIG. 5C I). Further characterization of polypeptides with substitutions 435N (UFV171004) and 435R (UFV171197) confirmed similar expression levels (OCTET), SEC profiles, and binding strength of mAbs CR9114 and CT149 (ELISA). However, the polypeptide with an asparagine (N) at position 435 displayed a ~4° C. higher thermal stability compared to the polypeptide with an arginine (R) substitution at this position (FIG. 5C II).

Polypeptides with amino acid substitutions at position 388, which position is at the top of the A-helix (M, V, I, L, F, Y, W, H, K, and R), were assessed for expression level (Octet) and trimer content by analytical SEC. The expression levels ranked from the methionine substitution (UFV180088) with 475 mg/L to the less favorable arginine substitution with an expression level of 192 mg/L. The SEC profiles all displayed trimeric polypeptide, indicating that the assessed residues at position 388 are all tolerated and do not affect the overall structure (FIG. 5D). The polypeptides with the amino acid substitutions at position 388 all eluted at a shorter retention time compared to the reference polypeptide (UFV180088) due to the difference in length of the C-terminal tag; Flag-linker-His-tag and C-tag respectively.

Taken together, single alternative amino acid substitutions in various optimization regions of the polypeptides of the invention are possible and well tolerated; expression level, trimer content and protein folding are only minimally affected.

Example 6: Definition of HA1 Head Deletion

Designs

Figure 1:
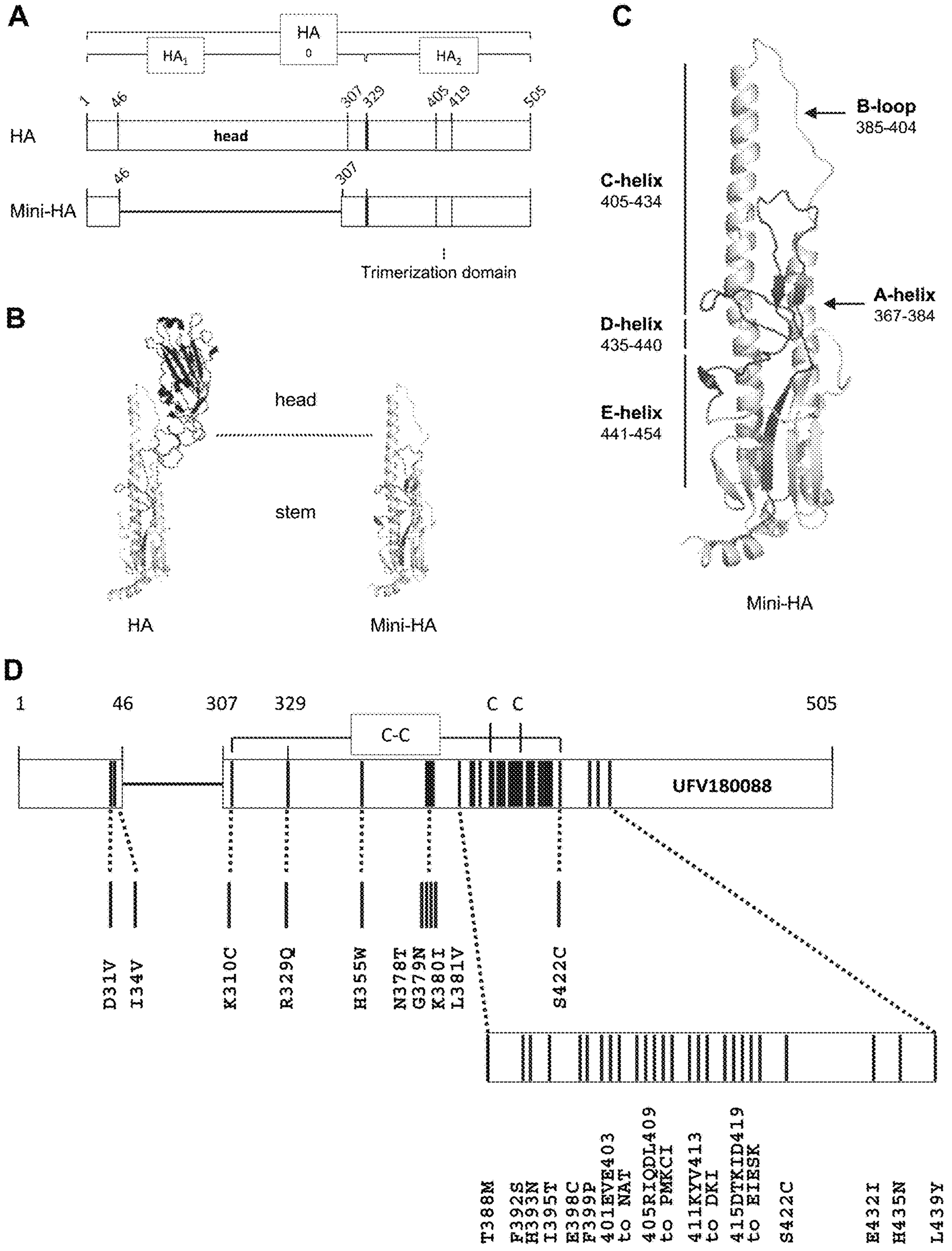
FIG. 1. A. Schematic overview of the polypeptides of the invention (lower figure); B. Removal of the head region of HA results in the stem polypeptides of the invention (mini-HA); C. Three-dimensional representation of a stem-based polypeptide monomer (mini-HA) of the invention; D. Schematic drawing of a polypeptide of the invention (in particular, the polypeptide UFV180088).

Stem polypeptides of the invention preferably comprise a deletion of the head region from position 47 up to and including the amino acid at position 306 (schematically shown in FIG. 1). In this example, alternative deletions and linkers derived from the head domain between the $HA_1$ ends that result after the deletion were explored (schematically shown in FIG. 6). First, alternative deletion positions for the $HA_1$ up strand were assessed (Table 3). The $HA_1$ ends as present in the reference design (UFV161908, with a deletion from the amino acid at position 47 up to and including the amino acid at position 306, replaced by a GPGS linker) are indicated in grey.

TABLE 3

| Connection between $HA_1$ ends after head deletion | | | | | | | | | | | | | | |
|---|---|---|---|---|---|---|---|---|---|---|---|---|---|---|
| | HA1 up strand | | | | | Connection AA position # | | | | | HA1 down strand | | | |
| UFV# | 41 | 42 | 43 | 44 | 45 | 46 | 47 | 48 | 49 | 50 | 307 | 308 | 309 | 310 |
| WT amino acid | E | L | V | Q | S | S | S | T | G | K | K | Y | V | K |
| UFV161908* | E | L | V | Q | S | G | P | G | S | — | K | Y | V | K |
| UFV170636 | E | L | V | Q | S | — | — | — | — | — | K | Y | V | K |
| UFV170637 | E | L | V | Q | S | S | — | — | — | — | K | Y | V | K |
| UFV170638 | E | L | V | Q | S | S | S | — | — | — | K | Y | V | K |

TABLE 3-continued

| Connection between $HA_1$ ends after head deletion | | | | | | | | | | | | | | |
|---|---|---|---|---|---|---|---|---|---|---|---|---|---|---|
| | HA1 up strand | | | | | | Connection AA position # | | | | HA1 down strand | | | |
| UFV# | 41 | 42 | 43 | 44 | 45 | 46 | 47 | 48 | 49 | 50 | 307 | 308 | 309 | 310 |
| UFV170639 | E | L | V | Q | S | S | S | T | — | — | K | Y | V | K |
| UFV170640 | E | L | V | Q | S | S | S | T | G | — | K | Y | V | K |

*Reference

Secondly, alternative deletion positions for the $HA_1$ up strand were combined with alternative deletion positions for the $HA_1$ down strains (Table 4').

TABLE 4

| Alternative connection between HA1 after head deletion | | | | | | | | | | | | | | |
|---|---|---|---|---|---|---|---|---|---|---|---|---|---|---|
| | HA1 up strand | | | | | | Connection AA position # | | | | HA1 down strand | | | |
| UFV# | 43 | 44 | 45 | 46 | 47 | 48 | 49 | 303 | 304 | 305 | 306 | 307 | 308 | 309 |
| WT amino acid | V | Q | S | S | S | T | G | G | A | C | P | K | Y | V |
| UFV160653* | V | Q | S | G | P | G | S | — | — | — | — | K | Y | V |
| UFV160764 | V | Q | S | — | — | — | — | — | — | — | P | K | Y | V |
| UFV160765 | V | Q | S | — | — | — | — | — | — | C | P | K | Y | V |
| UFV160766 | V | Q | S | — | — | — | — | — | A | C | P | K | Y | V |
| UFV160674 | V | Q | S | — | — | — | — | G | A | G* | P | K | Y | V |
| UFV160675 | V | Q | S | — | — | — | — | G | A | C | P | K | Y | V |
| UFV160767 | V | Q | S | S | — | — | — | — | A | C | P | K | Y | V |
| UFV160768 | V | Q | S | S | — | — | — | — | | C | P | K | Y | V |
| UFV160769 | V | Q | S | S | S | — | — | — | A | C | P | K | Y | V |
| UFV160770 | V | Q | S | S | S | — | — | — | — | C | P | K | Y | V |
| UFV160771 | V | Q | S | S | | — | — | — | — | — | P | K | Y | V |
| UFV160772 | V | Q | S | S | S | — | — | — | — | — | P | K | Y | V |

*Reference,
** Cysteine to glycine point mutation

Thirdly, the use of homologous linkers comprising amino acid sequences from the removed head domain to connect the $HA_1$ ends were explored (Table 5).

TABLE 5

| Alternative connections originating from residues strands from the removed head domain | | | | | | | | | | | | | | |
|---|---|---|---|---|---|---|---|---|---|---|---|---|---|---|
| | HA1 up strand | | | | | | Connection AA position # | | | | HA1 down strand | | | |
| UFV# | 41 | 42 | 43 | 44 | 45 | 46 | 47 | 48 | 49 | 50 | 307 | 308 | 309 | 310 |
| WT amino acid | E | L | V | Q | S | S | S | T | G | K | K | Y | V | K |
| UFV160321* | E | L | V | Q | S | G | G | G | G | — | K | Y | V | K |
| UFV160403 | E | L | V | Q | S | N | P | H | R | — | K | Y | V | K |
| UFV160404 | E | L | V | Q | S | G | D | P | H | — | K | Y | V | K |
| UFV160405 | E | L | V | Q | S | N | G | G | S | — | K | Y | V | K |
| UFV160406 | E | L | V | Q | S | G | G | S | N | — | K | Y | V | K |
| UFV160407 | E | L | V | Q | S | G | S | N | A | — | K | Y | V | K |
| UFV160408** | E | L | V | Q | S | G | P | G | S | — | K | Y | V | K |
| UFV160409 | E | L | V | Q | S | G | S | G | F | — | K | Y | V | K |
| UFV160410 | E | L | V | Q | S | G | S | G | — | — | K | Y | V | K |
| UFV160411 | E | L | V | Q | S | G | G | — | — | — | K | Y | V | K |
| UFV160412 | E | L | V | Q | S | G | G | S | — | — | K | Y | V | K |
| UFV160413 | E | L | V | Q | S | S | G | S | | — | K | Y | V | K |
| UFV160414 | E | L | V | Q | S | H | P | S | T | — | K | Y | V | K |
| UFV160415 | E | L | V | Q | S | I | P | N | I | — | K | Y | V | K |
| UFV160416 | E | L | V | Q | S | G | L | S | S | — | K | Y | V | K |
| UFV160417 | E | L | V | Q | S | K | P | G | D | — | K | Y | V | K |
| UFV160418 | E | L | V | Q | S | D | A | P | I | — | K | Y | V | K |

TABLE 5-continued

| Alternative connections originating from residues strands from the removed head domain | | | | | | | | | | | | | | |
|---|---|---|---|---|---|---|---|---|---|---|---|---|---|---|
| | HA1 up strand | | | | | Connection AA position # | | | | HA1 down strand | | | | |
| UFV# | 41 | 42 | 43 | 44 | 45 | 46 | 47 | 48 | 49 | 50 | 307 | 308 | 309 | 310 |
| UFV160419 | E | L | V | Q | S | T | P | N | — | — | K | Y | V | K |
| UFV160420 | E | L | V | Q | S | T | P | N | G | — | K | Y | V | K |

*Reference,
**Connection used as reference construct for the constructs of Table 1 and Table 2

Protein Expression in Mammalian Cells and Culture Supernatant Analysis

DNA fragments encoding the polypeptides of the invention were synthesized as described in Example 2. The polypeptides, including a C-terminal FLAG-Linker-His tag for screening purposes, were produced in eukaryotic Expi293F cells at microscale (200 μL) as described in Example 3. Expression, trimer content and folding (mAb binding of either CR9114 or CT149) of the polypeptides were assessed by AlphaLISA as described in Example 5. All data was normalized to their respective reference constructs UFV161908 (FIG. 6A), UFV160653 (FIG. 6B) and UFV160321 (FIG. 6C) which was set to 100%.

Results and Conclusion

Varying the head domain deletion position in the $HA_1$ up strand had only minimal effects on expression level, trimer yield and protein folding (i.e. antibody binding) (FIG. 6A). In contrast, expression of the polypeptides that include an alternative deletion position in both the HA1 up and down strand showed up to ~50% reduced expression levels and up to ~70% reduced binding of antibody CT149 (FIG. 6B). This indicates that within the tested range of positions in particular the position at which the HA1 down strand is deleted, affects both the expression and folding of the polypeptides.

An alternative approach to directly connecting the remaining $HA_1$ ends (i.w. the N-terminal HA1 fragment and the C-terminal HA1 fragment) after head domain removal is a connection via a homologous linking sequence. As shown in Table 5, to this end the $HA_1$ up strand (residue 45) was connected to the $HA_1$ down strand (residue 307) by means of a short sequence derived from the corresponding H3 HA head domain. This resulted in polypeptides with expression levels varying from 33% to 223% compared to the reference (FIG. 6C). Similarly, the binding of antibody CT149 showed a large spread with values ranging from 57% to 350% compared to the reference were observed. Polypeptides that expressed well displayed mostly also high antibody binding.

Overall, generation of trimeric and correctly folded stem polypeptides by means of deleting the HA head domain is not dependent on one exact deletion position. Directly connecting the $HA_1$ ends, and variations in deletion position in both the up and down strand of $HA_1$ were successfully generated. Alternatively, connecting the $HA_1$ end by introducing a homologous amino acid linker derived from the head domain was also possible and many peptides with different sequence composition and length (of at least 2 to 5 amino acids) could be selected to reconnect the $HA_1$ ends after head domain removal.

Example 7: Optimizing the B-Loop in Polypeptides of the Invention

Designs

After deleting the HA1 head domain, the B-loop (FIGS. 1B and C, comprising the amino acids 385-404) of the HA stem polypeptide becomes exposed. To partially shield this area from the immune system and to further stabilize the loop, glycosylation motifs and proline residues were introduced (FIG. 7). Glycosylation motifs (NxT) were introduced at position 401-403 by mutations E401N and E403T, for N-linked glycosylation at position 401 and tested in combination with N-linked glycan motifs at position 398-400 by mutating S398N (resulting in NxS motif) or at position 392-394 by mutating S392N and Q394T or at position 393-395 by mutating H393N and I395T (both resulking in NxT motif). Proline substitutions which may lower the helix propensity of the B-loop sequence were introduced by single point mutations at any of the positions between 385 and 406 and by double point mutations at 392 together with either 396 or 398.

Protein Expression in Mammalian Cells and Culture Supernatant Analysis

DNA fragments encoding the polypeptides of the invention were synthesized as described in Example 2. The polypeptides, including a C-terminal FLAG-Linker-His tag for screening purposes, were produced in the eukaryotic Expi293F cell line at microscale (200 μL) as described in Example 3. Expression, trimer content and folding (binding of mAb CR9114, CT149 (as described by Wu et al. (2015) and SD15013 (comprising the amino acid sequence of SEQ ID NO: 39) of the polypeptides were assessed by AlphaLISA as described in Example 5 (SD15013 binding was assessed using anti-His acceptor beads and Streptavidin donor beads in the presence of SD15013 at a concentration of 2 nM). Cell culture supernatants were analyzed by analytical SEC, as described in Example 2, at the day of harvest.

All data were normalized to their respective reference constructs UFV161686 (FIG. 8A), UFV161333 (FIGS. 7B and C) and UFV171187 (FIG. 7D) which was set to 100%.

Results and Conclusion

Introduction of a single glycosylation motif to the B-loop by mutation of residues at position 401, 402, and 403 to N, A, and T respectively, for N-linked glycosylation at position 401, resulted in a two-fold increase in expression level of the polypeptide. Similarly, a huge increase in binding of antibodies CR9114 and CT149, respectively 5 and 7-fold, and single domain SD15013 (10-fold) was observed (FIG. 7A).

Introduction of prolines to the B-loop did not affect the expression level of the polypeptides; values varied from 94% to 128% relative to the reference construct (FIG. 7B). In contrast, the addition of proline residues at positions 386, 387, 388, and 389 was detrimental for antibody binding. The minimal binding of CR9114, CT149 and SD15013 indicated that folding of the polypeptides is negatively impacted when a proline is introduced at the N-terminal end of the B-loop.

Introduction of a single proline at any of the positions from 390 to 405 or two prolines at positions 392 and 396 or positions 392 and 398 resulted in ~40% increased CR9114 binding while CT149 binding remained relatively similar or was reduced (~65% compared to the reference). SD15013 displayed the largest spread in these constructs with a relative binding ranging from ~50% to ~150% compared to the reference. The introduction of two prolines was tolerated well and binding of CR9114, CT149 and SD15013 was in general found to be the average of the antibody binding values for the single proline introductions. An exception was observed for SD15013 binding to UFV161708 that displayed 147% binding whereas for the single mutations at positions 392 and 396 a decrease in binding was observed (64% and 75% relative to reference).

Introduction of a second glycosylation motif to the B-loop was well tolerated (FIG. 7C); both polypeptides with the additional motif at position 393 (UFV161715) or 398 (UFV161721) showed relative similar expression levels compared to the reference, an increase in CR9114 binding (~145%), unaffected CT149 binding (~90%) and a small decrease in SD15013 binding (~60%).

Simultaneous introduction of proline residues and/or a second glycosylation motif (at position 392-395) resulted in polypeptides that expressed about 2-fold lower than the reference that contains single glycosylation motif at position 401-403 and no proline (FIG. 7D). Antibody binding (CR9114 and CT149) were hardly affected whereas a drop in SD15013 was observed (~48-88% relative to reference). As simultaneous glycosylation of N398 and N401 due to their proximity is unlikely, an additional glycan at N393 or N392 is preferred.

SEC-MALS analysis of EXPI-293 cell culture supernatants containing polypeptides of the invention with one N-linked glycan motif (UFV180208) or two N-linked glycan motifs and two prolines (UFV180217) shows a clear peak corresponding to the respective trimeric polypeptide (FIG. 7E).

Mutations to the B-loop in the form of stabilizing proline residues and additional N-linked glycosylation motifs were well tolerated. Although differences in expression and antibody binding were observed (most notably for SD15013 binding) the introduction of proline(s), except in the N-terminal region of the B-loop (position 392-389), and a second N-linked glycosylation motif was possible without affecting protein folding and trimerization.

Example 8: N-Linked Glycosylation Motif at Position 38 of the Polypeptides of the Invention Designs To evaluate the influence of the conserved glycosylation motif near the CR9114 epitope (position 38) on expression and folding, a polypeptide that contains the wild type motif 38-NAT-40 for N-linked glycosylation (UFV170282) was compared with a polypeptide in which the motif was knocked-out by point mutation T40I (UFV170278).

Protein Expression in Mammalian Cells, Culture Supernatant Analysis, Purification and Characterization DNA fragments encoding the polypeptides of the invention were synthesized, expressed and purified as described in Example 2. The level of expressed polypeptide in the culture supernatant was assessed through Bio-Layer Interferometry using the OCTET platform as described in Example 2 using immobilized mAb CT149 and a 25-fold diluted cell culture supernatant containing the polypeptide of the invention. The strength of antibody binding to the purified polypeptides was assessed by ELISA ($EC_{50}$) as described in Example 2.

Results and Conclusion

Upon removal of the N-linked glycosylation motif at position 38 (UFV170278) the expression level decreased by ~50% with respect to the polypeptide with the motif present (UFV170282), however, both polypeptides remained well expressing polypeptides with values above 255 mg per liter culture supernatant. As determined by ELISA the strength of antibody binding was not significantly different between the two polypeptides as evident by the $EC_{50}$ values of ~1 nM for CR9114 and CT149 (FIGS. 8A and B).

In conclusion, removal of the N-linked glycosylation motif at position 38, although a decrease in expression level is observed, was well tolerated and appeared to have no effect on folding of the polypeptide.

Example 9: Alternative Positions for the Intramolecular Disulfide Bridge Between HA1-HA2

Designs

The protomers of the trimeric stem polypeptides of the invention preferably are stabilized by an introduced disulfide bridge covalently linking the $HA_1$ down strand (position 310) to the C-helix of the $HA_2$ strand (position 422). Alternative options for this intra-protomeric disulfide bridge were evaluated by making small shifts in the exact position of the respective cysteines (positions 311/422 and 308/418). In addition to the 310/422 disulfide bridge a second pair of cysteines was evaluated to connect the $HA_1$ (position 26) with the C-terminal part of the $HA_2$ C-helix (position 433).

Protein Expression in Mammalian Cells and Culture Supernatant Analysis

DNA fragments encoding the polypeptides of the invention were synthesized as described in Example 2. The polypeptides were expressed in Expi-293 cells as described in Example 2 with the exception for the scale of the experiment were instead of micro scale (200 μL) the cultures were grown at medium scale (30 mL). Expression level and folding (binding of mAb CR9114 and CT149) of the polypeptides of the invention was assessed by AlphaLISA as described in Example 5 using CR9114 and CT149 concentrations of 2.5 nM and 1.25 nM, respectively.

Results and Conclusion

Repositioning the cysteines from residue 310 to 311 or to 308 (in combination with repositioning the cysteine at position 422 to 418) was well tolerated and did only minimally affected the expression level and folding of the polypeptides as evident by antibody binding (FIG. 9A). Introducing a second disulfide bridge in the region below the 310-422 disulfide bridge was in principle possible as shown by the unaffected expression level, however, the dramatic reduction in CR9114 and CT149 binding (2% and 48% to the reference respectively) indicated a negative effect on the folding of the desired conserved stem epitopes (FIG. 9B).

Example 10: Alternative Positions for Interprotomeric Disulfide Bridges

Designs

The protomers in the HA stem polypeptides are preferably covalently linked by means of an interprotomeric disulfide bridge in the top part of the trimeric HA protein (FIG. 4A). Two cysteine residues were introduced, one in the B-loop (position 398) and one in the C-helix (position 408) that both pair with the sterically close cysteines in the neighboring protomer within the trimer; i.e. cysteine 398 of protomer 1 forms a disulfide bond with cysteine 408 of protomer 2, cysteine 398 of protomer 2 forms a disulfide bond cysteine 408 of protomer 3, and cysteine 398 of protomer 3 forms a disulfide bond with cysteine 408 of protomer 1. Alternative options to this inter-protomeric disulfide bond were explored by making small up or down shifts in the exact position of the point mutations to cysteines (FIG. 10).

Protein Expression in Mammalian Cells and Culture Supernatant Analysis

DNA fragments encoding the polypeptides of the invention were synthesized as described in Example 2. The polypeptides, including a C-terminal FLAG-Linker-His tag for screening purposes, were produced in the eukaryotic Expi293F cell line at micro scale (200 μL) as described in Example 3. Expression, trimer content and folding (binding of mAb CR9114 or CT149) of the polypeptides of the invention was assessed by AlphaLISA as described in Example 5.

Results and Conclusion

Polypeptides with the introduced interprotomeric disulfides expressed ~1.8 fold lower compared to polypeptide without these cysteines. However, the difference in trimerization is dramatic (FIG. 10). Polypeptide with interprotomeric disulfides expressed at the same level and all displayed similarly high levels of trimer and binding affinity of antibodies CR9114 and CT149. This demonstrates the critical importance of the inter-protomeric disulfide bridge for trimerization and correct folding of the conserved stem epitopes. Furthermore, small changes in positioning the interprotomeric disulfide bridge were well tolerated.

Example 11: Alternative Truncations at the C-Terminus

Designs

Influenza virus hemagglutinin (HA) is a membrane protein that is located at the surface of the viral particle with the C-terminal part of the protein embedded in the viral membrane. For the soluble versions of the polypeptides of the invention the ectodomain can be truncated at different positions within the natural linker sequence (positions 500-513) that connects the C-terminal alpha helix of the ectodomain with the transmembrane (TM) and cytoplasmic domain.

Alternative C-terminal truncation positions were evaluated (Table 6).

TABLE 6

Alternative C-terminal truncations of the polypeptides of the invention, derived from the ectodomain of HA from A/Hong Kong/1/68.

| | C-terminus of last helix | | | | | | | | | | | | | natural Linker | |
|---|---|---|---|---|---|---|---|---|---|---|---|---|---|---|---|
| | 488 | 489 | 490 | 491 | 492 | 493 | 494 | 495 | 496 | 497 | 498 | 499 | 500 | 501 | 502 |
| A/HongKong/1/68 | H | D | V | Y | R | D | E | A | L | N | N | R | F | Q | I |
| UFV171272 | H | D | V | Y | R | D | E | A | L | N | N | R | F | Q | I |
| UFV171273 | H | D | V | Y | R | D | E | A | L | N | N | R | F | Q | I |
| UFV171274 | H | D | V | Y | R | D | E | A | L | N | N | R | F | Q | I |
| UFV171275 | H | D | V | Y | R | D | E | A | L | N | N | R | F | Q | I |
| UFV171276 | H | D | V | Y | R | D | E | A | L | N | N | R | F | Q | I |
| UFV171277 | H | D | V | Y | R | D | E | A | L | N | N | R | F | Q | I |
| UFV171278 | H | D | V | Y | R | D | E | A | L | N | N | R | F | Q | I |
| UFV171279 | H | D | V | Y | R | D | E | A | L | N | N | R | F | Q | |
| UFV171280 | H | D | V | Y | R | D | E | A | L | N | N | R | | | |

| | natural Linker | | | | | | | | | | | TM | | |
|---|---|---|---|---|---|---|---|---|---|---|---|---|---|---|
| | 503 | 504 | 505 | 506 | 507 | 508 | 509 | 510 | 511 | 512 | 513 | 514 | 515 | 516 |
| A/HongKong/1/68 | K | G | V | E | L | K | S | G | Y | K | D | W | I | L |
| UFV171272 | K | G | V | E | L | K | S | G | Y | K | D | W | I | |
| UFV171273 | K | G | V | E | L | K | S | G | Y | K | D | | | |
| UFV171274 | K | G | V | E | L | K | S | G | Y | | | | | |
| UFV171275 | K | G | V | E | L | K | S | | | | | | | |
| UFV171276 | K | G | V | E | L | | | | | | | | | |
| UFV171277 | K | G | V | | | | | | | | | | | |
| UFV171278 | K | | | | | | | | | | | | | |
| UFV171279 | | | | | | | | | | | | | | |
| UFV171280 | | | | | | | | | | | | | | |

Cell Culture Supernatant Analysis

DNA fragments encoding the polypeptides listed in Table 6 were synthesized as described in Example 3 and expressed in suspension EXPI-293 cell cultures as described in Example 4.

The harvested cell culture supernatants were analyzed for the levels of trimeric polypeptide by analytical SEC using the HPLC as described in Example 4A. Correct folding of the expressed polypeptides of the invention was assessed in the cell culture supernatant through Bio-Layer Interferometry using the OCTET platform (ForteBio) as described in Example 6. In short, supernatants, five-fold diluted in kinetics buffer (ForteBio), were assessed for binding of biotinylated human monoclonal antibodies CR9114 or CT149 (10 μg/mL) loaded onto Streptavidin biosensors (ForteBio). Curve fitting over the initial 100 seconds of the association step was performed to calculate $K_{ON}$ values and the curves were fitted in a 1:1 model. A MOCK sample was included as negative control.

Results and Conclusion

C-terminal truncations between residue 501 and 513 were well tolerated with only minor effects on trimer and expression levels as well as antibody binding. The truncated polypeptides display comparable trimeric peak patterns in SEC analysis (FIG. 11A) and a good, or improved $K_{ON}$ for CR9114 and CT149 binding in Octet analysis (FIG. 11B). Truncations (after position 499 in UFV171280) reaching the C-terminal helix of the ectodomain resulted in a clear drop in trimer expression and antibody binding levels, as shown by SEC and OCTET analysis.

Example 12: Alternative Mutations in the A-Helix of the Polypeptides of the Invention Designs The positioning and folding of the C-terminal part of the A-helix of the polypeptides of the invention is critical for the correct representation of conserved stem epitopes. To find the optimal conformation, three residues of the A-helix (378, 379, and 381) were mutated to residues originating in this position from either Group 1 HA (H1 A/Brisbane/59/07) or Group 2 HA (H3 A/Hong Kong/1/1968). Additionally, the putative A-helix stabilizing mutation G379A was assessed.

Protein Expression in Mammalian Cells, Culture Supernatant Analysis, Purification and Characterization DNA fragments encoding the polypeptides of the invention were synthesized as described in Example 2. The polypeptides, including a C-terminal FLAG-Linker-His tag for screening purposes, were produced in the eukaryotic Expi293F cell line at micro scale (200 μL) as described in Example 3. Expression, trimer content, and folding (by binding of 2.5 nM mAb CR9114 or CT149) of the polypeptides was assessed by AlphaLISA as described in Example 5. Additionally, the polypeptides were expressed at medium scale (50 mL) in EXPI-CHO cells as described in Example 4 and expression levels were determined by Bio-Layer Interferometry as described in Example 5 and crude cell culture supernatant was analyzed by SEC-MALS by means of High-Performance Liquid Chromatography (HPLC) as described in Example 3. Polypeptides were purified with a two-step protocol by Affinity Chromatography and Size Exclusion Chromatography as described in Example 4. The antigenicity of purified polypeptides was assessed by ELISA ($EC_{50}$ values of CR9114 and CT149 antibody binding) and the temperature at which 50% of the polypeptide unfolds was determined by DSF, both as described in Example 2.

Results and Conclusion

Gradually increasing the amount of H1 derived residues at positions 378, 379 and 381 affected the expression level of the polypeptide. Polypeptide UFV161448, containing all three H1-like residues, was the lowest expressing polypeptide (84%) whereas UFV161451, containing H1 like residues at positions 379 and 381, was the highest expressing polypeptide (163%). The polypeptides containing the putative A-helix stabilizing mutation 379A (UFV161459 and UFV161458) expressed worst (respectively 42 and 75%). The correct folding of the polypeptides was assessed in AlphaLISA. The relative signal for both CR9114 and CT149 binding showed a large spread. Polypeptide UFV161453 (379N) displayed the least binding, 61% and 24% for CR9114 and CT149 respectively. Polypeptide UFV161448 that contains all mutations towards H1 (378T, 379N and 381V) displayed the highest binding; 1706% and 841% for CR9114 and CT149, respectively (FIG. 12A).

The effect of A-helix mutations was further studied in the more stabilized trimeric stem polypeptides UFV171004 and (UFV171116) which included, amongst others, the H355W mutation and an alternative interprotomeric disulfide bridge (at 397/408). In three independent medium scale ExpiCHO productions, UFV171004 (which includes H1 residues in the A-helix at positions 378, 379, and 381), was expressed at a slightly higher level than polypeptide UFV171116 (which contains H3 residues at these positions).

Similarly, minimal differences were observed in the SEC-MALS analysis of the culture supernatants; for both constructs the peak corresponding to the trimeric fraction (retention time of ~8 minutes) was overlapping in shape and height. Binding of antibodies CR9114 and CT149 as a measure of correct protein folding was determined by ELISA and indicated strong binding ($EC_{50}$<0.01 nM). Temperature stability, as determined by DSF, indicated a significant difference between both polypeptides. Whereas 50% of polypeptide UFV171116 was unfolded at 66.2° C., polypeptide UFV171004 displayed a $Tm_{50}$ value of 68.0° C. (FIG. 12B).

Taken together, introducing H1 residues in the A-helix of the H3 based stem polypeptides resulted in polypeptides that were more thermostable and that displayed an increase in CR9114 and CT149 binding. The differences in antibody binding were less dramatic in the constructs UFV171004 and UFV171116 that include, amongst others, stabilizing mutation H355W.

Example 13: Introduction of Surface Mutations Towards H7

Designs

The trimeric stem polypeptides of the invention, as described in the previous Examples, are based on HA from the H3 influenza virus A/Hong Kong/1/1968. Despite the high degree of conservation in the stem of Group 2 H3 and H7 hemagglutinins, a few surface residues in the region of the conserved stem epitopes are different. In this Example, selected residues located at the polypeptide surface were stepwise mutated from H3 residues (as present in the references UFV172561 and UFV172562) to the corresponding H7 residues. These residues comprise positions in the 02/03 loop (residues 25 and 27), residues in the A-helix (residue 367) and residues in the lower part of the polypeptide (residues 475, 476, and 479).

Protein Expression in Mammalian Cells and Culture Supernatant Analysis

DNA fragments encoding the polypeptides of the invention were synthesized as described in Example 2. The polypeptides, including a C-terminal FLAG-Linker-His tag for screening purposes, were produced in the eukaryotic Expi293F cell line at micro scale (200 μL) as described in Example 3. Expression, trimer content and folding (by binding of mAb CR9114 and CT149) of the polypeptides of the invention was assessed by AlphaLISA as described in Example 5. All AlphaLISA data was normalized to their respective reference constructs UFV172561 and UFV172562. which were set to 100%. The first reference construct includes mutations to H1 residues at position 379 and 381, the second reference includes wild type H3 residues at positions 379 and 381. Additionally, culture supernatants were analyzed by analytical SEC, at the day of harvest, as described in Example 2.

Results and Conclusion

Introduction of H7 like residues at the β2/β loop, A-helix (including H1 like residues at positions 379 and 381), and lower part of the stem resulted in a slight decrease in expression and trimer yield and a relatively small variation in antibody binding (20%) to the trimeric stem polypeptides as determined by AlphaLISA. Similarly, SEC analysis of crude cell culture supernatants indicated a decrease in expression level for polypeptides including surface mutations towards H7 (FIG. 13A).

A similar effect is observed upon introducing the surface mutations in the backbone variant that includes H3 like residues at positions 379 and 381 (FIG. 13B).

Taken together, it is possible to modify the surface of the H3 HA derived stem polypeptides of the invention towards H7, especially in the presence of H1 like residues at the upper part of the A-helix.

Example 14: General Application to the Group 2 Mini-HA Approach

Designs

Design elements necessary for the generation of trimeric stem polypeptides of the invention were expressed in the H3 HA backbone (A/Hong Kong/1/1968) and also transferred in two alternative H3 backbones; i.e. A/Wisconsin/67/2005 and A/Singapore/INFIMH/16/0019/2016. The design elements were incrementally introduced; set I polypeptides contains a minimal set of mutations, set II includes additionally partial B-loop stabilization mutations, and set III includes all B-loop additional stabilizing mutations.

Protein Expression in Mammalian Cells and Culture Supernatant Analysis

DNA fragments encoding the polypeptides of the invention were synthesized as described in Example 2. The polypeptides, including a C-terminal FLAG-Linker-His tag for screening purposes, were produced in the eukaryotic Expi293F cell line at micro scale (200 μL) and crude cell culture supernatant was analyzed by analytical SEC, at the day of harvest, as described in Example 3.

Results and Conclusion

As was observed in the SEC-MALS analysis, transfer of the Set I design elements resulted in trimeric stem polypeptides for all 3 backbones, however, the trimer peak was most evident for the A/Wisconsin/67/2005 derived polypeptide and least for the A/Hong Kong/1/1968 derived polypeptide (FIG. 14A). Additional stabilizing mutations in the B-loop (Set II and Set III) resulted in significantly increased polypeptide expression levels and trimer content (FIG. 14B). Taken together, the results confirm that transferring the modifications of the polypeptides of the invention to other Group 2 backbones resulted in soluble trimeric mini-HA.

Example 15: Adenovirus-Driven In Vitro Expression of Correctly Folded, Trimeric Group 2 Mini-HA on the Cell Membrane of Human Lung Fibroblast Cells In this example, adenovirus 26 (Ad26.FLU.004)-driven expression and folding of trimeric UFV180480 (UFV18088 with native transmembrane domain) on the cell surface of human lung fibroblast (MRC-5) cells was evaluated. MRC-5 cells were transduced (5,000 VP/cells) in culture medium. After two days, cells were either lysed in lysis buffer to assess expression of trimeric UFV180480 by Western blotting analysis, or cell were harvested by trypsinization to assess cell-surface expression of correctly-folded UFV180480 using flow cytometry. In both cases, Ad26.Empty, lacking the transgene encoding for UFV180480, was included as negative control.

Protein lysates from Ad26.FLU.004 transduced cells, as well as the protein UFV180088 which serves as a positive control, were processed for SDS-PAGE under reduced conditions (ensuring complete unfolding of trimeric group 2 mini-HA proteins) or under non-reduced conditions (ensuring the trimeric nature of the mini-HA protein), and proteins were transferred to a nitrocellulose blot. Expression was tested by probing the blot with a group 2 mini-HA conformation-specific specific biotinylated antibody CR9114 and expression was visualized using HRP-conjugated streptavidin.

For testing cell-membrane associated expression of UFV180480 by flow cytometry, Ad26.FLU.004-transduced cells were trypsinized and resuspended in flow cytometry buffer. Non-permeabilized cells were probed with CR9114, and after extensive washing, with a PE-conjugated anti-human antibody to visualize UFV180480.

Results and Conclusion

Using flow cytometry analysis, we analyzed cell-surface expression of UFV180480. Compared to Ad26.Empty-transduced cells (FIG. 16A), the majority of Ad26.FLU.004-transduced MRC-5 cells (~96.3%) showed high levels of UFV180480 on the cell surface (FIG. 16B).

Flow cytometry analysis of UFV180480 expression in MRC-5 did not differentiate between expression of monomeric or trimeric UFV180480. Therefore, Western blotting analysis was performed. It was shown, based on molecular weight and by comparison to trimeric UFV180088, that Ad26.FLU.004 drives the expression of trimeric UFV180480 in MRC-5 cells (FIG. 16C). Based on the amino acid sequence of monomeric UFV180480, the molecular weight is estimated 34.4 kDa which yields a size of trimeric UFV180480 of around 103.2 kDa. Lysate from Ad26.FLU.004 transduced cells (5,000 VP/cell), but not from Ad26.Empty-transduced cells, showed a band around 103.2 kDa, and run slightly higher compared to trimeric UFV180088 (expected MW of 89.1 kDa) (compare FIG. 16C, lanes 1-3). No band was observed at around 34 kDa indicating that the majority of UFV180480 is in its trimeric form (FIG. 16C, lane 1). None of the samples showed a specific band when processed under reduced (i.e. completely unfolding) conditions (FIG. 16C, lanes 4-6).

According to the present invention, it thus has been confirmed that UFV180480 is expressed in vitro upon transduction of Ad26.FLU.004. Presence of trimeric protein on the cell surface of human cells was also confirmed.

Example 16: Polypeptides UFV170278 and UFV170282 of the Invention are Immunogenic and Induce Protection in a Lethal H3N2 A/Hong Kong/1/1968 Naïve Mouse Challenge Model In this example, the in vivo immunogenicity and the protective efficacy (based on survival proportion at the end of the follow-up period) of a dose range of 2% (v/v) Adjuplex-adjuvanted UFV170278 (with the conserved motif for an N-linked glycan at position 38) and UFV170282 (without the conserved motif for an N-linked glycan at position 38) in comparison to mock-immunized (PBS) animals was evaluated.

Groups of 10 female BALB/c mice (age 6-8 weeks) were intramuscularly immunized three times at a three-week interval with a dose range of soluble trimeric UFV170278 or UFV170282 adjuvanted with 2% (v/v) Adjuplex. The dose range consisted of 4 10-fold dilutions starting at 30 mcg up till 0.03 mcg. As a negative control 18 mice were immunized three times with PBS. Four weeks after the last immunization mice were bled to analyze the immune response and one day later the mice were challenged with 12.5×$LD_{50}$ mouse-adapted H3N2 A/Hong Kong/1/1968 challenge virus and monitored (survival, weight, clinical scores) for 3 weeks. Survival proportion at end of follow-up was the primary outcome parameter.

Results

It was shown that UFV170278 and UFV170282 are immunogenic as all doses of UFV170278 and UFV170282 induced significantly higher H3 A/Hong Kong/1/1968 HA stem-specific antibody titers (measured with a CR9114 competition assay) compared to the PBS group titers (P<0.001; ANOVA, with post-hoc t-test, step-wise testing (starting at the highest dose) and 2-fold Bonferroni correction for constructs), see FIG. 17A.

In addition, Adjuplex adjuvanted UFV170278 and UFV170282 provided significant protection (P<0.001; Fisher's exact test, step-wise testing (starting at the highest dose) and 2-fold Bonferroni correction for constructs) for all doses compared to the PBS group, see FIG. 17B. The bodyweight loss (defined by area under the curve) was significantly reduced (P<0.001; ANOVA, 2-fold Bonferroni correction over constructs, and step-wise testing, starting at highest dose) for all doses compared to the PBS group, see FIG. 17B.

Conclusion

According to the present invention, it thus has been shown that UFV170278 and UFV170282 are immunogenic and provide protection in a lethal H3N2 A/Hong Kong/1/1968 mouse challenge model.

Example 17: Polypeptides UFV180088, UFV180089 and UFV180090 of the Invention are Immunogenic in a Naïve Mouse Challenge Model In this example, the in vivo immunogenicity of a dose range of 2% (v/v) Adjuplex-adjuvanted UFV180088, UFV180089 and UFV180090 in comparison to mock-immunized (PBS) animals was evaluated.

Groups of 10 female BALB/c mice (age 6-8 weeks) were intramuscularly immunized one, two, or three times at a 3-week interval with 3 mcg of soluble trimeric UFV180088, UFV180089 or UFV180090. Final immunizations were given on the same day. As a negative control 18 mice were immunized three times with PBS. All immunizations were adjuvanted with 2% (v/v) Adjuplex. Four weeks after the final immunization mice were bled to analyze the immune response.

Results

It was shown that UFV180088, UFV180089 and UFV180090 are immunogenic as all constructs induced significantly higher H3 A/Hong Kong/1/1968 HA stem-specific antibody titers (measured with a CR9114 competition assay) after two or three immunizations compared to the PBS group titers (P<0.001; Wilcoxcon, 3-fold Bonferroni correction for multiple comparisons and stepwise testing, starting at the highest dose), see FIG. 18A. No construct induced significant stem-specific antibodies after one immunization.

All constructs induced significant higher H3 A/Hong Kong/1/1968 and H3 A/Texas/50/2012 HA-specific antibody titers (measured with a FL HA binding ELISAs) after two or three immunizations compared tot the PBS group titers (P<0.01; Wilcoxcon, 3-fold Bonferroni correction for multiple comparisons and stepwise testing, starting at the highest dose), see FIG. 18B. In addition, one immunization with UFV180088 and UFV180089 induced significant higher H3 A/Texas/50/2012 HA-specific antibody titers compared to the PBS group titers (P<0.01).

All construct induced significant higher H7 A/Netherlands/219/2003 HA-specific antibody titers (measured with a FL HA binding assay) after three immunizations compared tot the PBS group titers (P<0.001; Wilcoxcon, 3-fold Bonferroni correction for multiple comparisons and stepwise testing, starting at the highest dose), see FIG. 18B. Two immunizations with UFV180089 and UFV180090 induced significant higher titers compared to the PBS group antibody titers (P<0.001 and P<0.01, respectively), whereas no significant higher titers were detected after a single immunization.

Conclusion

According to the present invention, it thus has been shown that UFV180088, UFV180089 and UFV180090 are immunogenic in a naïve mouse model. All constructs induced significant HA stem-specific antibody titers and antibodies binding multiple phylogenetic distinct H3 (from strains isolated in different years) and H7 HA proteins.

Example 18: Polypeptides UFV180088, UFV180089 and UFV180090 of the Invention Induce Protection Against Lethal Challenge with H3N2 A/Hong Kong/1/1968 in a Naïve Mouse Challenge Model In this example, the in vivo protective efficacy (based on survival proportion at the end of the follow-up period) of a dose range of 2% (v/v) Adjuplex-adjuvanted UFV180088, UFV180089 and UFV180090 in comparison to mock-immunized (PBS) animals was evaluated.

Groups of 10 female BALB/c mice (age 6-8 weeks) were intramuscularly immunized one, two, or three times at a 3-week interval with 3 mcg of soluble trimeric UFV180088, UFV180089 or UFV180090. Final immunizations were given on the same day. As a negative control 18 mice were immunized three times with PBS. All immunizations were adjuvanted with 2% (v/v) Adjuplex. Four weeks after the final immunization mice were challenged with 25×$LD_{50}$ mouse-adapted H3N2 A/Hong Kong/1/1968 challenge virus and monitored (survival, weight, clinical scores) for 3 weeks. Survival proportion at end of follow-up was the primary outcome parameter.

Results

It was shown that UFV180088, UFV180089 and UFV180090 provide significant protection (P<0.001; Fisher's exact test, 2-fold Bonferroni correction over constructs, and step-wise testing, starting at highest dose) for two or three immunizations compared to the PBS group, see FIG. 19. No construct induced significant protection after one immunization. The bodyweight loss (defined by area under the curve) was significantly reduced (P<0.05; ANOVA, 2-fold Bonferroni correction over constructs, and step-wise testing, starting at highest dose) for all doses compared to the PBS group except after one immunization with UFV180089, see FIG. 19.

Conclusion

According to the present invention, it thus has been shown that UFV180088, UFV180089 and UFV180090 provide protection in a lethal H3N2 A/Hong Kong/1/1968 mouse challenge model.

TABLE 7

| Standard amino acids, abbreviations and properties | | | | |
|---|---|---|---|---|
| Amino Acid | 3-Letter | 1-Letter | Side chain polarity | Side chain charge (pH 7.4) |
| alanine | Ala | A | Nonpolar | Neutral |
| arginine | Arg | R | Polar | Positive |
| asparagine | Asn | N | Polar | Neutral |
| aspartic acid | Asp | D | Polar | Negative |
| cysteine | Cys | C | Nonpolar | Neutral |
| glutamic acid | Glu | E | Polar | Negative |
| glutamine | Gln | Q | Polar | Neutral |
| glycine | Gly | G | Nonpolar | Neutral |
| histidine | His | H | Polar | positive (10%) neutral (90%) |
| isoleucine | Ile | I | Nonpolar | Neutral |
| leucine | Leu | L | Nonpolar | Neutral |
| lysine | Lys | K | Polar | Positive |
| methionine | Met | M | Nonpolar | Neutral |
| phenylalanine | Phe | F | Nonpolar | Neutral |
| proline | Pro | P | Nonpolar | Neutral |
| serine | Ser | S | Polar | Neutral |
| threonine | Thr | T | Polar | Neutral |
| tryptophan | Trp | W | Nonpolar | Neutral |
| tyrosine | Tyr | Y | Polar | Neutral |
| valine | Val | V | Nonpolar | Neutral |

REFERENCES

Belongia et al. (2016), Lancet Infect. Dis. 16: 942-951.
Bommakanti et al. (2010), Proc. Natl. Acad. Sci. USA 107(31): 13701-13706.
Bommakanti et al. (2012), J Virol 86: 13434.
Ciani et al. (2010), Proc. Natl. Acad. Sci. USA 107(46): 19850-19855.
Corbett et al. (2019), mBio 10(1): e2810-2818.
Ekiert et al. (2009), Science 324(5924):246-51.
Das et al. (1985), Prog Nucleic Acid Res Mol Biol 32: 217-236.
Garten et al. (2017), MMWR Morb. Mortal Wkly Rep. 67: 634-642.
Gill et al. (2001), Gene Therapy 8: 1539-1546.
Kaufmann (2000), Mol Biotechnol 16: 151-160.
Letarov et al. (1993), Biochemistry Moscow 64: 817-823.
Lorieau et al. (2010), Proc. Natl. Acad. Sci. USA, 107: 11341.
S-Guthe et al. (2004), J. Mol. Biol. 337: 905-915.
Steel et al. (2010), mBio 1(1): 1-9.
Throsby et al. (2008), Plos One 12(3): 1-15.
Winter et al. (1981) Nature 292: 72-75.
Wu et al. (2015) Nature Communications 6(7708):1-11.

SEQUENCE LISTING

```
SEQ ID NO: 1 CAA24269.1 haemagglutinin (Influenza A virus
(A/Aichi/2/1968 (H3N2) (excluding signal sequence)
QDLPGNDNST ATLCLGHHAV PNGTLVKTIT DDQIEVTNAT ELVQSSSTGK    50
ICNNPHRILD GIDCTLIDAL LGDPHCDVFQ NETWDLFVER SKAFSNCYPY   100
DVPDYASLRS LVASSGTLEF ITEGFTWTGV TQNGGSNACK RGPGSGFFSR   150
LNWLTKSGST YPVLNVTMPN NDNFDKLYIW GIHHPSTNQE QTSLYVQASG   200
RVTVSTRRSQ QTIIPNIGSR PWVRGLSSRI SIYWTIVKPG DVLVINSNGN   250
LIAPRGYFKM RTGKSSIMRS DAPIDTCISE CITPNGSIPN DKPFQNVNKI   300
TYGACPKYVK QNTLKLATGM RNVPEKQTRG LFGAIAGFIE NGWEGMIDGW   350
YGFRHQNSEG TGQAADLKST QAAIDQINGK LNRVIEKTNE KFHQIEKEFS   400
EVEGRIQDLE KYVEDTKIDL WSYNAELLVA LENQHTIDLT DSEMNKLFEK   450
TRRQLRENAE EMGNGCFKIY HKCDNACIES IRNGTYDHDV YRDEALNNRF   500
QIKGVELKSG YKDWILWISF AISCFLLCVV LLGFIMWACQ RGNIRCNICI   550

SEQ ID NO 1: H3 Full length (A/Hong Kong/1/68)
MKTIIALSYIFCLALGQDLPGNDNSTATLCLGHHAVPNGTLVKTITDDQIEVTNATELVQSS
STGKICNNPHRILDGIDCTLIDALLGDPHCDVFQNETWDLFVERSKAFSNCYPYDVPDYASL
RSLVASSGTLEFITEGFTWTGVTQNGGSNACKRGPGSGFFSRLNWLTKSGSTYPVLNVTMPN
NDNFDKLYIWGVHHPSTNQEQTSLYVQASGRVTVSTRRSQQTIIPNIWSRPWVRGLSSRISI
YWTIVKPGDVLVINSNGNLIAPRGYFKMRTGKSSIMRSDAPIDTCISECITPNGSIPNDKPF
QNVNKITYGACPKYVKQNTLKLATGMRNVPEKQTRGLFGAIAGFIENGWEGMIDGWYGFRHQ
NSEGTGQAADLKSTQAAIDQINGKLNRVIEKTNEKFHQIEKEFSEVEGRIQDLEKYVEDTKI
DLWSYNAELLVALENQHTIDLTDSEMNKLFEKTRRQLRENAEDMGNGCFKIYHKCDNACIES
IRNGNYDHDVYRDEALNNRFQIKGVELKSGYKDWILWISFAISCFLLCVVLLGFIMWACQRG
NIRCNICI

CR6261 VH PROTEIN (SEQ ID NO: 3)
EVQLVESGAEVKKPGSSVKVSCKASGGPFRSYAISWVRQAPGQGPEWMGGIIPIFGTTKYAP
KFQGRVTITADDFAGTVYMELSSLRSEDTAMYYCAKHMGYQVRETMDVWGKGTTVTVSS

CR6261 VL PROTEIN (SEQ ID NO: 4)
QSVLTQPPSVSAAPGQKVTISCSGSSSNIGNDYVSWYQQLPGTAPKLLIYDNNKRPSGIPDR
FSGSKSGTSATLGITGLQTGDEANYYCATWDRRPTAYVVFGGGTKLTVL

CR8020 VH PROTEIN (SEQ ID NO: 5)
QVQLQQSGAEVKTPGASVKVSCKASGYTFTSFGVSWIRQAPGQGLEWIGWISAYNGDTYYAQ
KFQARVTMTTDTSTTTAYMEMRSLRSDDTAVYYCAREPPLFYSSWSLDNWGQGTLVTVSS

CR8020 VL PROTEIN (SEQ ID NO: 6)
EIVLTQSPGTLSLSPGERATLSCRASQSVSMNYLAWFQQKPGQAPRLLIYGASRRATGIPDR
ISGSGSGTDFTLTISRLEPADFAVYYCQQYGTSPRTFGQGAKVEIK

CR9114 VH PROTEIN (SEQ ID NO: 7)
QVQLVQSGAEVKKPGSSVKVSCKSSGGTSNNYAISWVRQAPGQGLDWMGGISPIFGSTAYAQ
KFQGRVTISADIFSNTAYMELNSLTSEDTAVYFCARHGNYYYYSGMDVWGQGTTVTVSS
```

-continued

SEQUENCE LISTING

CR9114 VL PROTEIN (SEQ ID NO: 8)
SYVLTQPPAVSGTPGQRVTISCSGSDSNIGRRSVNWYQQFPGTAPKLLIYSNDQRPSVVPDR
FSGSKSGTSASLAISGLQSEDEAEYYCAAWDDSLKGAVFGGGTQLTVL

FL HA OF Wisconsin/67/2005 (SEQ ID NO: 13)
MKTIIALSYILCLVFAQKLPGNDNSTATLCLGHHAVPNGTIVKTITNDQIEVTNATELVQSS
STGGICDSPHQILDGENCTLIDALLGDPQCDGFQNKKWDLFVERSKAYSNCYPYDVPDYASL
RSLVASSGTLEFNDESFNWTGVTQNGTSSSCKRRSNNSFFSRLNWLTHLKFKYPALNVTMPN
NEKFDKLYIWGVHHPVTDNDQIFLYAQASGRITVSTKRSQQTVIPNIGSRPRIRNIPSRISI
YWTIVKPGDILLINSTGNLIAPRGYFKIRSGKSSIMRSDAPIGKCNSECITPNGSIPNDKPF
QNVNRITYGACPRYVKQNTLKLATGMRNVPEKQTRGIFGAIAGFIENGWEGMVDGWYGFRHQ
NSEGIGQAADLKSTQAAINQINGKLNRLIGKTNEKFHQIEKEFSEVEGRIQDLEKYVEDTKI
DLWSYNAELLVALENQHTIDLTDSEMNKLFERTKKQLRENAEDMGNGCFKIYHKCDNACIGS
IRNGTYDHDVYRDEALNNRFQIKGVELKSGYKDWILWISFAISCFLLCVALLGFIMWACQKG
NIRCNICI FL HA OF A/Singapore/INFMH/16/0019/2016 (SEQ ID NO: 14)
MKTIIALSYILCLVFAQKIPGNDNSTATLCLGHHAVPNGTIVKTITNDRIEVTNATELVQNS
SIGEICDSPHQILDGENCTLIDALLGDPQCDGFQNKKWDLFVERSKAYSNCYPYDVPDYASL
RSLVASSGTLEFKNESFNWTGVTQNGTSSACIRGSSSSFFSRLNWLTHLNYKYPALNVTMPN
KEQFDKLYIWGVHHPGTDKDQIFPYAQSSGRITVSTKRSQQAVIPNIGSRPRIRGIPSRISI
YWTIVKPGDILLINSTGNLIAPRGYFKIRSGKSSIMRSDAPIGKCKSECITPNGSIPNDKPF
QNVNRITYGACPRYVKHSTLKLATGMRNVPEKQTRGIFGAIAGFIENGWEGMVDGWYGFRHQ
NSEGRGQAADLKSTQAAIDQINGKLNRLIGKTNEKFHQIEKEFSEVEGRVQDLEKYVEDTKI
DLWSYNAELLVALENQHTIDLTDSEMNKLFEKTKKQLRENAEDMGNGCFKIYHKCDNACIES
IRNETYDHNVYRDEALNNRFQIKGVELKSGYKDWILWISFAISCFLLCVALLGFIMWACQKG
NIRCNICI FL HA OF A/Perth/16/2009 (SEQ ID NO: 15)
MKTIIALSYILCLVFAQKLPGNDNSTATLCLGHHAVPNGTIVKTITNDQIEVTNATELVQSS
STGEICDSPHQILDGKNCTLIDALLGDPQCDGFQNKKWDLFVERSKAYSNCYPYDVPDYASL
RSLVASSGTLEFNNESFNWTGVTQNGTSSACIRRSKNSFFSRLNWLTHLNFKYPALNVTMPN
NEQFDKLYIWGVLHPGTDKDQIFLYAQASGRITVSTKRSQQTVSPNIGSRPRVRNIPSRISI
YWTIVKPGDILLINSTGNLIAPRGYFKIRSGKSSIMRSDAPIGKCNSECITPNGSIPNDKPF
QNVNRITYGACPRYVKQNTLKLATGMRNVPEKQTRGIFGAIAGFIENGWEGMVDGWYGFRHQ
NSEGRGQAADLKSTQAAIDQINGKLNRLIGKTNEKFHQIEKEFSEVEGRIQDLEKYVEDTKI
DLWSYNAELLVALENQHTIDLTDSEMNKLFEKTKKQLRENAEDMGNGCFKIYHKCDNACIGS
IRNGTYDHDVYRDEALNNRFQIKGVELKSGYKDWILWISFAISCFLLCVALLGFIMWACQKG
NIRCNICI FL HA OF A/Brisbane/10/2007 (SEQ ID NO: 16)
MKTIIALSYILCLVFTQKLPGNDNSTATLCLGHHAVPNGTIVKTITNDQIEVTNATELVQSS
STGEICDSPHQILDGENCTLIDALLGDPQCDGFQNKKWDLFVERSKAYSNCYPYDVPDYASL
RSLVASSGTLEFNNESENWTGVTQNGTSSACIRRSNNSFFSRLNWLTHLKFKYPALNVTMPN
NEKFDKLYIWGVHHPGTDNDQIFPYAQASGRITVSTKRSQQTVIPNIGSRPRVRNIPSRISI
YWTIVKPGDILLINSTGNLIAPRGYFKIRSGKSSIMRSDAPIGKCNSECITPNGSIPNDKPF
QNVNRITYGACPRYVKQNTLKLATGMRNVPEKQTRGIFGAIAGFIENGWEGMVDGWYGFRHQ
NSEGIGQAADLKSTQAAIDQINGKLNRLIGKTNEKFHQIEKEFSEVEGRIQDLEKYVEDTKI
DLWSYNAELLVALENQHTIDLTDSEMNKLFEKTKKQLRENAEDMGNGCFKIYHKCDNACIGS
IRNGTYDHDVYRDEALNNRFQIKGVELKSGYKDWILWISFAISCFLLCVALLGFIMWACQKG
NIRCNICI FL HA OF A/Panama/2007/1999 (SEQ ID NO: 17)
MKTIIALSYILCLVFAQKLPGNDNSTATLCLGHHAVSNGTLVKTITNDQIEVTNATELVQSS
STGRICDSPHQILDGENCTLIDALLGDPHCDGFQNKEWDLFVERSKAYSNCYPYDVPDYASL
RSLVASSGTLEFNNESENWTGVAQNGTSSACKRRSNKSFFSRLNWLHQLKYKYPALNVTMPN
NEKFDKLYIWGVHHPSTDSDQISIYAQASGRVTVSTKRSQQTVIPNIGSSPWVRGVSSRISI
YWTIVKPGDILLINSTGNLIAPRGYFKIRSGKSSIMRSDAPIGKCNSECITPNGSIPNDKPF
QNVNRITYGACPRYVKQNTLKLATGMRNVPEKQTRGIFGAIAGFIENGWEGMVDGWYGFRHQ
NSEGTGQAADLKSTQAAINQINGKLNRLIEKTNEKFHQIEKEFSEVEGRIQDLEKYVEDTKI
DLWSYNAELLVALENQHTIDLTDSEMNKLFERTKKQLRENAEDMGNGCFKIYHKCDNACIGS
IRNGTYDHDVYRDEALNNRFQIKGVELKSGYKDWILWISFAISCFLLCVVLLGFIMWACQKG
NIRCNICI CT149 VH PROTEIN (SEQ ID NO: 37)
QVQLVQSGAEVKKPGASVKVSCKTSGYSFSTYGVSWVRQAPGQGPEWVGWISAYTGITDYAQ
KFQGRVTLTTDATTATAFLDLRSLRPDDTATYFCARDKVQGRVEVGSGGRHDYWGQGTLVIV
SS CT149 VL PROTEIN (SEQ ID NO: 38)
EVVLTQSPGTLALPPGERATLSCRASHRVGSTYIAWYQQKSGQAPRRLIYGASNRATDIPDR
FSGSGSGTDFTLTIRRLEPEDSAVYYCQQFSVSPWTFGQGTRVEIK -continued

SEQUENCE LISTING

SD15013 (SEQ ID NO: 39)
EVQLVESGGGLVQAGDSLRISCAASGRTLSIYSMGWFRQAPGKEREFVATIGWNSGRTFYPD
SLKGRFTISRDNARNTLYLQMNNLRPEDTAVYYCAAAKGPLRLSSQADYWGQGTQVTVSSAA
AWSHPQFEKGAAWSHPQFEKGAAWSHPQFEK

SEQ ID NO 40: UFV180088
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVEPEA

SEQ ID NO 41: UFV180089
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADYK
STQAAIDQITNIVNRVIEKMNEKSNQTEKCPSNATGPMKCIEDKIEEIESKLWCYNAELLVA
LINQNTIDYTDSEMNKLFEKTRRQLRENAEDMGNGCFKIYHKCDDDCIASIRNGTYDHDVYR
DEALNNRFQIKGVEPEA

SEQ ID NO 42: UFV180090
MKTIIALSYIFCLALGQDLPGNDNSTATLCLGHHAVPNGTKVKTITEDQVEVTNATELVQSS
KYVCQNTLKLATGMRNVPEKQTQGLFGAIAGFIENGWEGMIDGWYGFRWQNSEGTGQAADYK
STQAAIDQITGILNRVIEKMNEKSNQTEKCPSNATGPMKCIEDKIEEIESKLWCYNAELLVA
LINQNTIDYTDSEMNKLFEKTRRQLRENAEDMGNGCFKIYHKCDNDCIASIRNGTYDHDVYR
DEALNNRFQIKGVEPEA

SEQ ID NO 43: UFV180141
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKCSSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 44: UFV180192
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKESSNATGRMKQIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 45: UFV180193
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRHQNSEGTGQAADLK
STQAAIDQITNIVNRVIEKMNEKSHQTEKCSSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 46: UFV180194
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKCSSNATGRIQCLEKYVEDTKIDLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 47: UFV180195
MKTIIALSYIFCLALGQDLPGNDNSTATLCLGHHAVPNGTLVKTITEDQVEVTNATELVQSS
KYVKQNTLKLATGMRNVPEKQTQGLFGAIAGFIENGWEGMIDGWYGFRWQNSEGTGQAADLK
STQAAIDQITNIVNRVIEKMNEKSHQTEKCSSNATGRMKCIEDKIEEIESKLWSYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 48: UFV180196
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQINGILNRVIEKMNEKSHQTEKCSSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 49: UFV180197
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTEKCSSNATGRMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

-continued

SEQUENCE LISTING

SEQ ID NO 50: UFV180198
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTEKCSSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 51: UFV180199
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKCSSNATGRMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 52: UFV180200
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKTNEKSHQTEKCSSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 53: UFV180201
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKCSSEVEGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 54: UFV180202
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQIEKCSSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 55: UFV180203
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKCSSNATGRMKCIEDKIEEIESKLWCYNAELLVA
LINQHTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 56: UFV180204
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKCSSNATGRMKCIEDKIEEIESKLWCYNAELLVA
LINQNTIDLTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 57: UFV180205
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKCSSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 58: UFV180206
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKFHQTEKCSSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 59: UFV180207
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKCFSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 60: UFV181034
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKFHQIEKCFSNATGRMKCIEDKIEEIESKLWCYNAELLVA
LINQHTIDLTDSEMNKLFEKTRRQLRENAEDMGNGCFKIYHKCDNACIESIRNGTYDHDVYR
DEALNNRFQIKGVHHHHHH

-continued

SEQUENCE LISTING

SEQ ID NO 61: UFV181036
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKFHQIEKCFSNATGRMKCIEDKIEEIESKLWCYNAELLVA
LINQNTIDLTDSEMNKLFEKTRRQLRENAEDMGNGCFKIYHKCDNACIESIRNGTYDHDVYR
DEALNNRFQIKGVHHHHHH

SEQ ID NO 62: UFV181038
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKFHQIEKCFSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVHHHHHH

SEQ ID NO 63: UFV181040
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSNQTEKCPSNATGPMKCIEDKIEEIESKLWCYNAELLVA
LENQHTIDLTDSEMNKLFEKTRRQLRENAEDMGNGCFKIYHKCDNACIESIRNGTYDHDVYR
DEALNNRFQIKGVHHHHHH

SEQ ID NO 64: UFV181042
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSNQTEKCPSNATGPMKCIEDKIEEIESKLWCYNAELLVA
LINQHTIDLTDSEMNKLFEKTRRQLRENAEDMGNGCFKIYHKCDNACIESIRNGTYDHDVYR
DEALNNRFQIKGVHHHHHH

SEQ ID NO 65: UFV161333
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 66: UFV161739
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 67: UFV161800
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIINGTYDHD
VYRDEALNNRFQIKGVELKSGYKDWIAAADYKDDDDKPGGGGSGGGGSGGGGSHHHHHH

SEQ ID NO 68: UFV161804
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRFQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIINGTYDHD
VYRDEALNNRFQIKGVELKSGYKDWIAAADYKDDDDKPGGGGSGGGGSGGGGSHHHHHH

SEQ ID NO 69: UFV170991
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 70: UFV171004
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTECESSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 71: UFV171190
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNFVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

-continued

SEQUENCE LISTING

SEQ ID NO 72: UFV171191
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTECESSNATGPMKCIEDKIEEIESKLWCYNAELLVA
LMNQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 73: UFV171192
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNFVNRVIEKMNEKSHQTECESSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 74: UFV171193
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNVVNRVIEKMNEKSHQTECESSNATGPMKCIEDKIEEIESKLWCYNAELLVA
LLNQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 75: UFV171194
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNMVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 76: UFV171195
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNTVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 77: UFV170611
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTECESSNATGRMKCIEDKIEEIESKLWCYNAEL
LVALENQHTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 78: UFV170612
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTECESSNATGRMKCIEDKIEEIESKLWCYNAEL
LVALENQKTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 79: UFV170613
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTECESSNATGRMKCIEDKIEEIESKLWCYNAEL
LVALENQNTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 80: UFV170614
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTECESSNATGRMKCIEDKIEEIESKLWCYNAEL
LVALENQQTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 81: UFV161908
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTECESSNATGRMKCIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 82: UFV171197
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTECESSNATGPMKCIEDKIEEIESKLWCYNAELLVA
LINQRTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

-continued

SEQUENCE LISTING

SEQ ID NO 83: UFV180666
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKTNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 84: UFV180667
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKVNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 85: UFV180668
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKINEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 86: UFV180669
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKLNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 87: UFV180670
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKFNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 88: UFV180671
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKYNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 89: UFV180672
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKWNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 90: UFV180673
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKHNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 91: UFV180674
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKKNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 92: UFV180675
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKRNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 93: UFV170636
MKTIIALSYIFCLALGQDLPGNDNSTATLCLGHHAVPNGTLVKTITEDQVEVTNAIELVQSK
YVCQNTLKLATGMRNVPEKQTRGLFGAIAGFIENGWEGMIDGWYGFRWQNSEGTGQAADLKS
TQAAIDQITNKVNRVIEKMNEKSHQTECESSNATGRMKCIEDKIEEIESKLWCYNAELLVAL
ENQRTIDYTDSEMNKLFEKTRRQLRENAEDMGNGCFKIYHKCDNACIESIRNGTYDHDVYRD
EALNNRFQIKGVELKSGYKDWIAAADYKDDDDKPGGGGSGGGGSGGGGSHHHHHH

-continued

SEQUENCE LISTING

SEQ ID NO 94: UFV170637
MKTIIALSYIFCLALGQDLPGNDNSTATLCLGHHAVPNGTLVKTITEDQVEVTNAIELVQSS
KYVCQNTLKLATGMRNVPEKQTRGLFGAIAGFIENGWEGMIDGWYGFRWQNSEGTGQAADLK
STQAAIDQITNKVNRVIEKMNEKSHQTECESSNATGRMKCIEDKIEEIESKLWCYNAELLVA
LENQRTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 95: UFV170638
MKTIIALSYIFCLALGQDLPGNDNSTATLCLGHHAVPNGTLVKTITEDQVEVTNAIELVQSS
SKYVCQNTLKLATGMRNVPEKQTRGLFGAIAGFIENGWEGMIDGWYGFRWQNSEGTGQAADL
KSTQAAIDQITNKVNRVIEKMNEKSHQTECESSNATGRMKCIEDKIEEIESKLWCYNAELLV
ALENQRTIDYTDSEMNKLFEKTRRQLRENAEDMGNGCFKIYHKCDNACIESIRNGTYDHDVY
RDEALNNRFQIKGVELKSGYKDWIAAADYKDDDDKPGGGGSGGGGSGGGGSHHHHHH

SEQ ID NO 96: UFV170639
MKTIIALSYIFCLALGQDLPGNDNSTATLCLGHHAVPNGTLVKTITEDQVEVTNAIELVQSS
STKYVCQNTLKLATGMRNVPEKQTRGLFGAIAGFIENGWEGMIDGWYGFRWQNSEGTGQAAD
LKSTQAAIDQITNKVNRVIEKMNEKSHQTECESSNATGRMKCIEDKIEEIESKLWCYNAELL
VALENQRTIDYTDSEMNKLFEKTRRQLRENAEDMGNGCFKIYHKCDNACIESIRNGTYDHDV
YRDEALNNRFQIKGVELKSGYKDWIAAADYKDDDDKPGGGGSGGGGSGGGGSHHHHHH

SEQ ID NO 97: UFV170640
MKTIIALSYIFCLALGQDLPGNDNSTATLCLGHHAVPNGTLVKTITEDQVEVTNAIELVQSS
STGKYVCQNTLKLATGMRNVPEKQTRGLFGAIAGFIENGWEGMIDGWYGFRWQNSEGTGQAA
DLKSTQAAIDQITNKVNRVIEKMNEKSHQTECESSNATGRMKCIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 98: UFV160653
MKTIIALSYIFCLALGQDLPGNDNSTATLCLGHHAVPNGTLVKTITDDQIEVTNATELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 99: UFV160764
MKTIIALSYIFCLALGQDLPGNDNSTATLCLGHHAVPNGTLVKTITDDQIEVTNATELVQSP
KYVCQNTLKLATGMRNVPEKQTRGLFGAIAGFIENGWEGMIDGWYGFRHQNSEGTGQAADLK
STQAAIDQITNKVNSVIEKMNEKSHQTEKESSNATGRMKQIEDKIEEIESKLWCYNAELLVA
LENQRTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 100: UFV160765
MKTIIALSYIFCLALGQDLPGNDNSTATLCLGHHAVPNGTLVKTITDDQIEVTNATELVQSC
PKYVCQNTLKLATGMRNVPEKQTRGLFGAIAGFIENGWEGMIDGWYGFRHQNSEGTGQAADL
KSTQAAIDQITNKVNSVIEKMNEKSHQTEKESSNATGRMKQIEDKIEEIESKLWCYNAELLV
ALENQRTIDYTDSEMNKLFEKTRRQLRENAEDMGNGCFKIYHKCDNACIESIRNGTYDHDVY
RDEALNNRFQIKGVELKSGYKDWIAAADYKDDDDKPGGGGSGGGGSGGGGSHHHHHH

SEQ ID NO 101: UFV160766
MKTIIALSYIFCLALGQDLPGNDNSTATLCLGHHAVPNGTLVKTITDDQIEVTNATELVQSA
CPKYVCQNTLKLATGMRNVPEKQTRGLFGAIAGFIENGWEGMIDGWYGFRHQNSEGTGQAAD
LKSTQAAIDQITNKVNSVIEKMNEKSHQTEKESSNATGRMKQIEDKIEEIESKLWCYNAELL
VALENQRTIDYTDSEMNKLFEKTRRQLRENAEDMGNGCFKIYHKCDNACIESIRNGTYDHDV
YRDEALNNRFQIKGVELKSGYKDWIAAADYKDDDDKPGGGGSGGGGSGGGGSHHHHHH

SEQ ID NO 102: UFV160674
MKTIIALSYIFCLALGQDLPGNDNSTATLCLGHHAVPNGTLVKTITDDQIEVTNATELVQSG
AGPKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 103: UFV160675
MKTIIALSYIFCLALGQDLPGNDNSTATLCLGHHAVPNGTLVKTITDDQIEVTNATELVQSG
ACPKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 104: UFV160767
MKTIIALSYIFCLALGQDLPGNDNSTATLCLGHHAVPNGTLVKTITDDQIEVTNATELVQSS
ACPKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

-continued

SEQUENCE LISTING

SEQ ID NO 105: UFV160768
MKTIIALSYIFCLALGQDLPGNDNSTATLCLGHHAVPNGTLVKTITDDQIEVTNATELVQSS
CPKYVCQNTLKLATGMRNVPEKQTRGLFGAIAGFIENGWEGMIDGWYGFRHQNSEGTGQAAD
LKSTQAAIDQITNKVNSVIEKMNEKSHQTEKESSNATGRMKQIEDKIEEIESKLWCYNAELL
VALENQRTIDYTDSEMNKLFEKTRRQLRENAEDMGNGCFKIYHKCDNACIESIRNGTYDHDV
YRDEALNNRFQIKGVELKSGYKDWIAAADYKDDDDKPGGGGSGGGGSGGGGSHHHHHH

SEQ ID NO 106: UFV160769
MKTIIALSYIFCLALGQDLPGNDNSTATLCLGHHAVPNGTLVKTITDDQIEVTNATELVQSS
SACPKYVCQNTLKLATGMRNVPEKQTRGLFGAIAGFIENGWEGMIDGWYGFRHQNSEGTGQA
ADLKSTQAAIDQITNKVNSVIEKMNEKSHQTEKESSNATGRMKQIEDKIEEIESKLWCYNAE
LLVALENQRTIDYTDSEMNKLFEKTRRQLRENAEDMGNGCFKIYHKCDNACIESIRNGTYDH
DVYRDEALNNRFQIKGVELKSGYKDWIAAADYKDDDDKPGGGGSGGGGSGGGGSHHHHHH

SEQ ID NO 107: UFV160770
MKTIIALSYIFCLALGQDLPGNDNSTATLCLGHHAVPNGTLVKTITDDQIEVTNATELVQSS
SCPKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 108: UFV160771
MKTIIALSYIFCLALGQDLPGNDNSTATLCLGHHAVPNGTLVKTITDDQIEVTNATELVQSS
PKYVCQNTLKLATGMRNVPEKQTRGLFGAIAGFIENGWEGMIDGWYGFRHQNSEGTGQAADL
KSTQAAIDQITNKVNSVIEKMNEKSHQTEKESSNATGRMKQIEDKIEEIESKLWCYNAELLV
ALENQRTIDYTDSEMNKLFEKTRRQLRENAEDMGNGCFKIYHKCDNACIESIRNGTYDHDVY
RDEALNNRFQIKGVELKSGYKDWIAAADYKDDDDKPGGGGSGGGGSGGGGSHHHHHH

SEQ ID NO 109: UFV160772
MKTIIALSYIFCLALGQDLPGNDNSTATLCLGHHAVPNGTLVKTITDDQIEVTNATELVQSS
SPKYVCQNTLKLATGMRNVPEKQTRGLFGAIAGFIENGWEGMIDGWYGFRHQNSEGTGQAAD
LKSTQAAIDQITNKVNSVIEKMNEKSHQTEKESSNATGRMKQIEDKIEEIESKLWCYNAELL
VALENQRTIDYTDSEMNKLFEKTRRQLRENAEDMGNGCFKIYHKCDNACIESIRNGTYDHDV
YRDEALNNRFQIKGVELKSGYKDWIAAADYKDDDDKPGGGGSGGGGSGGGGSHHHHHH

SEQ ID NO 110: UFV160321
MKTIIALSYIFCLALGQDLPGNDNSTATLCLGHHAVPNGTLVKTITDDQIEVTNATELVQSG
GGGKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 111: UFV160403
MKTIIALSYIFCLALGQDLPGNDNSTATLCLGHHAVPNGTLVKTITDDQIEVTNATELVQSN
PHRKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 112: UFV160404
MKTIIALSYIFCLALGQDLPGNDNSTATLCLGHHAVPNGTLVKTITDDQIEVTNATELVQSG
DPHKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 113: UFV160405
MKTIIALSYIFCLALGQDLPGNDNSTATLCLGHHAVPNGTLVKTITDDQIEVTNATELVQSN
GGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 114: UFV160406
MKTIIALSYIFCLALGQDLPGNDNSTATLCLGHHAVPNGTLVKTITDDQIEVTNATELVQSG
GSNKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 115: UFV160407
MKTIIALSYIFCLALGQDLPGNDNSTATLCLGHHAVPNGTLVKTITDDQIEVTNATELVQSG
SNAKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQUENCE LISTING

SEQ ID NO 116: UFV160408
MKTIIALSYIFCLALGQDLPGNDNSTATLCLGHHAVPNGTLVKTITDDQIEVTNATELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 117: UFV160409
MKTIIALSYIFCLALGQDLPGNDNSTATLCLGHHAVPNGTLVKTITDDQIEVTNATELVQSG
SGFKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 118: UFV160410
MKTIIALSYIFCLALGQDLPGNDNSTATLCLGHHAVPNGTLVKTITDDQIEVTNATELVQSG
SGKYVCQNTLKLATGMRNVPEKQTRGLFGAIAGFIENGWEGMIDGWYGFRHQNSEGTGQAAD
LKSTQAAIDQITNKVNSVIEKMNEKSHQTEKESSNATGRMKQIEDKIEEIESKLWCYNAELL
VALENQRTIDLTDSEMNKLFEKTRRQLRENAEDMGNGCFKIYHKCDNACIESIRNGTYDHDV
YRDEALNNRFQIKGVELKSGYKDWIAAADYKDDDDKPGGGGSGGGGSGGGGSHHHHHH

SEQ ID NO 119: UFV160411
MKTIIALSYIFCLALGQDLPGNDNSTATLCLGHHAVPNGTLVKTITDDQIEVTNATELVQSG
GKYVCQNTLKLATGMRNVPEKQTRGLFGAIAGFIENGWEGMIDGWYGFRHQNSEGTGQAADL
KSTQAAIDQITNKVNSVIEKMNEKSHQTEKESSNATGRMKQIEDKIEEIESKLWCYNAELLV
ALENQRTIDLTDSEMNKLFEKTRRQLRENAEDMGNGCFKIYHKCDNACIESIRNGTYDHDVY
RDEALNNRFQIKGVELKSGYKDWIAAADYKDDDDKPGGGGSGGGGSGGGGSHHHHHH

SEQ ID NO 120: UFV160412
MKTIIALSYIFCLALGQDLPGNDNSTATLCLGHHAVPNGTLVKTITDDQIEVTNATELVQSG
GSKYVCQNTLKLATGMRNVPEKQTRGLFGAIAGFIENGWEGMIDGWYGFRHQNSEGTGQAAD
LKSTQAAIDQITNKVNSVIEKMNEKSHQTEKESSNATGRMKQIEDKIEEIESKLWCYNAELL
VALENQRTIDLTDSEMNKLFEKTRRQLRENAEDMGNGCFKIYHKCDNACIESIRNGTYDHDV
YRDEALNNRFQIKGVELKSGYKDWIAAADYKDDDDKPGGGGSGGGGSGGGGSHHHHHH

SEQ ID NO 121: UFV160413
MKTIIALSYIFCLALGQDLPGNDNSTATLCLGHHAVPNGTLVKTITDDQIEVTNATELVQSS
GSKYVCQNTLKLATGMRNVPEKQTRGLFGAIAGFIENGWEGMIDGWYGFRHQNSEGTGQAAD
LKSTQAAIDQITNKVNSVIEKMNEKSHQTEKESSNATGRMKQIEDKIEEIESKLWCYNAELL
VALENQRTIDLTDSEMNKLFEKTRRQLRENAEDMGNGCFKIYHKCDNACIESIRNGTYDHDV
YRDEALNNRFQIKGVELKSGYKDWIAAADYKDDDDKPGGGGSGGGGSGGGGSHHHHHH

SEQ ID NO 122: UFV160414
MKTIIALSYIFCLALGQDLPGNDNSTATLCLGHHAVPNGTLVKTITDDQIEVTNATELVQSH
PSTKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 123: UFV160415
MKTIIALSYIFCLALGQDLPGNDNSTATLCLGHHAVPNGTLVKTITDDQIEVTNATELVQSI
PNIKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 124: UFV160416
MKTIIALSYIFCLALGQDLPGNDNSTATLCLGHHAVPNGTLVKTITDDQIEVTNATELVQSG
LSSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 125: UFV160417
MKTIIALSYIFCLALGQDLPGNDNSTATLCLGHHAVPNGTLVKTITDDQIEVTNATELVQSK
PGDKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 126: UFV160418
MKTIIALSYIFCLALGQDLPGNDNSTATLCLGHHAVPNGTLVKTITDDQIEVTNATELVQSD
APIKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

-continued

SEQUENCE LISTING

SEQ ID NO 127: UFV160419
MKTIIALSYIFCLALGQDLPGNDNSTATLCLGHHAVPNGTLVKTITDDQIEVTNATELVQST
PNKYVCQNTLKLATGMRNVPEKQTRGLFGAIAGFIENGWEGMIDGWYGFRHQNSEGTGQAAD
LKSTQAAIDQITNKVNSVIEKMNEKSHQTEKESSNATGRMKQIEDKIEEIESKLWCYNAELL
VALENQRTIDLTDSEMNKLFEKTRRQLRENAEDMGNGCFKIYHKCDNACIESIRNGTYDHDV
YRDEALNNRFQIKGVELKSGYKDWIAAADYKDDDDKPGGGGSGGGGSGGGGSHHHHHH

SEQ ID NO 128: UFV160420
MKTIIALSYIFCLALGQDLPGNDNSTATLCLGHHAVPNGTLVKTITDDQIEVTNATELVQST
PNGKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDLTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 129: UFV161686
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSEVEGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 130: UFV161722
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSQATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 131: UFV161723
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNAQGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 132: UFV161688
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIPKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 133: UFV161689
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEPMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 134: UFV161690
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKPNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 135: UFV161691
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMPEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 136: UFV161692
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNPKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 137: UFV161693
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEPSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

-continued

SEQUENCE LISTING

SEQ ID NO 138: UFV161694
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKPHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 139: UFV161695
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSPQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 140: UFV161696
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHPTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 141: UFV161697
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQPEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 142: UFV161698
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTPKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 143: UFV161699
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEPESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 144: UFV161700
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKPSSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 145: UFV161701
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKEPSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 146: UFV161702
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESPNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 147: UFV161703
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSPATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 148: UFV161704
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNPTGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

-continued

SEQUENCE LISTING

SEQ ID NO 149: UFV161705
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNAPGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 150: UFV161706
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATPRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 151: UFV161707
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGPMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 152: UFV161708
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKPHQTPKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 153: UFV161709
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKPHQTEKPSSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 154: UFV161715
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSNQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 155: UFV161721
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKNSSNATGRMKQIEDKIEEIESKLWCYNAEL
LVALENQRTIDYTDSEMNKLFEKTRRQLRENAEDMGNGCFKIYHKCDNACIESIRNGTYHDV
YRDEALNNRFQIKGVELKSGYKDWIAAADYKDDDDKPGGGGSGGGGSGGGGSHHHHHH

SEQ ID NO 156: UFV171187
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGRMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 157: UFV171120
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKnHTTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 158: UFV171121
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKnHTTECEPSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 159: UFV170994
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSNQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

-continued

SEQUENCE LISTING

SEQ ID NO 160: UFV170995
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSNQTECEPSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 161: UFV180208
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKFHQTEKCFSNATGRMKCIEDKIEEIESKLWCYNAELLVA
LINQHTIDLTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 162: UFV180217
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKFNQTEKCPSNATGPMKCIEDKIEEIESKLWCYNAELLVA
LINQHTIDLTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 163: UFV170278
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTEKCSSNATGRMKCIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIGAAEPEA

SEQ ID NO 164: UFV170282
MKTIIALSYIFCLALGQDLPGNDNSTATLCLGHHAVPNGTLVKTITEDQVEVTNATELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTEKCSSNATGRMKCIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIGAAEPEA

SEQ ID NO 165: UFV160595
MKTIIALSYIFCLALGQDLPGNDNSTATLCLGHHAVPNGTLVKTITDDQIEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 166: UFV161196
MKTIIALSYIFCLALGQDLPGNDNSTATLCLGHHAVPNGTLVKTITDDQIEVTNAIELVQSG
PGSKGPKCNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 167: UFV161198
MKTIIALSYIFCLALGQDLPGNDNSTATLCLGHHAVPNGTLVKTITDDQIEVTNAIELVQSG
PGSKCVPQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIECKLWAYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 168: UFV161169
MKTIIALSYIFCLALGQDLPGNDNSTATLCLGHHAVPNGTLCKTITDDQIEVTNAIELVQSG
PGSKYVCQNTLKLATGMRNVPEKQTRGLFGAIAGFIENGWEGMIDGWYGFRHQNSEGTGQAA
DLKSTQAAIDQITNKVNSVIEKMNEKSHQTEKESSNATGRMKQIEDKIEEIESKLWCYNAEL
LVALECQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 169: UFV170062
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 170: UFV170051
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTEKCSSNATGRMKCIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

-continued

SEQUENCE LISTING

SEQ ID NO 171: UFV170428
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTCKESSNATGRMKCIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 172: UFV170440
MKTIIALSYIFCLALGQDLPGNDNSTATLCLGHHAVPNGTLVKTITEDQVEVTNAIELVQSG
PGSKYVCQNTLKLATGMRNVPEKQTRGLFGAIAGFIENGWEGMIDGWYGFRWQNSEGTGQAA
DLKSTQAAIDQITNKVNRVIEKMNEKSHQTEKCSSNATGCMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 173: UFV171272
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKDWI

SEQ ID NO 174: UFV171273
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGYKD

SEQ ID NO 175: UFV171274
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKSGY

SEQ ID NO 176: UFV171275
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVELKS

SEQ ID NO 177: UFV171276
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGVEL

SEQ ID NO 178: UFV171277
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIKGV

SEQ ID NO 179: UFV171278
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQIK

SEQ ID NO 180: UFV171279
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNRFQ

SEQ ID NO 181: UFV171280
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKSHQTECESSNATGPMKCIEDKIEEIESKLWCYNAELLVA
LENQNTIDYTDSEMNKLFEKTRRQLRENAEDMGNGCFKIYHKCDNACIESIRNGTYDHDVYR
DEALNNR

SEQUENCE LISTING

SEQ ID NO 182: UFV161454
MKTIIALSYIFCLALGQDLPGNDNSTATLCLGHHAVPNGTLVKTITDDQIEVTNAIELVQSG
PGSKYVCQNTLKLATGMRNVPEKQTRGLFGAIAGFIENGWEGMIDGWYGFRHQNSEGTGQAA
DLKSTQAAIDQINGKLNRVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 183: UFV161453
MKTIIALSYIFCLALGQDLPGNDNSTATLCLGHHAVPNGTLVKTITDDQIEVTNAIELVQSG
PGSKYVCQNTLKLATGMRNVPEKQTRGLFGAIAGFIENGWEGMIDGWYGFRHQNSEGTGQAA
DLKSTQAAIDQINNKLNRVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 184: UFV161459
MKTIIALSYIFCLALGQDLPGNDNSTATLCLGHHAVPNGTLVKTITDDQIEVTNAIELVQSG
PGSKYVCQNTLKLATGMRNVPEKQTRGLFGAIAGFIENGWEGMIDGWYGFRHQNSEGTGQAA
DLKSTQAAIDQINAKLNRVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 185: UFV161451
MKTIIALSYIFCLALGQDLPGNDNSTATLCLGHHAVPNGTLVKTITDDQIEVTNAIELVQSG
PGSKYVCQNTLKLATGMRNVPEKQTRGLFGAIAGFIENGWEGMIDGWYGFRHQNSEGTGQAA
DLKSTQAAIDQINNKVNRVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 186: UFV161458
MKTIIALSYIFCLALGQDLPGNDNSTATLCLGHHAVPNGTLVKTITDDQIEVTNAIELVQSG
PGSKYVCQNTLKLATGMRNVPEKQTRGLFGAIAGFIENGWEGMIDGWYGFRHQNSEGTGQAA
DLKSTQAAIDQINAKVNRVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 187: UFV161450
MKTIIALSYIFCLALGQDLPGNDNSTATLCLGHHAVPNGTLVKTITDDQIEVTNAIELVQSG
PGSKYVCQNTLKLATGMRNVPEKQTRGLFGAIAGFIENGWEGMIDGWYGFRHQNSEGTGQAA
DLKSTQAAIDQITNKLNRVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 188: UFV161448
MKTIIALSYIFCLALGQDLPGNDNSTATLCLGHHAVPNGTLVKTITDDQIEVTNAIELVQSG
PGSKYVCQNTLKLATGMRNVPEKQTRGLFGAIAGFIENGWEGMIDGWYGFRHQNSEGTGQAA
DLKSTQAAIDQITNKVNRVIEKMNEKSHQTEKESSNATGRMKQIEDKIEEIESKLWCYNAEL
LVALENQRTIDYTDSEMNKLFEKTRRQLRENAEDMGNGCFKIYHKCDNACIESIRNGTYDHD
VYRDEALNNRFQIKGVELKSGYKDWIAAADYKDDDDKPGGGGSGGGGSGGGGSHHHHHH

SEQ ID NO 189: UFV171116
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQINGILNRVIEKMNEKSHQTECESSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVELKSGYKDWIAAADYKDDDDKPGGGGSGGGGSGGGGSHHHHHH

SEQ ID NO 190: UFV172561
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSNQTECEPSNATGPMKCIEDKIEEIESKLWCYNAELLVA
LINQRTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 191: UFV172563
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADYK
STQAAIDQITNIVNRVIEKMNEKSNQTECEPSNATGPMKCIEDKIEEIESKLWCYNAELLVA
LINQRTIDYTDSEMNKLFEKTRRQLRENAEDMGNGCFKIYHKCDDDCIASIRNGTYDHDVYR
DEALNNRFQIKGVAAADYKDDDDKPGGGGSGGGGSGGGGSHHHHHH

SEQ ID NO 192: UFV172564
MKTIIALSYIFCLALGQDLPGNDNSTATLCLGHHAVPNGTKVKTITEDQVEVTNATELVQSS
KYVCQNTLKLATGMRNVPEKQTQGLFGAIAGFIENGWEGMIDGWYGFRWQNSEGTGQAADYK
STQAAIDQITNIVNRVIEKMNEKSNQTECEPSNATGPMKCIEDKIEEIESKLWCYNAELLVA
LINQRTIDYTDSEMNKLFEKTRRQLRENAEDMGNGCFKIYHKCDDDCIASIRNGTYDHDVYR
DEALNNRFQIKGVAAADYKDDDDKPGGGGSGGGGSGGGGSHHHHHH

SEQUENCE LISTING

SEQ ID NO 193: UFV172571
MKTIIALSYIFCLALGQDLPGNDNSTATLCLGHHAVPNGTKVNTITEDQVEVTNATELVQSS
KYVCQNTLKLATGMRNVPEKQTQGLFGAIAGFIENGWEGMIDGWYGFRWQNSEGTGQAADYK
STQAAIDQITNIVNRVIEKMNEKSNQTECEPSNATGPMKCIEDKIEEIESKLWCYNAELLVA
LINQRTIDYTDSEMNKLFEKTRRQLRENAEDMGNGCFKIYHKCDNDCIASIRNGTYDHDVYR
DEALNNRFQIKGVAAADYKDDDDKPGGGGSGGGGSGGGGSHHHHHH

SEQ ID NO 194: UFV172562
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITGILNRVIEKMNEKSNQTECEPSNATGPMKCIEDKIEEIESKLWCYNAELLVA
LINQRTIDYTDSEMNKLFEKTRRQLRENAEDMGNGCFKIYHKCDNACIESIRNGTYDHDVYR
DEALNNRFQIKGVAAADYKDDDDKPGGGGSGGGGSGGGGSHHHHHH

SEQ ID NO 195: UFV172588
MKTIIALSYIFCLALGQDLPGNDNSTATLCLGHHAVPNGTKVKTITEDQVEVTNATELVQSS
KYVCQNTLKLATGMRNVPEKQTQGLFGAIAGFIENGWEGMIDGWYGFRWQNSEGTGQAADYK
STQAAIDQITGILNRVIEKMNEKSNQTECEPSNATGPMKCIEDKIEEIESKLWCYNAELLVA
LINQRTIDYTDSEMNKLFEKTRRQLRENAEDMGNGCFKIYHKCDNDCIASIRNGTYDHDVYR
DEALNNRFQIKGVAAADYKDDDDKPGGGGSGGGGSGGGGSHHHHHH

SEQ ID NO 196: UFV172583
MKTIIALSYIFCLALGQDLPGNDNSTATLCLGHHAVPNGTKVKTITEDQVEVTNATELVQSS
KYVCQNTLKLATGMRNVPEKQTQGLFGAIAGFIENGWEGMIDGWYGFRWQNSEGTGQAADYK
STQAAIDQITGILNRVIEKMNEKSNQTECEPSNATGPMKCIEDKIEEIESKLWCYNAELLVA
LINQRTIDYTDSEMNKLFEKTRRQLRENAEDMGNGCFKIYHKCDDDCIASIRNGTYDHDVYR
DEALNNRFQIKGVAAADYKDDDDKPGGGGSGGGGSGGGGSHHHHHH

SEQ ID NO 197: UFV172585
MKTIIALSYIFCLALGQDLPGNDNSTATLCLGHHAVPNGTKVNTITEDQVEVTNATELVQSS
KYVCQNTLKLATGMRNVPEKQTQGLFGAIAGFIENGWEGMIDGWYGFRWQNSEGTGQAADYK
STQAAIDQITGILNRVIEKMNEKSNQTECEPSNATGPMKCIEDKIEEIESKLWCYNAELLVA
LINQRTIDYTDSEMNKLFEKTRRQLRENAEDMGNGCFKIYHKCDDDCIASIRNGTYDHDVYR
DEALNNRFQIKGVAAADYKDDDDKPGGGGSGGGGSGGGGSHHHHHH

SEQ ID NO 198: UFV180642
MKTIIALSYILCLVFAQKIPGNDNSTATLCLGHHAVPNGTIVKTITNDRIEVTNATELVQNS
RYVCHSTLKLATGMRNVPEKQTQGIFGAIAGFIENGWEGMVDGWYGFRWQNSEGRGQAADLK
STQAAIDQITNKVNRLIGKMNEKFHQIEKCFSNATGRMKCIEDKIEEIESKLWCYNAELLVA
LENQHTIDLTDSEMNKLFEKTKKQLRENAEDMGNGCFKIYHKCDNACIESIRNETYDHNVYR
DEALNNRFQIKGVHHHHHH

SEQ ID NO 199: UFV180645
MKTIIALSYILCLVFAQKLPGNDNSTATLCLGHHAVPNGTIVKTITNDQIEVTNATELVQSS
RYVCQNTLKLATGMRNVPEKQTQGIFGAIAGFIENGWEGMVDGWYGFRWQNSEGIGQAADLK
STQAAINQITNKVNRLIGKMNEKFHQIEKCFSNATGRMKCIEDKIEEIESKLWCYNAELLVA
LENQHTIDLTDSEMNKLFERTKKQLRENAEDMGNGCFKIYHKCDNACIGSIRNGTYDHDVYR
DEALNNRFQIKGVHHHHHH

SEQ ID NO 200: UFV180647
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNKVNRVIEKMNEKFHQIEKCFSNATGRMKCIEDKIEEIESKLWCYNAELLVA
LENQHT IDLTDSEMNKLFEKTRRQLRENAEDMGNGCFKIYHKCDNACIESIRNGTYDHDVYR
DEALNNRFQIKGVHHHHHH

SEQ ID NO 201: UFV181106
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVHHHHHH

SEQ ID NO 202: UFV181107
MKTIIALSYILCLVFAQKLPGNDNSTATLCLGHHAVPNGTIVKTITNDQIEVTNATELVQSS
RYVCQNTLKLATGMRNVPEKQTQGIFGAIAGFIENGWEGMVDGWYGFRWQNSEGIGQAADLK
STQAAINQITNIVNRLIGKMNEKSNQTEKCPSNATGPMKCIEDKIEEIESKLWCYNAELLVA
LINQNTIDYTDSEMNKLFERTKKQLRENAEDMGNGCFKIYHKCDNACIGSIRNGTYDHDVYR
DEALNNRFQIKGVHHHHHH

SEQ ID NO 203: UFV181109
MKTIIALSYILCLVFAQKIPGNDNSTATLCLGHHAVPNGTIVKTITNDRIEVTNATELVQNS
RYVCHSTLKLATGMRNVPEKQTQGIFGAIAGFIENGWEGMVDGWYGFRWQNSEGRGQAADLK
STQAAIDQITNIVNRLIGKMNEKSNQTEKCPSNATGPMKCIEDKIEEIESKLWCYNAELLVA
LINQNTIDYTDSEMNKLFEKTKKQLRENAEDMGNGCFKIYHKCDNACIESIRNETYDHNVYR
DEALNNRFQIKGVHHHHHH

-continued

SEQUENCE LISTING

SEQ ID NO 204: UFV181117
MKTIIALSYIFCLALGQDLPGNDNSTATLCLGHHAVPNGTLVKTITDDQIEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSHQTEKCSSNATGRMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVHHHHHH

SEQ ID NO 205: UFV181118
MKTIIALSYILCLVFAQKLPGNDNSTATLCLGHHAVPNGTIVKTITNDQIEVTNATELVQSS
RYVCQNTLKLATGMRNVPEKQTQGIFGAIAGFIENGWEGMVDGWYGFRWQNSEGIGQAADLK
STQAAINQITNIVNRLIGKMNEKSHQTEKCSSNATGRMKCIEDKIEEIESKLWCYNAELLVA
LINQNTIDYTDSEMNKLFERTKKQLRENAEDMGNGCFKIYHKCDNACIGSIRNGTYDHDVYR
DEALNNRFQIKGVHHHHHH

SEQ ID NO 206: UFV181120
MKTIIALSYILCLVFAQKIPGNDNSTATLCLGHHAVPNGTIVKTITNDRIEVTNATELVQNS
RYVCHSTLKLATGMRNVPEKQTQGIFGAIAGFIENGWEGMVDGWYGFRWQNSEGRGQAADLK
STQAAIDQITNIVNRLIGKMNEKSHQTEKCSSNATGRMKCIEDKIEEIESKLWCYNAELLVA
LINQNTIDYTDSEMNKLFEKTKKQLRENAEDMGNGCFKIYHKCDNACIESIRNETYDHNVYR
DEALNNRFQIKGVHHHHHH

SEQ ID NO 207: UFV180480 (UFV180088 + native trans-
membrane (TM) domain)
MKTIIALSYIFCLALGQDLPGNDNSTATLCLGHHAVPNGTLVKTITEDQVEVTNATELVQSS
KYVCQNTLKLATGMRNVPEKQTQGLFGAIAGFIENGWEGMIDGWYGFRWQNSEGTGQAADLK
STQAAIDQITNIVNRVIEKMNEKSNQTEKCPSNATGPMKCIEDKIEEIESKLWCYNAELLVA
LINQNTIDYTDSEMNKLFEKTRRQLRENAEDMGNGCFKIYHKCDNACIESIRNGTYDHDVYR
DEALNNRFQIKGVELKSGYKDWILWISFAISCFLLCVVLLGFIMWACQRGNIRCNICI SEQ ID NO 208: nucleotide sequence encoding UFV180088
ATGAAAACCATTATCGCACTGAGTTACATCTTCTGCCTGGCTCTGGGACAGGATCTG
CCTGGGAACGACAACAGCACAGCAACACTGTGCCTGGGACACCATGCTGTGCCCAAC
GGGACCCTGGTCAAGACCATCACAGAGGATCAGGTGGAAGTGACTAATGCAACCGAA
CTGGTCCAGAGCTCCAAGTACGTGTGCCAGAACACCCTGAAACTGGCCACAGGCATG
AGAAATGTCCCTGAGAAGCAGACCCAGGGGCTGTTCGGCGCTATCGCAGGCTTCATC
GAGAACGGATGGGAAGGGATGATCGACGGCTGGTATGGATTCCGGTGGCAGAATTCC
GAGGGAACAGGGCAGGCCGCTGACCTGAAGTCTACTCAGGCAGCCATCGATCAGATT
ACCAACATCGTGAATCGCGTCATCGAGAAGATGAACGAAAAAAGCAATCAGACAGAG
AAGTGCCCCTCCAATGCCACTGGCCCCATGAAGTGTATTGAGGATAAGATCGAGGAA
ATCGAAAGTAAACTGTGGTGCTACAACGCCGAGCTGCTGGTGGCTCTGATCAATCAG
AATACAATCGACTATACTGATTCAGAGATGAACAAGCTGTTCGAAAAAACTAGGAGA
CAGCTGCGAGAGAACGCAGAAGACATGGGCAATGGATGTTTTAAGATCTACCACAAA
TGCGATAACGCCTGTATCGAGTCTATTAGGAATGGCACATACGACCATGACGTGTAC
CGGGACGAAGCACTGAACAATCGCTTTCAGATCAAGGGGGTGGAACCAGAGGCATAA
TAA SEQ ID NO 209: nucleotide sequence encoding UFV180480
(UFV180088 + TM domain)
ATGAAGACCATCATCGCCCTGTCTTACATCTTCTGCCTGGCCCTGGGACAGGACCTG
CCAGGCAACGATAATAGCACCGCCACCCTGTGCCTGGGACACCACGCAGTGCCCAAC
GGCACCCTGGTGAAGACCATCACAGAGGACCAGGTGGAGGTGACCAATGCCACAGAG
CTGGTGCAGAGCTCCAAGTACGTGTGCCAGAACACCCTGAAGCTGGCCACAGGCATG
AGAAATGTGCCCGAGAAGCAGACCCAGGGCCTGTTCGGAGCCATCGCCGGCTTTATC
GAGAACGGCTGGGAGGGCATGATCGATGGCTGGTATGGCTTTCGGTGGCAGAATAGC
GAGGGAACAGGACAGGCAGCAGACCTGAAGTCCACCCAGGCAGCCATCGATCAGATC
ACAAACATCGTGAATAGAGTGATCGAGAAGATGAACGAGAAGTCCAATCAGACCGAG
AAGTGCCCCTCTAACGCCACAGGCCCTATGAAGTGTATCGAGGACAAGATCGAGGAG
ATCGAGTCCAAGCTGTGGTGCTACAACGCCGAGCTGCTGGTGGCCCTGATCAACCAG
AATACCATCGACTATACAGATTCTGAGATGAATAAGCTGTTCGAGAAGACCCGGAGA
CAGCTGAGGGAGAACGCCGAGGACATGGGCAATGGCTGTTTTAAGATCTACCACAAG
TGCGATAACGCCTGTATCGAGAGCATCCGCAATGGCACATACGACCACGACGTGTAC
CGGGACGAGGCCCTGAACAATAGATTCCAGATCAAGGGCGTGGAGCTGAAGTCCGGC
TATAAGGATTGGATCCTGTGGATCTCTTTCGCCATCAGCTGCTTTCTGCTGTGCGTG
GTGCTGCTGGGCTTTATCATGTGGGCCTGTCAGAGGGGCAACATCCGCTGCAATATCTG
TATCTGATAA SEQ ID NO: 210 (minimal sequence of UFV180088)
QDLPGNDNSTATLCLGHHAVPNGTLVKTITEDQVEVTNATELVQSSKYVCQNTLKLA
TGMRNVPEKQTQGLFGAIAGFIENGWEGMIDGWYGFRWQNSEGTGQAADLKSTQAAI
DQITNIVNRVIEKMNEKSNQTEKCPSNATGPMKCIEDKIEEIESKLWCYNAELLVAL
INQNTIDYTDSEMNKLFEKTRRQLRENAEDMGNGCFKIYHKCDNACIESIRNGTYDH
DVYRDEALNNRFQIKGV SEQ ID NO: 211 (minimal sequence of UFV180089)
QDLPGNDNSTATLCLGHHAVPNGTLVKTITEDQVEVTNATELVQSSKYVCQNTLKLA
TGMRNVPEKQTQGLFGAIAGFIENGWEGMIDGWYGFRWQNSEGTGQAADYKSTQAAI -continued

| SEQUENCE LISTING |
| --- |
| DQITNIVNRVIEKMNEKSNQTEKCPSNATGPMKCIEDKIEEIESKLWCYNAELLVAL<br>INQNTIDYTDSEMNKLFEKTRRQLRENAEDMGNGCFKIYHKCDDDCIASIRNGTYDH<br>DVYRDEALNNRFQIKGV |
| SEQ ID NO: 212 (minimal sequence of UFV180090)<br>QDLPGNDNSTATLCLGHHAVPNGTKVKTITEDQVEVTNATELVQSSKYVCQNTLKLA<br>TGMRNVPEKQTQGLFGAIAGFIENGWEGMIDGWYGFRWQNSEGTGQAADYKSTQAAI<br>DQITGILNRVIEKMNEKSNQTEKCPSNATGPMKCIEDKIEEIESKLWCYNAELLVAL<br>INQNTIDYTDSEMNKLFEKTRRQLRENAEDMGNGCFKIYHKCDNDCIASIRNGTYDH<br>DVYRDEALNNRFQIKGV |

The invention claimed is:

1. A monomeric influenza A hemagglutinin (HA) stem polypeptide, comprising an HA1 and a HA2 domain of an HA of a group 2 influenza A virus, said HA stem polypeptide comprising an amino acid sequence which comprises:

a deletion of the head region from the HA1 domain;

a modification of the trimerization region in the HA2 domain;

at least two cysteine residues capable of forming at least one intramonomeric cysteine bridge;

and wherein in the amino acid sequence the amino acid at position 355 is W, wherein the numbering of the amino acid positions in the HA stem polypeptide amino acid sequence is H3 numbering corresponding to the full-length HA numbering of the reference strain H3N2 A/Aichi/2/68 (SEQ ID NO: 1).

2. The polypeptide according to claim 1, wherein:

a. the amino acid at position 432 is I, or the amino acid at position 432 is I and the amino acid at position 380 is I;

b. the amino acid at position 378 is T, the amino acid at position 379 is N and/or the amino acid at position 381 is V; and/or c. the polypeptide further comprises an introduced glycosylation motif at positions 401-403 for N-linked glycosylation at position 401.

3. The polypeptide according to claim 1, wherein said deletion of the head region in the HA1 domain comprises a deletion comprising at least the amino acid sequence from the amino acid corresponding to the amino acid at position 50 up to and including the amino acid corresponding to the amino acid at position 302, or wherein the deletion of the head region in the HA1 domain comprises at least the amino acid sequence from the amino acid at position 47 up to and including the amino acid at position 306.

4. The polypeptide according to claim 1, wherein the trimerization region in the HA2 domain comprises the amino acid sequence from the amino acid corresponding to the amino acid at position 405 up to and including the amino acid corresponding to the amino acid at position 419.

5. The polypeptide according to claim 1, wherein the modification of the trimerization region comprises the introduction of a heterologous trimerization domain.

6. The polypeptide according to claim 1, wherein:

a. the modification of the trimerization region comprises an alteration of the heptad repeat sequence in the C-helix; and/or b. the modified trimerization region in the HA2 domain comprises the amino acid sequence 405RMKQIEDKIEEIESK419 (SEQ ID NO: 9) or 405PMKQIEDKIEEIESK419 (SEQ ID NO: 10).

7. The polypeptide according to claim 1, comprising a cysteine at the amino acid position corresponding to position 310 in combination with a cysteine at the position corresponding to position 422; or a cysteine at the amino acid corresponding to position 311 in combination with a cysteine at the position corresponding to position 422; or a cysteine at the amino acid position corresponding to position 308 in combination with a cysteine at the position corresponding to position 418, wherein said cysteines are capable of forming an intramonomeric cysteine bridge.

8. The polypeptide according to claim 1, wherein the amino acid at position 388 is M.

9. The polypeptide according to claim 1, comprising at least one additional introduced glycosylation motif.

10. The polypeptide according to claim 1, wherein:
a. one or more of the amino acids in the B-loop are mutated into P;
b. the amino acid at position 31 is E and the amino acid at position 34 is V;
c. the amino acid at position 392 is S or P;
d. the amino acid at position 395 is T or P;
e. the amino acid at position 399 is S or P;
f. the amino acid at position 435 is N or R; and/or
g. the amino acid at position 439 is Y.

11. The polypeptide according to claim 1, wherein the HA stem polypeptide monomer does not comprise a protease cleavage site between the HA1 and HA2 domain.

12. The polypeptide according to claim 1, wherein the HA stem polypeptide monomer comprises a natural cleavage site or a polybasic cleavage site.

13. The polypeptide according to claim 1, wherein the HA1 and HA2 domain are from an influenza virus comprising HA of the H3 subtype.

14. The polypeptide according to claim 1, comprising a truncated HA2 domain.

15. The polypeptide according to claim 1, wherein the deletion of the head region in the HA1 domain has been replaced by a linking sequence of 1-10 amino acids.

16. The polypeptide according to claim 1, comprising a cysteine at the position corresponding to position 396 in combination with a cysteine at the position corresponding to position 408, or a cysteine at the position corresponding to position 397 in combination with a cysteine at the position corresponding to position 408; or a cysteine at the position corresponding to position 398 in combination with a cysteine at the position corresponding to position 408, or a cysteine at the position corresponding to position 398 in combination with a cysteine at the position corresponding to position 405.

17. A multimeric influenza A hemagglutinin (HA) stem polypeptide, comprising at least two HA stem polypeptide monomers according to claim 1.

18. A multimeric influenza A hemagglutinin (HA) stem polypeptide, comprising at least two HA stem polypeptide monomers according to claim 16, wherein a first HA stem polypeptide monomer is linked to a second monomer by an intermonomeric disulfide bridge between the cysteine at position 396, 397 or 398 of said first monomer and the cysteine at position 408 of the second monomer, or wherein a first HA stem polypeptide monomer is linked to a second monomer by an intermonomeric disulfide bridge between the cysteine at position 398 of said first monomer and the cysteine at position 405 of the second monomer.

19. The multimeric polypeptide according to claim 17, wherein the polypeptide is trimeric.

20. A nucleic acid encoding an HA stem polypeptide monomer according to claim 1.

21. A vector comprising a nucleic acid molecule according to claim 20.

22. A pharmaceutical composition comprising a monomeric HA stem polypeptide according to claim 1, and a pharmaceutically acceptable carrier.

23. A method of inducing an immune response against an influenza virus, wherein the method comprises administering a monomeric HA stem polypeptide according to claim 1.

24. A vaccine comprising the monomeric HA stem polypeptide according to claim 1.

25. The polypeptide according to claim 1, wherein the HA stem polypeptide is derived from HA of an influenza A virus selected from the group consisting of:

a. A/Hong Kong/1/68 with the amino acid sequence SEQ ID NO:2 consisting of one or more of the following modifications: the amino acid at position 432 is I, the amino acid at position 380 is I, the amino acid at position 378 is T, the amino acid at position 379 is N, the amino acid at position 381 is V; an introduced glycosylation motif at positions 401-403 for N-linked glycosylation at position 401; said deletion of the head region in the HA1 domain comprises a deletion comprising at least the amino acid sequence from the amino acid corresponding to the amino acid at position 50 up to and including the amino acid corresponding to the amino acid at position 302; the trimerization region in the HA2 domain comprises the amino acid sequence from the amino acid corresponding to the amino acid at position 405 up to and including the amino acid corresponding to the amino acid at position 419; the modification of the trimerization region comprises the introduction of a heterologous trimerization domain; the modification of the trimerization region comprises an alteration of the heptad repeat sequence in the C-helix; the modified trimerization region in the HA2 domain comprises the amino acid sequence 405RMKQIEDKIEEIESK419 (SEQ ID NO: 9) or 405PMKQIEDKIEEIESK419 (SEQ ID NO: 10); a cysteine at the amino acid position corresponding to position 310 in combination with a cysteine at the position corresponding to position 422; or a cysteine at the amino acid corresponding to position 311 in combination with a cysteine at the position corresponding to position 422; or a cysteine at the amino acid position corresponding to position 308 in combination with a cysteine at the position corresponding to position 418, wherein said cysteines are capable of forming an intramonomeric cysteine bridge; the amino acid at position 388 is M; the amino acid at position 31 is E and the amino acid at position 34 is V; the amino acid at position 392 is S or P; the amino acid at position 395 is T or P; the amino acid at position 399 is S or P; the amino acid at position 435 is N or R; the amino acid at position 439 is Y; the HA stem polypeptide monomer does not comprise a protease cleavage site between the HA1 and HA2 domain; the HA stem polypeptide monomer comprises a natural cleavage site or a polybasic cleavage site; a truncated HA2 domain; the deletion of the head region in the HA1 domain has been replaced by a linking sequence of 1-10 amino acids; and a cysteine at the position corresponding to position 396 in combination with a cysteine at the position corresponding to position 408, or a cysteine at the position corresponding to position 397 in combination with a cysteine at the position corresponding to position 408; or a cysteine at the position corresponding to position 398 in combination with a cysteine at the position corresponding to position 408, or a cysteine at the position corresponding to position 398 in combination with a cysteine at the position corresponding to position 405;

b. A/Wisconsin/67/2005 with the amino acid sequence of SEQ ID NO: 13, consisting of one or more of the following modifications: the amino acid at position 432 is I, or the amino acid at position 432 is I and the amino acid at position 380 is I; the amino acid at position 378 is T, the amino acid at position 379 is N and/or the amino acid at position 381 is V; an introduced glycosylation motif at positions 401-403 for N-linked glycosylation at position 401; said deletion of the head region in the HA1 domain comprises a deletion comprising at least the amino acid sequence from the amino acid corresponding to the amino acid at position 50 up to and including the amino acid corresponding to the amino acid at position 302; the trimerization region in the HA2 domain comprises the amino acid sequence from the amino acid corresponding to the amino acid at position 405 up to and including the amino acid corresponding to the amino acid at position 419; the modification of the trimerization region comprises the introduction of a heterologous trimerization domain; the modification of the trimerization region comprises an alteration of the heptad repeat sequence in the C-helix; the modified trimerization region in the HA2 domain comprises the amino acid sequence 405RMKQIEDKIEEIESK419 (SEQ ID NO: 9) or 405PMKQIEDKIEEIESK419 (SEQ ID NO: 10); a cysteine at the amino acid position corresponding to position 310 in combination with a cysteine at the position corresponding to position 422; or a cysteine at the amino acid corresponding to position 311 in combination with a cysteine at the position corresponding to position 422; or a cysteine at the amino acid position corresponding to position 308 in combination with a cysteine at the position corresponding to position 418, wherein said cysteines are capable of forming an intramonomeric cysteine bridge; the amino acid at position 388 is M; at least one additional introduced glycosylation motif; one or more of the amino acids in the B-loop are mutated into P; the amino acid at position 31 is E and the amino acid at position 34 is V; the amino acid at position 392 is S or P; the amino acid at position 395 is T or P; the amino acid at position 399 is S or P; the amino acid at position 435 is N or R; the amino acid at position 439 is Y; the HA stem polypeptide monomer does not comprise a protease cleavage site between the HA1 and HA2 domain; the HA stem polypeptide monomer comprises a natural cleavage site or a polybasic cleavage site; a truncated HA2 domain; the deletion of the head region in the HA1 domain has been replaced by a linking sequence of 1-10 amino acids; and a cysteine at the position corresponding to position 396 in combination with a cysteine at the position corresponding to position 408, or a cysteine at the position corresponding to position 397 in combination with a cysteine at the position corresponding to position 408; or a cysteine at the position corresponding to position 398 in combination with a cysteine at the position corresponding to position 408, or a cysteine at the position corresponding to position 398 in combination with a cysteine at the position corresponding to position 405;

c. A/Singapore/INFMH/16/0019/2016 with the amino acid sequence of SEQ ID NO: 14, consisting of one or more of the following modifications: the amino acid at position 432 is I, or the amino acid at position 432 is I and the amino acid at position 380 is I; the amino acid at position 378 is T, the amino acid at position 379 is N and/or the amino acid at position 381 is V; an introduced glycosylation motif at positions 401-403 for N-linked glycosylation at position 401; said deletion of the head region in the HA1 domain comprises a deletion comprising at least the amino acid sequence from the amino acid corresponding to the amino acid at position 50 up to and including the amino acid corresponding to the amino acid at position 302; the trimerization region in the HA2 domain comprises the amino acid sequence from the amino acid corresponding to the amino acid at position 405 up to and including the amino acid corresponding to the amino acid at position 419; the modification of the trimerization region comprises the introduction of a heterologous trimerization domain; the modification of the trimerization region comprises an alteration of the heptad repeat sequence in the C-helix; the modified trimerization region in the HA2 domain comprises the amino acid sequence 405RMKQIEDKIEEIESK419 (SEQ ID NO: 9) or 405PMKQIEDKIEEIESK419 (SEQ ID NO: 10); a cysteine at the amino acid position corresponding to position 310 in combination with a cysteine at the position corresponding to position 422; or a cysteine at the amino acid corresponding to position 311 in combination with a cysteine at the position corresponding to position 422; or a cysteine at the amino acid position corresponding to position 308 in combination with a cysteine at the position corresponding to position 418, wherein said cysteines are capable of forming an intramonomeric cysteine bridge; the amino acid at position 388 is M; at least one additional introduced glycosylation motif; one or more of the amino acids in the B-loop are mutated into P; the amino acid at position 31 is E and the amino acid at position 34 is V; the amino acid at position 392 is S or P; the amino acid at position 395 is T or P; the amino acid at position 399 is S or P; the amino acid at position 435 is N or R; the amino acid at position 439 is Y; the HA stem polypeptide monomer does not comprise a protease cleavage site between the HA1 and HA2 domain; the HA stem polypeptide monomer comprises a natural cleavage site or a polybasic cleavage site; a truncated HA2 domain; the deletion of the head region in the HA1 domain has been replaced by a linking sequence of 1-10 amino acids; and a cysteine at the position corresponding to position 396 in combination with a cysteine at the position corresponding to position 408, or a cysteine at the position corresponding to position 397 in combination with a cysteine at the position corresponding to position 408; or a cysteine at the position corresponding to position 398 in combination with a cysteine at the position corresponding to position 408, or a cysteine at the position corresponding to position 398 in combination with a cysteine at the position corresponding to position 405;

d. A/Perth/16/2009 with the amino acid sequence of SEQ ID NO: 15, consisting of one or more of the following modifications: the amino acid at position 432 is I, or the amino acid at position 432 is I and the amino acid at position 380 is I; the amino acid at position 378 is T, the amino acid at position 379 is N and/or the amino acid at position 381 is V; an introduced glycosylation motif at positions 401-403 for N-linked glycosylation at position 401; said deletion of the head region in the HA1 domain comprises a deletion comprising at least the amino acid sequence from the amino acid corresponding to the amino acid at position 50 up to and including the amino acid corresponding to the amino acid at position 302; the trimerization region in the HA2 domain comprises the amino acid sequence from the amino acid corresponding to the amino acid at position 405 up to and including the amino acid corresponding to the amino acid at position 419; the modification of the trimerization region comprises the introduction of a heterologous trimerization domain; the modification of the trimerization region comprises an alteration of the heptad repeat sequence in the C-helix; the modified trimerization region in the HA2 domain comprises the amino acid sequence 405RMKQIEDKIEEIESK419 (SEQ ID NO: 9) or 405PMKQIEDKIEEIESK419 (SEQ ID NO: 10); a cysteine at the amino acid position corresponding to position 310 in combination with a cysteine at the position corresponding to position 422; or a cysteine at the amino acid corresponding to position 311 in combination with a cysteine at the position corresponding to position 422; or a cysteine at the amino acid position corresponding to position 308 in combination with a cysteine at the position corresponding to position 418, wherein said cysteines are capable of forming an intra-monomeric cysteine bridge; the amino acid at position 388 is M; at least one additional introduced glycosylation motif; one or more of the amino acids in the B-loop are mutated into P; the amino acid at position 31 is E and the amino acid at position 34 is V; the amino acid at position 392 is S or P; the amino acid at position 395 is T or P; the amino acid at position 399 is S or P; the amino acid at position 435 is N or R; the amino acid at position 439 is Y; the HA stem polypeptide monomer does not comprise a protease cleavage site between the HA1 and HA2 domain; the HA stem polypeptide monomer comprises a natural cleavage site or a polybasic cleavage site; a truncated HA2 domain; the deletion of the head region in the HA1 domain has been replaced by a linking sequence of 1-10 amino acids; and a cysteine at the position corresponding to position 396 in combination with a cysteine at the position corresponding to position 408, or a cysteine at the position corresponding to position 397 in combination with a cysteine at the position corresponding to position 408; or a cysteine at the position corresponding to position 398 in combination with a cysteine at the position corresponding to position 408, or a cysteine at the position corresponding to position 398 in combination with a cysteine at the position corresponding to position 405;

e. A/Brisbane/10/2007 with the amino acid sequence of SEQ ID NO: 16, consisting of one or more of the following modifications: the amino acid at position 432 is I, or the amino acid at position 432 is I and the amino acid at position 380 is I; the amino acid at position 378 is T, the amino acid at position 379 is N and/or the amino acid at position 381 is V; an introduced glycosylation motif at positions 401-403 for N-linked glycosylation at position 401; said deletion of the head region in the HA1 domain comprises a deletion comprising at least the amino acid sequence from the amino acid corresponding to the amino acid at position 50 up to and including the amino acid corresponding to the amino acid at position 302; the trimerization region in the HA2 domain comprises the amino acid sequence from the amino acid corresponding to the amino acid at position 405 up to and including the amino acid corresponding to the amino acid at position 419; the modification of the trimerization region comprises the introduction of a heterologous trimerization domain; the modification of the trimerization region comprises an alteration of the heptad repeat sequence in the C-helix; the modified trimerization region in the HA2 domain comprises the amino acid sequence 405RMKQIEDKIEEIESK419 (SEQ ID NO: 9) or 405PMKQIEDKIEEIESK419 (SEQ ID NO: 10); a cysteine at the amino acid position corresponding to position 310 in combination with a cysteine at the position corresponding to position 422; or a cysteine at the amino acid corresponding to position 311 in combination with a cysteine at the position corresponding to position 422; or a cysteine at the amino acid position corresponding to position 308 in combination with a cysteine at the position corresponding to position 418, wherein said cysteines are capable of forming an intra-monomeric cysteine bridge; the amino acid at position 388 is M; at least one additional introduced glycosylation motif; one or more of the amino acids in the B-loop are mutated into P; the amino acid at position 31 is E and the amino acid at position 34 is V; the amino acid at position 392 is S or P; the amino acid at position 395 is T or P; the amino acid at position 399 is S or P; the amino acid at position 435 is N or R; the amino acid at position 439 is Y; the HA stem polypeptide monomer does not comprise a protease cleavage site between the HA1 and HA2 domain; the HA stem polypeptide monomer comprises a natural cleavage site or a polybasic cleavage site; a truncated HA2 domain; the deletion of the head region in the HA1 domain has been replaced by a linking sequence of 1-10 amino acids; and a cysteine at the position corresponding to position 396 in combination with a cysteine at the position corresponding to position 408, or a cysteine at the position corresponding to position 397 in combination with a cysteine at the position corresponding to position 408; or a cysteine at the position corresponding to position 398 in combination with a cysteine at the position corresponding to position 408, or a cysteine at the position corresponding to position 398 in combination with a cysteine at the position corresponding to position 405; and f. A/Panama/2007/1999 with the amino acid sequence of SEQ ID NO: 17, consisting of one or more of the following modifications: the amino acid at position 432 is I, or the amino acid at position 432 is I and the amino acid at position 380 is I; the amino acid at position 378 is T, the amino acid at position 379 is N and/or the amino acid at position 381 is V; an introduced glycosylation motif at positions 401-403 for N-linked glycosylation at position 401; said deletion of the head region in the HA1 domain comprises a deletion comprising at least the amino acid sequence from the amino acid corresponding to the amino acid at position 50 up to and including the amino acid corresponding to the amino acid at position 302; the trimerization region in the HA2 domain comprises the amino acid sequence from the amino acid corresponding to the amino acid at position 405 up to and including the amino acid corresponding to the amino acid at position 419; the modification of the trimerization region comprises the introduction of a heterologous trimerization domain; the modification of the trimerization region comprises an alteration of the heptad repeat sequence in the C-helix; the modified trimerization region in the HA2 domain comprises the amino acid sequence 405RMKQIEDKIEEIESK419 (SEQ ID NO: 9) or 405PMKQIEDKIEEIESK419 (SEQ ID NO: 10); a cysteine at the amino acid position corresponding to position 310 in combination with a cysteine at the position corresponding to position 422; or a cysteine at the amino acid corresponding to position 311 in combination with a cysteine at the position corresponding to position 422; or a cysteine at the amino acid position corresponding to position 308 in combination with a cysteine at the position corresponding to position 418, wherein said cysteines are capable of forming an intra-monomeric cysteine bridge; the amino acid at position 388 is M; at least one additional introduced glycosylation motif; one or more of the amino acids in the B-loop are mutated into P; the amino acid at position 31 is E and the amino acid at position 34 is V; the amino acid at position 392 is S or P; the amino acid at position 395 is T or P; the amino acid at position 399 is S or P; the amino acid at position 435 is N or R; the amino acid at position 439 is Y; the HA stem polypeptide monomer does not comprise a protease cleavage site between the HA1 and HA2 domain; the HA stem polypeptide monomer comprises a natural cleavage site or a polybasic cleavage site; a truncated HA2 domain; the deletion of the head region in the HA1 domain has been replaced by a linking sequence of 1-10 amino acids; and a cysteine at the position corresponding to position 396 in combination with a cysteine at the position corresponding to position 408, or a cysteine at the position corresponding to position 397 in combination with a cysteine at the position corresponding to position 408; or a cysteine at the position corresponding to position 398 in combination with a cysteine at the position corresponding to position 408, or a cysteine at the position corresponding to position 398 in combination with a cysteine at the position corresponding to position 405.

* * * * *